US010251396B2

(12) United States Patent
Mitsudera et al.

(10) Patent No.: US 10,251,396 B2
(45) Date of Patent: *Apr. 9, 2019

(54) AMIDE COMPOUND AND USE OF SAME FOR NOXIOUS ARTHROPOD CONTROL

(71) Applicant: SUMITOMO CHEMICAL COMPANY, LIMITED, Tokyo (JP)

(72) Inventors: Hiromasa Mitsudera, Takarazuka (JP); Mayumi Okajima, Takarazuka (JP); Ayano Kowata, Takarazuka (JP); Kenichiro Awasaguchi, Takarazuka (JP); Kazuya Ujihara, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/329,521

(22) PCT Filed: Jul. 21, 2015

(86) PCT No.: PCT/JP2015/070652

§ 371 (c)(1),
(2) Date: Jan. 26, 2017

(87) PCT Pub. No.: WO2016/017467

PCT Pub. Date: Feb. 4, 2016

(65) Prior Publication Data

US 2017/0295789 A1 Oct. 19, 2017

(30) Foreign Application Priority Data

Jul. 28, 2014 (JP) ................................ 2014-152615
Apr. 30, 2015 (JP) ................................ 2015-093089

(51) Int. Cl.

| | |
|---|---|
| ***A01N 43/80*** | (2006.01) |
| ***A01N 25/04*** | (2006.01) |
| ***A61K 31/42*** | (2006.01) |
| ***A61K 31/422*** | (2006.01) |
| ***C07D 413/12*** | (2006.01) |
| ***C07D 261/18*** | (2006.01) |
| ***A01N 25/06*** | (2006.01) |
| ***A01N 25/12*** | (2006.01) |
| ***A01N 25/14*** | (2006.01) |
| ***A01N 25/18*** | (2006.01) |
| ***A01N 25/28*** | (2006.01) |
| ***A01N 25/34*** | (2006.01) |

(52) U.S. Cl.

CPC ............ *A01N 43/80* (2013.01); *A01N 25/04* (2013.01); *A01N 25/06* (2013.01); *A01N 25/12* (2013.01); *A01N 25/14* (2013.01); *A01N 25/18* (2013.01); *A01N 25/28* (2013.01); *A01N 25/34* (2013.01); *A61K 31/42* (2013.01); *A61K 31/422* (2013.01); *C07D 261/18* (2013.01); *C07D 413/12* (2013.01)

(58) Field of Classification Search

CPC ................................ A01N 43/80; A01N 25/04
See application file for complete search history.

(56) References Cited

U.S. PATENT DOCUMENTS

| | | | | |
|---|---|---|---|---|
| 5,201,932 | A * | 4/1993 | Maywald | A01N 43/80 504/191 |
| 5,258,397 | A | 11/1993 | Lepage et al. | |
| 8,716,289 | B2 * | 5/2014 | Abouabdellah | C07D 401/14 514/248 |
| 2004/0102324 | A1 | 5/2004 | Annis et al. | |
| 2012/0094837 | A1 | 4/2012 | Mühlthau et al. | |
| 2012/0110705 | A1 | 5/2012 | Le Vezouet et al. | |

(Continued)

FOREIGN PATENT DOCUMENTS

| | | | |
|---|---|---|---|
| JP | 2004-521924 | A | 7/2004 |
| JP | 2012-532175 | A | 12/2012 |
| JP | 2013-535434 | A | 9/2013 |

(Continued)

OTHER PUBLICATIONS

Munster et al, Pestic. Sci., 1995, vol. 44, p. 21-27. (Year: 1995).*

(Continued)

*Primary Examiner* — Rebecca L Anderson
*Assistant Examiner* — Karen Cheng
(74) *Attorney, Agent, or Firm* — Birch, Stewart, Kolasch & Birch, LLP

(57) ABSTRACT

There is provided a noxious arthropod controlling agent containing an amide compound of formula (I):

(I)

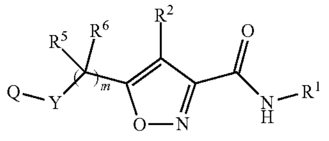

wherein $R^1$ represents a C1-C8 chain hydrocarbon group optionally having one or more groups selected from Group A, $R^2$ represents a hydrogen atom or the like, $R^3$ represents a hydrogen atom or the like, $R^5$ and $R^6$ are the same or different, and independently represent a hydrogen atom or the like, Y represents an oxygen atom or the like, m represents 0, 1, 2, 3, 4, 5, 6 or 7, and Q represents a C1-C8 chain hydrocarbon group optionally having one or more atoms or groups selected from Group D.

3 Claims, No Drawings

(56) References Cited

U.S. PATENT DOCUMENTS

| | | | |
|---|---|---|---|
| 2014/0100108 | A1 | 4/2014 | Willms et al. |
| 2015/0344466 | A1 | 12/2015 | Mitsudera et al. |

FOREIGN PATENT DOCUMENTS

| | | | |
|---|---|---|---|
| JP | 2015-51963 A | 3/2015 |
| WO | WO 91/08202 A1 | 6/1991 |
| WO | WO 02/058698 A2 | 8/2002 |
| WO | WO 03/090869 A1 | 11/2003 |
| WO | WO 2011/067272 A1 | 6/2011 |
| WO | WO 2013/003505 A1 | 1/2013 |
| WO | WO 2014/119696 A1 | 8/2014 |

OTHER PUBLICATIONS

International Preliminary Report on Patentability and Written Opinion of the International Searching Authority (Forms PCT/IB/326, PCT/IB/373, PCT/IB/338, and PCT/ISA/237) for International Application No. PCT/JP2015/070652, dated Feb. 9, 2017, with an English translation of the Written Opinion.
Machine translation for JP-2015-51963-A, published Mar. 19, 2015.
International Search Report issued in PCT/JP2015/070652 (PCT/ISA/210), dated Oct. 27, 2015.
Extended European Search Report for European Application No. 15826920.9, dated Jan. 31, 2018.

* cited by examiner

AMIDE COMPOUND AND USE OF SAME FOR NOXIOUS ARTHROPOD CONTROL

TECHNICAL FIELD

The present invention relates to an amide compound and noxious arthropod control use thereof.

BACKGROUND ART

Previously, many noxious arthropod controlling agents have been developed for controlling a noxious arthropod, and have been put into practical use. In addition, Patent Document 1 describes certain amide compounds.

PRIOR ART DOCUMENT

Patent Document

Patent Document 1: EP-A 0459887

DISCLOSURE OF THE INVENTION

Problems to be Solved by the Invention

The present invention provides a compound having excellent controlling efficacy on a noxious arthropod.

Means for Solving the Problems

In order to find out a compound having excellent controlling efficacy on a noxious arthropod, the present inventors intensively studied, and as a result, found out that an amide compound of following formula (I) has excellent controlling efficacy on a noxious arthropod, and thereby completing the present invention.

That is, the present invention encompasses:

[1] A noxious arthropod controlling agent containing an amide compound of formula (I):

(I)

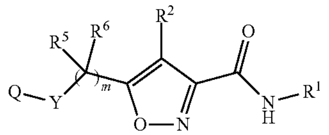

wherein $R^1$ represents a C1-C8 chain hydrocarbon group optionally having one or more groups selected from Group A, $R^2$ represents a C1-C3 hydrocarbon group optionally having one or more atoms or groups selected from the group consisting of an —$OR^3$ group and a halogen atom, a cyano group, a formyl group, a carboxy group, a (C1-C4 alkoxy)carbonyl group in which the C1-C4 alkoxy has optionally one or more halogen atoms, a carbamoyl group, a halogen atom, or a hydrogen atom, $R^3$ represents a —C(═S)$SR^4$ group or a hydrogen atom, $R^4$ represents a C1-C3 hydrocarbon group optionally having one or more halogen atoms, $R^5$ and $R^6$ are the same or different, and independently represent a C1-C4 alkyl group optionally having one or more halogen atoms, a halogen atom, a phenyl group optionally having one or more atoms or groups selected from Group B, or a hydrogen atom, Y represents a single bond, an oxygen atom or —$S(O)_u$—, wherein when Y is a single bond, m represents 0, and Q represents a C3-C8 chain hydrocarbon group, or a C1-C8 chain hydrocarbon group having one or more atoms or groups selected from Group C, and wherein when Y is an oxygen atom, or —$S(O)_u$—, m represents 0, 1, 2, 3, 4, 5, 6 or 7, and Q represents a C1-C8 chain hydrocarbon group optionally having one or more atoms or groups selected from Group D, or one group selected from Group E, and wherein u represents 0, 1, or 2;

Group A consisting of a halogen atom, a C1-C4 alkoxy group optionally having one or more halogen atoms, a $C_1$-$C_6$ alkylamino group, a di(C1-C6 alkyl)amino group, a hydroxy group, a (C1-C4 alkoxy)carbonyl group in which the C1-C4 alkoxy has optionally one or more halogen atoms, and a —$CONR^7R^8$ group, wherein $R^7$ and $R^8$ are the same or different, and independently represent a C1-C4 alkyl group optionally having one or more halogen atoms, a [(C1-C4 alkoxy)carbonyl]C1-C4 alkyl group in which the C1-C4 alkoxy has optionally one or more halogen atoms, a 3-tetrahydrofuranylmethyl group, a 4-tetrahydropyranylmethyl group or a hydrogen atom;

Group B consisting of a C1-C4 alkyl group optionally having one or more halogen atoms, a C1-C4 alkyl group having one or more benzyloxy groups, a $C_1$-$C_4$ alkoxy group optionally having one or more halogen atoms, a C1-C4 alkylthio group optionally having one or more halogen atoms, a C1-C4 alkylsulfinyl group optionally having one or more halogen atoms, a C1-C4 alkylsulfonyl group optionally having one or more halogen atoms, a (C1-C4 alkoxy)carbonyl group in which the C1-C4 alkoxy has optionally one or more halogen atoms, a vinyl group optionally having one or more atoms or groups selected from Group F, an ethynyl group optionally having an atom or group selected from Group F, a phenyl group, a phenoxy group, a cyano group, a nitro group, a carboxy group, a hydroxy group, a —$CONR^9R^{10}$ group, a methoxymethyl group and a halogen atom, wherein $R^9$ and $R^{10}$ are the same or different, and independently represent a $C_1$-$C_4$ alkyl group optionally having one or more halogen atoms, or a hydrogen atom;

Group C consisting of a $C_3$-$C_8$ cycloalkyl group optionally having one or more atoms or groups selected from Group B, an indanyl group optionally having one or more atoms or groups selected from Group B, a 1,2,3,4-tetrahydronaphthyl group optionally having one or more atoms or groups selected from Group B, a phenyl group optionally having one or more atoms or groups selected from Group B, a naphthyl group optionally having one or more atoms or groups selected from Group B, a pyridyl group optionally having one or more atoms or groups selected from Group B, a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B,
a benzothienyl group optionally having one or more atoms or groups selected from Group B,
a 1,3-benzodioxolyl group optionally having one or more atoms or groups selected from Group B,
a 1,4-benzodioxanyl group optionally having one or more atoms or groups selected from Group B,
a halogen atom, a (C1-C4 alkoxy)carbonyl group in which the C1-C4 alkoxy has optionally one or more halogen atoms, a cyano group, a nitro group, a carboxy group, a hydroxy group, and a —$CONR^9R^{10}$ group;

Group D consisting of
a C3-C8 cycloalkyl group optionally having one or more atoms or groups selected from Group B,
an indanyl group optionally having one or more atoms or groups selected from Group B,
a 1,2,3,4-tetrahydronaphthyl group optionally having one or more atoms or groups selected from Group B,
a phenyl group optionally having one or more atoms or groups selected from Group B,
a phenoxy group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B,
a benzothienyl group optionally having one or more atoms or groups selected from Group B,
a 1,3-benzodioxolyl group optionally having one or more atoms or groups selected from Group B,
a 1,4-benzodioxanyl group optionally having one or more atoms or groups selected from Group B,
a halogen atom, a (C1-C4 alkoxy)carbonyl group in which the C1-C4 alkoxy has optionally one or more halogen atoms, a cyano group, a nitro group, a carboxy group, a hydroxy group, and a —$CONR^9R^{10}$ group;

Group E consisting of
a C3-C8 cycloalkyl group optionally having one or more atoms or groups selected from Group B,
an indanyl group optionally having one or more atoms or groups selected from Group B,
a 1,2,3,4-tetrahydronaphthyl group optionally having one or more atoms or groups selected from Group B,
a phenyl group optionally having one or more atoms or groups selected from Group B,
a naphthyl group optionally having one or more atoms or groups selected from Group B,
a pyridyl group optionally having one or more atoms or groups selected from Group B,
a quinolyl group optionally having one or more atoms or groups selected from Group B,
a furyl group optionally having one or more atoms or groups selected from Group B,
a thienyl group optionally having one or more atoms or groups selected from Group B,
a benzofuranyl group optionally having one or more atoms or groups selected from Group B, and
a benzothienyl group optionally having one or more atoms or groups selected from Group B;

Group F consisting of
a C1-C4 alkyl group optionally having one or more halogen atoms and a halogen atom,
and an inert carrier.

[2] The noxious arthropod controlling agent according to [1], wherein the amide compound is a compound of formula (II):

(II)

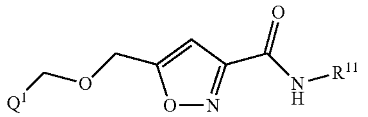

wherein $R^{11}$ represents a C1-C8 chain hydrocarbon group optionally having one or more groups selected from Group G, and $Q^1$ represents a phenyl group or naphthyl group:

Group G consisting of a C1-C4 alkoxy group, a (C1-C4 alkoxy)carbonyl group and a hydroxy group.

[3] The noxious arthropod controlling agent according to [1], wherein $R^1$ represents a $C_2$-$C_8$ chain hydrocarbon group having one or more substituents selected from the group consisting of a C1-C4 alkoxy group optionally having one or more halogen atoms, a C1-C6 alkylamino group, a di(C1-C6 alkyl)amino group and a hydroxy group, $R^2$ is a hydrogen atom, Y is a single bond, m is 0, Q is a $C_3$-$C_8$ chain hydrocarbon group optionally having one or more groups selected from Group C, wherein the one or more groups selected from Group C is a $C_3$-$C_8$ cycloalkyl group optionally having one or more atoms or groups selected from Group B, and wherein the one or more atoms or groups selected from Group B is selected from the group consists of a halogen atom and a cyano group.

[4] A method for controlling a noxious arthropod, which comprises applying an effective amount of an amide compound of formula (I) as defined in [1], to a noxious arthropod or a habitat of a noxious arthropod.

[5] The noxious arthropod controlling agent according to [1], wherein $R^1$ is a C2-C6 alkyl group optionally having one or more groups selected from the group consisting of a hydroxy group and a methoxy group, $R^2$ is a methyl group, a fluoromethyl group, a hydroxymethyl group, a 1-fluoroethyl group or a hydrogen atom, a group represented by Q-Y—$(CR^5R^6)_m$ is a $Q^a$-$CH_2$—O—$CH_2$ group, a $Q^a$-$CH_2$—$CH_2$—$CH_2$ group, a $Q^a$-O—$CH_2$ group, or a $Q^a$-$CH_2$ group, $Q^a$ is a phenyl group optionally having one or more atoms or groups selected from Group H or a naphthyl group optionally having one or more atoms or groups selected from Group H;

Group H consisting of a C1-C4 alkyl group, a C1-C4 alkoxy group and a halogen atom.

[6] The method for controlling a noxious arthropod according to [4], wherein $R^1$ is a C2-C6 alkyl group optionally having one or more groups selected from the group consisting of a hydroxy group and a methoxy group, $R^2$ is a methyl group, a fluoromethyl group, a hydroxymethyl group, a 1-fluoroethyl group or a hydrogen atom, a group represented by Q-Y—$(CR^5R^6)_m$ is a $Q^a$-$CH_2$—O—$CH_2$ group, a $Q^a$-$CH_2$—$CH_2$—$CH_2$ group, a $Q^a$-O—$CH_2$ group or a $Q^a$-$CH_2$ group, $Q^a$ is a phenyl group optionally having one or more atoms or groups selected from Group H or a naphthyl group optionally having one or more atoms or groups selected from Group H;

Group H consisting of a C1-C4 alkyl group, a C1-C4 alkoxy group, and a halogen atom.

[7] The method for controlling a noxious arthropod according to [4], wherein $R^1$ is a C2-C8 alkyl group having one or more groups selected from the group consisting of a hydroxy group, a methoxy group, a C1-C6 alkylamino group and a di(C1-C6 alkyl)amino group, $R^2$ is a methyl group, a fluoromethyl group, a hydroxymethyl group, a 1-fluoroethyl group or a hydrogen atom, and wherein a group represented by Q-Y—$(CR^5R^6)_m$ is a $Q^a$-$CH_2$—O—$CH_2$ group, a $Q^a$-$CH_2$—$CH_2$—$CH_2$ group, a $Q^a$-O—$CH_2$ group, a $Q^a$-$CH_2$—$CH_2$—O— group, a $Q^a$-$CH_2$ group, or a C3-C8 chain hydrocarbon group optionally having one or more substituents selected from the group consisting of a halogen atom and a cyano group, $Q^a$ is a phenyl group optionally having one or more substituents selected from Group H, or a naphthyl group optionally having one or more substituents selected from Group H;

Group H consisting of a C1-C4 alkyl group, a C1-C4 alkoxy group, and a halogen atom.

[8] The method for controlling a noxious arthropod according to [4], wherein $R^1$ is a C2-C8 alkyl group having one or more groups selected from the group consisting of a hydroxy group, a methoxy group, a C1-C6 alkylamino group and a di(C1-C6 alkyl)amino group, $R^2$ is a methyl group, a fluoromethyl group, a hydroxymethyl group, a 1-fluoroethyl group or a hydrogen atom, and wherein a group represented by Q-Y—$(CR^5R^6)_m$ is a C1-C4 alkoxy group, or a C3-C8 chain hydrocarbon group optionally having one or more substituents selected from the group consisting of a halogen atom, and a cyano group.

[9] Use of the amide compound of formula (I) as defined in claim 1 for controlling noxious arthropod.

Effect of the Invention

The present controlling agent has excellent controlling efficacy on a noxious arthropod, and is useful.

MODE FOR CARRYING OUT THE INVENTION

The compound disclosed in the present specification have isomers derived from an asymmetric carbon atom, and isomers derived from a double bond in some cases, and the compound includes such isomers and a mixture of isomers in an optional ratio.

Substituents described in the present specification will be explained.

The "halogen atom" means a fluorine atom, a chlorine atom, a bromine atom, and an iodine atom.

"Optionally having one or more halogen atoms" indicates that when a substituent has two or more halogen atoms, those halogen atoms may be the same or different from one another.

The expression of "CX-CY" in the present description means that the carbon atom number is X through Y. For example, the expression of "C1-C8" means that the number of carbon atom(s) is 1 to 8.

The "chain hydrocarbon group" represents an alkyl group, an alkenyl group and an alkynyl group.

In the present specification, examples of the "C1-C4 alkyl group optionally having one or more halogen atoms" include, for example, a methyl group, an ethyl group, a propyl group, an isopropyl group, a butyl group, an isobutyl group, a sec-butyl group, a tert-butyl group, an iodomethyl group, a bromomethyl group, a chloromethyl group, a fluoromethyl group, a difluoromethyl group, a chlorodifluoromethyl group, a trichloromethyl group, a trifluoromethyl group, a 2,2,2-trifluoroethyl group, a 1,1,2,2-tetrafluoroethyl group and a 1,1,2,2,2-pentafluoroethyl group.

In the present specification, examples of the "C1-C3 hydrocarbon group optionally having one or more halogen atoms" include, for example, a methyl group, an ethyl group, a propyl group, an isopropyl group, an iodomethyl group, a bromomethyl group, a chloromethyl group, a fluoromethyl group, a difluoromethyl group, a chlorodifluoromethyl group, a trichloromethyl group, a trifluoromethyl group, a 1-fluoroethyl group, a 2-fluoroethyl group, a 1-fluoropropyl group, a 2-fluoropropyl group, a 3-fluoropropyl group, a 1-fluoro-1-methylethyl group, a 1-chloroethyl group, a 1-chloropropyl group, a 1-chloro-1-methylethyl group, a 1-bromoethyl group, a 1-bromopropyl group, a 1-bromo-1-methylethyl group, a 2,2,2-trifluoroethyl group, a 1,1,2,2-tetrafluoroethyl group and a 1,1,2,2,2-pentafluoroethyl group.

In the present invention, examples of the "C3-C8 cycloalkyl group optionally having one or more atoms or groups selected from Group B" include, for example, a cyclopropyl group, a 1-methylcyclopropyl group, a 2,2-dichlorocyclopropyl group, a 2,2-difluorocyclopropyl group, a cyclopentyl group, a 1-methylcyclopentyl group, a 2-methylcyclopentyl group, a 3-methylcyclopentyl group, a 2-chlorocyclopentyl group, a 3-chlorocyclopentyl group, a 2-fluorocyclopentyl group, a 3-fluorocyclopentyl group, a 2,2-difluorocyclopentyl group, a 3,3-difluorocyclopentyl group, a 2-cyanocyclopentyl group, a 3-cyanocyclopentyl group, a cyclohexyl group, a 1-methylcyclohexyl group, a 2-methylcyclohexyl group, a 3-methylcyclohexyl group, a 4-methylcyclohexyl group, a 2-chlorocyclohexyl group, a 3-chlorocyclohexyl group, a 4-chlorocyclohexyl group, a 4,4-dichlorocyclohexyl group, a 4,4-difluorocyclohexyl group, a 4-cyanocyclohexyl group, a cycloheptyl group, and a cyclooctyl group.

In the present specification, examples of the "C1-C6 alkylamino group" include, for example, a methylamino group, an ethylamino group, a propylamino group, an isopropylamino group, a butylamino group, an isobutylamino group, a sec-butylamino group, a pentylamino group, and a hexylamino group.

In the present specification, examples of the "di(C1-C6 alkyl)amino group" include, for example, a dimethylamino group, a diethylamino group, a dipropylamino group, a diisopropylamino group, a methyl(ethyl)amino group, a methyl(isopropyl)amino group, a methyl(butyl)amino group, a methyl(pentyl)amino group and a methyl(hexyl) amino group.

In the present specification, examples of the "C1-C8 chain hydrocarbon group" in the "C1-C8 chain hydrocarbon group optionally having one or more groups selected from Group A" and the "C1-C8 chain hydrocarbon group optionally having one or more groups selected from Group G" include, for example, a "C1-C8 alkyl group" such as a methyl group, an ethyl group, an isopropyl group, a tert-butyl group, a propyl group, a sec-butyl group, an isobutyl group, a 1,1-dimethylpropyl group, a 2,2-dimethylpropyl group, a 1,2-dimethylpropyl group, a 1-ethylpropyl group, a butyl group, a 1-methylbutyl group, a 2-methylbutyl group, a 3-methylbutyl group, a 1,1-dimethylbutyl group, a 2,2-dimethylbutyl group, a 3,3-dimethylbutyl group, a 1-ethylbutyl group, a 2-ethylbutyl group, a pentyl group, a 1-methylpentyl group, a 2-methylpentyl group, a 3-methylpentyl group, a 4-methylpentyl group, a hexyl group, a heptyl group, an octyl group and the like;
a "C2-C8 alkenyl group" such as a vinyl group, a 1-propenyl group, a 2-propenyl group, a 1-methyl-1-propenyl group, a 1-methyl-2-propenyl group, a 1,2-dimethyl-1-propenyl group, a 1,1-dimethyl-2-propenyl group, a 1-ethyl-1-propenyl group, a 1-ethyl-2-propenyl group, a 1-butenyl group, a 2-butenyl group, a 3-butenyl group, a 1-methyl-1-butenyl group, a 2-methyl-1-butenyl group, a 2-methyl-2-butenyl group, a 2-methyl-3-butenyl group, a 3-methyl-3-butenyl group, a 1,1-dimethyl-3-butenyl group, a 1,1-dimethyl-2-butenyl group, a 1-ethyl-1-butenyl group, a 1-ethyl-2-butenyl group, a 1-ethyl-3-butenyl group, a 1-pentenyl group, a 2-pentenyl group, a 3-pentenyl group, a 4-pentenyl group, a 1-methyl-1-pentenyl group, a 1-methyl-2-pentenyl group, a 1-methyl-3-pentenyl group, a 1-methyl-4-pentenyl group, a 2-methyl-1-pentenyl group, a 2-methyl-2-pentenyl group, a 3-methyl-2-pentenyl group, a 3-methyl-3-pentenyl group, a 4-methyl-3-pentenyl group, a 4-methyl-4-pentenyl group, a 1,1-dimethyl-2-pentenyl group, a 1,1-dimethyl-3-pentenyl group, a 1,1-dimethyl-4-pentenyl group, a 1-ethyl-1-pentenyl group, a 1-ethyl-2-pentenyl group, a 1-ethyl-3-pentenyl group, a 1-ethyl-4-pentenyl group, a 1-hexenyl group, a 2-hexenyl group, a 3-hexenyl group, a 4-hexenyl group, a 5-hexenyl group, a 6-heptenyl group, and a 7-octenyl group;
a "C2-C8 alkynyl group" such as an ethynyl group, a 1-propynyl group, a 2-propynyl group, a 1-methyl-2-propynyl group, a 1,1-dimethyl-2-propynyl group, a 1-ethyl-2-propynyl group, a 1-butynyl group, a 2-butynyl group, a 3-butynyl group, a 1-methyl-2-butynyl group, a 1-methyl-3-butynyl group, a 1,1-dimethyl-2-butynyl group, a 1,1-dimethyl-3-butynyl group, a 1-ethyl-2-butynyl group, a 1-ethyl-3-butynyl group, a 1-pentynyl group, a 2-pentynyl group, a 3-pentynyl group, a 4-pentynyl group, a 1-methyl-2-pentynyl group, a 1-methyl-3-pentynyl group, a 1-methyl-4-pentynyl group, a 1,1-dimethyl-2-pentynyl group, a 1,1-dimethyl-3-pentynyl group, a 1,1-dimethyl-4-pentynyl group, a 1-ethyl-2-pentynyl group, a 1-ethyl-3-pentynyl group, a 1-ethyl-4-pentynyl group, a 1-hexynyl group, a 2-hexynyl group, a 3-hexynyl group, a 4-hexynyl group, a 5-hexynyl group, and a 7-octynyl group.

In the present specification, examples of the "C1-C8 chain hydrocarbon group optionally having one or more groups selected from Group A" include, for example, a methoxymethyl group, an ethoxymethyl group, a dimethoxymethyl group, a methoxycarbonylmethyl group, an ethoxycarbonylmethyl group, a hydroxymethyl group, a dimethylaminomethyl group, a diethylaminomethyl group, a methylethylaminomethyl group, a 1-methoxyethyl group, a 2-methoxyethyl group, a 1-ethoxyethyl group, a 2-ethoxyethyl group, a 1,1-dimethoxyethyl group, a 2,2-dimethoxyethyl group, a 1,1-diethoxyethyl group, a 2,2-diethoxyethyl group, a 1-(methoxycarbonyl)ethyl group, a 2-(methoxycarbonyl)ethyl group, a 1-(ethoxycarbonyl)ethyl group, a 2-(ethoxycarbonyl)ethyl group, a 1-hydroxyethyl group, a 2-hydroxyethyl group, a 1-(dimethylamino)ethyl group, a 2-(dimethylamino)ethyl group, a 1-(diethylamino)ethyl group, a 2-(diethylamino)ethyl group, a 1-{methyl(ethyl)amino}ethyl group, a 2-{methyl(ethyl)amino}ethyl group, a 1-methoxypropyl group, a 2-methoxypropyl group, a 3-methoxypropyl group, a 1-ethoxypropyl group, a 2-ethoxypropyl group, a 3-ethoxypropyl group, a 1,1-dimethoxypropyl group, a 2,2-dimethoxypropyl group, a 3,3-dimethoxypropyl group, a 1-methoxycarbonylpropyl group, a 1-hydroxypropyl group, a 2-hydroxypropyl group, a 3-hydroxypropyl group, a 1-(hydroxymethyl)ethyl group, a 3-(dimethylamino)propyl group, a 3-(diethylamino)propyl group, a 3-{methyl(ethyl)amino}propyl group, a 3-methoxy-2,2-dimethylpropyl group, a 3-methoxy-1,1-dimethylpropyl group, a 2-methoxy-1,1-dimethylpropyl group, a 2-methoxy-2-methylpropyl group, a 1-methoxy-2-methylpropyl group, a 1-hydroxy-2,2-dimethylpropyl group, a 3-hydroxy-2,2-dimethylpropyl group, a 3-hydroxy-1,1-dimethylpropyl group, a 2-hydroxy-1,1-dimethylpropyl group, a 2-hydorxy-2-methylpropyl group, a 1-hydroxy-2-methylpropyl group, a 1-(dimethylamino)propyl group, a 2-(dimethylamino)propyl group, a 3-(dimethylamino)propyl group, a N-(3-tetrahydrofuranylmethyl)carbamoylmethyl group, a N-(4-tetrahydropyranylmethyl)carbamoylmethyl group and a 2,2,2-trifluoroethyl group.

In the present specification, examples of the "C1-C8 chain hydrocarbon group optionally having one or more groups selected from Group G" include, for example, a methoxymethyl group, an ethoxymethyl group, a dimethoxymethyl group, a diethyoxymethyl group, a methoxycarbonylmethyl group, an ethoxycarbonylmethyl group, a 1-methoxyethyl group, a 2-methoxyethyl group, a 1-ethoxyethyl group, a 2-ethoxyethyl group, a 1,1-dimethoxyethyl group, a 2,2-dimethoxyethyl group, a 1,1-diethoxyethyl group, a 2,2-diethoxyethyl group, a 1-methoxycarbonylethyl group, a 2-methoxycarbonylethyl group, a 1-ethoxycarbonylethyl group, a 2-ethoxycarbonylethyl group, a 1-methoxypropyl group, a 2-methoxypropyl group, a 3-methoxypropyl group, a 1-(methoxymethyl)ethyl group, a 1-ethoxypropyl group, a 2-ethoxypropyl group, a 3-ethoxypropyl group, a 1,1-dimethoxypropyl group, a 2,2-dimethoxypropyl group, a 3,3-dimethoxypropyl group, a 1-(methoxycarbonyl)propyl group, a 2-(methoxycarbonyl)propyl group, a 3-(methoxycarbonyl)propyl group, a 1-methoxy-2,2-dimethylpropyl group, a 3-methoxy-2,2-dimethylpropyl group, a 3-methoxy-1,1-dimethylpropyl group, a 2-methoxy-1,1-dimethylpropyl group, a 2-methoxy-2-methylpropyl group, a 1-methoxy-2-methylpropyl group, a 2,2-dimethylpropyl group, a 2-hydroxy-1,3-dimethylbutyl group, a 2-hydroxyethyl group, a 3-hydroxypropyl group, a 4-hydroxybutyl group, a 2-hydroxypropyl group, a 3-hydroxy-2,2-dimethylpropyl group, and a 2-hydroxy-2-methylpropyl group.

In the present specification, examples of the "[(C1-C4 alkoxy)carbonyl]C1-C4 alkyl group in which the C1-C4 alkoxy has optionally one or more halogen atoms" include: a (methoxycarbonyl)methyl group, an (ethoxycarbonyl)methyl group, a (propoxycarbonyl)methyl group, an (isopropoxycarbonyl)methyl group, a (butoxycarbonyl)methyl group, a 1-(methoxycarbonyl)ethyl group, a 2-(methoxycarbonyl)ethyl group, a 3-(methoxycarbonyl)propyl group, and a 4-(methoxycarbonyl)butyl group.

In the present specification, examples of the "indanyl group optionally having one or more atoms or groups selected from Group B" include:

a "1-indanyl group optionally having one or more atoms or groups selected from Group B" such as a 1-indanyl group, a 4-methyl-1-indanyl group, a 5-methyl-1-indanyl group, a 4-cyano-1-indanyl group, a 4-carboxy-1-indanyl group, 4-hydroxy-1-indanyl group, a 4-trifluoromethyl-1-indanyl group, a 4-trifluoromethoxy-1-indanyl group, a 4-trifluoromethylthio-1-indanyl group, a 4-trifluoromethanesulfinyl-1-indanyl group, a 4-trifluoromethanesulfonyl-1-indanyl group, a 4-fluoro-1-indanyl group, a 4-chloro-1-indanyl group, and a 4-bromo-1-indanyl group;

a "2-indanyl group optionally having one or more atoms or groups selected from Group B" such as:

a 2-indanyl group, a 4-methyl-2-indanyl group, a 5-methyl-2-indanyl group, a 6-methyl-2-indanyl group, a 7-methyl-2-indanyl group, a 4-cyano-2-indanyl group, a 4-carboxy-2-indanyl group, a 4-hydroxy-2-indanyl group, a 4-trifluoromethyl-2-indanyl group, a 4-trifluoromethoxy-2-indanyl group, a 4-trifluoromethylthio-2-indanyl group, a 4-trifluoromethanesulfinyl 2-indanyl group, a 4-trifluoromethanesulfonyl-2-indanyl group, a 4-fluoro-2-indanyl group, a 4-chloro-2-indanyl group, and a 4-bromo-2-indanyl group.

In the present specification, examples of the "phenyl group optionally having one or more atoms or groups selected from Group B" include, for example, a phenyl group, a 2-cyanophenyl group, a 3-cyanophenyl group, a 4-cyanophenyl group, a 2-nitrophenyl group, a 2-carboxyphenyl group, a 2-hydroxyphenyl group, a 2-(methylaminocarbonyl)phenyl group, a 2-(dimethylaminocarbonyl)phenyl group, a 2-methylphenyl group, a 3,4-dimethylphenyl group, a 2,6-dimethylphenyl group, a 2-ethylphenyl group, a 2-trifluoromethylphenyl group, a 2-methoxyphenyl group, a 2-trifluoromethoxyphenyl group, a 2-methylthiophenyl group, a 2-methylsulfinylphenyl group, a 2-methylsulfonylphenyl group, a 2-trifluoromethylthiophenyl group, a 2-trifluoromethylsulfinylphenyl group, a 2-trifluoromethylsulfonylphenyl group, a 2-methoxycarbonylphenyl group, a 2-vinylphenyl group, a 2-(2,2-difluorovinyl)phenyl group, a 2-ethynylphenyl group, a 2-(2-fluoroethynyl)phenyl group, a 2-fluorophenyl group, a pentafluorophenyl group, and a 2-chlorophenyl group.

In the present specification, examples of the "phenoxy group optionally having one or more atoms or groups selected from Group B" include, for example, a phenoxy group, a 2-cyanophenoxy group, a 3-cyanophenoxy group, a 4-cyanophenoxy group, a 2-nitrophenoxy group, a 2-carboxyphenoxy group, a 2-hydroxyphenoxy group, a 2-(methylaminocarbonyl)phenoxy group, a 2-(dimethylaminocarbonyl)phenoxy group, a 2-methylphenoxy group, a 3,4-dimethylphenoxy group, a 2,6-dimethylphenoxy group, a 2-ethylphenoxy group, a 2-trifluoromethylphenoxy group, a 2-methoxyphenoxy group, a 2-trifluoromethoxyphenoxy group, a 2-methylthiophenoxy group, a 2-methylsulfinylphenoxy group, a 2-methylsulfonylphenoxy group, a 2-trifluoromethylthiophenoxy group, a 2-trifluoromethylsulfinylphenoxy group, a 2-trifluoromethylsulfonylphenoxy group, a 2-methoxycarbonylphenoxy group, a 2-vinylphenoxy group, a 2-(2,2-difluorovinyl)phenoxy group, a 2-ethynylphenoxy group, a 2-(2-fluoroethynyl)phenoxy group, a 2-fluorophenoxy group, a pentafluorophenoxy group, and a 2-chlorophenoxy group.

In the present specification, examples of the "naphthyl group optionally having one or more atoms or groups selected from Group B" include, for example, a "1-naphthyl group optionally having one or more atoms or groups selected from Group B" such as a 1-naphthyl group, a 2-cyano-1-naphthyl group, a 3-cyano-1-naphthyl group, a 4-cyano-1-naphthyl group, a 2-nitro-1-naphthyl group, a 2-carboxy-1-naphthyl group, a 2-hydroxy-1-naphthyl group, a 2-methyl-1-naphthyl group, a 2-trifluoromethyl-1-naphthyl group, a 2-methoxy-1-naphthyl group, a 2-trifluoromethoxy-1-naphthyl group, a 2-trifluoromethylthio-1-naphthyl group, a 2-trifluoromethylsulfinyl-1-naphthyl group, a 2-trifluoromethylsulfonyl-1-naphthyl group, a 2-methoxycarbonyl-1-naphthyl group, a 2-vinyl-1-naphthyl group, a 2-(2,2-difluorovinyl)-1-naphthyl group, a 2-ethynyl-1-naphthyl group, a 2-(2-fluoroethynyl)-1-naphthyl group, a 2-fluoro-1-naphthyl group, and a 2-chloro-1-naphthyl group;

a "2-naphthyl group optionally having one or more atoms or groups selected from Group B" such as a 2-naphthyl group, a 1-cyano-2-naphthyl group, a 3-cyano-2-naphthyl group, a 4-cyano-2-naphthyl group, a 1-nitro-2-naphthyl group, a 1-carboxy-2-naphthyl group, a 1-hydroxy-2-naphthyl group, a 1-methyl-2-naphthyl group, a 1-trifluoromethyl-2-naphthyl group, a 1-methoxy-2-naphthyl group, a 1-trifluoromethoxy-2-naphthyl group, a 1-trifluoromethylthio-2-naphthyl group, a 1-trifluoromethylsulfinyl-2-naphthyl group, a 1-trifluoromethylsulfonyl-2-naphthyl group, a 1-methoxycarbonyl-2-naphthyl group, a 1-vinyl-2-naphthyl group, a 1-(2,2-difluorovinyl)-2-naphthyl group, a 1-ethynyl-2-naphthyl group, a 1-fluoro-2-naphthyl group, and a 1-chloro-2-naphthyl group.

In the present specification, examples of the "pyridyl group optionally having one or more atoms or groups selected from Group B" include:

a "2-pyridyl group optionally having one or more atoms or groups selected from Group B" such as a 2-pyridyl group, a 3-cyano-2-pyridyl group, a 4-cyano-2-pyridyl group, a 5-cyano-2-pyridyl group, a 6-cyano-2-pyridyl group, a 3-nitro-2-pyridyl group, a 3-carboxy-2-pyridyl group, a 3-hydroxy-2-pyridyl group, a 3-methyl-2-pyridyl group, a 3-trifluoromethyl-2-pyridyl group, a 3-methoxy-2-pyridyl group, a 3-trifluoromethoxy-2-pyridyl group, a 3-methoxycarbonyl-2-pyridyl group, a 3-vinyl-2-pyridyl group, a 3-(2,2-difluorovinyl)-2-pyridyl group, a 3-ethynyl-2-pyridyl group, a 3-(2-fluoroethynyl)-2-pyridyl group, a 3-fluoro-2-pyridyl group, a 3-chloro-2-pyridyl group and the like;

a "3-pyridyl group optionally having one or more atoms or groups selected from Group B" such as a 3-pyridyl group, a 2-cyano-3-pyridyl group, a 4-cyano-3-pyridyl group, a 5-cyano-3-pyridyl group, a 6-cyano-3-pyridyl group, a 2-nitro-3-pyridyl group, a 2-carboxy-3-pyridyl group, a 2-hydroxy-3-pyridyl group, a 2-methyl-3-pyridyl group, a 2-trifluoromethyl-3-pydiryl group, a 2-methoxy-3-pyridyl group, a 2-trifluoromethoxy-3-pyridyl group, a 2-methoxycarbonyl-3-pyridyl group, a 2-vinyl-3-pyridyl group, a 2-(2,2-difluorovinyl)-3-pyridyl group, a 2-ethynyl-3-pyridyl group, a 2-(2-fluoroethynyl)-3-pyridyl group, a 2-fluoro-3-pyridyl group, a 2-chloro-3-pyridyl group and the like;

a "4-pyridyl group optionally having one or more atoms or groups selected from Group B" such as a 4-pyridyl group, a 2-cyano-4-pyridyl group, a 2-nitro-4-pyridyl group, a 2-carboxy-4-pyridyl group, a 2-hydroxy-4-pyridyl group, a 2-methyl-4-pyridyl group, a 2-trifluoromethyl-4-pyridyl group, a 2-methoxy-4-pyridyl group, a 2-trifluoromethoxy-4-pyridyl group, a 2-methoxycarbonyl-4-pyridyl group, a 2-vinyl-4-pyridyl group, a 2-(2,2-difluorovinyl)-4-pyridyl group, a 2-ethynyl-4-pyridyl group, a 2-(2-fluoroethynyl)-4-pyridyl group, a 2-fluoro-4-pyridyl group, and a 2-chloro-4-pyridyl group.

In the present specification, examples of the "quinolyl group optionally having one or more atoms or groups selected from Group B" include a "2-quinolyl group optionally having one or more atoms or groups selected from Group B" such as a 2-quinolyl group, a 5-cyano-2-quinolyl group, a 6-cyano-2-quinolyl group, a 7-cyano-2-quinolyl group, a 8-cyano-2-quinolyl group, a 5-nitro-2-quinolyl group, a 5-carboxy-2-quinolyl group, a 5-hydroxy-2-quinolyl group, a 5-methyl-2-quinolyl group, a 5-trifluoromethyl-2-quinolyl group, a 5-methoxy-2-quinolyl group, a 5-trifluoromethoxy-2-quinolyl group, a 5-methoxycarbonyl-2-quinolyl group, a 5-vinyl-2-quinolyl group, a 5-(2,2-difluorovinyl)-2-quinolyl group, a 5-ethynyl-2-quinolyl group, a 5-(2-fluoroethynyl)-2-quinolyl group, a 5-fluoro-2-quinolyl group, a 5,6,7,8-tetrafluoro-2-quinolyl group, and a 5-chloro-2-quinolyl group;

a "3-quinolyl group optionally having one or more atoms or groups selected from Group B" such as a 3-quinolyl group, a 5-cyano-3-quinolyl group, a 6-cyano-3-quinolyl group, a 7-cyano-3-quinolyl group, a 8-cyano-3-quinolyl group, a 5-nitro-3-quinolyl group, a 5-carboxy-3-quinolyl group, a 5-hydroxy-3-quinolyl group, a 5-methyl-3-quinolyl group, a 5-trifluoromethyl-3-quinolyl group, a 5-methoxy-3-quinolyl group, a 5-trifluoromethoxy-3-quinolyl group, a 5-methoxycarbonyl-3-quinolyl group, a 5-vinyl-3-quinolyl group, a 5-(2,2-difluorovinyl)-3-quinolyl group, a 5-ethynyl-3-quinolyl group, a 5-(2-fluoroethynyl)-3-quinolyl group, a 5-fluoro-3-quinolyl group, a 5,6,7,8-tetrafluoro-3-quinolyl group, a 5-chloro-3-quinolyl group, a 6-chloro-3-quinolyl group, a 7-chloro-3-quinolyl group, and a 8-chloro-3-quinolyl group;

a "4-quinolyl group optionally having one or more atoms or groups selected from Group B" such as a 4-quinolyl group, a 2-cyano-4-quinolyl group, a 3-cyano-4-quinolyl group, a 2-nitro-4-quinolyl group, a 2-carboxy-4-quinolyl group, a 2-hydroxy-4-quinolyl group, a 2-methyl-4-quinolyl group, a 2-trifluoromethyl-4-quinolyl group, a 2-methoxy-4-quinolyl group, a 2-trifluoromethoxy-4-quinolyl group, a 2-methoxycarbonyl-4-quinolyl group, a 2-vinyl-4-quinolyl group, a 2-(2,2-difluorovinyl)-4-quinolyl group, a 2-ethynyl-4-quinolyl group, a 2-(2-fluoroethynyl)-4-quinolyl group, a 2-fluoro-4-quinolyl group, and a 2-chloro-4-quinolyl group.

In the present specification, examples of the "furyl group optionally having one or more atoms or groups selected from Group B" include, for example, a "2-furyl group optionally having one or more atoms or groups selected from Group B" such as a 2-furyl group, a 3-cyano-2-furyl group, a 4-cyano-2-furyl group, a 5-cyano-2-furyl group, a 3-nitro-2-furyl group, a 3-carboxy-2-furyl group, a 3-hydroxy-2-furyl group, a 3-methyl-2-furyl group, a 3-trifluoromethyl-2-furyl group, a 3-methoxy-2-furyl group, a 3-trifluoromethoxy-2-furyl group, a 3-methoxycarbonyl-2-furyl group, a 3-vinyl-2-furyl group, a 3-(2,2-difluorovinyl)-2-furyl group, a 3-ethynyl-2-furyl group, a 3-(2-fluoroethynyl)-2-furyl group, a 3-fluoro-2-furyl group, and a 3-chloro-2-furyl group;

a "3-furyl group optionally having one or more atoms or groups selected from Group B" such as a 3-furyl group, a 2-cyano-3-furyl group, a 4-cyano-3-furyl group, a 5-cyano-3-furyl group, a 2-nitro-3-furyl group, a 2-carboxy-3-furyl group, a 2-hydroxy-3-furyl group, a 2-methyl-3-furyl group, a 2-trifluoromethyl-3-furyl group, a 2-methoxy-3-furyl group, a 2-trifluoromethoxy-3-furyl group, a 2-methoxycarbonyl-3-furyl group, a 2-vinyl-3-furyl group, a 2-(2,2-difluorovinyl)-3-furyl group, a 2-ethynyl-3-furyl group, a 2-(2-fluoroethynyl)-3-furyl group, a 2-fluoro-3-furyl group, and a 2-chloro-3-furyl group.

In the present specification, examples of the "thienyl group optionally having one or more atoms or groups selected from Group B" include:

a "2-thienyl group optionally having one or more atoms or groups selected from Group B" such as a 2-thienyl group, a 3-cyano-2-thienyl group, a 4-cyano-2-thienyl group, a 5-cyano-2-thienyl group, a 3-nitro-2-thienyl group, a 3-carboxy-2-thienyl group, a 3-hydroxy-2-thienyl group, a 3-methyl-2-thienyl group, a 3-trifluoromethyl-2-thienyl group, a 3-methoxy-2-thienyl group, a 3-trifluoromethoxy-2-thienyl group, a 3-methoxycarbonyl-2-thienyl group, a 3-vinyl-2-thienyl group, a 3-(2,2-difluorovinyl)-2-thienyl group, a 3-ethynyl-2-thienyl group, a 3-(2-fluoroethynyl)-2-thienyl group, a 3-fluoro-2-thienyl group, a 3-chloro-2-thienyl group and the like;

a "3-thienyl group optionally having one or more atoms or groups selected from Group B" such as a 3-thienyl group, a 2-cyano-3-thienyl group, a 4-cyano-3-thienyl group, a 5-cyano-3-thienyl group, a 2-nitro-3-thienyl group, a 2-carboxy-3-thienyl group, a 2-hydroxy-3-thienyl group, a 2-methyl-3-thienyl group, a 2-trifluoromethyl-3-thienyl group, a 2-methoxy-3-thienyl group, a 2-trifluoromethoxy-3-thienyl group, a 2-methoxycarbonyl-3-thienyl group, a 2-vinyl-3-thienyl group, a 2-(2,2-difluorovinyl)-3-thienyl group, a 2-ethynyl-3-thienyl group, a 2-(2-fluoroethynyl)-3-thienyl group, a 2-fluoro-3-thienyl group, a 2-chloro-3-thienyl group and the like.

In the present specification, examples of the "benzofuranyl group optionally having one or more atoms or groups selected from Group B" include:

a "2-benzofuranyl group optionally having one or more atoms or groups selected from Group B" such as a 2-benzofuranyl group, a 4-cyano-2-benzofuranyl group, a 5-cyano-2-benzofuranyl group, a 6-cyano-2-benzofuranyl group, a 7-cyano-2-benzofuranyl group, a 4-nitro-2-benzofuranyl group, a 4-carboxy-2-benzofuranyl group, a 4-hydroxy-2-benzofuranyl group, a 4-methyl-2-benzofuranyl group, a 4-trifluoromethyl-2-benzofuranyl group, a 4-methoxy-2-benzofuranyl group, a 4-trifluoromethoxy-2-benzofuranyl group, a 4-methoxycarbonyl-2-benzofuranyl group, 4-vinyl-2-benzofuranyl group, a 4-(2,2-difluorovinyl)-2-benzofuranyl group, a 4-ethynyl-2-benzofuranyl group, a 4-(2-fluoroethynyl)-2-benzofuranyl group, a 4-fluoro-2-benzofuranyl group, a 4,5,6,7-tetrafluoro-2-benzofuranyl group, a 4-chloro-2-benzofuranyl group and the like; a "5-benzofuranyl group optionally having one or more atoms or groups selected from Group B" such as a 5-benzofuranyl group, a 4-cyano-5-benzofuranyl group, a 3-cyano-5-benzofuranyl group, a 6-cyano-5-benzofuranyl group, a 7-cyano-5-benzofuranyl group, a 4-nitro-5-benzofuranyl group, a 4-carboxy-5-benzofuranyl group, a 4-hydroxy-5-benzofuranyl group, a 4-methyl-5-benzofuranyl group, a 4-trifluoromethyl-5-benzofuranyl group, a 4-methoxy-5-benzofuranyl group, a 4-trifluoromethoxy-5-benzofuranyl group, a 4-methoxycarbonyl-5-benzofuranyl group, a 4-vinyl-5-benzofuranyl group, a 4-(2,2-difluorovinyl)-5-benzofuranyl group, a 4-ethynyl-5-benzofuranyl group, a 4-(2-fluoroethynyl)-5-benzofuranyl group, a 4-fluoro-5-benzofuranyl group, a 3,4,6,7-tetrafluoro-5-benzofuranyl group, a 4-chloro-5-benzofuranyl group and the like.

In the present specification, examples of the "benzothienyl group optionally having one or more atoms or groups selected from Group B" include, for example, a "2-benzothienyl group optionally having one or more atoms or groups selected from Group B" such as a 2-benzothienyl group, a 4-cyano-2-benzothienyl group, a 5-cyano-2-benzothienyl group, a 6-cyano-2-benzothienyl group, a 7-cyano-2-benzothienyl group, a 4-nitro-2-benzothienyl group, a 4-carboxy-2-benzothienyl group, a 4-hydroxy-2-benzothienyl group, a 4-methyl-2-benzothienyl group, a 4-trifluoromethyl-2-benzothienyl group, a 4-methoxy-2-benzothienyl group, a 4-trifluoromethoxy-2-benzothienyl group, a 4-methoxycarbonyl-2-benzothienyl group, a 4-vinyl-2-benzothienyl group, a 4-(2,2-difluorovinyl)-2-benzothienyl group, a 4-ethynyl-2-benzothienyl group, a 4-(2-fluoroethynyl)-2-benzothienyl group, a 4-fluoro-2-benzothienyl group, a 4,5,6,7-tetrafluoro-2-benzothienyl group, and a 4-chloro-2-benzothienyl group;

a "5-benzothienyl group optionally having one or more atoms or groups selected from Group B" such as a 5-benzothienyl group, a 4-cyano-5-benzothienyl group, a 3-cyano-5-benzothienyl group, a 6-cyano-5-benzothienyl group, a 7-cyano-5-benzothienyl group, a 4-nitro-5-benzothienyl group, a 4-carboxy-5-benzothienyl group, a 4-hydroxy-5-benzothienyl group, a 4-methyl-5-benzothienyl group, a 4-trifluoromethyl-5-benzothienyl group, a 4-methoxy-5-benzothienyl group, a 4-trifluoromethoxy-5-benzothienyl group, a 4-methoxycarbonyl-5-benzothienyl group, a 4-vinyl-5-benzothienyl group, a 4-(2,2-difluorovinyl)-5-benzothienyl group, a 4-ethynyl-5-benzothienyl group, a 4-(2-fluoroethynyl)-5-benzothienyl group, a 4-fluoro-5-benzothienyl group, a 4,5,6,7-tetrafluoro-5-benzothienyl group, and a 4-chloro-5-benzothienyl group.

In the present specification, examples of the "1,3-benzodioxolanyl group optionally having one or more atoms or groups selected from Group B" include, for example, a 1,3-benzodioxolanyl group, a 4-cyano-1,3-benzodioxolanyl group, a 4-nitro-1,3-benzodioxolanyl group, a 4-carboxy-1,3-benzodioxolanyl group, a 4-hydroxy-1,3-benzodioxolanyl group, a 4-methyl-1,3-benzodioxolanyl group, a 4-trifluoromethyl-1,3-benzodioxolanyl group, a 4-methoxy-1,3-benzodioxolanyl group, a 4-trifluoromethoxy-1,3-benzodioxolanyl group, a 4-methoxycarbonyl-1,3-benzodioxolanyl group, a 4-vinyl-1,3-benzodioxolanyl group, a 4-ethynyl-1,3-benzodioxolanyl group, a 4-fluoro-1,3-benzodioxolanyl group, a 4,5,6,7-tetrafluoro-1,3-benzodioxolanyl group, and a 4-chloro-1,3-benzodioxolanyl group.

In the present specification, examples of the "1,4-benzodioxanyl group optionally having one or more atoms or groups selected from Group B" include, for example, a 1,4-benzodioxanyl group, a 5-cyano-1,4-benzodioxanyl group, a 5-nitro-1,4-benzodioxanyl group, a 5-carboxy-1,4-benzodioxanyl group, a 5-hydroxy-1,4-benzodioxanyl group, a 5-methyl-1,4-benzodioxanyl group, a 5-trifluoromethyl-1,4-benzodioxanyl group, a 5-methoxy-1,4-benzodioxanyl group, a 5-trifluoromethoxy-1,4-benzodioxanyl group, a 5-methoxycarbonyl-1,4-benzodioxanyl group, a 5-vinyl-1,4-benzodioxanyl group, a 5-ethynyl-1,4-benzodioxanyl group, a 5-fluoro-1,4-benzodioxanyl group, a 4,5,6,7-tetrafluoro-1,4-benzodioxanyl group, and a 5-chloro-1,4-benzodioxanyl group.

In the present specification, examples of the "C1-C8 chain hydrocarbon group optionally having one or more atoms or groups selected from Group D" include, for example, a benzyl group, a phenyldifluoromethyl group, a 1-phenylethyl group, a 2,2,2-trifluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 7-phenylheptyl group, a 1,1-difluoro-7-phenylheptyl group, a 8-phenyloctyl group, a 1,1-difluoro-8-phenyloctyl group, a 4-cyanobenzyl group, a 4-nitrobenzyl group, a 4-carboxybenzyl group, a 4-hydroxybenzyl group, a 4-(methylaminocarbonyl)benzyl group, a 4-(dimethylaminocarbonyl)benzyl group, a 4-methylbenzyl group, a 4-(trifluoromethyl)benzyl group, a 4-methoxybenzyl group, a 4-(trifluoromethoxy)benzyl group, a 4-(methylthio)benzyl group, a 4-(methylsulfinyl)benzyl group, a 4-(methylsulfonyl)benzyl group, a 4-(methoxycarbonyl)benzyl group, a 4-vinylbenzyl group, a 4-(2,2-difluorovinyl)benzyl group, a 4-ethynylbenzyl group, a 4-(2-fluoroethynyl)benzyl group, a 4-fluorobenzyl group, a 4-chlorobenzyl group, a 3,4-dichlorobenzyl group, a (4-cyanophenyl)difluoromethyl group, a 1-naphthylmethyl group, a (1-naphthyl)difluoromethyl group, a 1-(1-naphthyl)ethyl group, a 2,2,2-trifluoro-1-(1-naphthyl)ethyl group, a 1,1,2,2,2-pentafluoro-1-(1-naphthyl)ethyl group, a 2-(1-naphthyl)ethyl group, a 1,1-difluoro-2-(1-naphthyl)ethyl group, a 2,2-difluoro-2-(1-naphthyl)ethyl group, a 1,1,2,2-tetrafluoro-2-(1-naphthyl)ethyl group, a 3-(1-naphthyl)propyl group, a 1,1-difluoro-3-(1-naphthyl)propyl group, a 2,2-difluoro-3-(1-naphthyl)propyl group, a 3,3-difluoro-3-(1-naphthyl)propyl group, a 1,1,2,2,3,3-hexafluoro-3-(1-naphthyl)propyl group, a 4-(1-naphthyl)butyl group, a 1,1-difluoro-4-(1-naphthyl)butyl group, a 2,2-difluoro-4-(1-naphthyl)butyl group, a 3,3-difluoro-4-(1-naphthyl)butyl group, a 4,4-difluoro-4-(1-naphthyl)butyl group, a 1,1,2,2,3,3,4,4-octafluoro-4-(1-naphthyl)butyl group, a 5-(1-naphthyl)pentyl group, a 1,1-difluoro-5-(1-naphthyl)pentyl group, a 2,2-difluoro-5-(1-naphthyl)pentyl group, a 3,3-difluoro-5-(1-naphthyl)pentyl group, a 4,4-difluoro-5-(1-naphthyl)pentyl group, a 5,5-difluoro-5-(1-naphthyl)pentyl group, a 6-(1-naphthyl)hexyl group, a 1,1-difluoro-6-(1-naphthyl)hexyl group, a 7-(1-naphthyl)heptyl group, a 1,1-difluoro-7-(1-naphthyl)heptyl group, a 8-(1-naphthyl)octyl group, a 1,1-difluoro-8-(1-naphthyl)octyl group, a 2-naphthylmethyl group, a (2-naphthyl)difluoromethyl group, a 1-(2-naphthyl)ethyl group, a 2,2,2-trifluoro-1-(2-naphthyl)ethyl group, a 1,1,2,2,2-pentafluoro-1-(2-naphthyl)ethyl group, a 2-(2-naphthyl)ethyl group, a 1,1-difluoro-2-(2-naphthyl)ethyl group, a 2,2-difluoro-2-(2-naphthyl)ethyl group, a 1,1,2,2-tetrafluoro-2-(2-naphthyl)ethyl group, a 3-(2-naphthyl)propyl group, a 1,1-difluoro-3-(2-naphthyl)propyl group, a 2,2-difluoro-3-(2-naphthyl)propyl group, a 3,3-difluoro-3-(2-naphthyl)propyl group, a 1,1,2,2,3,3-hexafluoro-3-(2-naphthyl)propyl group, a 4-(2-naphthyl)butyl group, a 1,1-difluoro-4-(2-naphthyl)butyl group, a 2,2-difluoro-4-(2-naphthyl)butyl group, a 3,3-difluoro-4-(2-naphthyl)butyl group, a 4,4-difluoro-4-(2-naphthyl)butyl group, a 1,1,2,2,3,3,4,4-octafluoro-4-(2-naphthyl)butyl group, a 5-(2-naphthyl)pentyl group, a 1,1-difluoro-5-(2-naphthyl)pentyl group, a 2,2-difluoro-5-(2-naphthyl)pentyl group, a 3,3-difluoro-5-(2-naphthyl)pentyl group, a 4,4-difluoro-5-(2-naphthyl)pentyl group, a 5,5-difluoro-5-(2-naphthyl)pentyl group, a 6-(2-naphthyl)hexyl group, a 1,1-difluoro-6-(2-naphthyl)hexyl group, a 7-(2-naphthyl)heptyl group, a 1,1-difluoro-7-(2-naphthyl)heptyl group, a 8-(2-naphthyl)octyl group, a 1,1-difluoro-8-(2-naphthyl)octyl group, a 2-pyridylmethyl group, a 1-(2-pyridyl)ethyl group, a 2-(2-pyridyl)ethyl group, a 3-(2-pyridyl)propyl group, a 4-(2-pyridyl)butyl group, a 5-(2-pyridyl)pentyl group, a 6-(2-pyridyl)hexyl group, a 7-(2-pyridyl)heptyl group, a 8-(2-pyridyl)octyl group, a 3-pyridylmethyl group, a 4-pyridylmethyl group, a 2-quinolylmethyl group, a 3-quinolylmethyl group, a 4-quinolylmethyl group, a 2-furylmethyl group, a 3-furylmethyl group, a 2-thienylmethyl group, a 3-thienylmethyl group, a 2-benzofuranylmethyl group, a fluoromethyl group, a 1-fluoroethyl group, a 1,1-difluoroethyl group, a 2-fluoroethyl group, a 2,2-difluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 3,3,4,4,4-pentafluorobutyl group, a 5-fluoropentyl group, a 6-fluorohexyl group, a 7-fluoroheptyl group, a 8-fluorooctyl group, a chloromethyl group, a bromomethyl group, a (methoxycarbonyl)methyl group, a cyanomethyl group, a nitromethyl group, a (carboxy)methyl group, a hydroxymethyl group and the like.

In the present specification, examples of the "C1-C8 chain hydrocarbon group having one or more atoms or groups selected from Group C" include:

a benzyl group, a phenyldifluoromethyl group, a 1-phenylethyl group, a 2,2,2-trifluoro-1-phenylethyl group, a 2-phenylethyl group, a 1,1-difluoro-2-phenylethyl group, a 2,2-difluoro-2-phenylethyl group, a 1,1,2,2-tetrafluoro-2-phenylethyl group, a 3-phenylpropyl group, a 1,1-difluoro-3-phenylpropyl group, a 2,2-difluoro-3-phenylpropyl group, a 3,3-difluoro-3-phenylpropyl group, a 1,1,2,2,3,3-hexafluoro-3-phenylpropyl group, a 4-phenylbutyl group, a 1,1-difluoro-4-phenylbutyl group, a 2,2-difluoro-4-phenylbutyl group, a 3,3-difluoro-4-phenylbutyl group, a 4,4-difluoro-4-phenylbutyl group, a 1,1,2,2,3,3,4,4-octafluoro-3-4-phenylbutyl group, a 5-phenylpentyl group, a 1,1-difluoro-5-phenylpentyl group, a 2,2-difluoro-5-phenylpentyl group, a 3,3-difluoro-5-phenylpentyl group, a 4,4-difluoro-5-phenylpentyl group, a 5,5-difluoro-5-phenylpentyl group, a 6-phenylhexyl group, a 1,1-difluoro-6-phenylhexyl group, a 7-phenylheptyl group, a 1,1-difluoro-7-phenylheptyl group, a 8-phenyloctyl group, a 1,1-difluoro-8-phenyloctyl group, a 4-cyanobenzyl group, a 4-nitrobenzyl group, a 4-carboxybenzyl group, a 4-hydroxybenzyl group, a 4-(methylaminocarbonyl)benzyl group, a 4-(dimethylaminocarbonyl)benzyl group, a 4-methylbenzyl group, a 4-(trifluoromethyl)benzyl group, a 4-methoxybenzyl group, a 4-(trifluoromethoxy)benzyl group, a 4-(methylthio)benzyl group, a 4-(methylsulfinyl)benzyl group, a 4-(methylsulfonyl)benzyl group, a 4-(methoxycarbonyl)benzyl group, a 4-vinylbenzyl group, a 4-(2,2-difluorovinyl)benzyl group, a 4-ethynylbenzyl group, a 4-(2-fluoroethynyl)benzyl group, a 4-fluorobenzyl group, a 4-chlorobenzyl group, a 3,4-dichlorobenzyl group, a (4-cyanophenyl)difluoromethyl group, a 1-naphthylmethyl group, a (1-naphthyl)difluoromethyl group, a 1-(1-naphthyl)ethyl group, a 2,2,2-trifluoro-1-(1-naphthyl)ethyl group, a 2-(1-naphthyl)ethyl group, a 1,1-difluoro-2-(1-naphthyl)ethyl group, a 2,2-difluoro-2-(1-naphthyl)ethyl group, a 1,1,2,2-tetrafluoro-2-(1-naphthyl)ethyl group, a 3-(1-naphthyl)propyl group, a 1,1-difluoro-3-(1-naphthyl)propyl group, a 2,2-difluoro-3-(1-naphthyl)propyl group, a 3,3-difluoro-3-(1-naphthyl)propyl group, a 1,1,2,2,3,3-hexafluoro-3-(1-naphthyl)propyl group, a 4-(1-naphthyl)butyl group, a 1,1-difluoro-4-(1-naphthyl)butyl group, a 2,2-difluoro-4-(1-naphthyl)butyl group, a 3,3-difluoro-4-(1-naphthyl)butyl group, a 4,4-difluoro-4-(1-naphthyl)butyl group, a 1,1,2,2,3,3,4,4-octafluoro-4-(1-naphthyl)butyl group, a 5-(1-naphthyl)pentyl group, a 1,1-difluoro-5-(1-naphthyl)pentyl group, a 2,2-difluoro-5-(1-naphthyl)pentyl group, a 3,3-difluoro-5-(1-naphthyl)pentyl group, a 4,4-difluoro-5-(1-naphthyl)pentyl group, a 5,5-difluoro-5-(1-naphthyl)pentyl group, a 6-(1-naphthyl)hexyl group, a 1,1-difluoro-6-(1-naphthyl)hexyl group, a 7-(1-naphthyl)heptyl group, a 1,1-difluoro-7-(1-naphthyl)heptyl group, a 8-(1-naphthyl)octyl group, a 2-naphthylmethyl group, a (2-naphthyl)difluoromethyl group, a 1-(2-naphthyl)ethyl group, a 2,2,2-trifluoro-1-(2-naphthyl)ethyl group, a 2-(2-naphthyl)ethyl group, a 1,1-difluoro-2-(2-naphthyl)ethyl group, a 2,2-difluoro-2-(2-naphthyl)ethyl group, a 1,1,2,2-tetrafluoro-2-(2-naphthyl)ethyl group, a 3-(2-naphthyl)propyl group, a 1,1-difluoro-3-(2-naphthyl)propyl group, a 2,2-difluoro-3-(2-naphthyl)propyl group, a 3,3-difluoro-3-(2-naphthyl)propyl group, a 1,1,2,2,3,3-hexafluoro-3-(2-naphthyl)propyl group, a 4-(2-naphthyl)butyl group, a 1,1-difluoro-4-(2-naphthyl)butyl group, a 2,2-difluoro-4-(2-naphthyl)butyl group, a 3,3-difluoro-4-(2-naphthyl)butyl group, a 4,4-difluoro-4-(2-naphthyl)butyl group, a 1,1,2,2,3,3,4,4-octafluoro-4-(2-naphthyl)butyl group, a 5-(2-naphthyl)pentyl group, a 1,1-difluoro-5-(2-naphthyl)pentyl group, a 2,2-difluoro-5-(2-naphthyl)pentyl group, a 3,3-difluoro-5-(2-naphthyl)pentyl group, a 4,4-difluoro-5-(2-naphthyl)pentyl group, a 5,5-difluoro-5-(2-naphthyl)pentyl group, a 6-(2-naphthyl)hexyl group, a 1,1-difluoro-6-(2-naphthyl)hexyl group, a 7-(2-naphthyl)heptyl group, a 1,1-difluoro-7-(2-naphthyl)heptyl group, a 8-(2-naphthyl)octyl group, a 1,1-difluoro-8-(2-naphthyl)octyl group, a 2-pyridylmethyl group, a 1-(2-pyridyl)ethyl group, a 2-(2-pyridyl)ethyl group, a 3-(2-pyridyl)propyl group, a 4-(2-pyridyl)butyl group, a 5-(2-pyridyl)pentyl group, a 6-(2-pyridyl)hexyl group, a 7-(2-pyridyl)heptyl group, a 8-(2-pyridyl)octyl group, a 3-pyridylmethyl group, a 4-pyridylmethyl group, a 2-quinolylmethyl group, a 3-quinolylmethyl group, a 4-quinolylmethyl group, a 2-furylmethyl group, a 3-furylmethyl group, a 2-thienylmethyl group, a 3-thienylmethyl group, a 2-benzofuranylmethyl group, a (5-cyano-2-benzofuranyl)methyl group, a (5-nitro-2-benzofuranyl)methyl group, a (5-carboxy-2-benzofuranyl)methyl group, a (5-hydroxy-2-benzofuranyl)methyl group, a [5-(methylaminocarbonyl)-2-benzofuranyl]methyl group, a [5-(dimethylaminocarbonyl)-2-benzofuranyl]methyl group, a (5-methyl-2-benzofuranyl)methyl group, a (5-trifluoromethyl-2-benzofuranyl)methyl group, a (5-methoxy-2-benzofuranyl)methyl group, a (5-trifluoromethoxy-2-benzofuranyl)methyl group, a (5-methylthio-2-benzofuranyl)methyl group, a (5-methylsulfinyl-2-benzofuranyl)methyl group, a (5-methylsulfonyl-2-benzofuranyl)methyl group, a (5-methoxycarbonyl-2-benzofuranyl)methyl group, a (5-vinyl-2-benzofuranyl)methyl group, a [5-(2,2-difluorovinyl)-2-benzofuranyl]methyl group, a (5-ethynyl-2-benzofuranyl)methyl group, a [5-(2-fluoroethynyl)-2-benzofuranyl]methyl group, a (5-fluoro-2-benzofuranyl)methyl group, a (5-chloro-2-benzofuranyl) methyl group, a 5-benzofuranylmethyl group, a (3-cyano-5-benzofuranyl)methyl group, a (3-nitro-5-benzofuranyl)methyl group, a (3-carboxy-5-benzofuranyl)methyl group, a (3-hydroxy-5-benzofuranyl)methyl group, a [3-(methylaminocarbonyl)-5-benzofuranyl]methyl group, a [3-(dimethylaminocarbonyl)-5-benzofuranyl]methyl group, a (3-methyl-5-benzofuranyl)methyl group, a (3-trifluoromethyl-5-benzofuranyl)methyl group, a (3-methoxy-5-benzofuranyl)methyl group, a (3-trifluoromethoxy-5-benzofuranyl)methyl group, a (3-methylthio-5-benzofuranyl)methyl group, a (3-methylsulfinyl-5-benzofuranyl)methyl group, a (3-methylsulfonyl-5-benzofuranyl)methyl group, a (3-methoxycarbonyl-5-benzofuranyl)methyl group, a (3-vinyl-5-benzofuranyl) methyl group, a [3-(2,2-difluorovinyl)-5-benzofuranyl] methyl group, a (3-ethynyl-5-benzofuranyl)methyl group, a [3-(2-fluoroethynyl)-5-benzofuranyl]methyl group, a (3-fluoro-5-benzofuranyl)methyl group, a (3-chloro-5-benzofuranyl) methyl group, a 2-benzothienylmethyl group, a (5-cyano-2-benzothienyl) methyl group, a (5-nitro-2-benzothienyl)methyl group, a (5-carboxy-2-benzothienyl)methyl group, a (5-hydroxy-2-benzothienyl)methyl group, a [5-(methylaminocarbonyl)-2-benzothienyl]methyl group, a [5-(dimethylaminocarbonyl)-2-benzothienyl]methyl group, a (5-methyl-2-benzothienyl) methyl group, a (5-trifluoromethyl-2-benzothienyl)methyl group, a (5-methoxy-2-benzothienyl)methyl group, a (5-trifluoromethoxy-2-benzothienyl)methyl group, a (5-methylthio-2-benzothienyl)methyl group, a (5-methylsulfinyl-2-benzothienyl)methyl group, a (5-methylsulfonyl-2-benzothienyl)methyl group, a (5-methoxycarbonyl-2-benzothienyl)methyl group, a (5-vinyl-2-benzothienyl) methyl group, a [5-(2,2-difluorovinyl)-2-benzothienyl] methyl group, a (5-ethynyl-2-benzothienyl)methyl group, a [5-(2-fluoroethynyl)-2-benzothienyl]methyl group, a (5-fluoro-2-benzothienyl)methyl group, a (5-chloro-2-benzothienyl) methyl group, a 5-benzothienylmethyl group, a (3-cyano-5-benzothienyl) methyl group, a (3-nitro-5-benzothienyl)methyl group, a (3-carboxy-5-benzothienyl)methyl group, a (3-hydroxy-5-benzothienyl)methyl group, a [3-(methylaminocarbonyl)-5-benzothienyl]methyl group, a [3-(dimethylaminocarbonyl)-5-benzothienyl]methyl group, a (3-methyl-5-benzothienyl) methyl group, a (3-trifluoromethyl-5-benzothienyl)methyl group, a (3-methoxy-5-benzothienyl)methyl group, a (3-trifluoromethoxy-5-benzothienyl)methyl group, a (3-methylthio-5-benzothienyl)methyl group, a (3-methylsulfinyl-5-benzothienyl)methyl group, a (3-methylsulfonyl-5-benzothienyl)methyl group, a (3-methoxycarbonyl-5-benzothienyl)methyl group, a (3-vinyl-5-benzothienyl) methyl group, a [3-(2,2-difluorovinyl)-5-benzothienyl] methyl group, a (3-ethynyl-5-benzothienyl)methyl group, a [3-(2-fluoroethynyl)-5-benzothienyl]methyl group, a (3-fluoro-5-benzothienyl)methyl group, a (3-chloro-5-benzothienyl) methyl group, a fluoromethyl group, a 1-fluoroethyl group, a 1,1-difluoroethyl group, a 2-fluoroethyl group, a 2,2-difluoroethyl group, a 2,2,2-trifluoroethyl group, a 3-fluoropropyl group, a 3,3,3-trifluoropropyl group, a 4-fluorobutyl group, a 4,4,4-trifluorobutyl group, a 3,3,4,4,4-pentafluorobutyl group, a 5-fluoropentyl group, a 6-fluorohexyl group, a 7-fluoroheptyl group, a 8-fluorooctyl group, a chloromethyl group, a bromomethyl group, a (methoxycarbonyl)methyl group, a cyanomethyl group, a nitromethyl group, a (carboxy)methyl group, a hydroxymethyl group, a 1-hydroxyethyl group and the like.

In the present specification, examples of the "C1-C4 alkyl group having one or more benzyloxy groups" include, for example, a benzyloxymethyl group, a 1-(benzyloxy)ethyl group, a 2-(benzyloxy)ethyl group, a 1-(benzyloxy)propyl group, a 2-(benzyloxy)propyl group, a 3-(benzyloxy)propyl group, a 1-(benzyloxy)-1-methylethyl group, a 1-(benzyloxy)butyl group, a 2-(benzyloxy)butyl group, a 3-(benzyloxy)butyl group, a 4-(benzyloxy)butyl group, a 1-(benzyloxy)-1-methylpropyl group, a 2-(benzyloxy)-1-methylpropyl group, a 1-(benzyloxy)-2-methylpropyl group, and a 2-(benzyloxy)-2-methylpropyl group.

In the present specification, examples of the "C1-C4 alkoxy group" include:

a methoxy group, an ethoxy group, a propoxy group, an isopropoxy group, an isobutoxy group and the like.

In the present specification, examples of the "C1-C4 alkoxy group optionally having one or more halogen atoms" include:

a methoxy group, an ethoxy group, a propoxy group, an isopropoxy group, an isobutoxy group, a difluoromethoxy group, a trifluoromethoxy group, a trichloromethoxy group, a 2,2,2-trifluoroethoxy group, a 1,1,2,2-tetrafluoroethoxy group and a 1,1,2,2,2-pentafluoroethoxy group.

In the present specification, examples of the "C1-C4 alkylthio group optionally having one or more halogen atoms" include, for example, a methylthio group, an ethylthio group, a 1-propylthio group, a 2-propylthio group, an isobutylthio group, a difluoromethylthio group, a trifluoromethylthio group, a trichloromethylthio group, a 2,2,2-trifluoroethylthio group, a 1,1,2,2-tetrafluoroethylthio group and a 1,1,2,2,2-pentafluoroethylthio group.

In the present specification, examples of the "C1-C4 alkylsulfinyl group optionally having one or more halogen atoms" include, for example, a methanesulfinyl group, an ethanesulfinyl group, a 1-propanesulfinyl group, a 2-propanesulfinyl group, an isobutanesulfinyl group, a difluoromethanesulfinyl group, a trifluoromethanesulfinyl group, a trichloromethanesulfinyl group, a 2,2,2-trifluoroethanesulfinyl group, a 1,1,2,2-tetrafluoroethanesulfinyl group and a 1,1,2,2,2-pentafluoroethanesulfinyl group.

In the present specification, examples of the "C1-C4 alkylsulfonyl group optionally having one or more halogen atoms" include, for example, a methanesulfonyl group, an ethanesulfonyl group, a 1-propanesulfonyl group, a 2-propanesulfonyl group, an isobutanesulfonyl group, a difluoromethanesulfonyl group, a trifluoromethanesulfonyl group, a trichloromethanesulfonyl group, a 2,2,2-trifluoroethanesulfonyl group, a 1,1,2,2-tetrafluoroethanesulfonyl group and a 1,1,2,2,2-pentafluoroethanesulfonyl group.

In the present specification, examples of the "(C1-C4 alkoxy)carbonyl group" include, for example, a methoxycarbonyl group, an ethoxycarbonyl group, a propoxycarbonyl group, an isopropoxycarbonyl group, a butoxycarbonyl group, and a tert-butoxycarbonyl group.

In the present specification, examples of the "(C1-C4 alkoxy)carbonyl group in which the C1-C4 alkoxy has optionally one or more halogen atoms" include, for example, a methoxycarbonyl group, an ethoxycarbonyl group, a propoxycarbonyl group, an isopropoxycarbonyl group, a butoxycarbonyl group, a tert-butoxycarbonyl group, a difluoromethoxycarbonyl group, a trifluoromethoxycarbonyl group, a trichloromethoxycarbonyl group, a 2,2,2-trifluoroethoxycarbonyl group, a 1,1,2,2-tetrafluoroethoxycarbonyl group and a 1,1,2,2,2-pentafluoroethoxycarbonyl group.

In the present specification, examples of the "vinyl group optionally having one or more atoms or groups selected from Group E" include, for example, a vinyl group, a 2-fluorovinyl group, a 2,2-difluorovinyl group and: a 2,2-dichlorovinyl group.

In the present specification, examples of the "ethynyl group optionally having an atom or group selected from Group E" include, for example, an ethynyl group, and a 2-fluoroethynyl group.

In the present specification, examples of the "C1-C3 hydrocarbon group having one or more atoms or groups selected from the group consisting of a hydroxy group and a halogen atom" include, for example, a hydroxymethyl group, a fluoromethyl group, a chloromethyl group, a bromomethyl group, a difluoromethyl group, a trifluoromethyl group, a 1-hydroxyethyl group, a 1-fluoroethyl group, a 2-hydroxyethyl group, a 1,1-difluoroethyl group, a 1-chloroethyl group, a 2-chloroethyl group, a 1-bromoethyl group, a 1-hydroxypropyl group, a difluoromethyl group, a 1-hydroxy-2,2,2-trifluoroethyl group, a 1-hydroxy-2,2,3,3-pentafluoropropyl group and a 1-hydroxy-3,3,3-trifluoropropyl group.

In the present specification, examples of the "C1-C3 hydrocarbon group" include, for example, a C1-C3 alkyl group, and examples of the "C1-C3 hydrocarbon group optionally having one or more atoms or groups selected from the group consisting of a hydroxy group and a halogen atom" include, for example, a methyl group, an ethyl group, a propyl group, a hydroxymethyl group, a fluoromethyl group, a chloromethyl group, a bromomethyl group, a difluoromethyl group, a trifluoromethyl group, a 1-hydroxyethyl group, a 1-fluoroethyl group, a 2-hydroxyethyl group, a 1,1,-difluoroethyl group, a 1-chloroethyl group, a 2-chloroethyl group, a 1-bromoethyl group, a 1-hydroxypropyl group, a 1-hydroxy-2,2,2-trifluoroethyl group, a 1-hydroxy-2,2,3,3,3-pentafluoropropyl group and a 1-hydroxy-3,3,3-trifluoropropyl group.

In the present specification, examples of the "C2-C6 alkyl group optionally having one or more groups selected from the group consisting of a hydroxy group and a methoxy group" include:

an isobutyl group, a 1,1-dimethylpropyl group, a 2-methoxypropyl group, a 2-methoxy-2-methylpropyl group, a 2,2-dimethoxyethyl group, a 2-methoxyethyl group, a 3-methoxypropyl group, a 3-methoxy-2,2-dimethylpropyl group, a 2-hydroxypropyl group, a 3-hydroxy-2,2-dimethylpropyl group, and a 1-(methoxymethyl)-2-methoxyethyl group.

In the present specification, examples of the "phenyl group optionally having one or more atoms or groups selected from Group H" include:

a 2-fluorophenyl group, a 3-fluorophenyl group, a 4-fluorophenyl group, a 3-chlorophenyl group, a 4-chlorophenyl group, a 4-bromophenyl group, a 3-methylphenyl group, a 4-methylphenyl group, a 4-methoxyphenyl group, a 2-fluoro-4-chlorophenyl group, a 3-fluoro-4-chlorophenyl group, a 2,4-difluorophenyl group, a 2,3-difluorophenyl group, a 3,4-difluorophenyl group, a 3,5-difluorophenyl group, and a 2,3,4-trifluorophenyl group.

Examples of the present noxious arthropod controlling agent include, for example, the followings.

[1-1] A noxious arthropod controlling agent containing an amide compound of formula (I-1):

(I-1)

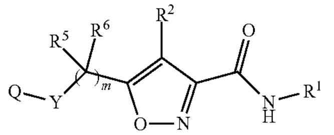

wherein $R^1$ represents a C1-C8 chain hydrocarbon group optionally having one or more groups selected from Group A-1, $R^2$, $R^3$, $R^5$, $R^6$, Y, Q, and u are the same as defined in [1] with respect to formula (I);

Group A-1 consisting of a C1-C4 alkoxy group optionally having one or more halogen atoms, a C1-C6 alkylamino group, a di(C1-C3 alkyl)amino group, a hydroxy group, a (C1-C4 alkoxy)carbonyl group in which the C1-C4 alkoxy has optionally one or more halogen atoms, and a —$CONR^7R^8$ group, wherein $R^7$ and $R^8$ are the same or different, and independently represent a C1-C4 alkyl group optionally having one or more halogen atoms, a [(C1-C4 alkoxy)carbonyl]C1-C4 alkyl group in which the C1-C4 alkoxy has optionally one or more halogen atoms, a 3-tetrahydrofuranylmethyl group, a 4-tetrahydropyranylmethyl group or a hydrogen atom, and an inert carrier.

[2-1] The noxious arthropod controlling agent according to [1-1], wherein the amide compound is a compound of formula (II-1):

(II)

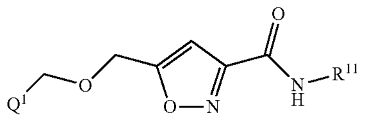

wherein $R^{11}$ represents a C1-C8 chain hydrocarbon group optionally having one or more groups selected from Group G, and $Q^1$ represents a phenyl group or a naphthyl group; Group G consisting of a C1-C4 alkoxy group, a (C1-C4 alkoxy) carbonyl group and a hydroxy group.

[3-1] A method for controlling a noxious arthropod, which comprises applying an effective amount of the amide compound of formula (I-1) as defined in [1-1] to a noxious arthropod or a habitat of a noxious arthropod.

[4-1] The noxious arthropod controlling agent according to [1-1], wherein $R^1$ is a C2-C6 alkyl group optionally having one or more groups selected from the group consisting of a hydroxy group and a methoxy group, $R^2$ is a methyl group, a fluoromethyl group, a hydroxymethyl group, a 1-fluoroethyl group or a hydrogen atom, and a group represented by Q-Y— $(CR^5R^6)_m$ is a $Q^a$-$CH_2$—O—$CH_2$ group, a $Q^a$-$CH_2$—$CH_2$—$CH_2$ group, a $Q^a$-O—$CH_2$ group or a $Q^a$-$CH_2$ group, $Q^a$ is a phenyl group optionally having one or more atoms or groups selected from Group H or a naphthyl group optionally having one or more atoms or groups selected from Group H;

Group H consisting of a C1-C4 alkyl group, a C1-C4 alkoxy group, and a halogen atom.

[5-1] The method for controlling a noxious arthropod according to [3-1], wherein $R^1$ is a C2-C6 alkyl group optionally having one or more groups selected from the group consisting of a hydroxy group and a methoxy group, $R^2$ is a methyl group, a fluoromethyl group, a hydroxymethyl group, a 1-fluoroethyl group or a hydrogen atom, a group represented by Q-Y—$(CR^5R^6)_m$ is a $Q^a$-$CH_2$—O—$CH_2$ group, a $Q^a$-$CH_2$—$CH_2$—$CH_2$ group, a $Q^a$-O—$CH_2$ group or a $Q^a$-$CH_2$ group, $Q^a$ is a phenyl group optionally having one or more atoms or groups selected from Group H or a naphthyl group optionally having one or more atoms or groups selected from Group H consisting of a C1-C4 alkyl group, a C1-C4 alkoxy group and a halogen atom.

Examples of the amide compound of formula (I) include, for example, an amide compound of formula (I) as defined in [1], wherein $R^1$ is a group of following formula (IV):

(IV)

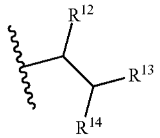

wherein $R^{12}$ represents a C1-C2 chain hydrocarbon group optionally having one or more groups selected from Group G, a C1-C4 alkoxy group, or a hydrogen atom, and $R^{13}$ and $R^{14}$ are the same or different, and independently represent a C1-C2 chain hydrocarbon group optionally having one or more groups selected from Group G, or a C1-C4 alkoxy group;

Group G consisting of a C1-C4 alkoxy group, and wherein $R^2$, $R^5$, $R^6$, Q, Y and m are the same as defined in [1] with respect to the formula (I).

Further examples of the amide compound of formula (I) include, for example, the following amide compounds;

an amide compound in which $R^2$ is a C1-C2 hydrocarbon group optionally having one or more atoms or groups selected from the group consisting of a hydroxy group and a halogen atom in formula (I);

an amide compound in which $R^5$ and $R^6$ are a hydrogen atom in formula (I);

an amide compound in which m is 1, Y is an oxygen atom, and Q is a C1-C8 chain hydrocarbon group optionally having one or more atoms or groups selected from Group D in formula (I);

an amide compound in which m is 0, Y is an oxygen atom, and Q is a C1-C8 chain hydrocarbon group optionally having one or more atoms or groups selected from Group D in formula (I);

an amide compound in which m is 1, Y is an oxygen atom, and Q is a phenyl group optionally having one or more atoms or groups selected from Group B in formula (I);

an amide compound in which m is 0, Y is a single bond, and Q is a C1-C8 chain hydrocarbon group having one or more atoms or groups selected from Group C in formula (I);

an amide compound in which m is 1, Y is an oxygen atom, $R^2$ is a methyl group, $R^5$ and $R^6$ are a hydrogen atom, and Q is a C1-C8 chain hydrocarbon group optionally having one or more atoms or groups selected from Group D in formula (I);

an amide compound in which m is 1, Y is an oxygen atom, $R^2$, $R^5$ and $R^6$ are a hydrogen atom, and Q is a C1-C8 chain hydrocarbon group optionally having one or more atoms or groups selected from Group D in formula (I);

an amide compound in which m is 1, Y is an oxygen atom, $R^2$ is a C1-C2 hydrocarbon group optionally having one or more atoms or groups selected from the group consisting of a hydroxy group and a halogen atom, $R^5$ and $R^6$ are a hydrogen atom, and Q is a phenyl group optionally having one or more atoms or groups selected from Group B in formula (I);

an amide compound in which m is 1, Y is an oxygen atom, $R^2$ is a methyl group, $R^5$ and $R^6$ are a hydrogen atom, and Q is a phenyl group optionally having one or more atoms or groups selected from Group B in formula (I);

an amide compound in which m is 1, Y is an oxygen atom, $R^2$, $R^5$ and $R^6$ are a hydrogen atom, and Q is a phenyl group optionally having one or more atoms or groups selected from Group B in formula (I);

an amide compound in which m is 0, Y is an oxygen atom, $R^2$ is a methyl group, and Q is a C1-C8 chain hydrocarbon group optionally having one or more atoms or groups selected from Group D in formula (I);

an amide compound in which m is 0, Y is a single bond, $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having one or more atoms or groups selected from Group C in formula (I);

an amide compound in which m is 0, Y is a single bond, $R^2$ is a methyl group, $R^5$ and $R^6$ are a hydrogen atom, and Q is a C1-C8 chain hydrocarbon group having one or more atoms or groups selected from Group C in formula (I);

an amide compound in which m is 0, Y is a single bond, $R^2$, $R^5$ and $R^6$ are a hydrogen atom, and Q is a C1-C8 chain hydrocarbon group having one or more atoms or groups selected from Group C in formula (I);

an amide compound in which m is 1, Y is an oxygen atom, $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^2$ is a methyl group, $R^5$ and $R^6$ are a hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^2$ is a methyl group, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^2$, $R^5$ and $R^6$ are hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^2$, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^2$ is a C1-C2 hydrocarbon group optionally having one or more atoms or groups selected from the group consisting of a hydroxy group and a halogen atom, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^2$ is a C1-C2 hydrocarbon group optionally having one or more atoms or groups selected from the group consisting of a hydroxy group and a halogen atom, $R^5$ and $R^6$ are a hydrogen atom, and Q is a methyl group optionally having a naphthyl group optionally having one or more atoms or groups selected from Group B in formula (I);

an amide compound in which m is 1, Y is an oxygen atom, $R^2$ is a methyl group, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^2$ is a methyl group, $R^5$ and $R^6$ are a hydrogen atom, and Q is a methyl group optionally having a naphthyl group optionally having one or more atoms or groups selected from Group B in formula (I);

an amide compound in which m is 1, Y is an oxygen atom, $R^2$, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^2$, $R^5$ and $R^6$ are a hydrogen atom, and Q is a methyl group optionally having a naphthyl group optionally having one or more atoms or groups selected from Group B in formula (I);

an amide compound in which m is 0, Y is a single bond, $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^2$ is a methyl group, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^2$, $R^5$ and $R^6$ are a hydrogen atom, and Q is a C1-C8 chain hydrocarbon group having a naphthyl group optionally having one or more atoms or groups selected from Group B in formula (I);

an amide compound in which m is 0, Y is a single bond, $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^2$ is a methyl group, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^2$, $R^5$ and $R^6$ are a hydrogen atom, and Q is a C1-C8 chain hydrocarbon group having a naphthyl group optionally having one or more atoms or groups selected from Group B in formula (I);

an amide compound in which m is 0, Y is a single bond, $R^2$ is a C1-C2 hydrocarbon group optionally having one or more atoms or groups selected from the group consisting of a hydroxy group and a halogen atom, $R^5$ and $R^6$ are a hydrogen atom, and Q is a propyl group having a phenyl group optionally having one or more atoms or groups selected from Group B in formula (I);

an amide compound in which m is 0, Y is a single bond, $R^2$ is a methyl group, $R^5$ and $R^6$ are a hydrogen atom, and Q is a propyl group having a phenyl group optionally having one or more atoms or groups selected from Group B in formula (I);

an amide compound in which m is 0, Y is a single bond, $R^2$, $R^5$ and $R^6$ are a hydrogen atom, and Q is a propyl group having a naphthyl group optionally having one or more atoms or groups selected from Group B in formula (I);

an amide compound in which m is 0, Y is a single bond, $R^2$ is a C1-C2 hydrocarbon group optionally having one or more atoms or groups selected from the group consisting of a hydroxy group and a halogen atom, $R^5$ and $R^6$ are a hydrogen atom, and Q is a propyl group having a phenyl group optionally having one or more atoms or groups selected from Group B in formula (I);

an amide compound in which m is 0, Y is a single bond, $R^2$ is a methyl group, $R^5$ and $R^6$ are a hydrogen atom, and Q is a propyl group having a phenyl group optionally having one or more atoms or groups selected from Group B in formula (I);

an amide compound in which m is 0, Y is a single bond, $R^2$, $R^5$ and $R^6$ are a hydrogen atom, and Q is a propyl group having a naphthyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a C1-C8 chain hydrocarbon group optionally having one or more atoms or groups selected from Group D in formula (I);

an amide compound in which m is 1, Y is an oxygen atom, $R^1$ is a group of formula (IV), $R^2$, $R^5$ and $R^6$ are a hydrogen atom, and Q is a C1-C8 chain hydrocarbon group optionally having one or more atoms or groups selected from Group D in formula (I);

an amide compound in which m is 1, Y is an oxygen atom, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a phenyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a phenyl group optionally having one or more atoms or groups selected from Group B in formula (I);

an amide compound in which m is 1, Y is an oxygen atom, $R^1$ is a group of formula (IV), $R^2$, $R^5$ and $R^6$ are a hydrogen atom, and Q is a phenyl group optionally having one or more atoms or groups selected from Group B in formula (I);

an amide compound in which m is 0, Y is a single bond, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having one or more atoms or groups selected from Group C in formula (I);

an amide compound in which m is 0, Y is a single bond, $R^1$ is a group of formula (IV), $R^2$ is a methyl group, $R^5$ and $R^6$ are a hydrogen atom, and Q is a C1-C8 chain hydrocarbon group having one or more atoms or groups selected from Group C in formula (I);

an amide compound in which m is 0, Y is a single bond, $R^1$ is a group of formula (IV), $R^2$, $R^5$ and $R^6$ are a hydrogen atom, and Q is a C1-C8 chain hydrocarbon group having one or more atoms or groups selected from Group C in formula (I);

an amide compound in which m is 1, Y is an oxygen atom, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^1$ is a group of formula (IV), $R^2$, $R^5$ and $R^6$ are a hydrogen atom, and Q is a C1-C8 chain hydrocarbon group optionally having a phenyl group optionally having one or more atoms or groups selected from Group B in formula (I);

an amide compound in which m is 1, Y is an oxygen atom, $R^1$ is a group of formula (IV), $R^2$, $R^5$ and $R^6$ are a hydrogen atom, and Q is a C1-C8 chain hydrocarbon group optionally having a naphthyl group optionally having one or more atoms or groups selected from Group B in formula (I);

an amide compound in which m is 1, Y is an oxygen atom, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a methyl group optionally having a naphthyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^1$ is a group of formula (IV), $R^2$ is a methyl group, $R^5$ and $R^6$ are a hydrogen atom, and Q is a methyl group optionally having a naphthyl group optionally having one or more atoms or groups selected from Group B in formula (I);

an amide compound in which m is 1, Y is an oxygen atom, $R^1$ is a group of formula (IV), $R^2$, $R^5$ and $R^6$ are a hydrogen atom, and Q is a methyl group optionally having a phenyl group optionally having one or more atoms or groups selected from Group B in formula (I);

an amide compound in which m is 1, Y is an oxygen atom, $R^1$ is a group of formula (IV), $R^2$, $R^5$ and $R^6$ are a hydrogen atom, and Q is a methyl group optionally having a naphthyl group optionally having one or more atoms or groups selected from Group B in formula (I);

an amide compound in which m is 0, Y is a single bond, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is single bond, $R^1$ is a group of formula (IV), $R^2$ is a methyl group, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^1$ is a group of formula (IV), $R^2$, $R^5$ and $R^6$ are a hydrogen atom, and Q is a C1-C8 chain hydrocarbon group having a naphthyl group optionally having one or more atoms or groups selected from Group B in formula (I);

an amide compound in which m is 0, Y is a single bond, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^1$ is a group of formula (IV), $R^2$ is a methyl group, $R^5$ and $R^6$ are a hydrogen atom, and Q is a C1-C8 chain hydrocarbon group having a phenyl group optionally having one or more atoms or groups selected from Group B in formula (I);

an amide compound in which m is 0, Y is a single bond, $R^1$ is a group of formula (IV), $R^2$, $R^5$ and $R^6$ are a hydrogen atom, and Q is a C1-C8 chain hydrocarbon group having a naphthyl group optionally having one or more atoms or groups selected from Group B in formula (I);

an amide compound in which m is 0, Y is a single bond, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a propyl group having a phenyl group optionally having one or more atoms or groups selected from Group B in formula (I);

an amide compound in which m is 0, Y is a single bond, $R^1$ is a group of formula (IV), $R^2$ is a methyl group, $R^5$ and $R^6$ are a hydrogen atom, and Q is a propyl group having a phenyl group optionally having one or more atoms or groups selected from Group B in formula (I);

an amide compound in which m is 0, Y is a single bond, $R^1$ is a group of formula (IV), $R^2$, $R^5$ and $R^6$ are a hydrogen atom, and Q is a propyl group having a naphthyl group optionally having one or more atoms or groups selected from Group B in formula (I);

an amide compound in which m is 0, Y is a single bond, $R^1$ is a group of formula (IV), $R^2$ is a C1-C2 hydrocarbon group optionally having one or more atoms or groups selected from the group consisting of a hydroxy group and a halogen atom, $R^5$ and $R^6$ are a hydrogen atom, and Q is a propyl group having a phenyl group optionally having one or more atoms or groups selected from Group B in formula (I);

an amide compound in which m is 0, Y is a single bond, $R^1$ is a group of formula (IV), $R^2$ is a methyl group, $R^5$ and $R^6$ are a hydrogen atom, and Q is a propyl group having a phenyl group optionally having one or more atoms or groups selected from Group B in formula (I);

an amide compound in which m is 0, Y is a single bond, $R^1$ is a group of formula (IV), $R^2$, $R^5$ and $R^6$ are a hydrogen atom, and Q is a propyl group having a naphthyl group optionally having one or more atoms or groups selected from Group B in formula (I);

an amide compound in which m is 1, Y is an oxygen atom, $R^2$, $R^5$ and $R^6$ are a hydrogen atom, Q is a C1-C4 alkyl group having a phenyl group, and $R^1$ is a C1-C8 chain hydrocarbon group optionally having one or more groups selected from the group consisting of a halogen atom, a C1-C4 alkoxy group, a C1-C6 alkylamino group, a di(C1-C6 alkyl)amino group, a hydroxy group, a (C1-C4 alkoxy)carbonyl group and a —$CONR^7R^8$ group, wherein $R^7$ and $R^8$ are the same or different, and independently represent a C1-C4 alkyl group optionally having one or more halogen atoms, or a hydrogen atom, in formula (I);

an amide compound in which m is 1, Y is an oxygen atom, $R^2$, $R^5$ and $R^6$ are a hydrogen atom, Q is a C1-C4 alkyl group having a naphthyl group, and $R^1$ is a C1-C8 chain hydrocarbon group optionally having one or more groups selected from the group consisting of a halogen atom, a C1-C4 alkoxy group, a C1-C6 alkylamino group, a di(C1-C6 alkyl) amino group, a hydroxy group and a —$CONR^7R^8$ group, wherein $R^7$ and $R^8$ are the same or different, and independently represent a C1-C4 alkyl group optionally having one or more halogen atoms, or a hydrogen atom in formula (I);

an amide compound in which Y is a single bond, $R^2$, $R^5$ and $R^6$ are a hydrogen atom, Q is a C1-C8 alkyl group optionally having one or more halogen atoms, and $R^1$ is a C1-C8 chain hydrocarbon group optionally having one or more groups selected from the group consisting of a halogen atom, a C1-C4 alkoxy group, a C1-C6 alkylamino group and a di(C1-C6 alkyl)amino group in formula (I);

an amide compound in which m is 1, Y is an oxygen atom, $R^2$, $R^5$ and $R^6$ are a hydrogen atom, Q is a C1-C4 alkyl group having a phenyl group, and $R^1$ is a C1-C8 chain hydrocarbon group optionally having one or more groups selected from the group consisting of a C1-C6 alkylamino group, a di(C1-C6 alkyl)amino group, a hydroxy group, a C1-C4 alkoxy group, a (C1-C4 alkoxy)carbonyl group and a —$CONR^7R^8$ group, wherein $R^7$ and $R^8$ are the same or different, and independently represent a C1-C4 alkyl group optionally having one or more halogen atoms, or a hydrogen atom, in formula (I);

an amide compound in which m is 1, Y is an oxygen atom, $R^2$, $R^5$ and $R^6$ are a hydrogen atom, Q is a C1-C4 alkyl group having a naphthyl group, and $R^1$ is a C1-C8 chain hydrocarbon group optionally having one or more groups selected from the group consisting of a C1-C6 alkylamino group, a di(C1-C6 alkyl)amino group, a hydroxy group and a C1-C4 alkoxy group in formula (I);

an amide compound in which Y is a single bond, $R^2$, $R^5$ and $R^6$ are a hydrogen atom, Q is a C1-C8 alkyl group optionally having one or more halogen atoms, and $R^1$ is a C1-C8 chain hydrocarbon group optionally having one or more groups selected from the group consisting of a C1-C6 alkylamino group, and a di(C1-C6 alkyl)amino group in formula (I).

Then, a process for producing the amide compound will be illustrated.

The amide compound can be produced, for example, in accordance with the following Production Processes.

Production Process 1

The amide compound can be produced by reacting a compound of formula (1A) and a compound of formula (2A) in the presence of a condensing agent:

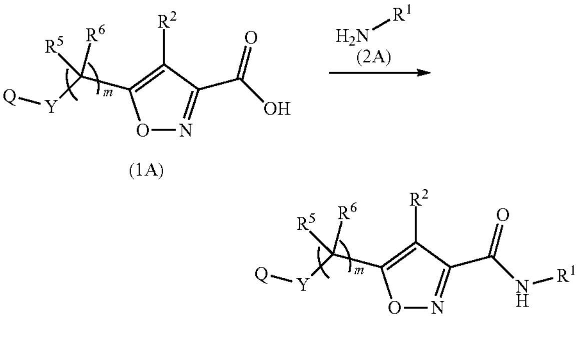

(1A)
(I)

wherein symbols are as defined above.

A reaction is performed usually in the presence of a condensing agent in a solvent.

Examples of the condensing agent used in the reaction include 1-ethyl-3-(3-dimethylaminopropyl)carbodiimide hydrochloride (hereinafter, referred to as EDCD), dicyclohexylcarbodiimide, benzotriazol-1-yloxytris(dimethylamino)phosphonium hexafluorophosphate and (benzotriazol-1-yloxy)tripyrrolidinophosphonium hexafluorophosphate.

The reaction may be performed in the presence of a base.

Examples of the base used in the reaction include carbonates such as sodium carbonate and potassium carbonate (hereinafter, referred to as carbonates), tertiary amines such as triethylamine, diisopropylethylamine, 1,8-diazabicyclo [5.4.0]undeca-7-ene, and 1,5-diazabicyclo[4.3.0]non-5-ene (hereinafter, referred to as tertiary amines) and nitrogen-containing aromatic compounds such as pyridine, and 4-dimethylaminopyridine (hereinafter, referred to as nitrogen-containing aromatic compounds).

Examples of the solvent used in the reaction include aromatic hydrocarbons such as benzene and toluene (hereinafter, referred to as aromatic hydrocarbons), aliphatic hydrocarbons such as hexane (hereinafter, referred to as aliphatic hydrocarbons), ethers such as diethyl ether and tetrahydrofuran (hereinafter, referred to as ethers), halogenated hydrocarbons such as dichloromethane, chloroform, 1,2-dichloroethane, and chlorobenzene (hereinafter, referred to as halogentated hydrocarbons), acid amides such as dimethylformamide (hereinafter, referred to as DMF) (hereinafter, referred to as acid amides), and esters such as ethyl acetate, and butyl acetate (hereinafter, referred to as esters).

The reaction can be also performed by adding 1-hydroxybenzotriazole (hereinafter, referred to as HOBT), 1-hydroxy-7-azabenzotriazole, or N-hydroxysuccinic acid imide in place of the base, or in addition to the base. An amount of them that may be used is usually 0.01 mole to 1 mole, preferably 0.05 mole to 0.2 mole per mol of the compound of formula (1A).

A reaction time of the reaction is usually in a range of 5 minutes to 72 hours.

A reaction temperature of the reaction is usually in a range of −20° C. to 100° C. (provided that when a boiling point of a solvent to be used is lower than 100° C., −20° C. to a boiling point of a solvent).

In the reaction, the amount ratio of the compound of formula (1A) and the compound of formula (2A) can be set preferably at an equimolar or similar ratio, for example, a ratio of 1 mole to 3 moles of the compound of formula (2A) per mole of the compound of formula (1A).

The condensing agent can be usually used in an amount of 1 mole to an excessive amount, preferably 1 mole to 3 moles per mol of the compound of formula (1A).

The base can be used usually in an amount of 1 mole to an excessive amount, preferably 1 mole to 3 moles per mole of the compound of formula (1A).

After completion of the reaction, the amide compound can be isolated by performing ordinary post-treatment operation such as organic solvent extraction and concentration after addition of the reaction mixture to water. In addition, the isolated amide compound can be also purified by operation such as chromatography, recrystallization and distillation.

Production Process 2

The amide compound can be produced by reacting a compound of formula (3A) and a compound of formula (2A) in the presence of a base.

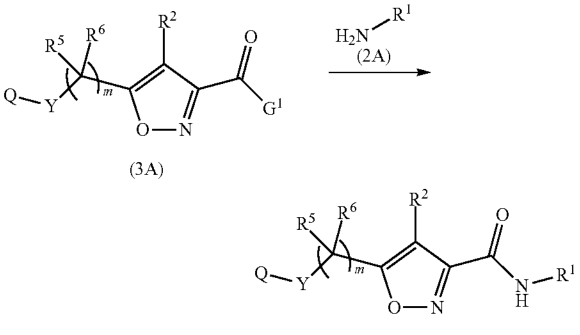

(3A)

(I)

wherein $G^1$ represents a leaving group such as a chlorine atom, and other symbols are as defined above.

The reaction is performed in the presence of a base usually in a solvent.

Examples of the base used in the reaction include carbonates, tertiary amines and nitrogen-containing aromatic compounds.

Examples of the solvent used in the reaction include ethers, aliphatic hydrocarbons, aromatic hydrocarbons, halogenated hydrocarbons, esters, nitriles such as acetonitrile and butyronitrile (hereinafter, referred to as nitriles), acid amides, sulfoxides such as dimethyl sulfoxide and a mixture thereof.

A reaction time of the reaction is usually in a range of 5 minutes to 72 hours.

A reaction temperature of the reaction is usually in a range of −20 to 100° C.

In the reaction, a use molar ratio of the compound of formula (3A) and the compound of formula (2A) can be arbitrarily set at preferably an equimolar or similar ratio, specifically, 0.5 to 3 moles of the compound of formula (2A), per mole of the compound of formula (3A).

The base used in the reaction can be used at an arbitrary ratio of usually 1 mole to an excessive amount, preferably 1 to 3 moles per mol of the compound of formula (3A).

After completion of the reaction, the amide compound can be isolated by performing ordinary post-treatment operation such as organic solvent extraction and concentration after addition of the reaction mixture to water. In addition, the isolated amide compound can be also purified by operation such as chromatography, recrystallization and distillation.

Production Process 3

A compound of formula (I-w) can be produced by reacting a compound of formula (4A) and a compound of formula (5A) in the presence of a base.

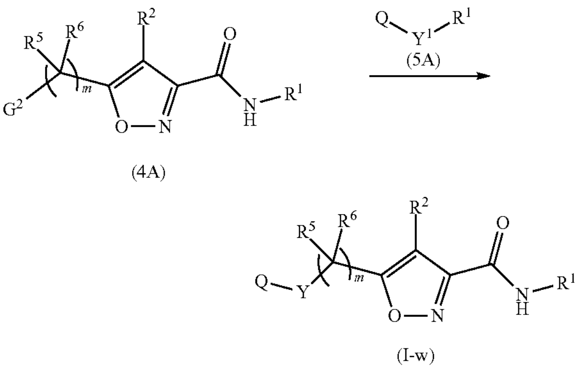

(4A)

(I-w)

wherein $G^2$ represents a leaving group (e.g. chlorine atom, bromine atom, iodine atom, methanesulfonyloxy group, trifluoromethanesulfonyloxy group or p-toluenesulfonyloxy group etc.), $Y^1$ represents an oxygen atom or a sulfur atom, and other symbols are as defined above.

A reaction is performed in the presence of a base usually in a solvent.

Examples of the base used in the reaction include metal hydride compounds such as sodium hydride and potassium hydride, carbonates, alkali metal alkoxides such as potassium-tert-butoxide, tertiary amines and nitrogen-containing aromatic compounds.

Examples of the solvent used in the reaction include ethers, aliphatic hydrocarbons, aromatic hydrocarbons, halogenated hydrocarbons, esters, nitriles, acid amides, sulfoxides such as dimethyl sulfoxide and a mixture thereof.

A reaction time of the reaction is usually in a range of 5 minutes to 72 hours.

A reaction temperature of the reaction is usually in a range of −20 to 100° C.

In the reaction, a use molar ratio of the compound of formula (4A) and the compound of formula (5A) can be arbitrarily set at preferably an equimolar or similar ratio, specifically, 0.5 to 3 moles of the compound of formula (5A) per mole of the compound of formula (4A).

The base used in the reaction can be used at an arbitrary ratio of usually 1 mole to an excessive amount, preferably 1 to 3 moles per mole of the compound of formula (5A).

After completion of the reaction, the amide compound can be isolated by performing ordinary post-treatment operation such as organic solvent extraction and concentration after addition of the reaction mixture to water. In addition, the isolated amide compound can be also purified by operation such as chromatography, recrystallization and distillation.

Production Process 4

A compound of formula (I-s) can be produced, for example, by a route shown in the following scheme according to the method described in European Journal of Organic Chemistry, 4852-4860, (2006).

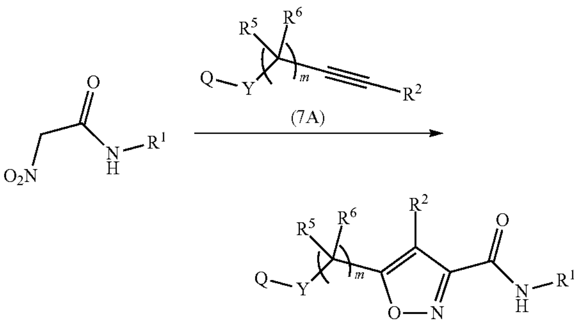

(7A)

(I-s)

wherein symbols are as defined above.

Production Process 5

A compound of formula (I-w) can be produced by subjecting a compound of formula (12A) to a coupling reaction.

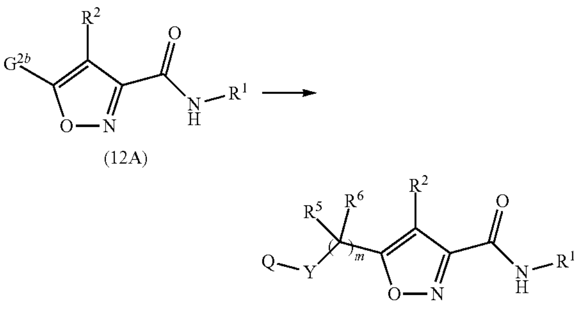

(12A)

(I-w)

wherein $G^{2b}$ represents a leaving group (e.g. chlorine atom, bromine atom and iodine atom etc.), and other symbols are as defined above.

Examples of the coupling reaction include:

(1) Negishi coupling reaction (2) Stille coupling reaction (3) Suzuki coupling reaction (4) a method using an organic metal reagent such as a Grignard reagent, an organocopper reagent and an organolithium reagent.

As one example, (1) a method by the Negishi coupling reaction will be mentioned specifically.

A reaction is performed usually under the inert gas atmosphere such as nitrogen, usually in the presence of a transition metal catalyst, inorganic zinc salts and an organic metal reagent, if necessary, in the presence of a ligand in a solvent.

Examples of the transition metal catalyst used in the reaction include palladium catalysts such as palladium acetate, palladium dichloride, dichlorobis(triphenylphosphine)palladium, and tetrakis(triphenylphosphine)palladium.

Examples of the ligand used in the reaction include phosphines such as trimethylphosphine, tricyclohexylphosphine, and triphenylphosphine, imidazolium salts such as 1,3-bis(2,4,6-trimethylphenyl)imidazolium chloride, diketones such as acetylacetone, and octafluoroacetylacetone, 1,1'-bis(diphenylphosphino)ferrocene, and 2-dicyclohexylphosphino-2',6'-dimethoxybiphenyl.

Examples of the inorganic zinc salts used in the reaction include zinc chloride.

Examples of the organic metal reagent used in the reaction include organomagnesium halides such as methylmagnesium chloride, ethylmagnesium chloride, propylmagnesium chloride, butylmagnesium chloride, pentylmagnesium bromide, and hexylmagnesium chloride, and organolithium compounds such as methyllithium, and ethyllithium.

Examples of the solvent used in the reaction include aromatic hydrocarbons, aliphatic hydrocarbons, and ethers.

A reaction time of the reaction is usually in a range of 5 minutes to 72 hours.

A reaction temperature of the reaction is usually in a range of −20° C. to 100° C. (provided that when a boiling point of a solvent to be used is lower than 100° C., −20° C. to a boiling point of a solvent).

An amount of the transition metal catalyst that can be usually used from 0.001 to 0.5 mole per mole of the compound of formula (12A).

An amount of the ligand that can be usually used is 0.001 mole to 0.5 mole per mole of the compound of formula (12A).

The inorganic zinc salts can be usually used in an amount of 1 mole to an excessive amount, preferably 1 mole to 3 moles per mole of the compound of formula (12A).

The organic metal reagent can be usually used in an amount of 1 mole to an excessive amount, preferably 1 mole to 3 moles per mole of the compound of formula (12A).

After completion of the reaction, the amide compound can be isolated by performing ordinary post-treatment operation such as organic solvent extraction and concentration after addition of the reaction mixture to water. In addition, the isolated amide compound can be also purified by operation such as chromatography, recrystallization and distillation.

Production Process 6

A compound of formula (I-y) can be produced by reacting a compound of formula (I-x) with a base, and thereafter, reacting the resultant with an electrophile.

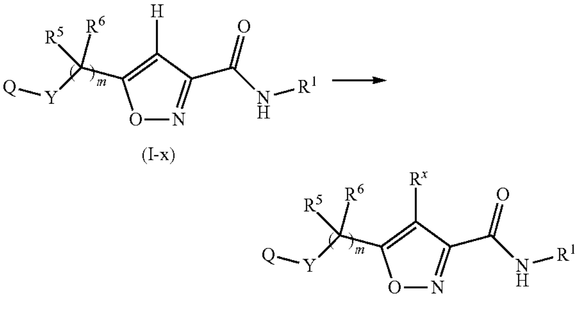

(I-x)

(I-y)

wherein $R^x$ represents a C1-C3 hydrocarbon group optionally having one or more atoms or groups selected from the group consisting of a hydroxy group and a halogen atom, a halogen atom, a formyl group, or a carboxy group, and other symbols are as defined above.

A reaction is performed usually under the inert gas atmosphere such as nitrogen, in the presence of a base in a solvent.

Examples of the base used in the reaction include metal amides such as sodium amide, lithium diisopropylamide, and sodium bis(trimethylsilyl)amide, alkali metal alkoxides such as potassium-tert-butoxide, organolithium compounds such as methyllithium, ethyllithium, n-butyllithium, sec-butyllithium, tert-butyllithium, and 2,4,6-trimethylphenyllithium, organomagnesium halides such as methylmagnesium chloride, ethylmagnesium chloride, propylmagnesium chloride, butylmagnesium chloride, pentylmagnesium bromide, and hexylmagnesium chloride, and a 2,2,6,6-tetramethylpiperidinylmagnesium chloride-lithium chloride complex.

Examples of the electrophile used in the reaction include DMF, formaldehyde, paraformaldehyde, acetaldehyde, propionaldehyde, iodomethane, iodoethane, 1,2-dibromoethane, 1-bromo-2-chloroethane, 1-chloropropane, 1-bromopropane, 1-iodopropane, dimethyl sulfate, diethyl sulfate, methyl tosylate, bromine, iodine, N-bromosuccinimide, N-chlorosuccinimide, N-iodosuccinimide, carbon dioxide, N-fluoropyridinium salts such as N-fluoro-2,4,6-trimethylpyridinium triflate, and electrophilic fluorinating agents such as N-fluoro-N'-(chloromethyl)triethylenediaminebis(tetrafluoroborate), and N-fluorobenzenesulfonimide.

Examples of the solvent used in the reaction include aliphatic hydrocarbons, aromatic hydrocarbons, ethers and a mixture thereof.

A reaction time of the reaction is usually in a range of 5 minutes to 72 hours.

A reaction temperature of the reaction is usually in a range of −100° C. to 40° C. (provided that when a boiling point of a solvent to be used is lower than 40° C., −100° C. to a boiling point of a solvent).

The base used in the reaction can be used at an arbitrary ratio of usually 1 mole to an excessive amount, preferably 2 mole to 3 moles per mole of the compound of formula (I-x).

The electrophile can be usually used in an amount of 1 mole to an excessive amount, preferably 1 mole to 3 moles per mole of the compound of formula (I-x).

After completion of the reaction, the compound can be isolated by performing ordinary post-treatment operation such as organic solvent extraction and concentration after addition of the reaction mixture to water. In addition, the isolated compound can be also purified by operation such as chromatography, recrystallization and distillation.

Production Process 7

A compound of formula (I-u) can be produced by reacting a compound of formula (I-t) with a halogenating agent, and thereafter, reacting the resultant with a nucleophile.

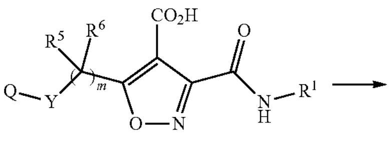

(I-t)

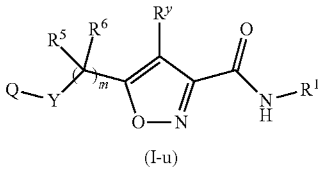

(I-u)

wherein $R^y$ represents a (C1-C4 alkoxy)carbonyl group in which the C1-C4 alkoxy has optionally one or more halogen atoms, or a carbamoyl group, and other symbols are as defined above.

A reaction is performed usually under the inert gas atmosphere such as nitrogen, in the presence of a halogenating agent, if necessary, in the presence of DMF in a solvent.

Examples of the halogenating agent used in the reaction include thionyl chloride, oxalyl chloride and phosphorus oxychloride.

Examples of the nucleophile used in the reaction include C1-C4 alcohols such as methyl alcohol, ethyl alcohol, propanol and butanol, and ammonia.

Examples of the solvent used in the reaction include esters, ethers, aliphatic hydrocarbons, aromatic hydrocarbons, halogenated hydrocarbons and a mixture thereof.

A reaction time of the reaction is usually in a range of 5 minutes to 24 hours.

A reaction temperature of the reaction is usually in a range of 0 to 100° C. (provided that when a boiling point of a solvent to be used is lower than 100° C., 0° C. to a boiling point of a solvent).

The halogenating agent can be usually used in an amount of 1 mole to an excessive amount, preferably 1 to 5 moles, per mole of the compound of formula (1-t).

DMF which may be used usually in an amount of 0.01 mole to an excessive amount, preferably 0.01 to 0.1 mole per mole of the compound of formula (I-t).

The nucleophile can be usually used in an amount of 1 mole to an excessive amount, preferably 1 mole to 5 moles per mole of the compound of formula (I-t).

After completion of the reaction, the compound can be isolated by performing ordinary post-treatment operation such as organic solvent extraction and concentration after addition of the reaction mixture to water. In addition, the isolated compound can be also purified by operation such as chromatography, recrystallization and distillation.

Production Process 8

A compound of formula (I-m) can be produced by reacting a compound of formula (I-1) with a nucleophile.

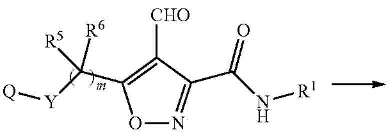

(I-l)

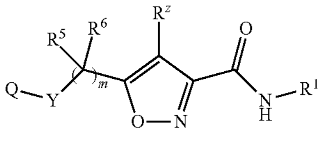

(I-m)

wherein $R^z$ represents a C1-C3 hydrocarbon group having one or more atoms or groups selected from the group consisting of a hydroxy group and a halogen atom, and other symbols are as defined above.

A reaction is performed usually in a solvent.

Examples of the nucleophile used in the reaction include organomagnesium halides such as methylmagnesium chloride, ethylmagnesium chloride, and propylmagnesium chloride, organolithium compounds such as methyllithium, ethyllithium, and propyllithium, metal hydrides such as sodium borohydride, organozinc reagents such as dimethylzinc, and diethylzinc, and nucleophilic fluorinating agents such as (diethylamino)sulfur trifluoride, and bis(2-methoxyethyl) aminosulfur trifluoride.

Examples of the solvent used in the reaction include ethers, aliphatic hydrocarbons, aromatic hydrocarbons, halogenated hydrocarbons, alcohols such as methyl alcohol, and ethyl alcohol and a mixture thereof.

A reaction time of the reaction is usually in a range of 5 minutes to 72 hours.

A reaction temperature of the reaction is usually in a range of −40 to 60° C. (provided that when a boiling point of a solvent to be used is lower than 60° C., −40° C. to a boiling point of a solvent).

The nucleophile can be usually used in an amount of 1 mole to an excessive amount, preferably 1 to 5 moles per mole of the compound of formula (I-1).

After completion of the reaction, the compound can be isolated by performing ordinary post-treatment operation such as organic solvent extraction and concentration after addition of the reaction mixture to water. In addition, the isolated compound can be also purified by operation such as chromatography, recrystallization and distillation.

Production Process 9

A compound of formula (I-o) can be produced by reacting a compound of formula (I-n) and a fluorinating agent.

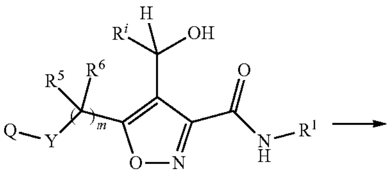

(I-n)

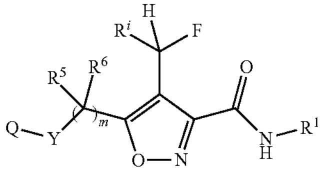

(I-o)

wherein $R^i$ represents a C1-C2 hydrocarbon group optionally having one or more halogen atoms or a hydrogen atom, and other symbols are as defined above.

A reaction is performed in the presence of a fluorinating agent usually in a solvent.

Examples of the fluorinating agent used in the reaction include 4-tert-butyl-2,6-dimethylphenylsulfur trifluoride (Fluolead (registered trademark)), bis(2-methoxyethyl) aminosulfur trifluoride (Deoxo-Fluor (registered trademark)), (diethylamino)sulfur trifluoride (DAST), (diethylamino)difluorosulfonium tetrafluoroborate (XtalFluor-E (registered trademark)), and difluoro(morpholino)sulfonium tetrafluoroborate (XtalFluor-M (registered trademark)).

Examples of the solvent used in the reaction include ethers, aliphatic hydrocarbons, aromatic hydrocarbons, halogenated hydrocarbons, esters, nitriles, acid amides, sulfoxides such as dimethyl sulfoxide and a mixture thereof.

A reaction time of the reaction is usually in a range of 5 minutes to 72 hours.

A reaction temperature of the reaction is usually in a range of −78 to 100° C. (provided that when a boiling point of a solvent to be used is lower than 100° C., −78° C. to a boiling point of a solvent).

The fluorinating agent can be usually used in an amount of 1 mole to an excessive amount, preferably 1 to 5 moles per mole of the compound of formula (I-n).

After completion of the reaction, the compound can be isolated by performing ordinary post-treatment operation such as organic solvent extraction and concentration after addition of the reaction mixture to dilute hydrochloric acid or water. In addition, the isolated compound can be also purified by operation such as chromatography, recrystallization and distillation.

Production Process 10

A compound of formula (I-p) and a compound of formula (I-q) can be produced, for example, by a route shown in the following scheme according to the method described in Journal of Organic Chemistry, 63, 4011-4017 (1998).

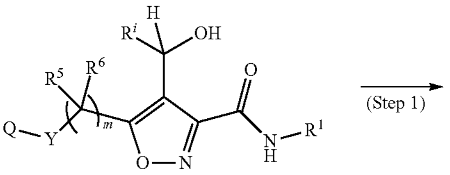

(I-n)

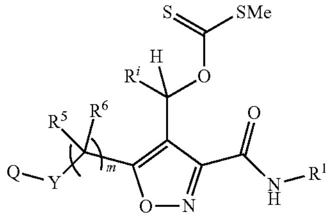

(I-p)

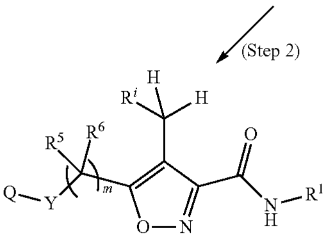

(I-q)

wherein symbols are as defined above.

(Step 1)

A reaction is performed usually under the inert gas atmosphere such as nitrogen, in the presence of a base and carbon disulfide in a solvent, and post-treatment with a methylating agent is further performed.

Examples of the base used in the reaction include organolithium compounds such as n-butyllithium, sec-butyllithium, tert-butyllithium, and 2,4,6-trimethylphenyllithium, lithium diisopropylamide, lithium hexamethyldisilazide, and sodium hydride.

Examples of the methylating agent used in the reaction include methyl iodide, dimethyl sulfate, and methyl tosylate.

Examples of the solvent used in the reaction include aromatic hydrocarbons, aliphatic hydrocarbons, and ethers.

A reaction time of the reaction is usually in a range of 1 minute to 72 hours.

A reaction temperature of the reaction is usually in a range of −78° C. to 100° C. (provided that when a boiling point of a solvent to be used is lower than 100° C., −78° C. to a boiling point of a solvent).

The base can be usually used in an amount of 1 mole to an excessive amount, preferably 1 mole to 3 moles per mole of the compound of formula (I-n).

Carbon disulfide can be usually used in an amount of 1 mole to an excessive amount, preferably 1 mole to 5 moles per mole of the compound of formula (I-n).

The methylating agent can be usually used in an amount of 1 mole to an excessive amount, preferably 1 to 5 moles per mole of the compound of formula (I-n).

After completion of the reaction, the compound of formula (I-p) can be isolated by performing ordinary post-treatment operation such as organic solvent extraction and concentration after addition of the reaction mixture to dilute hydrochloric acid or water. In addition, the isolated compound of formula (I-p) can be also purified by operation such as chromatography, recrystallization and distillation.

(Step 2)

A reaction is performed usually under the inert gas atmosphere such as nitrogen, in the presence of tributyltin hydride and a radical initiator in a solvent.

Examples of the radical initiator used in the reaction include azo compounds such as azobisisobutyronitrile (AIBN), and 1,1'-azobis(cyclohexanecarbonitrile) (ABCN), organic peroxides such as di-tert-butyl peroxide, and benzoyl peroxide (BPO), triethylborane and diethylzinc.

Examples of the solvent used in the reaction include aromatic hydrocarbons, halogenated hydrocarbons such as chloroform, and chlorobenzene, aliphatic hydrocarbons, and ethers.

A reaction time of the reaction is usually in a range of 1 minute to 72 hours.

A reaction temperature of the reaction is usually in a range of 0° C. to 100° C.

Tributyltin hydride used in the reaction can be used at an arbitrary ratio of usually 1 mole to an excessive amount, preferably 1 mole to 3 moles per mole of the compound of formula (I-p).

The radical initiator used in the reaction can be used at an arbitrary ratio of usually 0.01 mole to an excessive amount, preferably 0.1 mole to 1 mole per mole of the compound of formula (I-p).

After completion of the reaction, the compound of formula (I-q) can be isolated by performing ordinary post-treatment operation such as concentration. In addition, the isolated compound of formula (I-q) can be also purified by operation such as chromatography, recrystallization and distillation.

Production Process 11

A compound of formula (I-f) can be produced by subjecting a compound of formula (I-e) and a compound of formula (8A) to the Sonogashira reaction.

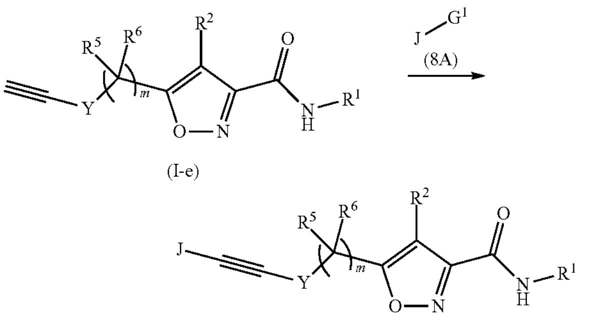

(I-e)

(I-f)

wherein J represents one group selected from Group I, and other symbols are as defined above.

Group I: a group consisting of an indanyl group optionally having one or more atoms or groups selected from Group B, a 1,2,3,4-tetrahydronaphthyl group optionally having one or more atoms or groups selected from Group B, a phenyl group optionally having one or more atoms or groups selected from Group B, a naphthyl group optionally having one or more atoms or groups selected from Group B, a pyridyl group optionally having one or more atoms or groups selected from Group B, a quinolyl group optionally having one or more atoms or groups selected from Group B, a furyl group optionally having one or more atoms or groups selected from Group B, a thienyl group optionally having one or more atoms or groups selected from Group B, a benzofuranyl group optionally having one or more atoms or groups selected from Group B, and a benzothienyl group optionally having one or more atoms or groups selected from Group B.

A reaction is performed usually under the inert gas atmosphere such as nitrogen, usually in the presence of a transition metal catalyst, inorganic copper salts and a base in a solvent.

Examples of the transition metal catalyst used in the reaction include palladium catalysts such as palladium acetate, palladium dichloride, dichlorobis(triphenylphosphine)palladium, and tetrakis(triphenylphosphine)palladium.

Examples of the inorganic copper salts used in the reaction include copper (I) bromide and copper (I) iodide.

Examples of the base used in the reaction include carbonates, tertiary amines and nitrogen-containing aromatic compounds.

Examples of the solvent used in the reaction include aromatic hydrocarbons, aliphatic hydrocarbons, ethers, halogenated hydrocarbons, acid amides, and esters.

A reaction time of the reaction is usually in a range of 5 minutes to 72 hours.

A reaction temperature of the reaction is usually in a range of −20° C. to 100° C. (provided that when a boiling point of a solvent to be used is lower than 100° C., −20° C. to a boiling point of a solvent).

An amount of the transition metal catalyst that can be used is usually 0.001 to 0.5 mole per mole of the compound of formula (I-e).

An amount of the inorganic copper salts that can be used in the reaction is usually 0.001 to 0.5 mole per mole of the compound of formula (I-e).

An amount of compound of formula (8A) that can be usually used is 1 mole to an excessive amount, preferably 1 mole to 5 moles per mole of the compound of formula (I-e).

An amount of the base that can be usually used is 1 mole to an excessive amount, preferably 1 mole to 3 moles per mole of the compound of formula (I-e).

After completion of the reaction, the compound of formula (I-f) can be obtained by performing ordinary post-treatment operation such as organic solvent extraction and concentration after addition of the reaction mixture to water. In addition, the obtained compound of formula (I-f) can be purified by operation such as chromatography, recrystallization and distillation.

Production Process 12

A compound of formula (I-h) can be produced by reacting the compound represented by formula (I-g) and a compound of formula (2a) in the presence of a condensing agent.

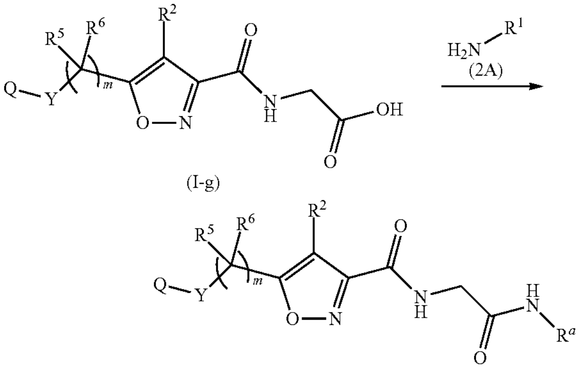

(2A)

(I-g)

(I-h)

wherein $R^a$ represents a C1-C4 alkyl group optionally having one or more halogen atoms, a [(C1-C4 alkoxy)carbonyl] C1-C4 alkyl group in which the C1-C4 alkoxy has optionally one or more halogen atoms, a 3-tetrahydrofuranylmethyl group, or a 4-tetrahydropyranylmethyl group, and other symbols are as defined above.

A reaction is performed usually in the presence of a condensing agent, if necessary, in the presence of a base in a solvent.

Examples of the condensing agent used in the reaction include dicyclohexylcarbodiimide, EDCD, benzotriazol-1-yloxytris(dimethylamino)phosphonium hexafluorophosphate and (benzotriazol-1-yloxy)tripyrrolidinophosphonium hexafluorophosphate.

Examples of the base used in the reaction include carbonates, tertiary amines and nitrogen-containing aromatic compounds.

Examples of the solvent used in the reaction include aromatic hydrocarbons, aliphatic hydrocarbons, ethers, halogenated hydrocarbons, acid amides, and esters.

The reaction can be also performed by, if necessary, adding HOBT, 1-hydroxy-7-azabenzotriazole, or N-hydroxysuccinic acid imide in an amount of usually 0.01 mole to 1 mole, preferably 0.05 mole to 0.2 mole per mole of the compound of formula (I-g).

A reaction time of the reaction is usually in a range of 5 minutes to 72 hours.

A reaction temperature of the reaction is usually in a range of −20° C. to 100° C. (provided that when a boiling point of a solvent to be used is lower than 100° C., −20° C. to a boiling point of a solvent).

In the reaction, the amount ratio of the compound of formula (I-g) and the compound of formula (2a) is preferably an equimolar or similar ratio, for example, 1 mole to 3 moles of the compound of formula (2a), per mole of the compound of formula (I-g).

The condensing agent can be usually used in an amount of 1 mole to an excessive amount, preferably 1 mole to 3 moles per mole of the compound of formula (I-g).

The base used can be usually used in an amount of 1 mole to an excessive amount, preferably 1 mole to 3 moles, per mole of the compound of formula (I-g).

After completion of the reaction, the compound can be isolated by performing ordinary post-treatment operation such as organic solvent extraction and concentration after addition of the reaction mixture to water. In addition, the isolated compound can be also purified by operation such as chromatography, recrystallization and distillation.

Production Process 13

A compound of formula (I-j) can be produced from a compound of formula (I-i) according to the method described in W. Green et al., Protective Groups in Organic Synthesis, 4 edition, pp. 860 to 861, 2007, John Wiley & Sons, INC.

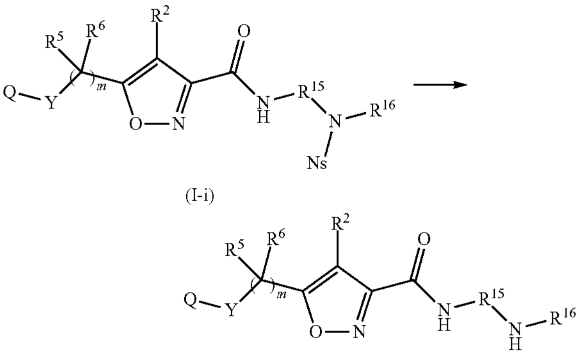

(I-i)

(I-j)

wherein Ns represents a 2-nitrobenzenesulfonyl group or a 4-nitrobenzenesulfonyl group, $R^{15}$ represents a C2-C8 alkylene group, $R^{16}$ represents a C1-C6 alkyl group, and other symbols are as defined above.

Then, a process for producing intermediates for production of the compound will be illustrated.

Reference Production Process 1

A compound of formula (1A) can be produced by subjecting the compound of formula (13A) to a hydrolysis reaction in the presence of a base.

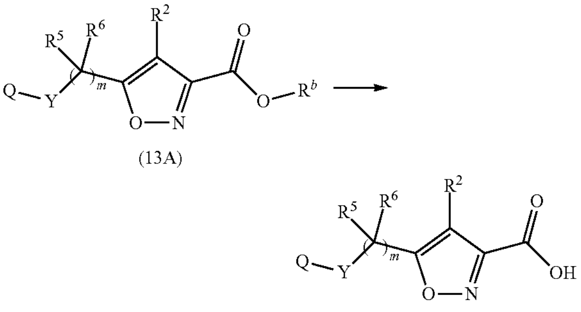

(13A)

(1A)

wherein $R^b$ represents a methyl group or an ethyl group, and other symbols are as defined above.

A reaction is performed in the presence of a base, in the presence of water and an organic solvent.

Examples of the base used in the reaction include alkali metal hydroxides such as lithium hydroxide, sodium hydroxide, and potassium hydroxide.

Examples of the solvent used in the reaction include ethers, aromatic hydrocarbons, halogenated hydrocarbons, nitriles, alcohols such as methanol, ethanol, and propanol and a mixture thereof.

A reaction time of the reaction is usually in a range of 5 minutes to 72 hours.

A reaction temperature of the reaction is usually in a range of 0° C. to 100° C. (provided that when a boiling point of a solvent to be used is lower than 100° C., 0° C. to a boiling point of a solvent).

The base is usually used in an amount of 1 mole to an excessive amount, preferably 1 mole to 5 moles per mole of the compound of formula (13A).

After completion of the reaction, the compound of formula (1A) can be obtained by adding the reaction mixture to water, washing the resultant with an organic solvent, neutralizing the aqueous layer with acidic water (hydrochloric acid etc.), and performing ordinary post-treatment operation such as organic solvent extraction and concentration. In addition, the resulting compound of formula (1A) can be usually used in a reaction at a next step without purification, and if necessary, can be also purified by operation such as chromatography and recrystallization.

Reference Production Process 2

A compound of formula (3B) can be produced, for example, by reacting a compound of formula (1B) with a halogenating agent.

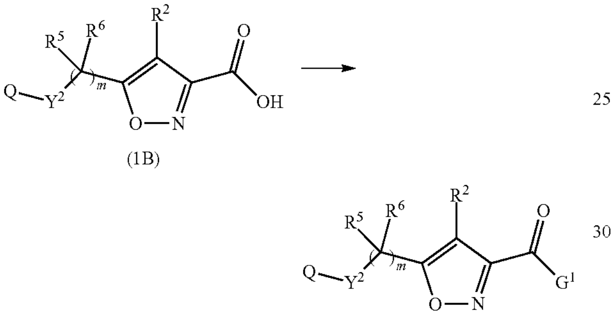

(1B)

(3B)

wherein $Y^2$ represents —$CR^8R^9$—, an oxygen atom, or —$S(O)_2$—, and other symbols are as defined above.

A reaction is performed in a solvent, if necessary.

Examples of the halogenating agent used in the reaction include thionyl chloride, oxalyl chloride and phosphorus oxychloride.

Examples of the solvent used in the reaction include ethers, aliphatic hydrocarbons, aromatic hydrocarbons, halogenated hydrocarbons and a mixture thereof.

A reaction time of the reaction is usually in a range of 5 minutes to 24 hours.

A reaction temperature of the reaction is usually in a range of 0 to 100° C.

The halogenating agent is usually used in an amount of 1 mole to an excessive amount, preferably 1 to 5 moles, per mole of the compound of formula (1B).

After completion of the reaction, the compound of formula (3B) can be isolated by performing post-treatment operation such as concentration of the reaction mixture as it is. The isolated compound of formula (3B) can be usually used in a reaction at a next step without purification, and if necessary, can be purified by distillation or the like.

Reference Production Process 3

The compound of formula (13) can be produced, for example, by a route shown in the following scheme according to the method described in Journal of Chemical Society, Perkin Trans., 14, 1716, (2001).

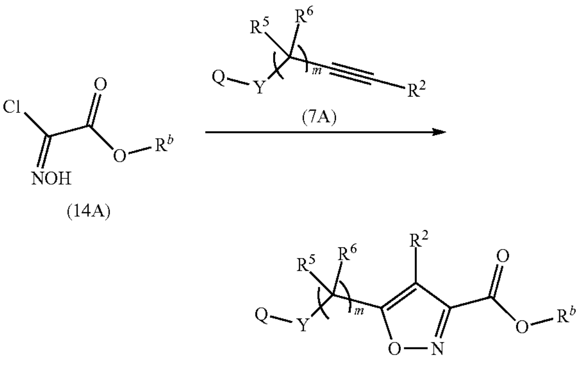

(14A)

(7A)

(13A)

wherein symbols in the scheme are as defined above.

Reference Production Process 4

A compound of formula (13) can be produced, for example, by a route shown in the following scheme according to the method described in European Journal of Organic Chemistry, 4852-4860, (2006).

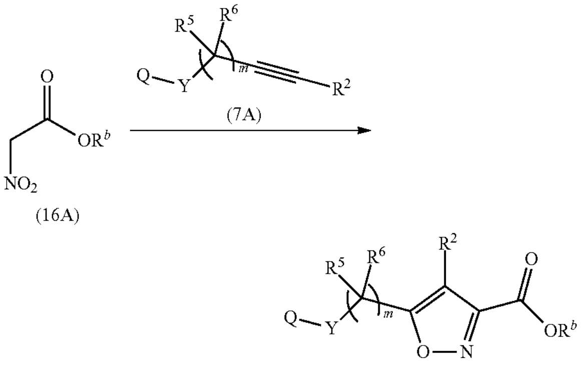

(16A)

(7A)

(13A)

wherein symbols in the scheme are as defined above.

Reference Production Process 5

A compound of formula (13) can be produced, for example, according to the method described in Bioorganic & Medicinal Chemistry Letters, 23, 273-280 (2013), in accordance with a route shown in the following scheme.

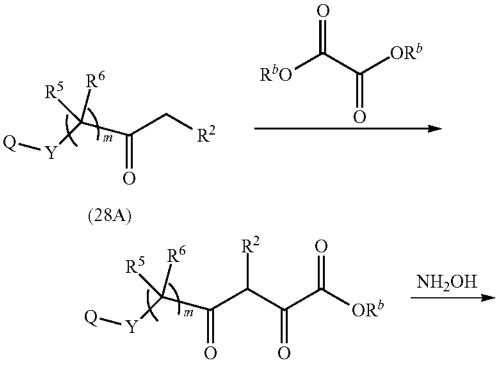

(28A)

(29A)

-continued

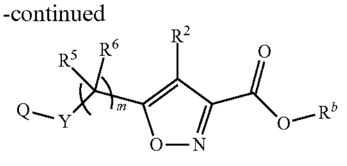

(13A)

wherein symbols are as defined above.

Reference Production Process 6

A compound of formula (14A) can be produced by reacting a compound of formula (35A) and a compound of formula (5A), in the presence of a base.

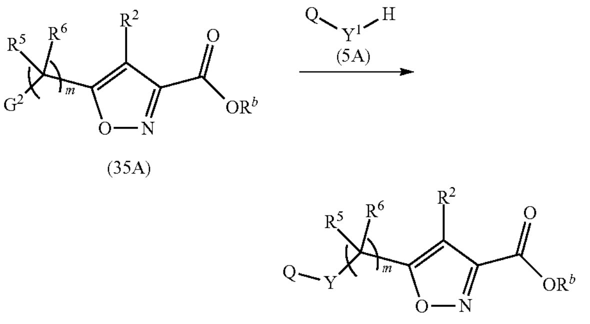

(5A)

(35A)

(14A)

wherein symbols are as defined above.

A reaction is performed in the presence of a base usually in a solvent.

Examples of the base used in the reaction include metal hydride compounds such as sodium hydride and potassium hydride, carbonates, alkali metal alkoxides such as potassium-tert-butoxide, tertiary amines and nitrogen-containing aromatic compounds.

Examples of the solvent used in the reaction include ethers, aliphatic hydrocarbons, aromatic hydrocarbons, halogenated hydrocarbons, esters, nitriles, acid amides, sulfoxides such as dimethyl sulfoxide and a mixture thereof.

A reaction time of the reaction is usually in a range of 5 minutes to 72 hours.

A reaction temperature of the reaction is usually in a range of −20 to 100° C.

In the reaction, the amount ratio of the compound of formula (35A) and the compound of formula (5A) is preferably an equimolar or similar ratio, specifically, 0.5 mole to 3 moles of the compound of formula (5A) per mole of the compound of formula (35A).

The base is be usually used in an amount of 1 mole to an excessive amount, preferably 1 to 3 moles, per mole of the compound of formula (35A).

After completion of the reaction, the compound can be isolated by performing ordinary post-treatment operation such as organic solvent extraction and concentration after addition of the reaction mixture to water. In addition, the isolated compound can be also purified by operation such as chromatography, recrystallization and distillation.

Reference Production Process 7

Among the compound of formula (35A), a compound of formula (35-a) can be produced, for example, by a route shown in the following scheme according to the method described in Journal of Chemical Society, Parkin Transl, 206-215 (2001).

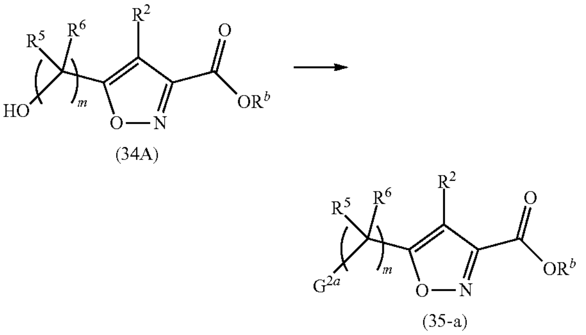

(34A)

(35-a)

wherein $G^{2a}$ represents a leaving group (e.g. methanesulfonyloxy group, trifluoromethanesulfonyloxy group or p-toluenesulfonyloxy group etc.), and other symbols are as defined above.

Reference Production Process 8

Among the compound of formula (35A), a compound of formula (35-b) can be produced, for example, by a route shown in the following scheme according to the method described in Chemistry-A European Journal, 993-1005 (2001).

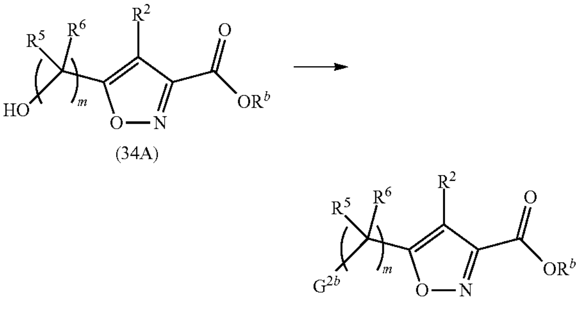

(34A)

(35-b)

wherein symbols are as defined above.

Reference Production Process 9

A compound of formula (36A) can be produced, for example, by performing the Mitsunobu reaction shown in the following scheme according to the method described in Strategic applications of named reactions in organic synthesis, 294-295 (2005, Elsevier Academic Press).

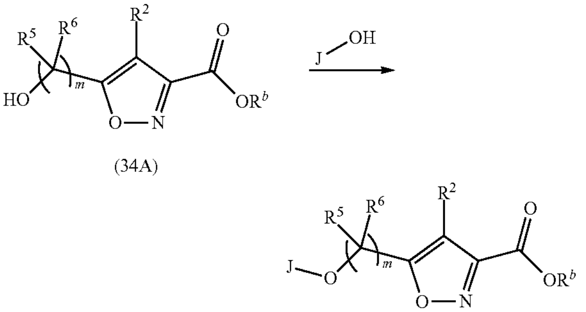

(34A)

(36A)

wherein symbols are as defined above.

Reference Production Process 10

A compound of formula (I-i) can be produced by reacting a compound of formula (1A) and a compound of formula (2b).

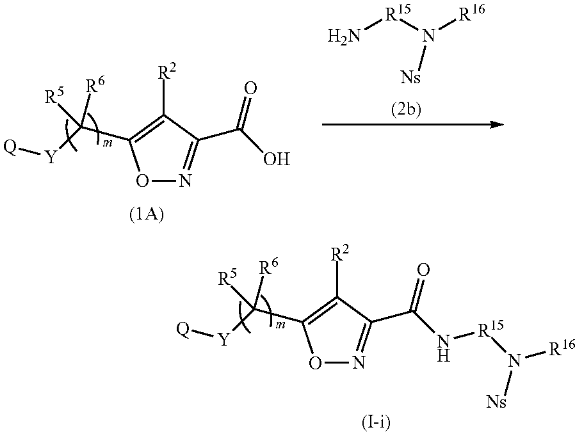

(2b)

(1A)

(I-i)

wherein symbols are as defined above.

The reaction can be carried out according to the method described in Production Process 1.

Reference Production Process 11

A compound of formula (12A) can be produced, for example, by subjecting the compound of formula (A) and the compound of formula (2c) to a condensing reaction according to the method described in International Publication WO 2011-070029.

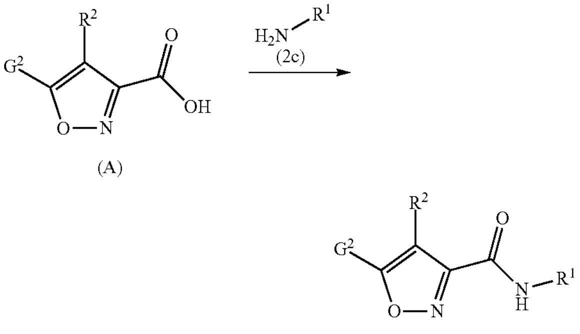

(2c)

(A)

(12A)

wherein symbols are as defined above.

Reference Production Process 12

A compound of formula (4) can be produced, for example, from a compound of formula (B).

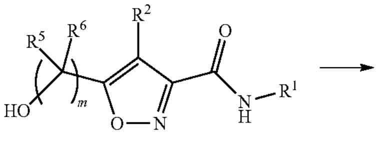

(B)

-continued

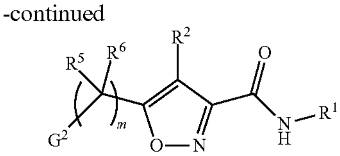

(4A)

wherein symbols are as defined above.

The noxious arthropod on which the amide compound has a control effect includes noxious insects and noxious mites. More specifically, examples are as described below.

Hemiptera: Delphacidae such as *Laodelphax striatellus, Nilaparvatalugens* and *Sogatella furcifera;*

Deltocephalidae such as *Nephotettix cincticeps* and *Nephotettix virescens;*

Aphididae such as *Aphis gossypii* and *Myzus persicae;*

Pentatomidae such as *Nezara antennata, Riptortus clavetus, Eysarcoris lewisi, Bemisia argentifolii, Eysarcoris parvus, Plautia stali, Halyomorpha mista, Stenotus rubrovittatus* and *Trigonotylus ruficornis;*

Aleyrodidae such as *Trialeurodes vaporariorum* and *Bemisia argentifolii;*

Coccidae such as *Aonidiella aurantii, Comstockaspis perniciosa, Unaspis citri, Ceroplastes rubens* and *Icerya purchasi;*

Tingidae;

Cimicoidea such as *Cimex lectularius;*

Psyliidae, etc.;

Lepidoptera: Pyralidae such as *Chilo suppressalis, Cnaphalocrocis medinalis, Notarcha derogata* and *Plodia interpunctella;*

Noctuidae such as *Spodoptera litura, Pseudaletia separata, Trichoplusia* spp., *Heliothis* spp., and *Helicoverpa* spp.;

Pieridae such as *Pieris rapae;*

Tortricidae such as *Adoxophyes* spp., *Grapholita molesta* and *Cydia pomonella;*

Carposinidae such as *Carposina niponensis;*

Lyonetiidae such as *Lyonetia* spp.;

Lymantriidae such as *Lymantria* spp. and *Euproctis* spp.;

Yponomeutidae such as *Plutella xylostella;*

Gelechiidae such as *Pectinophora gossypiella;*

Arctiidae such as *Hyphantria cunea;*

Tineidae such as *Tinea translucens* and *Tineolabisselliella*, etc.;

Diptera: Culices such as *Culex pipiens pallens, Culex tritaeniorhynchus* and *Culex quinquefasciatus; Aedes* spp. such as *Aedes aegypti* and *Aedes albopictus; Anopheles* spp. such as *Anopheles sinensis;*

Chironomidae;

Muscidae such as *Musca domestica* and *Muscina stabulans;*

Calliphoridae;

Sarcophagidae;

Fanniidae;

Anthomyiidae such as *Delia platura* and *Delia antiqua;*

Agromyzidae such as *Liriomyza trifolii;*

Tephritidae;

Drosophilidae;

Phoridae such as *Megaselia spiracularis;*

Psychodidae such as *Clogmia albipunctata;*

Simuliidae;

Tabanidae, *Stomoxys*, etc.;

Coleoptera: *Diabrotica* spp. such as *Diabrotica virgifera virgifera* and *Diabrotica undecimpunctata howardi;*

Scarabaeidae such as *Anomala cuprea* and *Anomala* rufocuprea;

Curculionidae such as *Sitophilus zeamais, Lissorhoptrus oryzophilus* and *Callosobruchuys chienensis;*

Heteromera such as *Tenebrio molitor* and *Tribolium castaneum;*

Chrysomelidae such as *Oulema oryzae, Aulacophora femoralis, Phyllotreta striolata* and *Leptinotarsa decemlineata;*

Dermestidae such as *Dermestes maculates;*

Anobiidae;

*Epilachna* such as *Epilachna vigintioctopunctata;*

Lyctidae, Bostrychidae, Ptinidae, Cerambycidae, *Paederus fuscipes*, etc.;

Blattodea: *Blattella germanica, Periplaneta fuliginosa, Periplaneta americana, Periplaneta brunnea, Blatta orientalis*, etc.;

Thysanoptera: *Thrips palmi, Thrips tabaci, Frankliniella occidentalis, Frankliniella intonsa*, etc.;

Hymenoptera: Formicidae such as *Monomorium pharaosis, Formica fusca japonica, Ochetellus glaber, Pristomyrmex pungens* and *Pheidole noda;*

Vespidae;

Bethylidae;

Tenthredinidae such as *Athalia japonica*, etc.;

Orthoptera: Gryllotalpidae, Acrididae, Grylloidea, etc.;

Siphonaptera: *Ctenocephalides felis, Ctenocephalides canis, Pulex irritans, Xenopsylla cheopis*, etc.;

Anoplura: *Pediculus humanus* corporis, Phthirus pubis, *Haematopinus eurysternus, Dalmalinia ovis, Haematopinus suis*, etc.;

Termitidae: Subterranean termites such as *Reticulitermes speratus, Coptotermes formosanus, Reticulitermes flavipes, Reticulitermes hesperus, Reticulitermes virginicus, Reticulitermes tibialis* and *Heterotermes aureus;*

Drywood termites such as *Incisitermes minor;*

Dampwood termites such as Zootermopsis *nevadensis*, etc.;

Acari: Tetranychidae such as *Tetranychus urticae, Tetranychus kanzawai, Panonychus citri, Panonychus ulmi* and *Oligonychus* spp.;

Eriophyidae such as Aculops lycopers, Aculops pelekassi and *Aculus schlechtendali;*

Tarsonemidae such as *Polyphagotarsonemus* latu;

Tenuipalpidae;

Tuckerellidae;

Ixodidae such as *Haemaphysalis longicornis, Haemaphysalis flava, Dermacentor variabilis, Haemaphysalis flava, Dermacentor taiwanicus, Ixodes ovatus, Ixodes persulcatus, Ixodes scapularis, Boophilus microplus, Amblyomma americanum* and *Rhipicephalus sanguineus;*

Acaridae such as *Tyrophagus putrescentiae;*

Pyroglyphidae such as *Dermatophagoides farinae* and *Dermatophagoides pteronyssinus;*

Cheyletidae such as *Cheyletus eruditus, Cheyletus malaccensis* and *Cheyletus moorei;*

Dermanyssidae such as *Ornithonyssus bacoti, Ornithonyssus sylvairum* and *Dermanyssus gallinae;*

Trombiculidae such as *Leptotrombidium akamushi*, etc.;

Araneae: *Chiracanthium japonicum, Latrodectus hasseltii*, etc.;

Chilopoda: *Thereuonema hilgendorfi, Scolopendra subspinipes*, etc.;

Diplopoda: *Oxidus gracilis, Nedyopus tambanus*, etc.;

Isopoda: *Armadillidium vulgare*, etc.

The noxious arthropod controlling agent of the present invention contains an active ingredient compound, typically the amide compound of formula (I), and an inert carrier. In the present specification, the inert carrier represents a bulking agent, a diluent or the like which is used in the epidemic prevention and agricultural fields. The noxious arthropod controlling agent of the present invention is usually formulated into a formulation such as an emulsifiable concentrate, an oil solution, a dust formulation, a granule, a wettable powder, a flowable, a microcapsule, an aerosol, a fumigant, a poisonous bait, a resin formulation or the like, by mixing the amide compound with an inert carrier such as a solid carrier, a liquid carrier, a gaseous carrier and the like and, if necessary, adding a surfactant, and other auxiliaries for formulation. These formulations usually contain the amide compound at 0.01 to 95% by weight.

Examples of the solid carrier which is used in the formulation include fine powder and granules of clay materials (kaolin clay, diatomaceous earth, bentonite, Fubasami clay, acid clay, etc.), synthetic hydrated silicon oxide, talc, ceramics, other inorganic minerals (sericite, quartz, sulfur, activated carbon, calcium carbonate, hydrated silica, etc.), chemical fertilizers (ammonium sulfate, ammonium phosphate, ammonium nitrate, urea, ammonium chloride, etc.) and the like.

Examples of the liquid carrier include water, alcohols (methanol, ethanol, isopropyl alcohol, butanol, hexanol, benzyl alcohol, ethylene glycol, propylene glycol, phenoxyethanol, etc.), ketones (acetone, methyl ethyl ketone, cyclohexanone, etc.), aromatic hydrocarbons (toluene, xylene, ethylbenzene, dodecylbenzene, phenylxylylethane, methylnaphthalene, etc.), aliphatic hydrocarbons (hexane, cyclohexane, kerosene, light oil, etc.), esters (ethyl acetate, butyl acetate, isopropyl myristate, ethyl oleate, diisopropyl adipate, diisobutyl adipate, propylene glycol monomethyl ether acetate, etc.), nitriles (acetonitrile, isobutyronitrile, etc.), ethers (diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, 3-methoxy-3-methyl-1-butanol, etc.), acid amides (N,N-dimethylformamide, N,N-dimethylacetamide, etc.), halogenated hydrocarbons (dichloromethane, trichloroethane, carbon tetrachloride, etc.), sulfoxides (dimethyl sulfoxide, etc.), and propylene carbonate and vegetable oils (soybean oil, cottonseed oil, etc).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ether, polyoxyethylene alkylaryl ether and polyethylene glycol fatty acid ester, and anionic surfactants such as alkylsulfonates, alkylbenzene sulfonates and alkylsulfates.

The other auxiliaries for formulation include fixing agents, dispersants, colorants and stabilizers, specifically, for example, casein, gelatin, polysaccharides (starch, arabic gum, cellulose derivatives, alginic acid, etc.), lignin derivatives, bentonite, synthetic water-soluble polymers (polyvinyl alcohol, polyvinyl pyrrolidone, polyacrylic acid, etc.), PAP (isopropyl acid phosphate), BHT (2,6-di-tert-butyl-4-methylphenol) and BHA (mixtures of 2-tert-butyl-4-methoxyphenol and 3-tert-butyl-4-methoxyphenol).

A noxious arthropod can be controlled, for example, by applying the noxious arthropod controlling agent of the present invention to a noxious arthropod directly, and/or a habitat of a noxious arthropod. Alternatively, by applying the noxious arthropod controlling agent of the present invention to a place where one wants to repel a noxious arthropod, a noxious arthropod can be repelled from the place, or biting from a noxious arthropod at the place can be inhibited.

In the noxious arthropod controlling method, a method therefor is not particularly limited as far as it is an aspect that the amide compound can be substantially applied, and for example, the method can be performed by applying an effective amount of the amide compound to a noxious arthropod, a habitat of a noxious arthropod or a place where one wants to repel a noxious arthropod. In the noxious arthropod controlling method of the present invention, the active ingredient compound is used in a form of the noxious arthropod controlling agent of the present invention.

The habitat where noxious arthropod inhabits includes paddy fields, fields, orchards, non-agricultural lands, houses and the like.

The application can be carried out by the application method similar to the conventional one, as long as the amide compound can be brought into contact with or ingested by a noxious arthropod.

Examples of the application method include spraying treatment, soil treatment, seed treatment and water culture medium treatment.

When the noxious arthropod controlling agent of the present invention is used in noxious arthropod controlling in the field of agriculture, the application amount is usually 1 to 10000 g in an amount of the active ingredient compound per 10000 $m^2$. When the noxious arthropod controlling agent of the present invention is formulated into an emulsifiable concentrate, a wettable powder, a flowable or the like, the noxious arthropod controlling agent is usually diluted with water so as to have a concentration of the active ingredient of 0.01 to 10000 ppm, and dust formulations, granules and the like are usually applied as they are.

These formulations and formulation solutions diluted with water may be directly treated by being sprayed on a noxious arthropod or a plant such as crops which should be protected from a noxious arthropod, and also may be treated on a soil in order to control a noxious arthropod that inhabits in the soil of cultivated land.

Also, the resin formulation processed into a sheet or string can be also treated by a method such as winding it around crops, spreading it in the vicinity of crops, or spreading it to the soil around crop roots.

When the noxious arthropod controlling agent of the present invention is used in controlling the noxious arthropod that inhabits in the house, the application amount thereof is usually 0.01 to 1000 mg per 1 $m^2$ of an area to be treated, in the case of using it on a planar area, and the amount is usually 0.01 to 500 mg per 1 $m^3$ of a space to be treated, in the case of using it in a space. When the noxious arthropod controlling agent of the present invention is formulated into an emulsifiable concentrate, a wettable powder, a flowable or the like, the noxious arthropod controlling agent is usually diluted with water so as to have a concentration of the active ingredient of 0.1 to 1000 ppm to apply, and oil formulations, aerosols, fumigants, poisonous baits and the like are applied as they are.

The present controlling agent can be used in the farmland where the following crops are grown.

Crops; corn, rice, wheat, barley, rye, oat, sorghum, cotton, soybean, peanut, sarrazin, sugar beet, rapeseed, sunflower, sugar cane, tobacco, etc.

Vegetables; Solanaceae vegetables (eggplant, tomato, green pepper, hot pepper, potato, etc.), Cucurbitaceae vegetables (cucumber, pumpkin, zucchini, watermelon, melon, etc.), Cruciferae vegetables (Japanese radish, turnip, horseradish, kohlrabi, Chinese cabbage, cabbage, brown mustard, broccoli, cauliflower, etc.), Compositae vegetables (burdock, garland chrysanthemum, artichoke, lettuce, etc.), Liliaceae vegetables (Welsh onion, onion, garlic, asparagus, etc.), Umbelliferae vegetables (carrot, parsley, celery, parsnip, etc.), Chenopodiaceae vegetables (spinach, Swiss chard, etc.), Labiatae vegetables (Japanese mint, mint, basil, etc.), strawberry, sweat potato, yam, aroid, etc.

Flowers;

Foliage plants;

Fruit trees; pomaceous fruits (apple, common pear, Japanese pear, Chinese quince, quince, etc.), stone fleshy fruits (peach, plum, nectarine, Japanese plum, cherry, apricot, prune, etc.), citrus plants (Satsuma mandarin, orange, lemon, lime, grapefruits, etc.), nuts (chestnut, walnut, hazel nut, almond, pistachio, cashew nut, macadamia nut, etc.), berry fruits (blueberry, cranberry, blackberry, raspberry, etc.), grape, persimmon, olive, loquat, banana, coffee, date palm, coconut palm, etc.;

Trees other than fruit trees; tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew), etc.

The crops also include genetically modified crops.

The noxious arthropod controlling agent of the present invention can be used as a mixture with or in combination with other insecticide, miticide, nematicide, fungicide, plant growth regulator, herbicide or synergist. Examples of the active ingredient of said insecticide, miticide, nematicide, fungicide, plant growth regulator, herbicide and synergist are shown below.

Active Ingredients of Insecticide (1) Organic Phosphorus Compounds acephate, Aluminium phosphide, butathiofos, cadusafos, chlorethoxyfos, chlorfenvinphos, chlorpyrifos, chlorpyrifos-methyl, cyanophos, diazinon, DCIP (dichlorodiisopropyl ether), dichlofenthion, dichlorvos, dimethoate, dimethylvinphos, disulfoton, EPN, ethion, ethoprophos, etrimfos, fenthion, fenitrothion, fosthiazate, formothion, Hydrogen phosphide, isofenphos, isoxathion, malathion, mesulfenfos, methidathion, monocrotophos, naled, oxydeprofos, parathion, phosalone, phosmet, pirimiphos-methyl, pyridafenthion, quinalphos, phenthoate, profenofos, propaphos, prothiofos, pyraclorfos, salithion, sulprofos, tebupirimfos, temephos, tetrachlorvinphos, terbufos, thiometon, trichlorphon, vamidothion, phorate, and cadusafos.

(2) Carbamate Compounds alanycarb, bendiocarb, benfuracarb, carbaryl, carbofuran, carbosulfan, cloethocarb, ethiofencarb, fenobucarb, fenothiocarb, fenoxycarb, furathiocarb, isoprocarb: MIPC, metolcarb, methomyl, methiocarb, oxamyl, pirimicarb, propoxur, XMC, thiodicarb, xylylcarb, and aldicarb.

(3) Pyrethroid Compounds acrinathrin, allethrin, beta-cyfluthrin, bifenthrin, cycloprothrin, cyfluthrin, cyhalothrin, cypermethrin, deltamethrin, esfenvalerate, etofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS,3RS;1RS,3SR)-2,2-dimethyl-3-prop-1-enylcyclopropanecarboxylate, 2,3,5,6-tetrafluoro-4-methylbenzyl (EZ)-(1RS,3RS;1RS,3SR)-2,2-dimethyl-3-prop-1-enylcyclopropanecarboxylate, and 2,3,5,6-tetrafluoro-4-(methoxymethyl)benzyl (1RS, 3RS;1RS,3SR)-2,2-dimethyl-3-(2-methyl-1-propenyl)cyclopropanecarboxylate.

(4) Nereistoxin Compounds cartap, bensultap, thiocyclam, monosultap, and bisultap.

(5) Neonicotinoid Compounds imidacloprid, nitenpyram, acetamiprid, thiamethoxam, thiacloprid, dinotefuran, and clothianidin.

(6) Benzoyl Urea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron.

(7) Phenylpyrazole-Based Compounds acetoprole, ethiprole, fipronil, vaniliprole, pyriprole, and pyrafluprole.

(8) Bt Toxins

Living spores derived from *Bacillus thuringiensis* and produced crystalline toxins and mixtures thereof.

(9) Hydrazine Compounds chromafenozide, halofenozide, methoxyfenozide, and tebufenozide.

(10) Organic Chlorine Compounds aldrin, dieldrin, dienochlor, endosulfan, and methoxychlor.

(11) Other Active Ingredients of Insecticide machine oil and nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, DDT, DSP, flufenerim, flonicamid, flurimfen, formetanate, metam-ammonium, metam-sodium, Methyl bromide, Potassium oleate, protrifenbute, spiromesifen, sulfoxaflor, Sulfur, metaflumizone, spirotetramat, pyrifluquinazone, spinetoram, chlorantraniliprole, tralopyril, and cyantraniliprole.

Active Ingredients of Miticide acequinocyl, amitraz, benzoximate, bifenaate, bromopropylate, chinomethionat, chlorobenzilate, CPCBS (chlorfenson), clofentezine, cyflumetofen, dicofol, etoxazole, fenbutatin oxide, fenothiocarb, fenpyroximate, fluacrypyrim, fluproxyfen, hexythiazox, propargite: BPPS, polynactins, pyridaben, pyrimidifen, tebufenpyrad, tetradifon, spirodiclofen, spiromesifen, spirotetramat, amidoflumet, and cyenopyrafen.

Active Ingredients of Nematicide

DCIP, fosthiazate, levamisol hydrochloride (levamisol), methylisothiocyanate, morantel tartarate, and imicyafos.

Active Ingredients of Fungicide

Azole fungicidal compounds such as propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, and flutriafol;

Cyclic amine fungicidal compounds such as fenpropimorph, tridemorph, and fenpropidin;

Benzimidazole fungicidal compounds such as carbendezim, benomyl, thiabendazole, and thiophanate-methyl; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil, and tiadinil.

Active Ingredients of Plant Growth Regulator ethephon, chlormequat-chloride, mepiquat-chloride, Gibberellin A, a representative of which is Gibberellin A3, abscisic acid, Kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, and 5-(trifluoromethyl)benzo[b]thiophene-2-carboxylic acid.

Active Ingredients of Herbicide (1) Phenoxy Fatty Acid Herbicidal Compounds 2,4-PA, MCP, MCPB, phenothiol, mecoprop, fluroxypyr, triclopyr, clomeprop, and naproanilide.

(2) Benzoate Herbicidal Compounds 2,3,6-TBA, dicamba, clopyralid, picloram, aminopyralid, quinclorac, and quinmerac.

(3) Urea Herbicidal Compounds diuron, linuron, chlortoluron, isoproturon, fluometuron, isouron, tebuthiuron, methabenzthiazuron, cumyluron, daimuron, and methyl-daimuron.

(4) Triazine Herbicidal Compounds atrazine, ametoryn, cyanazine, simazine, propazine, simetryn, dimethametryn, prometryn, metribuzin, triaziflam, and indaziflam.

(5) Bipyridinium Herbicidal Compounds paraquat, and diquat.

(6) Hydroxybenzonitrile Herbicidal Compounds bromoxynil, and ioxynil.

(7) Dinitroaniline Herbicidal Compounds pendimethalin, prodiamine, and trifluralin.

(8) Organophosphorus Herbicidal Compounds amiprofos-methyl, butamifos, bensulide, piperophos, anilofos, glyphosate, glufosinate, glufosinate-P, and bialaphos.

(9) Carbamate Herbicidal Compounds di-allate, tri-allate, EPIC, butylate, benthiocarb, esprocarb, molinate, dimepiperate, swep, chlorpropham, phenmedipham, phenisopham, pyributicarb, and asulam.

(10) Acid Amide Herbicidal Compounds propanil, propyzamide, bromobutide, and etobenzanid.

(11) Chloroacetanilide Herbicidal Compounds acetochlor, alachlor, butachlor, dimethenamid, propachlor, metazachlor, metolachlor, pretilachlor, thenylchlor, and pethoxamid.

(12) Diphenyl Ether Herbicidal Compounds acifluorfen-sodium, bifenox, oxyfluorfen, lactofen, fomesafen, chlomethoxynil, and aclonifen.

(13) Cyclic Imide Herbicidal Compounds oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, and saflufenacil.

(14) Pyrazole Herbicidal Compounds benzofenap, pyrazolate, pyrazoxyfen, topramezone, and pyrasulfotole.

(15) Triketone Herbicidal Compounds isoxaflutole, benzobicyclon, sulcotrione, mesotrione, tembotrione, and tefuryltrione.

(16) Aryloxyphenoxypropionate Herbicidal Compounds
clodinafop-propargyl, cyhalofop-butyl, diclofop-methyl, fenoxaprop-ethyl, fluazifop-butyl, haloxyfop-methyl, and quizalofop-ethyl, metamifop.
(17) Trione Oxime Herbicidal Compounds
alloxydim-sodium, sethoxydim, butroxydim, clethodim, cloproxydim, cycloxydim, tepraloxydim, tralkoxydim, and profoxydim.
(18) Sulfonyl Urea Herbicidal Compounds
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl-sodium, foramsulfuron, mesosulfuron-methyl, trifloxysulfuron, tritosulfuron, orthosulfamuron, flucetosulfuron, and propyrisulfuron.
(19) Imidazolinone Herbicidal Compounds
imazamethabenz-methyl, imazamethapyr, imazamox, imazapyr, imazaquin, and imazethapyr.
(20) Sulfonamide Herbicidal Compounds
flumetsulam, metosulam, diclosulam, florasulam, cloransulam-methyl, penoxsulam, and pyroxsulam.
(21) Pyrimidinyloxybenzoate Herbicidal Compounds
pyrithiobac-sodium, bispyribac-sodium, pyriminobac-methyl, pyribenzoxim, pyriftalid, and pyrimisulfan.
(22) Other Herbicidal Compounds
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and methiozolin.
Active Ingredients of Synergist piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, and ETN.

EXAMPLES

The present invention will be illustrated more specifically below by way of Production Examples, Formulation Examples and Test Examples, but the present invention is not limited to these Examples.

In Examples, a room temperature usually indicates 10 to 30° C. $^1$H NMR indicates a proton nuclear magnetic resonance spectrum, and chemical shift (6) is expressed in ppm, using tetramethylsilane as an internal standard substance.

Production Example 1

5-Benzyloxymethyl-isoxazole-3-carboxylic acid (hereinafter, referred to as intermediate compound (1)) (0.3 g, 1.3 mmol), isobutylamine (0.15 mL, 1.5 mmol), and HOBT (0.02 g, 0.1 mmol) were added to chloroform (Amylene-added product) (3 mL). After EDCD (0.3 g, 1.5 mmol) was added to the mixed liquid at room temperature, the mixture was stirred at room temperature for 2 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.29 g of a compound of following formula:

(1)

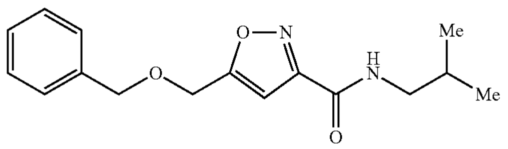

(hereinafter, referred to as compound (1)).

$^1$H-NMR ($CDCl_3$, TMS, δ(ppm)): 0.97 (3H, s), 0.98 (3H, s), 1.84-1.94 (1H, m), 3.27 (2H, t), 4.61 (2H, s), 4.65 (2H, s), 6.73 (1H, s), 6.85 (1H, br s), 7.30-7.40 (5H, m).

Production Example 2

The intermediate compound (1) (0.24 g, 1.0 mmol), 1,2-dimethylpropylamine (0.14 mL, 1.2 mmol) and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature for 2 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.23 g of a compound of following formula:

(2)

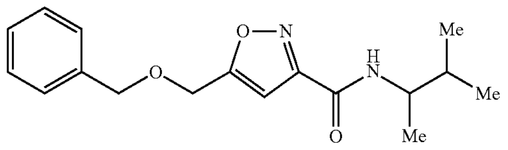

(hereinafter, referred to as compound (2)).

$^1$H-NMR ($CDCl_3$, TMS, δ(ppm)): 0.96 (6H, dd), 1.19 (3H, d), 1.76-1.84 (1H, m), 3.99-4.08 (1H, m), 4.60 (2H, s), 4.65 (2H, s), 6.64 (1H, brs), 6.72 (1H, s), 7.30-7.40 (5H, m).

Production Example 3

2-Methylallylamine hydrochloride (0.13 g, 1.2 mmol), and triethylamine (0.17 mL, 1.2 mmol) were added to chloroform (Amylene-added product) (2.5 mL), and the mixture was stirred at room temperature for 30 minutes. After the intermediate compound (1) (0.24 g, 1.0 mmol), HOBT (0.01 g, 0.1 mmol) and EDCD (0.24 g, 1.2 mmol) were added to the mixed liquid, the mixture was stirred at room temperature overnight. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.26 g of a compound of following formula:

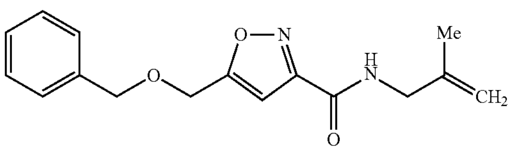

(3)

(hereinafter, referred to as compound (3))

$^1$H-NMR ($CDCl_3$, TMS, δ(ppm)): 1.79 (3H, s), 3.99-4.00 (2H, m), 4.61 (2H, s), 4.65 (2H, s), 4.89-4.92 (2H, m), 6.74 (1H, s), 6.94 (1H, brs), 7.31-7.40 (5H, m).

Production Example 4

2-Methoxypropylamine hydrochloride (0.16 g, 1.2 mmol), and triethylamine (0.17 mL, 1.2 mmol) were added to chloroform (Amylene-added product) (2.5 mL), and the mixture was stirred at room temperature for 30 minutes.

After the intermediate compound (1) (0.24 g, 1.0 mmol), HOBT (0.01 g, 0.1 mmol) and EDCD (0.24 g, 1.2 mmol) were added to the mixed liquid, the mixture was stirred at room temperature for 2 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.18 g of a compound of following formula:

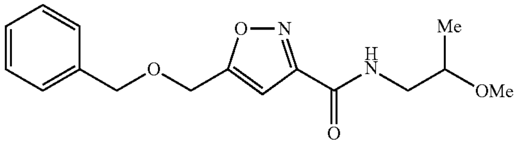

(4)

(hereinafter, referred to as compound (4)).

$^1$H-NMR ($CDCl_3$, TMS, δ(ppm)): 1.19 (3H, d), 3.24-3.30 (1H, m), 3.37 (3H, s), 3.49-3.56 (1H, m), 3.67-3.74 (1H, m), 4.61 (2H, s), 4.65 (2H, s), 6.73 (1H, s), 7.15 (1H, brs), 7.31-7.40 (5H, m).

Production Example 5

The intermediate compound (1) (0.24 g, 1.0 mmol), 2-methoxyethylamine (0.11 mL, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature for 3.5 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.20 g of a compound of following formula:

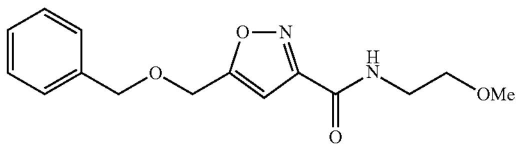

(5)

(hereinafter, referred to as compound (5)).

$^1$H-NMR ($CDCl_3$, TMS, δ(ppm)): 3.38 (3H, s), 3.53-3.56 (2H, m), 3.62-3.66 (2H, m), 4.60 (2H, s), 4.65 (2H, s), 6.72 (1H, s), 7.15 (1H, br s), 7.30-7.39 (5H, m).

Production Example 6

The intermediate compound (1) (0.24 g, 1.0 mmol), 3-methoxypropylamine (0.13 mL, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature for 3.5 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel chromatography to obtain 0.21 g of a compound of following formula:

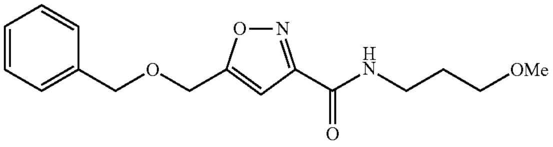

(6)

(hereinafter, referred to as compound (6)).

$^1$H-NMR ($CDCl_3$, TMS, δ(ppm)): 1.85-1.91 (2H, m), 3.37 (3H, s), 3.50-3.58 (4H, m), 4.60 (2H, s), 4.64 (2H, s), 6.72 (1H, s), 7.30-7.39 (6H, m).

Production Example 7

3-Methoxy-2,2-dimethylpropylamine hydrochloride (0.19 g, 1.2 mmol), and triethylamine (0.17 mL, 1.2 mmol) were added to chloroform (Amylene-added product) (2.5 mL), and the mixture was stirred at room temperature for 30 minutes.

After the intermediate compound (1) (0.24 g, 1.0 mmol), HOBT (0.01 g, 0.1 mmol) and EDCD (0.24 g, 1.2 mmol) were added to the mixed liquid, the mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.28 g of a compound of following formula:

(7)

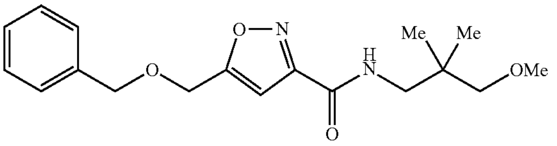

(hereinafter, referred to as compound (7)).

$^1$H-NMR ($CDCl_3$, TMS, δ(ppm)): 0.97 (6H, s), 3.21 (2H, s), 3.36 (2H, d), 3.38 (3H, s), 4.61 (2H, s), 4.65 (2H, s), 6.72 (1H, s), 7.30-7.40 (5H, m), 7.56 (1H, br s).

Production Example 8

The intermediate compound (1) (0.24 g, 1.0 mmol), 2-methoxy-2-methylpropylamine (0.13 g, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.24 g of a compound of following formula:

(8)

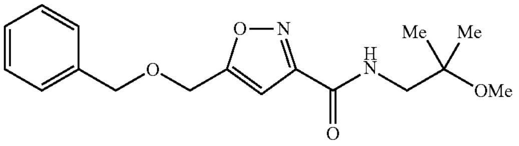

(hereinafter, referred to as compound (8)).

$^1$H-NMR ($CDCl_3$, TMS, δ(ppm)): 1.21 (6H, s), 3.23 (3H, s), 3.46 (2H, d), 4.61 (2H, s), 4.65 (2H, s), 6.73 (1H, s), 7.10 (1H, br s), 7.30-7.40 (5H, m).

Production Example 9

The intermediate compound (1) (0.70 g, 3.0 mmol), 1-amino-2-propanol (0.28 mL, 3.6 mmol), and HOBT (0.04 g, 0.3 mmol) were added to chloroform (Amylene-added product) (7 mL). After EDCD (0.69 g, 3.6 mmol) was added to the mixed liquid at room temperature, the mixture was stirred at room temperature for 4 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.64 g of a compound of following formula:

(9)

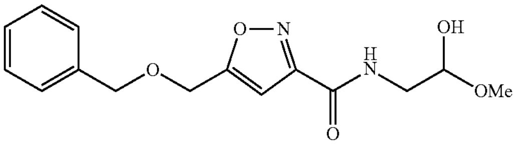

(hereinafter, referred to as compound (9)).

$^1$H-NMR ($CDCl_3$, TMS, δ(ppm)): 1.25 (3H, d), 2.52 (1H, br), 3.27-3.34 (1H, m), 3.60-3.66 (1H, m), 4.00-4.07 (1H, m), 4.60 (2H, s), 4.64 (2H, s), 6.73 (1H, s), 7.30-7.40 (6H, m).

Production Example 10

The intermediate compound (1) (0.70 g, 3.0 mmol), 3-amino-2,2-dimethylpropanol (0.37 g, 3.6 mmol), and HOBT (0.04 g, 0.3 mmol) were added to chloroform (Amylene-added product) (7 mL). After EDCD (0.69 g, 3.6 mmol) was added to the mixed liquid at room temperature, the mixture was stirred at room temperature for 4.5 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.83 g of a compound of following formula:

(10)

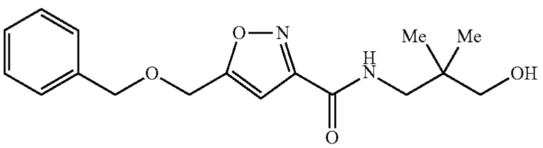

(hereinafter, referred to as compound (10)).

$^1$H-NMR ($CDCl_3$, TMS, δ(ppm)): 0.95 (6H, s), 3.26 (2H, s), 3.31 (2H, d), 3.48 (br, 1H), 4.61 (2H, s), 4.65 (2H, s), 6.73 (1H, s), 7.27-7.39 (6H, m).

Production Example 11

The intermediate compound (1) (0.24 g, 1.0 mmol), aminoacetaldehyde dimethyl acetal (0.13 mL, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature overnight. Thereafter, dilute hydrochloric acid was added to the reaction mixture, followed by extraction with chloroform two times. After organic layer was passed through a short column to remove impurities, this was concentrated under reduced pressure. The residue was subjected to silica gel column chromatography to obtain 0.27 g of a compound of following formula:

(11)

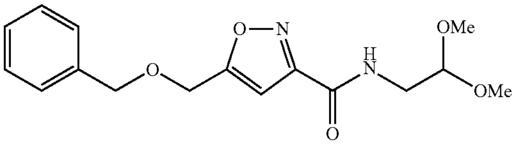

(hereinafter, referred to as compound (11)).

$^1$H-NMR ($CDCl_3$, TMS, δ(ppm)): 3.43 (6H, s), 3.59 (2H, t), 4.48 (1H, t), 4.61 (2H, s), 4.65 (2H, s), 6.72 (1H, s), 6.99 (1H, br s), 7.30-7.40 (5H, m).

Production Example 12

The intermediate compound (1) (0.24 g, 1.0 mmol), 1,3-dimethoxypropane-2-amine (0.15 g, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature overnight. Thereafter, dilute hydrochloric acid was added to the reaction mixture, followed by extraction with chloroform two times. After organic layer was passed through a short column to remove impurities, this was concentrated under reduced pressure. The residue was subjected to silica gel column chromatography to obtain 0.26 g of a compound of following formula:

(12)

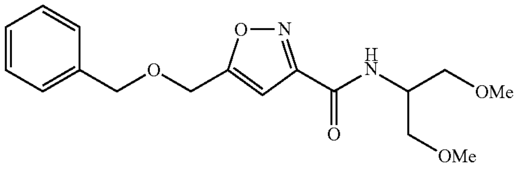

(hereinafter, referred to as compound (12)).

$^1$H-NMR ($CDCl_3$, TMS, δ(ppm)): 3.38 (6H, s), 3.49-3.53 (2H, m), 3.57-3.61 (2H, m), 4.36-4.43 (1H, m), 4.60 (2H, s), 4.65 (2H, s), 6.72 (1H, s), 7.14 (1H, brs), 7.30-7.40 (5H, m).

Production Example 13

Glycine methyl ester hydrochloride (0.61 g, 4.8 mmol), and triethylamine (0.67 mL, 4.8 mmol) were added to chloroform (Amylene-added product) (10 mL), and the mixture was stirred at room temperature for 30 minutes. After the intermediate compound (1) (0.94 g, 4.0 mmol), HOBT (0.05 g, 0.4 mmol) and EDCD (0.93 g, 4.8 mmol) were added to the mixed liquid, the mixture was stirred at room temperature for 4 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 1.0 g of a compound of following formula:

(13)

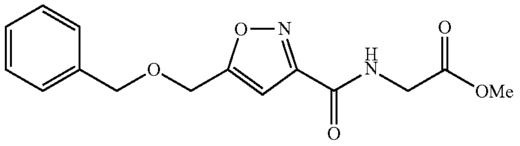

(hereinafter, referred to as compound (13)).

$^1$H-NMR ($CDCl_3$, TMS, δ(ppm)): 3.80 (3H, s), 4.23 (2H, d), 4.61 (2H, s), 4.65 (2H, s), 6.73 (1H, s), 7.31-7.39 (6H, m).

Production Example 14

β-alanine methyl ester hydrochloride (0.17 g, 1.2 mmol), and triethylamine (0.17 mL, 1.2 mmol) were added to chloroform (Amylene-added product) (2.5 mL), and the mixture was stirred at room temperature for 30 minutes. After the intermediate compound (1) (0.24 g, 1.0 mmol), HOBT (0.01 g, 0.1 mmol) and EDCD (0.24 g, 1.2 mmol) were added to the mixed liquid, mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.25 g of a compound of following formula:

(14)

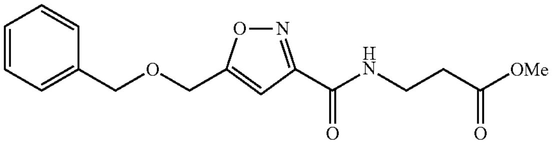

(hereinafter, referred to as compound (14)).

$^1$H-NMR ($CDCl_3$, TMS, δ(ppm)): 2.66 (2H, t), 3.70-3.74 (5H, m), 4.60 (2H, s), 4.64 (2H, s), 6.71 (1H, s), 7.30-7.40 (6H, m).

Production Example 15

(Tetrahydrofuran-3-ylmethyl)amine hydrochloride (0.11 g, 0.82 mmol) and triethylamine (0.11 mL, 0.82 mmol) were added to chloroform (Amylene-added product) (2.0 mL), and the mixture was stirred at room temperature for 15 minutes. After [(5-benzyloxymethyl-isoxazole-3-carbonyl)amino]acetic acid (hereinafter, referred to as intermediate compound (2)) (0.2 g, 0.68 mmol), HOBT (0.01 g, 0.06 mmol) and EDCD (0.16 g, 0.82 mmol) were added to the mixed liquid, the mixture was stirred at room temperature for 2.5 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.18 g of a compound of following formula:

(15)

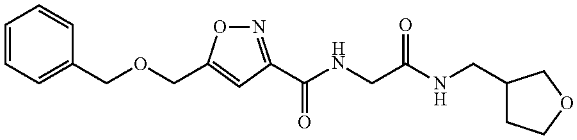

(hereinafter, referred to as compound (15)).

$^1$H-NMR ($CDCl_3$, TMS, δ(ppm)): 1.59-1.63 (1H, m), 2.00-2.08 (1H, m), 2.46-2.52 (1H, m), 3.32 (2H, t), 3.52-3.55 (1H, m), 3.69-3.75 (1H, m), 3.77-3.81 (1H, m), 3.85-3.90 (1H, m), 4.10 (2H, d), 4.62 (2H, s), 4.66 (2H, s), 6.19 (1H, br s), 6.73 (1H, s), 7.31-7.40 (5H, m), 7.44 (1H, br s).

Production Example 16

Glycine methyl ester hydrochloride (0.10 g, 0.82 mmol), and triethylamine (0.11 mL, 0.82 mmol) were added to chloroform (Amylene-added product) (2.0 mL), and the mixture was stirred at room temperature for 15 minutes.

After the intermediate compound (2) (0.2 g, 0.68 mmol), HOBT (0.01 g, 0.06 mmol) and EDCD (0.16 g, 0.82 mmol) were added to the mixed liquid, the mixture was stirred at room temperature for 2 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.18 g of a compound of following formula:

(16)

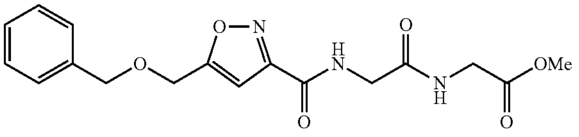

(hereinafter, referred to as compound (16)).

$^1$H-NMR ($CDCl_3$, TMS, δ(ppm)): 3.76 (3H, s), 4.10 (2H, d), 4.19 (2H, d), 4.61 (2H, s), 4.65 (2H, s), 6.61 (1H, br s), 6.73 (1H, s), 7.31-7.39 (5H, m), 7.54 (1H, brs).

Production Example 17

The intermediate compound (2) (0.2 g, 0.68 mmol), 2,2,2-trifluoroethylamine (0.06 mL, 0.82 mmol), and HOBT (0.01 g, 0.06 mmol) were added to chloroform (Amylene-added product) (4.0 mL). After EDCD (0.16 g, 0.82 mmol) was added to the mixed liquid at room temperature, the mixture was stirred at room temperature for 2 hours. Thereafter, after dilute hydrochloric acid was added to the reaction mixture, insolubles were dissolved in methanol, and this was concentrated under reduced pressure, water was added to the residue, followed by extraction with ethyl acetate two times. After the organic layer was dried on magnesium sulfate, this was concentrated under reduced pressure, and the precipitated solid was suction-filtered to obtain 0.18 g of a compound of following formula:

(17)

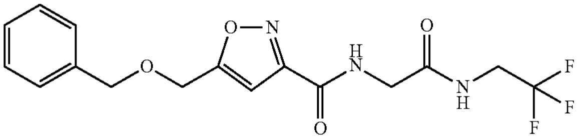

(hereinafter, referred to as compound (17)).

$^1$H-NMR ($CDCl_3$, TMS, δ(ppm)): 3.91-3.99 (2H, m), 4.20 (2H, d), 4.62 (2H, s), 4.66 (2H, s), 6.88 (1H, br s), 6.72 (1H, s), 7.31-7.40 (5H, m), 7.54 (1H, br s).

Production Example 18

L-alanine methyl ester hydrochloride (0.17 g, 1.2 mmol), and triethylamine (0.17 mL, 1.2 mmol) were added to chloroform (Amylene-added product) (2.5 mL), and the mixture was stirred at room temperature for 30 minutes. After the intermediate compound (1) (0.24 g, 1.0 mmol), HOBT (0.01 g, 0.1 mmol) and EDCD (0.24 g, 1.2 mmol) were added to the mixed liquid, the mixture was stirred at room temperature overnight. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.24 g of a compound of following formula:

(18)

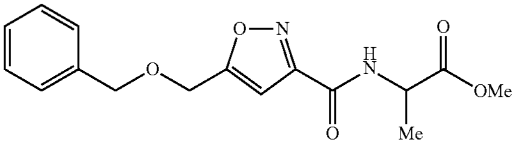

(hereinafter, referred to as compound (18)).

$^1$H-NMR ($CDCl_3$, TMS, δ(ppm)): 1.53 (3H, d), 3.79 (3H, s), 4.61 (2H, s), 4.65 (2H, s), 4.73-4.80 (1H, m), 6.72 (1H, s), 7.30-7.40 (6H, m).

Production Example 19

L-valine methyl ester hydrochloride (0.21 g, 1.2 mmol), and triethylamine (0.17 mL, 1.2 mmol) were added to chloroform (Amylene-added product) (2.5 mL), and the mixture was stirred at room temperature for 30 minutes. After the intermediate compound (1) (0.24 g, 1.0 mmol), HOBT (0.01 g, 0.1 mmol) and EDCD (0.24 g, 1.2 mmol) were added to the mixed liquid, the mixture was stirred at room temperature overnight. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.27 g of a compound of following formula:

(19)

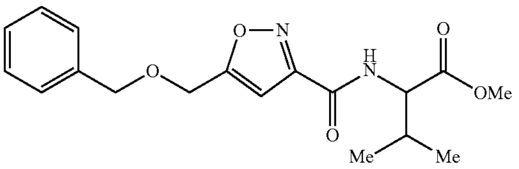

(hereinafter, referred to as compound (19)).

$^1$H-NMR ($CDCl_3$, TMS, δ(ppm)): 0.98-1.02 (6H, m), 2.24-2.32 (1H, m), 3.78 (3H, s), 4.61 (2H, s), 4.65 (2H, s), 4.71-4.74 (1H, m), 6.72 (1H, s), 7.24 (1H, brs), 7.30-7.40 (5H, m).

Production Example 20

Isobutylamine (0.18 g, 2.40 mmol) was added to chloroform (Amylene-added product) (5 mL). After 5-(2-naphthylmethoxymethyl)isoxazole-3-carboxylic acid (hereinafter, referred to as intermediate compound (3)) (0.57 g, 2.00 mmol), HOBT (0.03 g, 0.24 mmol) and EDCD (0.46 g, 2.4 mmol) were added to the mixed liquid at room temperature, the mixture was stirred at room temperature for 5 hours. Dilute hydrochloric acid was added to the reaction mixture, followed by extraction with chloroform two times. After the organic layer was washed with an aqueous saturated sodium bicarbonate solution, and dried with anhydrous sodium sulfate, this was filtered, and the filtrate was concentrated under reduced pressure. The residue was subjected to silica gel column chromatography to obtain 0.48 g of a compound of following formula:

(20)

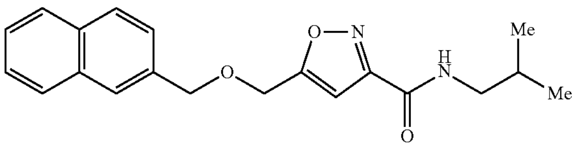

(hereinafter, referred to as compound (20)).

MS (ESI) m/z $[M+H]^+$: 339

Production Example 21

2-Methoxypropylamine hydrochloride (0.15 g, 1.2 mmol) and triethylamine (0.17 mL, 1.2 mmol) were added to chloroform (Amylene-added product) (3 mL), and the mixture was stirred at room temperature for 30 minutes.

After the intermediate compound (3) (0.24 g, 1.0 mmol), HOBT (0.01 g, 0.1 mmol) and EDCD (0.24 g, 1.2 mmol) were added to the mixed liquid, the mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.31 g of a compound of following formula:

(21)

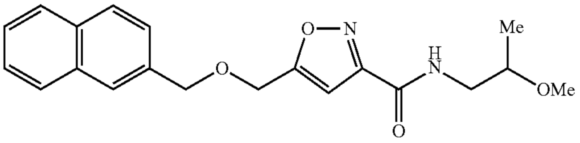

(hereinafter, referred to as compound (21)).

$^1$H-NMR ($CDCl_3$, TMS, δ(ppm)): 1.20 (3H, d), 3.24-3.31 (1H, m), 3.37 (3H, s), 3.49-3.56 (1H, m), 3.68-3.74 (1H, m), 4.68 (2H, s), 4.77 (2H, s), 6.75 (1H, s), 7.14 (1H, br), 7.46-7.52 (3H, m), 7.80 (1H, s), 7.83-7.87 (3H, m).

Production Example 22

The intermediate compound (1) (0.24 g, 1.0 mmol), N,N-dimethylethylenediamine (0.13 mL, 1.2 mmol), and HOBT (0.01 g, 0.1 mmol) were added to chloroform (Amylene-added product) (2.5 mL). After EDCD (0.24 g, 1.2 mmol) was added to the mixed liquid at room temperature, the mixture was stirred at room temperature for 4 hours. Thereafter, water was added to the reaction mixture, followed by extraction with chloroform two times. After the organic layer was passed through a short column to remove impurities, this was concentrated under reduced pressure. The residue was subjected to silica gel column chromatography to obtain 0.19 g of a compound of following formula:

(22)

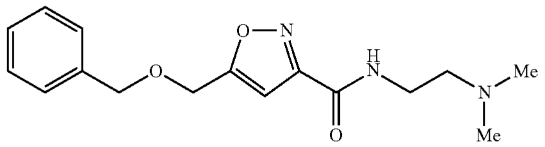

(hereinafter, referred to as compound (22)).

$^1$H-NMR ($CDCl_3$, TMS, δ(ppm)): 2.34 (6H, s), 2.60 (2H, m), 3.56 (2H, m), 4.60 (2H, s), 4.64 (2H, s), 6.72 (1H, s), 7.30-7.39 (5H, m), 7.49 (1H, br s).

Production Example 23

The intermediate compound (1) (0.24 g, 1.0 mmol), N,N-dimethylpropane-1,3-diamine (0.15 mL, 1.2 mmol), and HOBT (0.01 g, 0.1 mmol) were added to chloroform (Amylene-added product) (2.5 mL).

After EDCD (0.24 g, 1.2 mmol) was added to the mixed liquid at room temperature, the mixture was stirred at room temperature for 4 hours. Thereafter, water was added to the reaction mixture, followed by extraction with chloroform two times. After the organic layer was passed through a short column to remove impurities, this was concentrated under reduced pressure. The residue was subjected to silica gel column chromatography to obtain 0.19 g of a compound of following formula:

(23)

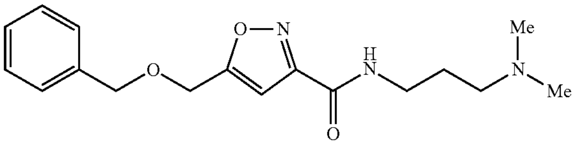

(hereinafter, referred to as compound (23)).

$^1$H-NMR ($CDCl_3$, TMS, δ(ppm)): 1.76-1.83 (2H, m), 2.31 (6H, s), 2.49-2.52 (2H, m), 3.51-3.56 (2H, m), 4.60 (2H, s), 4.64 (2H, s), 6.71 (1H, s), 7.30-7.39 (5H, m), 8.24 (1H, br s).

Production Example 24

The intermediate compound (1) (0.24 g, 1.0 mmol), 1-amino-2-methylpropane-2-ol (0.11 g, 1.2 mmol), and HOBT (0.01 g, 0.1 mmol) were added to chloroform (Amylene-added product) (234.5 mL).

After EDCD (0.24 g, 1.2 mmol) was added to the mixed liquid at room temperature, the mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure.

The residue was subjected to silica gel column chromatography to obtain 0.26 g of a compound of following formula:

(24)

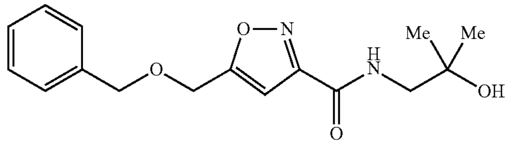

(hereinafter, referred to as compound (24)).

$^1$H-NMR ($CDCl_3$, TMS, δ(ppm)): 1.29 (6H, s), 2.16 (1H, br), 3.46 (2H, d), 4.61 (2H, s), 4.65 (2H, s), 6.74 (1H, s), 7.27 (1H, br), 7.30-7.40 (5H, m).

Production Example 25

The intermediate compound (3) (0.29 g, 1.0 mmol), 1-amino-2-methylpropane-2-ol (0.11 g, 1.2 mmol), and HOBT (0.01 g, 0.1 mmol) were added to chloroform (Amylene-added product) (2.5 mL).

After EDCD (0.24 g, 1.2 mmol) was added to the mixed liquid at room temperature, the mixture was stirred at room temperature for 3 hours. Thereafter, dilute hydrochloric acid was added to the reaction mixture, followed by extraction with chloroform two times. After the organic layer was passed through a short column to remove impurities, this was concentrated under reduced pressure. The residue was subjected to silica gel column chromatography to obtain 0.33 g of a compound of following formula:

(25)

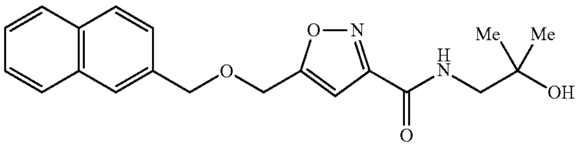

(hereinafter, referred to as compound (25))

$^1$H-NMR ($CDCl_3$, TMS, δ(ppm)): 1.29 (6H, s), 2.21 (1H, br), 3.46 (2H, d), 4.68 (2H, s), 4.76 (2H, s), 6.76 (1H, s), 7.26 (1H, br), 7.46-7.52 (3H, m), 7.79 (1H, s), 7.83-7.86 (3H, m).

Production Example 26

The intermediate compound (1) (0.50 g, 2.15 mmol) was dissolved in DMF (1.0 mL), and $N^2$,$N^2$,2-trimethylpropane-1,2-diamine (hereinafter, referred to as intermediate compound (5)) (0.3 mL, 2.58 mmol), propylphosphonic anhydride (50% ethyl acetate solution) (1.0 mL, 3.22 mmol) and diisopropylethylamine (1.2 mL, 6.44 mmol) were added at room temperature. After the mixture was stirred at room temperature for 16 hours, cold water was added to the reaction mixture, followed by extraction with ethyl acetate two times. After the organic layer was dried with anhydrous sodium sulfate, and filtered, and the filtrate was concentrated under reduced pressure. The residue was subjected to silica gel column chromatography to obtain 0.31 g of a compound of following formula:

(26)

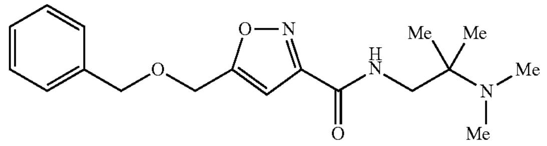

(hereinafter, referred to as compound (26)).

$^1$H-NMR ($CDCl_3$, TMS, δ(ppm)): 7.56-7.47 (1H, m), 7.42-7.30 (5H, m), 6.73 (1H, d), 4.65 (2H, s), 4.61 (2H, s), 3.35 (2H, d), 2.23 (6H, s), 1.06 (6H, s).

Production Example 27

According to the method described in Production Example 26, $N^2$,2-dimethylpropane-1,2-diamine was used in place of the intermediate compound (5), to obtain a compound of following formula:

(27)

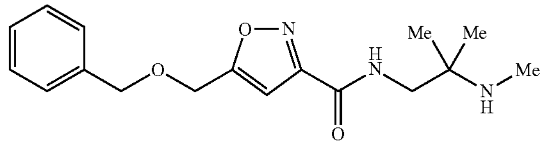

(hereinafter, referred to as compound (27)).

$^1$H-NMR ($CDCl_3$, TMS, δ(ppm)): 7.42-7.30 (5H, m), 6.73 (1H, s), 4.65 (2H, s), 4.61 (2H, s), 3.34 (2H, d), 2.34 (3H, s), 1.13 (6H, s).

Production Example 28

The intermediate compound (1) (0.30 g, 1.3 mmol), $N^1$,$N^1$,2,2-tetramethylpropane-1,3-diamine (hereinafter, referred to as intermediate compound (6)) (0.25 mL, 1.5 mmol), and HOBT (0.02 g, 0.13 mmol) were added to chloroform (Amylene-added product) (4.3 mL). After triethylamine (0.21 mL, 1.5 mmol) was added to the mixed liquid, and the mixture was stirred at room temperature for 30 minutes, EDCD (0.30 g, 1.5 mmol) was added, and the mixture was stirred at room temperature overnight. Thereafter, an aqueous saturated sodium bicarbonate solution was added to the reaction mixture, followed by extraction with chloroform two times. After the organic layer was dried with anhydrous magnesium sulfate, this was filtered, and the filtrate was concentrated under reduced pressure. The residue was subjected to silica gel column chromatography to obtain 0.23 g of a compound of following formula:

(28)

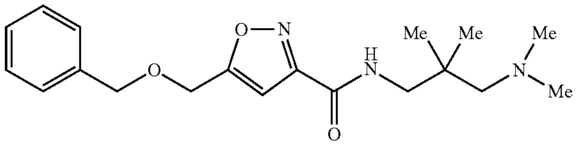

(hereinafter, referred to as compound (28)).

$^1$H-NMR ($CDCl_3$, TMS, δ(ppm)): 9.41-9.33 (1H, m), 7.40-7.30 (5H, m), 6.71 (1H, s), 4.64 (2H, s), 4.61 (2H, s), 3.34 (2H, d), 2.34 (6H, s), 2.31 (2H, s), 0.98 (6H, s).

According to the method described in Production Example 28, 2,2,2-trifluoroethylamine was used in place of the intermediate compound (6), to obtain a compound of following formula:

(41)

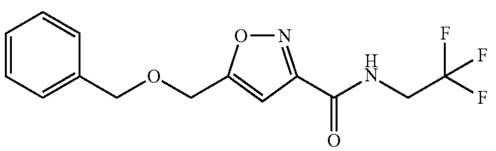

(hereinafter, referred to as compound (41)).

$^1$H-NMR ($CDCl_3$, TMS, δ(ppm)): 4.10 (2H, m), 4.62 (2H, s), 4.66 (2H, s), 6.76 (1H, s), 7.09 (1H, brs), 7.29-7.41 (5H, m).

Production Example 29

In Production Example 28, 5-butylisoxazole-3-carboxylic acid (hereinafter, referred to as intermediate compound (4)) was used in place of the intermediate compound (1), and further, any of amines ($H_2N$—$R^1$) corresponding to $R^1$s described in Table 1 was used in place of the intermediate compound (6) to produce the compound described in Table 1.

The compounds of formula (I-A) in which $R^1$ is shown in Table 1:

(I-A)

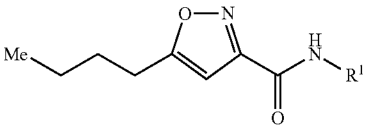

TABLE 1

| Compound | $R^1$ |
|---|---|
| 29 | $CH_2$ $CMe_2$ $NMe_2$ |
| 31 | $CH_2$ $CMe_2$ $CH_2$ $NMe_2$ |
| 32 | $CH_2$ $CMe_2$ NHMe |
| 38 | $CH_2$ $CH_2$ $CH_2$ $NMe_2$ |
| 39 | $CH_2$ $CMe_2$ N (Me) (Et) |
| 40 | $CH_2$ $CMe_2$ $CH_2$ NHMe |
| 44 | CH (Me) $CH_2NMe_2$ |
| 49 | $CH_2CMe_2NEt_2$ |
| 50 | $CH_2CMe_2OMe$ |
| 51 | $CH_2CMe_2CH_2CH_2NMe_2$ |
| 54 | $CH_2C$ (Me) (iPR) $NMe_2$ |
| 56 | $CH_2C$ (Me) (Et) N (Me) (Et) |
| 57 | $CH_2CMe_2N$ (Me) (nBu) |
| 69 | $CH_2CH$ (iBU) $NMe_2$ |
| 70 | $CH_2CH$ (sBU) $NMe_2$ |

In the formula iPr represents isopropyl, nPr represents n-propyl, nBu represents n-butyl, iBU represents isobutyl, and sBu represents sec-butyl.

Compound (29)

$^1$H-NMR ($CDCl_3$, TMS, δ(ppm)): 7.53-7.38 (1H, m), 6.43 (1H, s), 3.34 (2H, d), 2.79 (2H, t), 2.22 (6H, s), 1.73-1.66 (2H, m), 1.40 (2H, td), 1.05 (6H, s), 0.94 (3H, t).

Compound (31)

$^1$H-NMR ($CDCl_3$, TMS, δ(ppm)): 9.18-9.11 (1H, m), 6.42 (1H, s), 3.33 (2H, d), 2.78 (2H, t), 2.34 (6H, s), 2.29 (2H, s), 1.73-1.66 (2H, m), 1.40 (2H, td), 0.97 (6H, s), 0.94 (3H, t).

Compound (32)

$^1$H-NMR ($CDCl_3$, TMS, δ(ppm)): 7.32 (1H, brs), 6.43 (1H, s), 3.34 (2H, d), 2.81-2.75 (2H, m), 2.34 (3H, s), 1.78-1.62 (3H, m), 1.45-1.34 (2H, m), 1.12 (6H, s), 0.94 (3H, t).

Compound (38)

$^1$H-NMR ($CDCl_3$, TMS, δ(ppm)): 8.08 (1H, brs), 6.42-6.41 (1H, m), 3.55-3.48 (2H, m), 2.81-2.75 (2H, m), 2.44-2.39 (2H, m), 2.25 (6H, s), 1.78-1.69 (4H, m), 1.44-1.36 (2H, m), 0.94 (3H, t).

Compound (39)

$^1$H-NMR ($CDCl_3$, TMS, δ(ppm)): 0.94 (3H, t), 1.05-1.09 (9H, m), 1.35-1.45 (2H, m), 1.66-1.73 (2H, m), 2.19 (3H, s), 2.38-2.43 (2H, m), 2.78 (2H, t), 3.31 (2H, d), 6.43 (1H, s), 7.52 (1H, br s).

Compound (40)

$^1$H-NMR ($CDCl_3$, TMS, δ(ppm)): 8.43-8.39 (1H, m), 6.42 (1H, s), 3.49 (1H, s), 3.35 (2H, d), 2.78 (2H, t), 2.55 (2H, s), 2.52 (3H, s), 1.73-1.66 (2H, m), 1.45-1.35 (2H, m), 1.02 (6H, s), 0.94 (3H, t).

Compound (44)

$^1$H-NMR ($CDCl_3$, TMS, δ(ppm)): 7.05-6.96 (1H, m), 6.42 (1H, s), 2.78 (2H, t), 2.24 (1H, dd), 2.25 (1H, dd), 2.25 (6H, s), 1.73-1.65 (2H, m), 1.59 (1H, m), 1.44-1.32 (2H, m), 1.27 (3H, d), 0.94 (3H, t).

Compound (49)

$^1$H-NMR ($CDCl_3$, TMS, δ(ppm)): 7.59 (1H, brs), 6.42 (1H, s), 3.28 (2H, d), 2.76-2.80 (2H, m), 2.57 (4H, q), 1.66-1.74 (2H, m), 1.37-1.43 (2H, m), 1.04-1.10 (12H, m), 0.94 (3H, t).

Compound (50)

$^1$H-NMR ($CDCl_3$, TMS, δ(ppm)): 7.08 (1H, brs), 6.43 (1H, s), 3.45 (2H, d), 3.22 (3H, s), 2.77-2.81 (2H, m), 1.66-1.74 (2H, m), 1.36-1.45 (2H, m), 1.21 (6H, s), 0.95 (3H, t).

Compound (51)

$^1$H-NMR ($CDCl_3$, TMS, δ(ppm)): 9.06-8.86 (1H, m), 6.41 (1H, s), 3.23 (2H, d), 2.77 (2H, t), 2.43-2.34 (2H, m), 2.29 (6H, s), 1.73-1.65 (2H m), 1.48 (2H, t), 1.45-1.33 (2H, m), 0.96 (6H, s), 0.94 (3H, t).

Compound (54)

$^1$H-NMR($CDCl_3$, TMS, δ(ppm)): 7.40 (1H, brs), 6.42 (1H, s), 3.73-3.65 (1H, m), 3.15-3.07 (1H, m), 2.81-2.75 (2H, m), 2.39 (6H, s), 2.35-2.28 (1H, m), 2.00-1.91 (1H, m), 1.74-1.64 (2H, m), 1.45-1.34 (2H, m), 1.02-0.91 (11H, m).

Compound (56)

$^1$H-NMR($CDCl_3$, TMS, δ(ppm)): 7.55 (1H, brs), 6.42 (1H, s), 3.30-3.39 (2H, m), 2.78 (2H, t), 2.42-2.47 (2H, m), 2.22 (3H, s), 1.66-1.73 (2H, m), 1.35-1.59 (4H, m), 1.07 (3H, t), 1.02 (3H, s), 0.92 (3H, t), 0.88 (3H, t).

Compound (57)

$^1$H-NMR ($CDCl_3$, TMS, δ(ppm)): 7.51 (1H, brs), 6.42 (1H, s), 3.33 (2H, d), 2.79 (2H, t), 2.32-2.36 (2H, m), 2.18 (3H, s), 1.66-1.73 (2H, m), 1.29-1.48 (6H, m), 1.06 (6H, s), 0.88-0.96 (6H, m).

Compound (69)

$^1$H-NMR($CDCl_3$, TMS, δ(ppm)): 7.55-7.48 (1H, m), 6.43 (1H, s), 3.73-3.64 (1H, m), 3.03-2.96 (1H, m), 2.78 (2H, t), 2.68-2.61 (1H, m), 2.25 (6H, s), 1.73-1.65 (2H, m), 1.45-1.36 (2H, m), 1.37-1.33 (2H, m), 1.13-1.04 (1H, m), 0.94 (3H, t), 0.93 (3H, d), 0.89 (3H, d).

Compound (70)

$^1$H-NMR ($CDCl_3$, TMS, δ(ppm)): 7.42-7.35 (1H, m), 6.43 (1H, s), 3.72-3.63 (2H, m), 3.21-3.13 (1H, m), 2.78 (2H, t), 2.38 (6H, s), 1.74-1.65 (2H, m), 1.60-1.47 (1H, m), 1.43-1.36 (2H, m), 0.96 (3H, t), 0.96 (3H, t), 0.93-0.85 (5H, m).

Production Example 30

According to the method described in Production Example 28, the intermediate compound (3) was used in place of the intermediate compound (1), and the intermediate compound (5) was used in place of the intermediate compound (6), to obtain a compound of following formula:

(30)

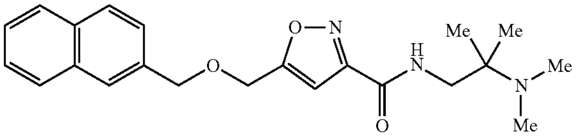

(hereinafter, referred to as compound (30)).

$^1$H-NMR ($CDCl_3$, TMS, δ(ppm)): 1.07 (6H, s), 2.24 (6H, s), 3.36 (2H, d), 4.68 (2H, s), 4.77 (2H, s), 6.75 (1H, s), 7.46-7.50 (3H, m), 7.54 (1H, br s), 7.80-7.87 (4H, m).

Production Example 31

The intermediate compound (4) (0.20 g, 1.18 mmol) was dissolved in ethyl acetate (6.0 mL), and DMF (0.01 mL) was added. Thionyl chloride (0.12 mL, 1.42 mmol) was added to the mixed liquid, and the mixture was stirred at 80 degree for 1 hour. Thereafter, the reaction mixture was cooled to room temperature, and concentrated under reduced pressure. Toluene (0.2 mL) was added to the resulting residue. This solution was added to a mixed liquid of $N^1,N^1$,2-trimethylpropane-1,2-diamine (hereinafter, referred to as intermediate compound (7)) (0.14 mL, 1.42 mmol) and a 1N aqueous sodium hydroxide solution (3 mL) under ice-cooling. After the mixture was stirred at the same temperature for 1 hour, ethyl acetate was added to the reaction mixture, followed by extraction. After the organic layer was dried with anhydrous magnesium sulfate, this was filtered, and filtrate was concentrated under reduced pressure. The residue was subjected to silica gel column chromatography to obtain 134 mg of a compound of following formula:

(33)

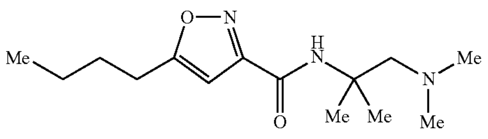

(hereinafter, referred to as compound (33)).

$^1$H-NMR ($CDCl_3$, TMS, δ(ppm)): 7.37-7.35 (1H, m), 6.38 (1H, s), 2.77 (2H, t), 2.49 (2H, s), 2.36 (6H, s), 1.72-1.64 (2H, m), 1.45 (6H, s), 1.39 (2H, dd), 0.94 (3H, t).

Production Example 32

According to the method described in Production Example 30, 5-(3-fluoropropyl)isoxazole-3-carboxylic acid was used in place of the intermediate compound (3), to obtain 0.04 g of a compound of following formula:

(36)

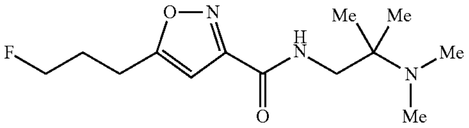

(hereinafter, referred to as compound (36)).

$^1$H-NMR ($CDCl_3$, TMS, δ(ppm)): 7.45 (1H, brs), 6.49-6.48 (1H, m), 4.51 (2H, dt), 3.34 (2H, d), 2.96 (2H, m), 2.22 (6H, s), 2.19-2.04 (2H, m), 1.05 (6H, s).

Production Example 33

According to the method described in Production Example 31, N,N-dimethylethylenediamine was used in place of the intermediate compound (7), to obtain a compound of following formula:

(37)

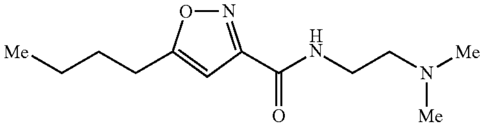

(hereinafter, referred to as compound (37)).

$^1$H-NMR ($CDCl_3$, TMS, δ(ppm)): 7.25 (1H, brs), 6.43-6.42 (1H, m), 3.53-3.47 (2H, m), 2.81-2.76 (2H, m), 2.51-2.47 (2H, m), 2.25 (6H, s), 1.74-1.65 (2H, m), 1.45-1.34 (2H, m), 0.94 (3H, t).

Production Example 34

Compounds (42) and (43) as defined in Table 2 below were produced in a similar manner as in the production process of Production Example 31 by using an amine compound having each $R^1$ group as defined in Table 2 in place of the intermediate compound of formula (7).

Compound of Formula (I-A):

(I-A)

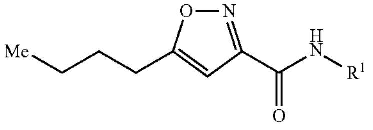

TABLE 2

| Compound | $R^1$ |
|---|---|
| 42 | $CMe_2CH_2CH_2NMe_2$ |
| 43 | $CH_2CH_2CMe_2NMe_2$ |

Compound (42)

$^1$H-NMR ($CDCl_3$, TMS, δ(ppm)): 9.27-9.14 (1H, m), 6.36 (1H, s), 2.76 (2H, t), 2.48 (2H, t), 2.28 (6H, s), 1.77-1.72 (2H, m), 1.72-1.63 (2H, m), 1.49 (6H, s), 1.39 (2H, td), 0.93 (3H, t).

Compound (43)

$^1$H-NMR ($CDCl_3$, TMS, δ(ppm)): 9.14-8.98 (1H, m), 6.40 (1H, s), 3.57-3.52 (2H, m), 2.77 (2H, t), 2.28 (6H, s), 1.73-1.65 (4H, m), 1.39 (2H, td), 0.97 (6H, s), 0.94 (3H, t).

Production Example 35

According to the method described in Production Example 30, 5-pentylisoxazole-3-carboxylic acid was used in place of the intermediate compound (3), to obtain a compound of following formula:

(34)

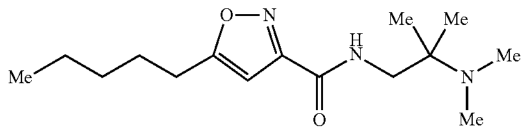

(hereinafter, referred to as compound (34)).

$^1$H-NMR ($CDCl_3$, TMS, δ(ppm)): 7.44 (1H, brs), 6.43-6.42 (1H, m), 3.33 (2H, d), 2.81-2.75 (2H, m), 2.22 (6H, s), 1.76-1.68 (2H, m), 1.40-1.31 (4H, m), 1.05 (6H, s), 0.93-0.87 (3H, m).

Production Example 36

Compound of formula (I-B) wherein $R^1$ is as defined in Table 3 below was produced in a similar manner as in Production Example 28 by using 5-isopropylisoxazole-3-carboxylic acid, hereinafter referred to as intermediate compound (9), in place of the intermediate compound (1), and using an amine compound having any one of $R^1$ groups as defined in Table 3.

Compound of formula (I-B):

(I-B)

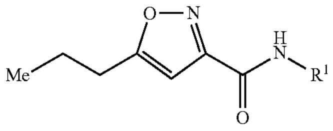

TABLE 3

| Compound | $R^1$ |
|---|---|
| 35 | $CH_2CMe_2NMe_2$ |
| 62 | $CH_2C$ (Me) (Et) $NMe_2$ |
| 63 | $CH_2CMe_2N$ (Me) (Et) |
| 64 | $CH_2CMe_2CH_2NMe_2$ |
| 65 | $CH_2CH_2CH_2NMe_2$ |
| 68 | $CMe_2CH_2NMe_2$ |

Compound (35)

$^1$H-NMR ($CDCl_3$, TMS, δ(ppm)): 7.44 (1H, brs), 6.44-6.43 (1H, m), 3.33 (2H, d), 2.80-2.73 (2H, m), 2.22 (6H, s), 1.81-1.70 (2H, m), 1.05 (6H, s), 1.00 (3H, t).

Compound (62)

$^1$H-NMR ($CDCl_3$, TMS, δ(ppm)): 7.45 (1H, brs), 6.44 (1H, s), 3.36-3.37 (2H, m), 2.76 (2H, t), 2.25 (6H, s), 1.70-1.79 (2H, m), 1.44-1.57 (2H, m), 0.98-1.02 (6H, m), 0.89 (3H, t).

Compound (63)

$^1$H-NMR ($CDCl_3$, TMS, δ(ppm)): 7.52 (1H, brs), 6.43 (1H, s), 3.33 (2H, d), 2.76 (2H, t), 2.38-2.43 (2H, m), 2.19 (3H, s), 1.70-1.79 (2H, m), 1.05-1.09 (9H, m), 1.00 (3H, t).

Compound (64)

$^1$H-NMR ($CDCl_3$, TMS, δ(ppm)): 9.17 (1H, brs), 6.43 (1H, s), 3.33 (2H, d), 2.75 (2H, t), 2.34 (6H, s), 2.30 (2H, s), 1.70-1.79 (2H, m), 0.97-1.01 (9H, m).

Compound (65)

$^1$H-NMR ($CDCl_3$, TMS, δ(ppm)): 8.10 (1H, brs), 6.43 (1H, s), 3.49-3.54 (2H, m), 2.76 (2H, t), 2.42 (2H, t), 2.26 (6H, s), 1.70-1.79 (4H, m), 0.99 (3H, t).

Compound (68)

$^1$H-NMR ($CDCl_3$, TMS, δ(ppm)): 7.37 (1H, brs), 6.39 (1H, s), 2.75 (2H, t), 2.50 (2H, s), 2.36 (6H, s), 1.69-1.78 (2H, m), 1.45 (6H, s), 0.99 (3H, t).

Production Example 37

Intermediate compound (9) (0.23 g, 1.5 mmol) was dissolved in ethyl acetate (7.5 mL), and DMF (0.01 mL, 0.15 mmol) was added there to. Oxalyl chloride (0.15 mL, 1.8 mmol) was added thereto and stirred for 1 and half hours at room temperature. Then ethyl acetate was added to the reaction mixture, and concentrated under reduced pressure. To the obtained residue was added ethyl aceate (0.5 mL). The obtained solution was added to a mixture of intermediate compound (7) (0.21 g, 1.8 mmol) and 2N aqueous sodium hydroxide solution (2.7 mL) under ice cooling, stirred at the temperature for 1 hr and then extracted with ethyl acetated from the reaction mixture. Obtained organic layers were combined and dried over anhydrous sodium sulfate, filtered and the obtained filtrate was concentrated under r educed pressure to give a residue, which was then subjected to column chromatography to give 0.19 g of a compound of following formula:

(68)

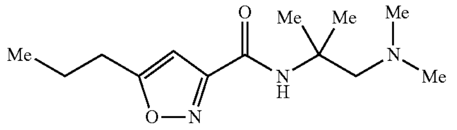

(hereinafter, referred to as compound (68)).

$^1$H-NMR ($CDCl_3$, TMS, δ(ppm)): 0.99 (3H, t), 1.45 (6H, s), 1.69-1.78 (2H, m), 2.36 (6H, s), 2.50 (2H, s), 2.75 (2H, t), 6.39 (1H, s), 7.37 (1H, brs).

Production Example 38

Compound of formula (I-C) wherein $R^1$ is as defined in Table 4 was produced in a similar manner as in Production Example 37 by using intermediate compound (8) in place of intermediate compound (9) and using an amine of formula $R^1$—$NH_2$ wherein $R^1$ is as defined in Table 4 in place of intermediate compound (7).

Compound of Formula (I-C):

(I-C)

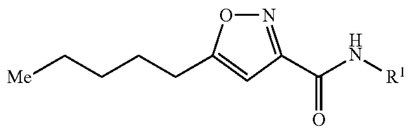

TABLE 4

| Compound | $R^1$ |
|---|---|
| 67 | $CH(Me)CMe_2NMe_2$ |

Compound (67)

$^1$H-NMR ($CDCl_3$, TMS, δ(ppm)): 7.20 (1H, brs), 6.42 (1H, s), 4.21-4.11 (1H, m), 2.77 (2H, t), 2.22 (6H, s), 1.76-1.65 (2H, m), 1.39-1.32 (4H, m), 1.26 (3H, d), 1.03-0.88 (9H, m).

Production Example 39

Compound of formula (I-A) wherein $R^1$ is as defined in Table 5 was produced in a similar manner as in Production Example 37 by using intermediate compound (7) in place of intermediate compound (9), and using an amine compound of formula $R^1$—$NH_2$ wherein $R^1$ is as defined in Table 5 in place of intermediate compound (7).

Compound of Formula (I-A):

(I-A)

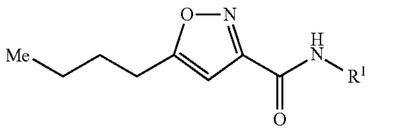

TABLE 5

| Compound | $R^1$ |
|---|---|
| 45 | $CH_2CH_2NMe_2$ |
| 46 | $CH_2CH_2OMe$ |
| 47 | $CH_2C$ (Me) (Et) $NMe_2$ |
| 48 | $CH_2CEt_2NMe_2$ |
| 55 | $CH_2CH$ (iPr) $NMe_2$ |
| 58 | CH (Me) C (Me) (Et) $NMe_2$ |
| 59 | CH (Me) C (Me) (Et) $NMe_2$ |
| 66 | CH (Me) $CMe_2NMe_2$ |
| 77 | tBu |

Compound (45)

$^1$H-NMR ($CDCl_3$, TMS, δ(ppm)): 7.25 (1H, brs), 6.42 (1H, s), 3.53-3.47 (2H, m), 2.81-2.76 (2H, m), 2.51-2.47 (2H, m), 2.25 (6H, s), 1.74-1.65 (2H, m), 1.45-1.34 (2H, m), 0.94 (3H, t).

Compound (46)

$^1$H-NMR ($CDCl_3$, TMS, δ(ppm)): 7.10 (1H, brs), 6.42 (1H, s), 3.66-3.60 (2H, m), 3.56-3.52 (2H, m), 3.38 (3H, s), 2.82-2.75 (2H, m), 1.74-1.65 (2H, m), 1.45-1.36 (2H, m), 0.94 (3H, t).

Compound (47)

$^1$H-NMR ($CDCl_3$, TMS, δ(ppm)): 7.44 (1H, brs), 6.43 (1H, s), 3.37-3.34 (2H, m), 2.81-2.76 (2H, m), 2.24 (6H, s), 1.74-1.65 (2H, m), 1.58-1.35 (4H, m), 0.99 (3H, s), 0.94 (3H, t), 0.89 (3H, t).

Compound (48)

$^1$H-NMR ($CDCl_3$, TMS, δ(ppm)): 7.47 (1H, brs), 6.43 (1H, s), 3.37-3.34 (2H, m), 2.81-2.76 (2H, m), 2.34 (6H, s), 1.74-1.58 (4H, m), 1.52-1.37 (4H, m), 0.97-0.88 (9H, m).

Compound (55)

$^1$H-NMR ($CDCl_3$, TMS, δ(ppm)): 7.40 (1H, brs), 6.42 (1H, s), 3.72-3.65 (1H, m), 3.15-3.07 (1H, m), 2.81-2.76 (2H, m), 2.39 (6H, s), 2.37-2.29 (1H, m), 2.01-1.91 (1H, m), 1.74-1.65 (2H, m), 1.45-1.34 (2H, m), 1.01-0.91 (9H, m).

Compound (58)

$^1$H-NMR ($CDCl_3$, TMS, δ(ppm)): 7.37 (1H, brs), 6.42 (1H, s), 4.23-4.14 (1H, m), 2.80-2.75 (2H, m), 2.34 (6H, s), 1.74-1.65 (2H, m), 1.61-1.34 (4H, m), 1.27 (3H, d), 1.04 (3H, s), 0.97-0.90 (6H, m).

Compound (59)

$^1$H-NMR ($CDCl_3$, TMS, δ(ppm)): 7.67 (1H, brs), 6.41 (1H, s), 4.08-3.98 (1H, m), 2.82-2.74 (2H, m), 2.24 (6H, s), 1.75-1.50 (4H, m), 1.45-1.29 (5H, m), 1.00-0.90 (9H, m).

Compound (66)

$^1$H-NMR ($CDCl_3$, TMS, δ(ppm)): 7.20 (1H, brs), 6.42 (1H, s), 4.20-4.10 (1H, m), 2.78 (2H, t), 2.22 (6H, s), 1.74-1.65 (2H, m), 1.45-1.35 (2H, m), 1.29-1.23 (3H, m), 1.03-0.91 (9H, m).

Compound (77)

$^1$H-NMR ($CDCl_3$, TMS, δ(ppm)): 6.64 (1H, brs), 6.39 (1H, s), 2.77 (2H, t), 1.73-1.64 (2H, m), 1.45 (9H, s), 1.44-1.34 (2H, m), 0.94 (3H, t).

Production Example 40

Compound (52) was produced in a similar manner as in Production EXample 28 by using 5-(ethylthiomethyl)isoxazole-3-carboxylic acid, intermediate compound (10), in place of intermediate compound (1) and using intermediate compound (5) in place of intermediate compound (6).

(52)

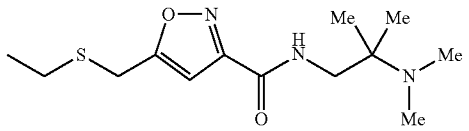

$^1$H-NMR ($CDCl_3$, TMS, δ(ppm)): 7.46 (1H, brs), 6.61 (1H, s), 3.81 (2H, d), 3.33 (2H, d), 2.59 (2H, q), 2.22 (6H, s), 1.27 (3H, t), 1.05 (6H, s).

Production Example 41

Compound (53) was produced in a similar manner as in Production EXample 40 by using 5-(ethoxymethyl)isoxazole-3-carboxylic acid in place of intermediate compound (10).

(53)

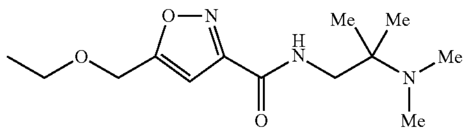

$^1$H-NMR ($CDCl_3$, TMS, δ(ppm)): 7.46 (1H, brs), 6.69 (1H, s), 4.62 (2H, d), 3.59 (2H, q), 3.34 (2H, d), 2.22 (6H, s), 1.24 (3H, t), 1.05 (6H, s).

Production Example 42

Compound (72) was produced in a similar manner as in Production EXample 28 by using 4-methyl-5-propoxyisoxazole-3-carboxylic acid, intermediate compound (11), in place of intermediate compound (1), and using intermediate compound (5) in place of intermediate compound (6).

(72)

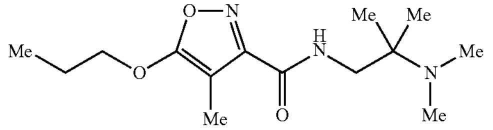

$^1$H-NMR ($CDCl_3$, TMS, δ(ppm)): 7.36-7.30 (1H, m), 4.31 (2H, t), 3.31 (2H, d), 2.21 (6H, s), 2.05 (3H, s), 1.87-1.77 (2H, m), 1.05 (6H, s), 1.03 (3H, t).

Production Example 43

Compound (73) was produced in a similar manner as in Product ion Example 42 by using intermediate compound (7) in place of intermediate compound (6).

(73)

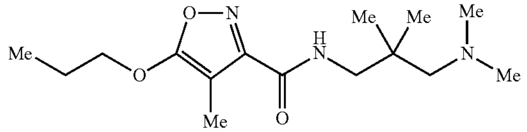

$^1$H-NMR ($CDCl_3$, TMS, δ(ppm)): 8.88-8.81 (1H, m), 4.31 (2H, t), 3.30 (2H, d), 2.33 (6H, s), 2.28 (2H, s), 2.05 (3H, s), 1.82 (2H, td), 1.03 (3H, t), 0.96 (6H, s).

Production Example 44

Compound (74) was produced in a similar manner as in Product ion Example 42 by using 4-methyl-5-butylisoxazole-3-carboxylic acid, intermediate compound (12), in place of intermediate compound (11).

(74)

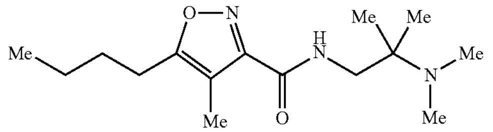

$^1$H-NMR ($CDCl_3$, TMS, δ(ppm)): 7.41 (1H, brs), 3.31 (2H, d), 2.74-2.68 (2H, m), 2.22 (6H, s), 2.17 (3H, s), 1.70-1.58 (2H, m), 1.41-1.30 (2H, m), 1.05 (6H, s), 0.93 (3H, t).

Production Example 45

Compound (75) was produced in a similar manner as in Product ion Example 42 by using the intermediate compound (12) in place of intermediate compound (11), and using intermediate (7) in place of intermediate compound (6).

(75)

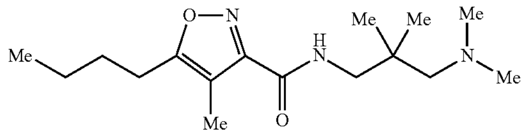

$^1$H-NMR ($CDCl_3$, TMS, δ(ppm)): 8.93 (1H, brs), 3.32 (2H, d), 2.73-2.68 (2H, m), 2.33 (6H, s), 2.28 (2H, s), 2.18 (3H, s), 1.71-1.62 (2H, m), 1.41-1.30 (m, 2H), 0.97 (6H, s), 0.93 (3H, t).

Production Example 46

Compound (77) (3.86 g, 17.2 mmol) was dissolved in THF (40 mL). The resulting solution was cooled to −70° C. and then n-butyl lithium (1.63 mol/L, 1.3 mL, 37.9 mmol) was dropwaise added to the solution over 15 min., stirred at −70° C. for 10 minutes, and methyl iodide 1.3 mL, 20.7 mmol) was added thereto and stirred for 1 hour at a temperature lower than −5° C. Then 6N hydrochloric acid (7 mL), and methyl t-butyl ether were added to the reaction mixture and extracted. Obtained organic layers were washed with water and saturated aqueous sodium chloride solution, and dried over anhydrous magnesium sulfated. Dried solution was filtered and collected filtrate was concentrated under reduced pressure to give a residue, which was then subjected to column chromatography to give 2.10 g of a compound of following formula:

(73)

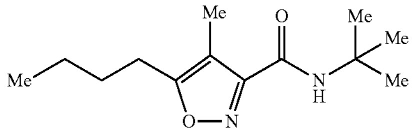

(hereinafter, referred to as compound (73)).

$^1$H-NMR ($CDCl_3$, TMS, δ(ppm)): 6.66 (1H, brs), 2.70 (2H, t), 2.16 (3H, s), 1.69-1.60 (2H, m), 1.45 (9H, s), 1.40-1.29 (2H, m), 0.93 (3H, t).

Production Examples of intermediate compounds will be shown as Reference Production Examples. Herein, Et represents an ethyl group.

Reference Production Example 1

Ethyl nitroacetate (4.80 g, 40 mmol), benzyl propargyl ether (3.55 g, 27 mmol) and 1,4-diazabicyclo[2.2.2]octane (0.61 g, 5.4 mmol) were added to chloroform (Amylene-added product) (10 mL). The mixture was heated to reflux for 48 hours, and cooled to room temperature, and dilute hydrochloric acid was added, followed by extraction with ethyl acetate two times. The organic layer was washed with an aqueous saturated sodium chloride solution, dried with anhydrous sodium sulfate, and concentrated under reduced pressure. The residue was subjected to silica gel column chromatography to obtain 5.37 g of ethyl 5-(benzyloxymethyl)isoxazole-3-carboxylate of following formula:

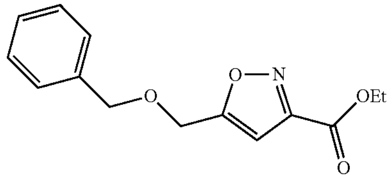 [SMILES: CCOC(=O)c1cc(COCc2ccccc2)on1]

$^1$H-NMR ($CDCl_3$, TMS, δ(ppm)): 1.42 (3H, t), 4.45 (2H, q), 4.62 (2H, s), 4.67 (2H, s), 6.70 (1H, d), 7.33-7.39 (5H, m).

Reference Production Example 2

Ethyl 5-(benzyloxymethyl)isoxazole-3-carboxylate (10.9 g, 42 mmol) was added to ethanol (80 mL), potassium hydroxide (3.49 g, 62.3 mmol) and water (40 mL) were further added, and the mixture was stirred at room temperature overnight, followed by concentration under reduced pressure. Dilute hydrochloric acid was added to the concentrate, followed by extraction with ethyl acetate two times. The organic layer was washed with an aqueous saturated sodium chloride solution, dried with anhydrous sodium sulfate, and concentrated under reduced pressure. The residue was subjected to silica gel column chromatography, and crystallized with t-butyl methyl ether/hexane to obtain 8.27 g of an intermediate compound (1) of following formula:

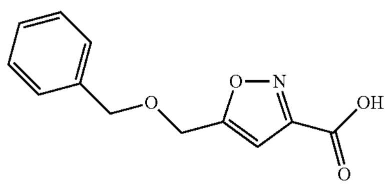 [SMILES: O=C(O)c1cc(COCc2ccccc2)on1]

$^1$H-NMR ($CDCl_3$, TMS, δ(ppm)): 7.40-7.32 (5H, m), 6.75 (1H, d), 4.69 (2H, s), 4.64 (2H, s).

Reference Production Example 3

Ethyl nitroacetate (1.49 g, 12.5 mmol), (2-naphthylmethyl) propargyl ether (1.96 g, 10 mmol) and 1,4-diazabicyclo[2.2.2]octane (0.56 g, 5 mmol) were added to chloroform (Amylene-added product) (3 mL), the mixture was heated to reflux for 24 hours, and cooled to room temperature, and dilute hydrochloric acid was added, followed by extraction with ethyl acetate two times. The organic layer was washed with an aqueous saturated sodium chloride solution, dried with anhydrous sodium sulfate, and concentrated under reduced pressure. The residue was subjected to silica gel column chromatography to obtain 1.58 g of ethyl 5-(2-naphthylmethoxymethyl)isoxazole-3-carboxylate of following formula:

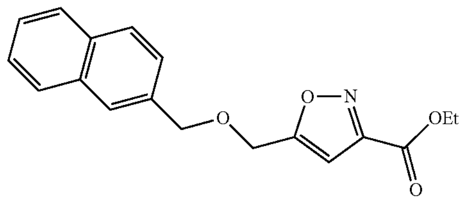 [SMILES: CCOC(=O)c1cc(COCc2ccc3ccccc3c2)on1]

$^1$H-NMR($CDCl_3$, TMS, δ(ppm)): 1.42 (3H, t), 4.45 (2H, q), 4.70 (2H, d), 4.78 (2H, s), 6.72 (1H, s), 7.46-7.51 (3H, m), 7.83-7.85 (4H, m).

Reference Production Example 4

Ethyl 5-(2-naphthylmethoxymethyl)isoxazole-3-carboxylate (1.58 g, 5.1 mmol) was added to ethanol (60 mL), potassium hydroxide (0.58 g, 10.2 mmol) and water (10 mL) were further added, and the mixture was stirred at room temperature overnight, followed by concentration under reduced pressure. Dilute hydrochloric acid was added to the concentrate, followed by extraction with ethyl acetate two times. The organic layer was washed with an aqueous saturated sodium chloride solution, dried with anhydrous sodium sulfate, and concentrated under reduced pressure. The residue was subjected to silica gel column chromatography, and crystallized with t-butyl methyl ether/hexane to obtain 1.23 g of intermediate compound (3) of following formula:

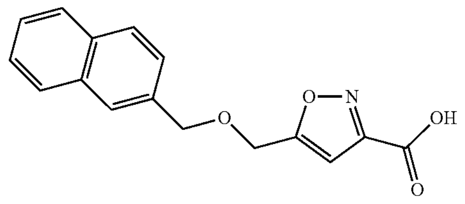 [SMILES: O=C(O)c1cc(COCc2ccc3ccccc3c2)on1]

$^1$H-NMR($CDCl_3$, TMS, δ(ppm)): 4.72 (2H, d), 4.80 (2H, s), 6.77 (1H, s), 7.47-7.52 (3H, m), 7.83-7.86 (4H, m).

Reference Production Example 5

The compound (13) (0.8 g, 2.6 mmol) was dissolved in ethanol (10 mL), an aqueous solution obtained by dissolving potassium hydroxide (0.29 g, 5.2 mmol) in water (5 mL) was added at room temperature, and the mixture was stirred for 3 hours. The reaction liquid was concentrated under reduced pressure to remove ethanol, and dilute hydrochloric acid was added to the residue to a pH of 2. This reaction mixture was extracted with ethyl acetate three times, the organic layer was washed with an aqueous saturated sodium chloride solution, and dried with anhydrous magnesium sulfate, this was filtered, and the filtrate was concentrated under reduced pressure. The residue was washed with hexane to obtain 0.6 g of the intermediate compound (2) of following formula:

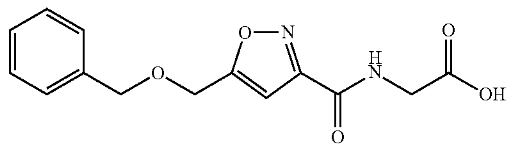 [SMILES: O=C(O)CNC(=O)c1cc(COCc2ccccc2)on1]

$^1$H-NMR ($CDCl_3$, TMS, δ(ppm)): 4.30 (2H, d), 4.61 (2H, s), 4.66 (2H, s), 6.75 (1H, s), 7.31-7.39 (7H, m).

Reference Production Example 6

Ethyl 5-hydroxy-4-methylisoxazol-3-caroxylate (1.50 g, 8.76 m mol), 1-propanol (0.79 g, 13 mmol) and triphenylphosphine (3.40 g, 13.1 mmol) were added to tetrahydrofuran (66 mL). The resulting solution was cooled to 0° C., and diisopropyl azodicaroxylate (approximately 1.9 M toluene solution) (6.9 ml) was added thereto below 5° C. and stirred for 2 hrs at 0° C. Then the reaction mixture was concentrated under reduced pressure. Obtained residue was subjected to column chromatography to give ethyl 4-methyl-5-propoxyisoxazol-3-carboxylate of the following formula (1.23 g).

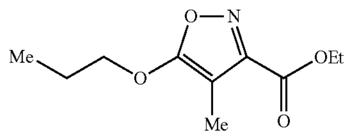 [SMILES: CCCOc1onc(C(=O)OCC)c1C]

$^1$H-NMR ($CDCl_3$, TMS, δ(ppm)): 4.42 (2H, q), 4.34 (2H, t), 2.01 (3H, s), 1.87-1.77 (2H, m), 1.41 (3H, t), 1.03 (3H, t).

Reference Production Example 7

Ethyl 4-methyl-5-propylisoxazol-3-carboxylate (1.23 g, 5.77 mmol) was added to ethanol (23 mL) and 1N aqueous potassium hydroxide solution (12 mL) was added thereto. The resulting solution was stirred at room temperature for 2 hrs. To the mixture was added dilute hydrochloric acid and extracted with ethyl acetate twice. Obtained organic layers were dried over anhydrous magnesium sulfate, and after filtration filtrate was concentrated under reduced pressure and the residue was washed with toluene to give the following intermediate compound (11) (1.02 g).

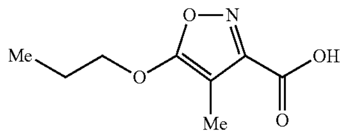 [SMILES: CCCOc1onc(C(=O)O)c1C]

$^1$H-NMR ($CDCl_3$, TMS, δ(ppm)): 4.37 (2H, t), 2.04 (3H, s), 1.84 (2H, td), 1.04 (3H, t).

Reference Production Example 8

Compound (73) (1.50 g) was added to trifluoroacetic acid (9 mL), and water (1 mL) was added thereto and stirred at 100° C. for 14 hrs. Then the mixture was concentrated under reduced pressure. The concentrated residue was diluted with methyl t-butyl ether and extracted with aqueous sosium hydrogencarbonate. To the aqueous phase was added 12N hydrochloric acid to adjust the pH of the aqueous phase to pH12 and extracted with ethyl acetate. Obtained organic phase was washed with saturated aqueous sodium chloride solution and dried over magnesium sulfate. Then obtained filtrate by filtration was concentrated under reduced pressure to give a residue, which was then subjected to column chromatography to give intermediate compound (12) (1.02 g.

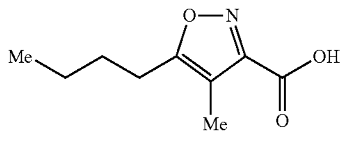 [SMILES: CCCCc1onc(C(=O)O)c1C]

$^1$H-NMR ($CDCl_3$, TMS, δ(ppm)): 2.76 (2H, t), 2.17 (3H, s), 1.74-1.63 (2H, m), 1.42-1.31 (2H, m), 0.94 (3H, t).

Amide compounds of formula (Y-1) to the formula (Y-946) (hereinafter, referred to as compounds A) can be obtained according to the aforementioned processes. In the following formulas, Me represents methyl, Et represents ethyl, Pr represents propyl, Bu represents butyl, Ph represents phenyl, NA1 represents naphthalen-1-yl, NA2 represents naphthalen-2-yl, IN1 represents indan-1-yl, IN2 represents indan-2-yl, Py2 represents 2-pyridyl, Qun2 represents 2-quinolyl, Fur2 represents 2-furyl, Thi2 represents 2-thienyl, BF5 represents 5-benzofuranyl, BF2 represents 2-benzofuranyl, BT5 represents 5-benzothienyl, BT2 represents 2-benzothienyl, BDXO5 represents 1,3-benzodioxol-5-yl, BDXA6 represents 1,4-benzodioxan-6-yl, 3Cy represents cyclopropyl, 5Cy represents cyclopentyl, and 8Cy represents cyclooctyl.

For example, [$CH_2CH_2CH_2Ph$] represents a 3-phenylpropyl group, [$CH_2CH_2$(8-F-NA2)] represents a 2-(8-fluoronaphthalen-2-yl)ethyl group, and [$CH_2CH_2$(2,2-$F_2$-3Cy)] represents a 2-(2,2-difluorocyclopropyl)ethyl group.

(Y-1)

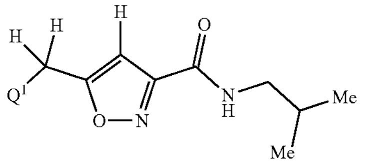

(Y-2)

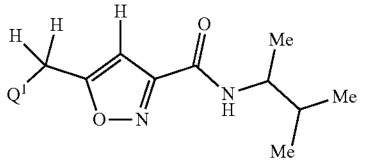

(Y-5)

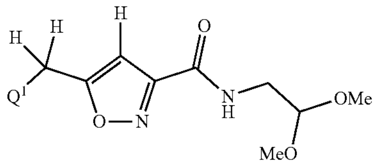

(Y-6)

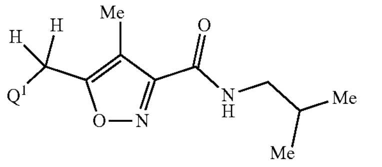

(Y-9)

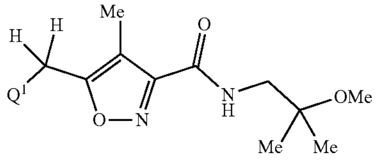

(Y-10)

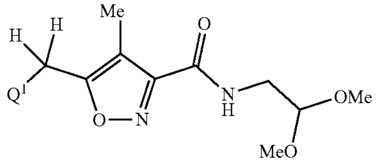

(Y-13)

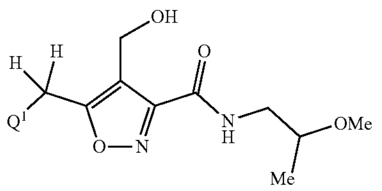

(Y-14)

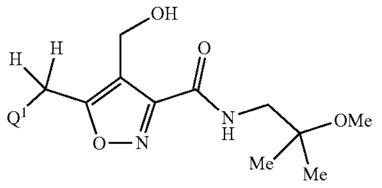

-continued
(Y-17)
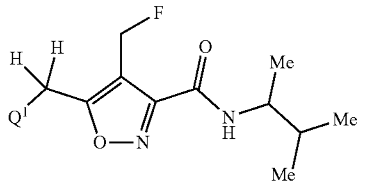
(Y-18)
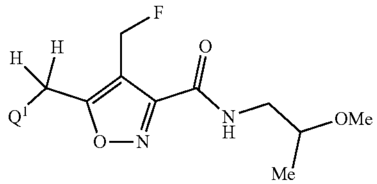
(Y-21)
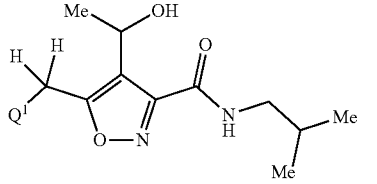
(Y-22)
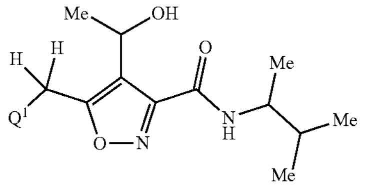
(Y-25)
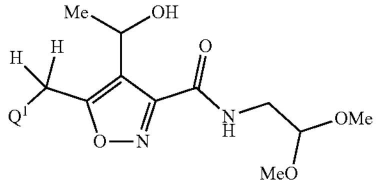
(Y-26)
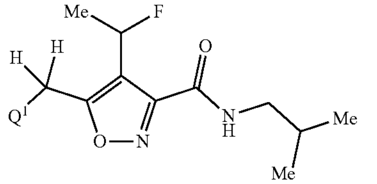
(Y-29)
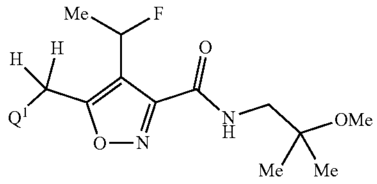
(Y-30)
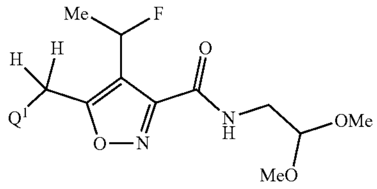
-continued
(Y-31)
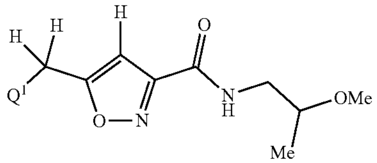
(Y-32)
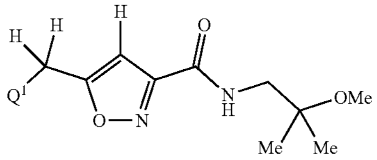
(Y-33)
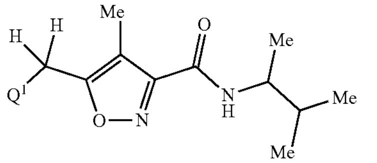
(Y-34)
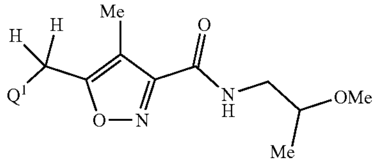
(Y-35)
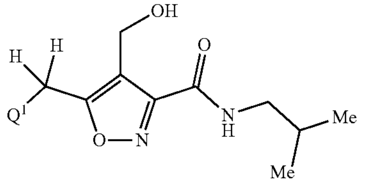
(Y-36)
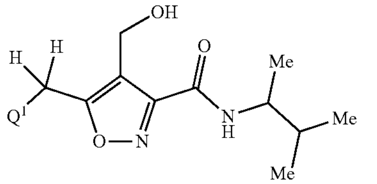
(Y-37)
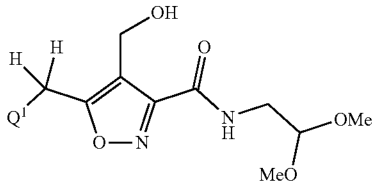
(Y-38)
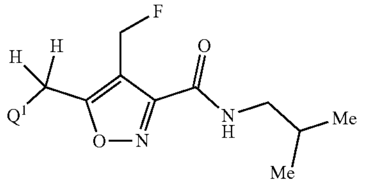

-continued
(Y-39)
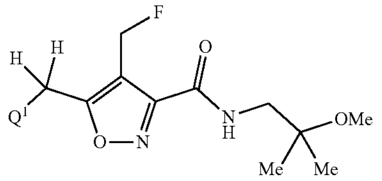
(Y-40)
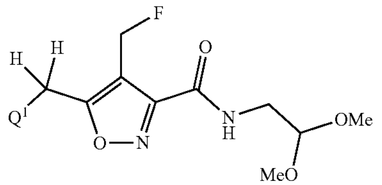
(Y-41)
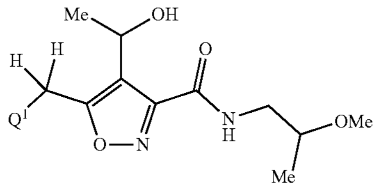
(Y-42)
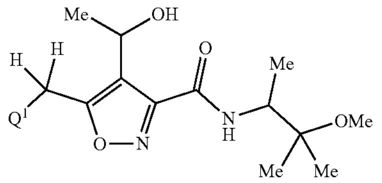
(Y-43)
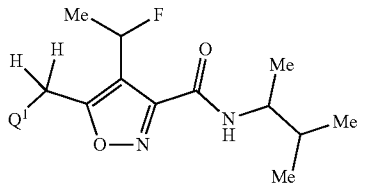
(Y-44)
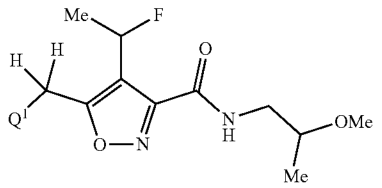
(Y-75)
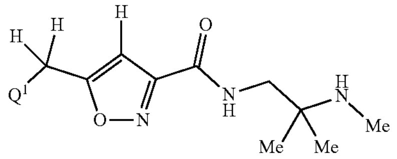
(Y-76)
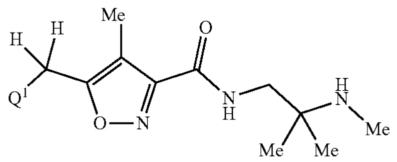
-continued
(Y-77)
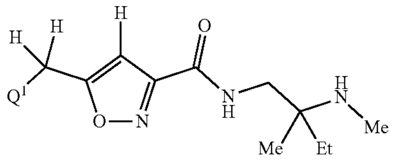
(Y-78)
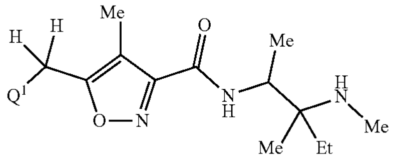
(Y-79)
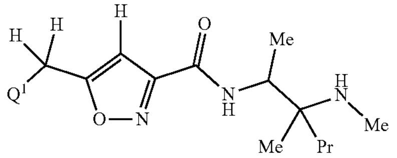
(Y-80)
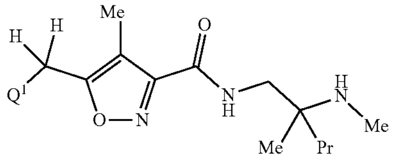
(Y-81)
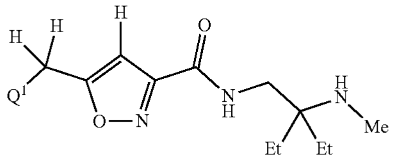
(Y-82)
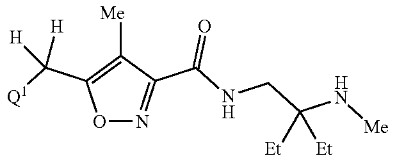
(Y-83)
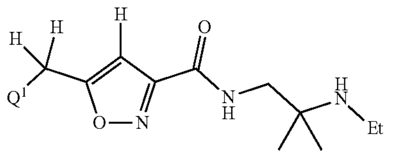
(Y-84)
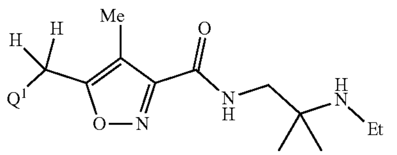
(Y-85)
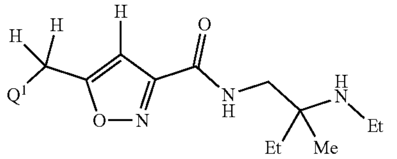

-continued
(Y-86)
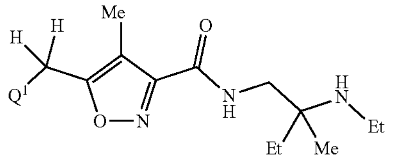
(Y-87)
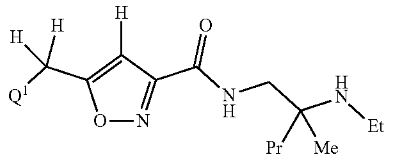
(Y-88)
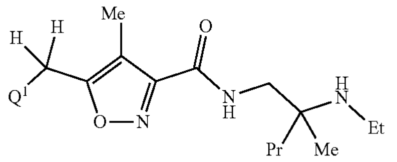
(Y-89)
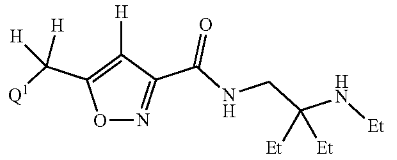
(Y-90)
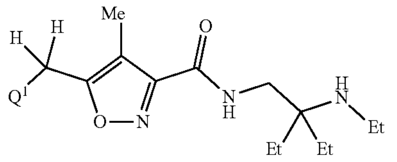
(Y-91)
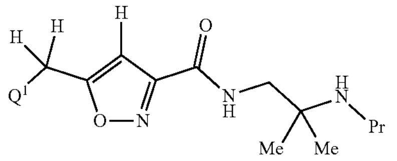
(Y-92)
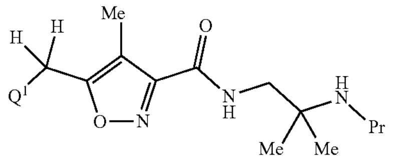
(Y-93)
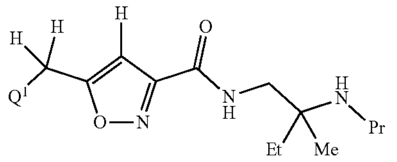
(Y-94)
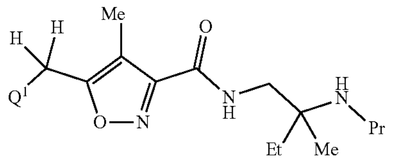
-continued
(Y-95)
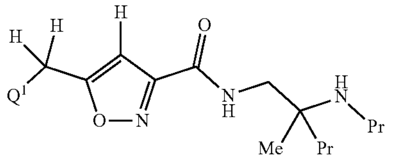
(Y-96)
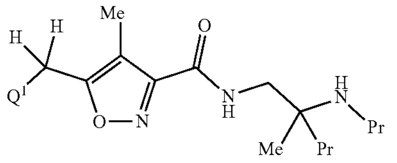
(Y-97)
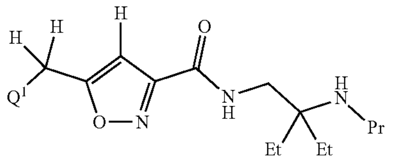
(Y-98)
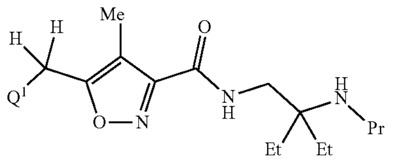
(Y-99)
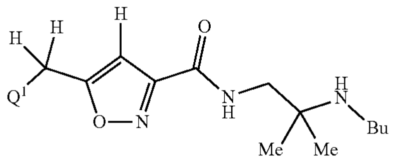
(Y-100)
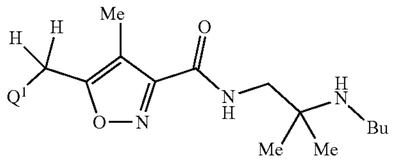
(Y-101)
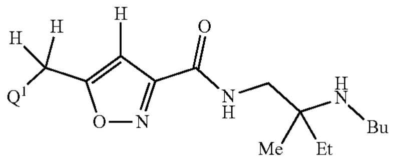
(Y-102)
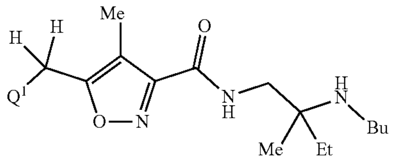
(Y-103)
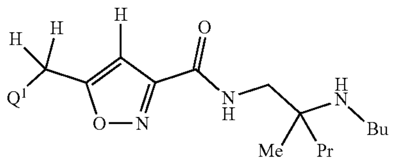

-continued
(Y-104)
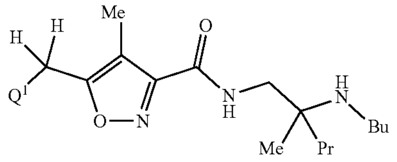
(Y-162)
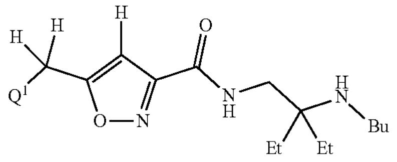
(Y-105)
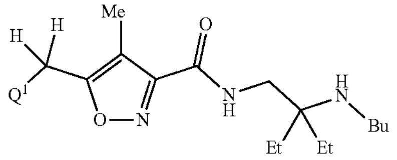
(Y-106)
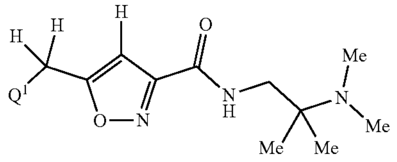
(Y-107)
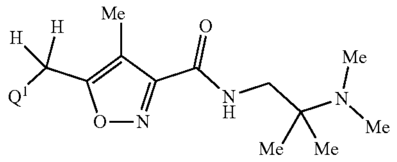
(Y-108)
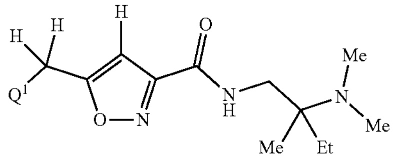
(Y-109)
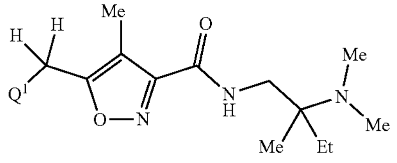
(Y-110)
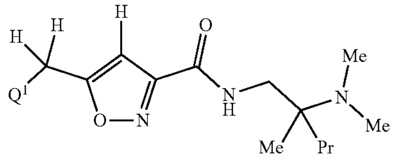
(Y-111)
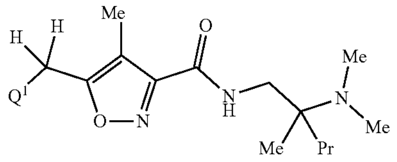
-continued
(Y-112)
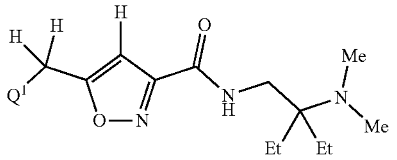
(Y-113)
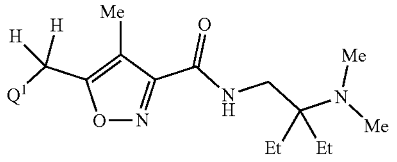
(Y-114)
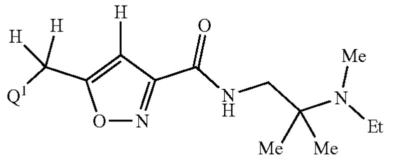
(Y-115)
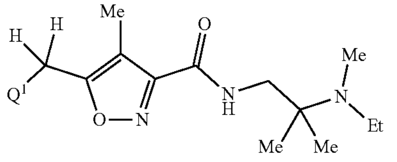
(Y-116)
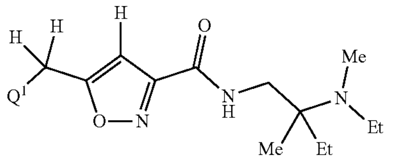
(Y-117)
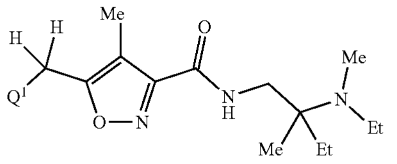
(Y-118)
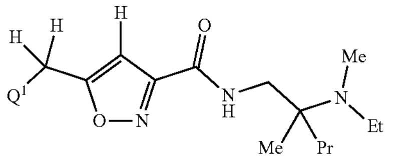
(Y-119)
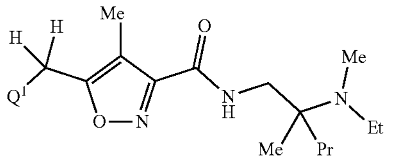
(Y-120)
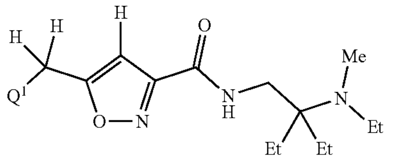

-continued
(Y-121)
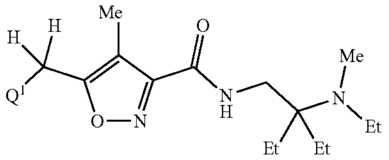
(Y-122)
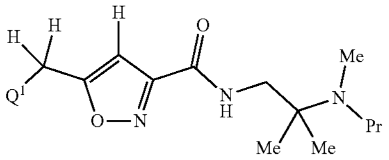
(Y-123)
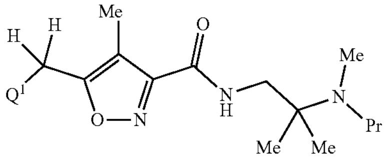
(Y-124)
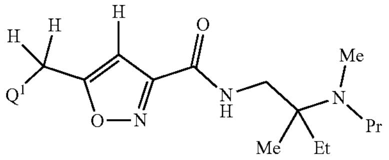
(Y-125)
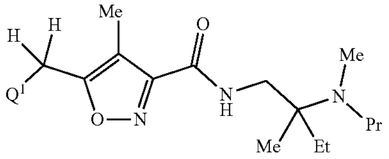
(Y-126)
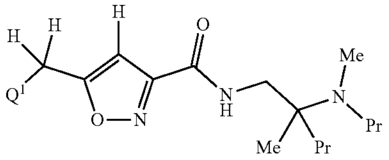
(Y-127)
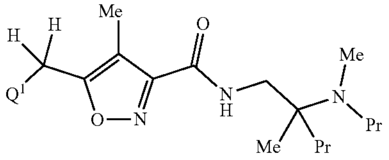
(Y-128)
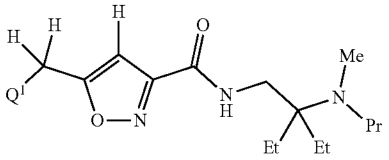
(Y-129)
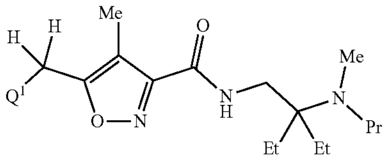
-continued
(Y-130)
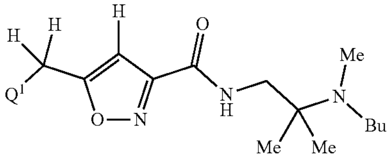
(Y-131)
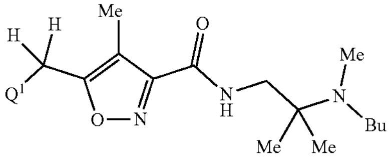
(Y-132)
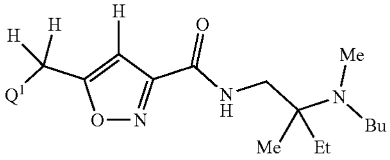
(Y-133)
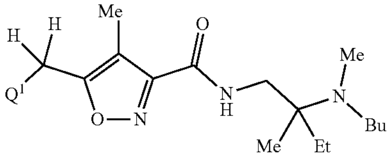
(Y-134)
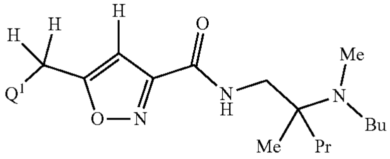
(Y-135)
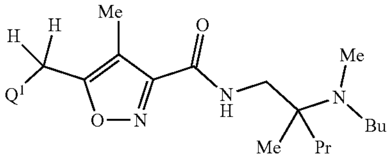
(Y-136)
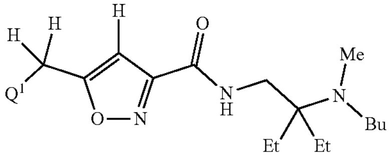
(Y-137)
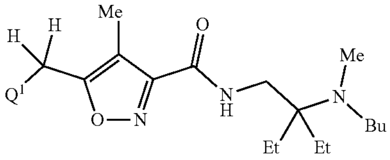
(Y-138)
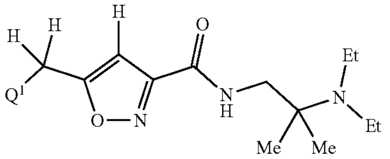

-continued
(Y-139)
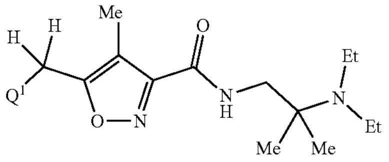
(Y-140)
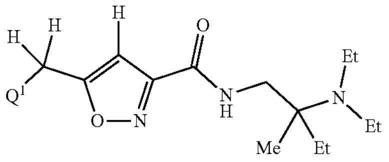
(Y-141)
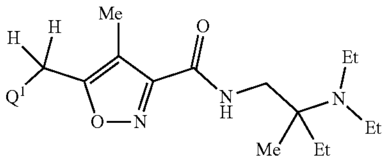
(Y-142)
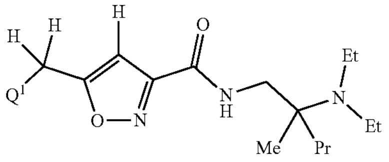
(Y-143)
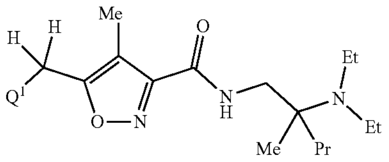
(Y-144)
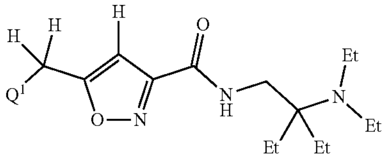
(Y-145)
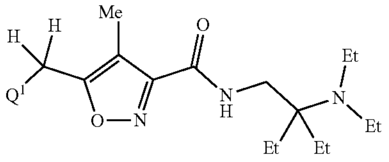
(Y-146)
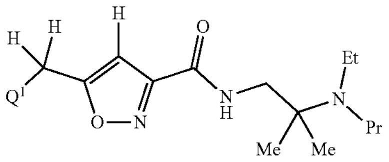
(Y-147)
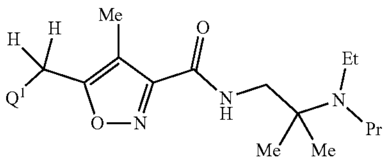
-continued
(Y-148)
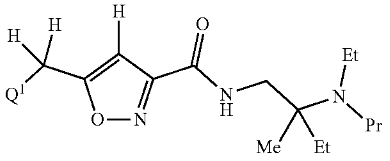
(Y-149)
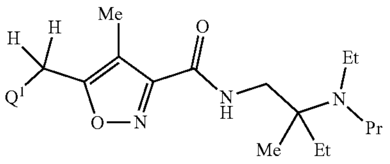
(Y-150)
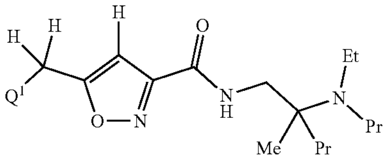
(Y-151)
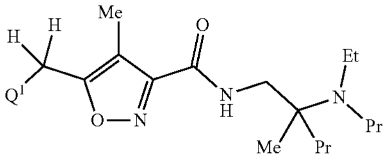
(Y-152)
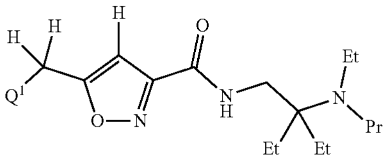
(Y-153)
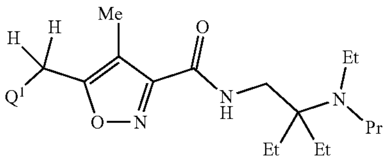
(Y-154)
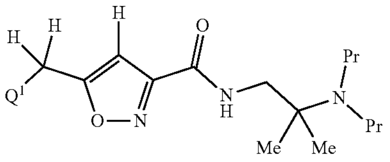
(Y-155)
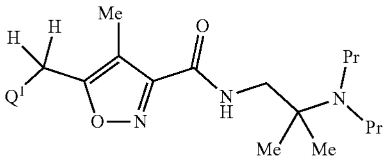
(Y-156)
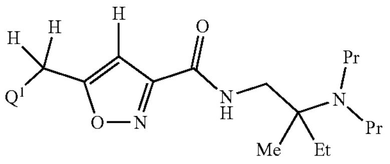

-continued
(Y-157)
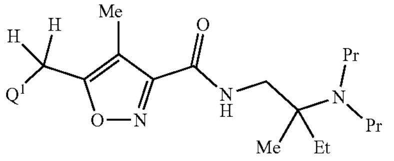
(Y-158)
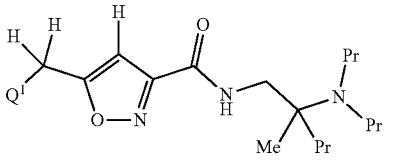
(Y-159)
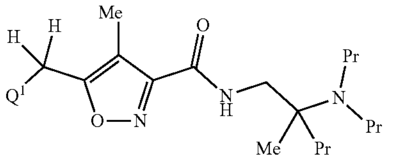
(Y-160)
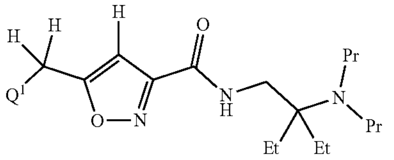
(Y-161)
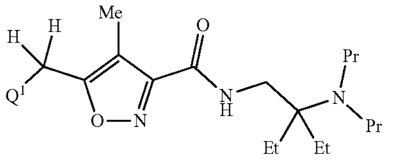
(Y-250)
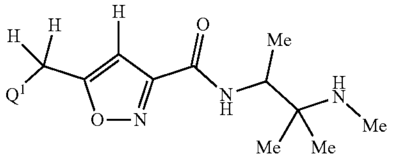
(Y-163)
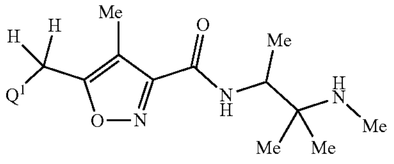
(Y-164)
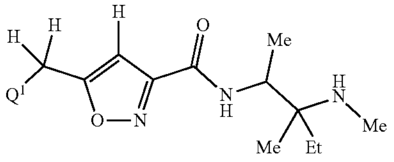
(Y-165)
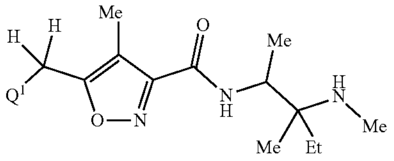
-continued
(Y-166)
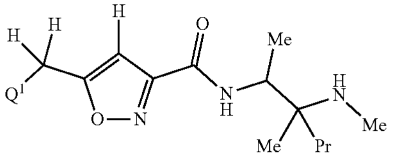
(Y-167)
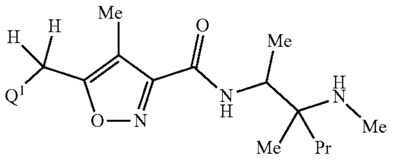
(Y-168)
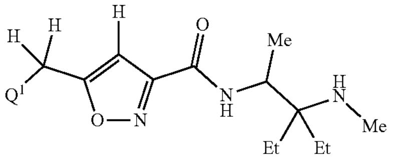
(Y-169)
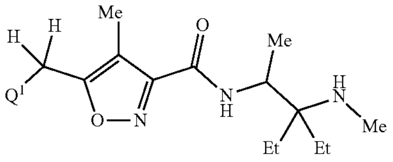
(Y-170)
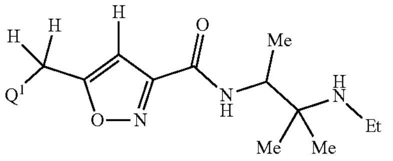
(Y-171)
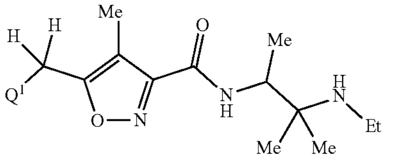
(Y-172)
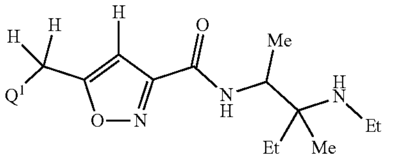
(Y-173)
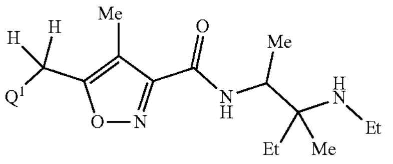
(Y-174)
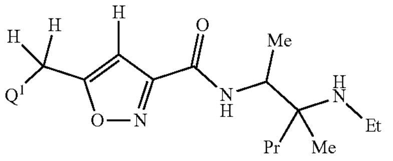

-continued
(Y-175)
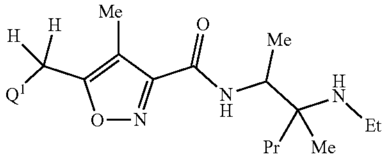
(Y-176)
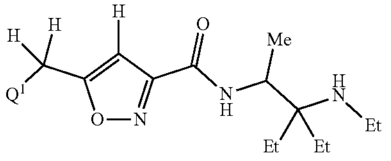
(Y-177)
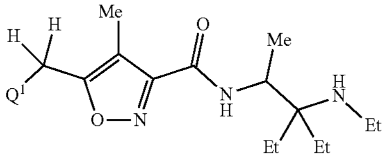
(Y-178)
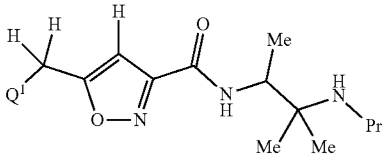
(Y-179)
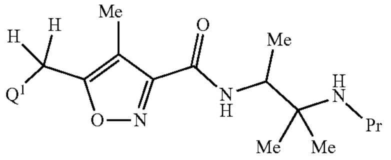
(Y-180)
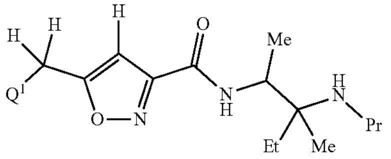
(Y-181)
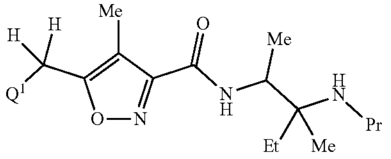
(Y-182)
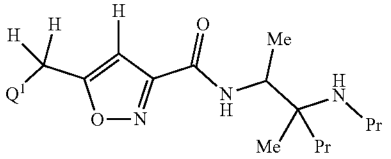
(Y-183)
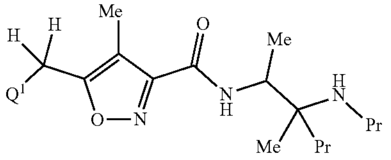
-continued
(Y-184)
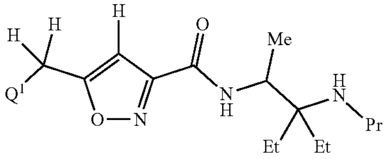
(Y-185)
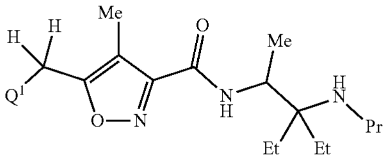
(Y-186)
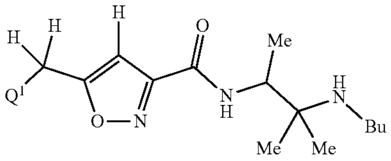
(Y-187)
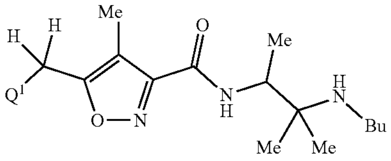
(Y-188)
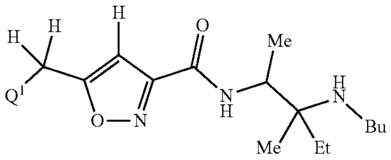
(Y-189)
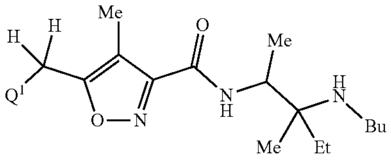
(Y-190)
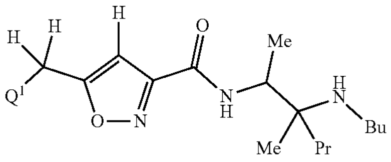
(Y-191)
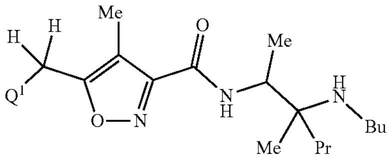
(Y-192)
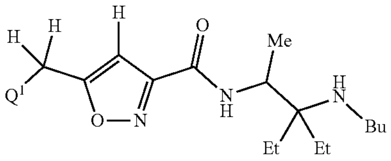

-continued
(Y-193)
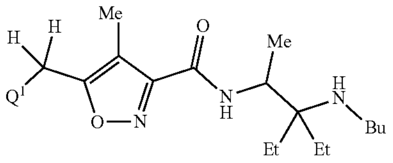
(Y-194)
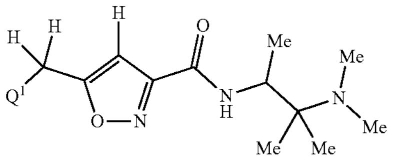
(Y-195)
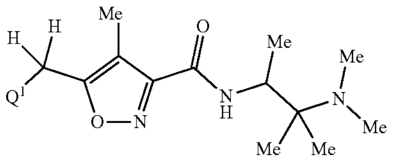
(Y-196)
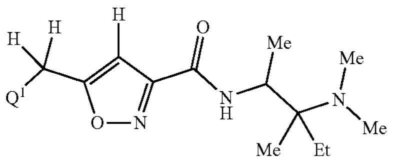
(Y-197)
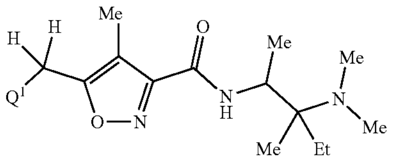
(Y-198)
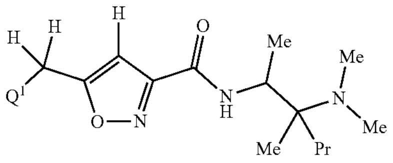
(Y-199)
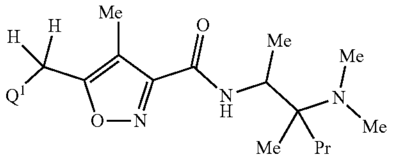
(Y-200)
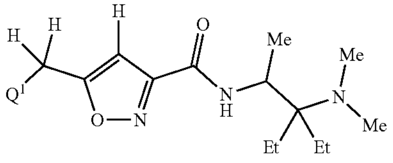
(Y-201)
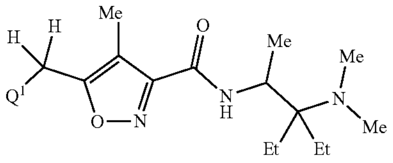
-continued
(Y-202)
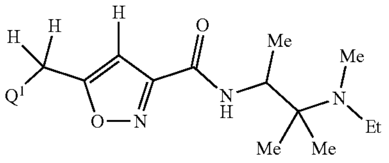
(Y-203)
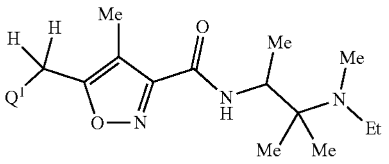
(Y-204)
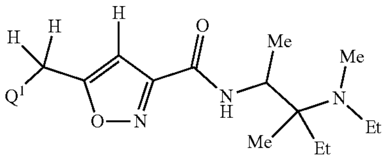
(Y-205)
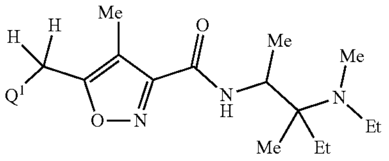
(Y-206)
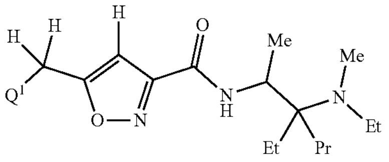
(Y-207)
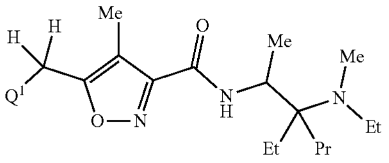
(Y-208)
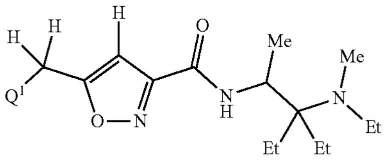
(Y-209)
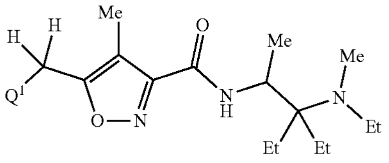
(Y-210)
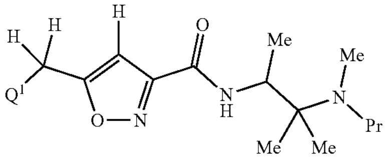

-continued
(Y-211)
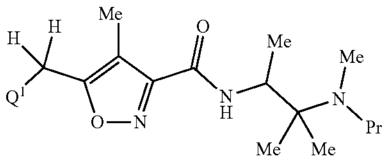
(Y-212)
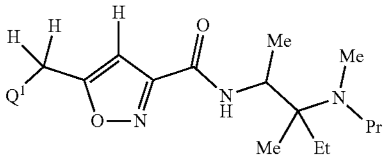
(Y-213)
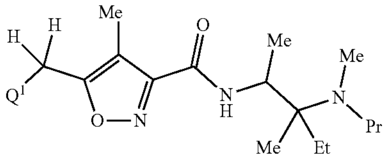
(Y-214)
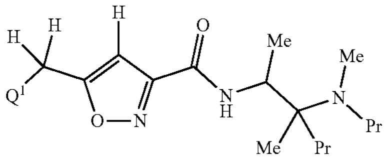
(Y-215)
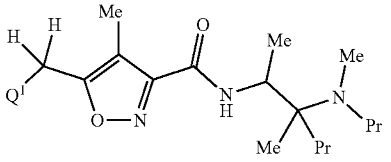
(Y-216)
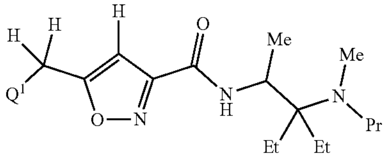
(Y-217)
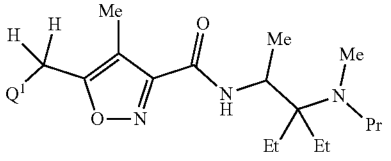
(Y-218)
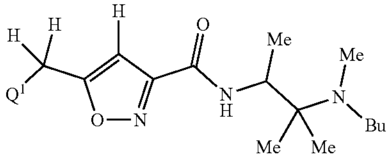
(Y-219)
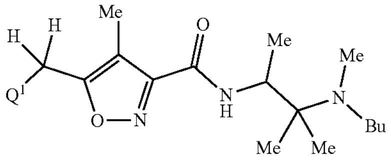
-continued
(Y-220)
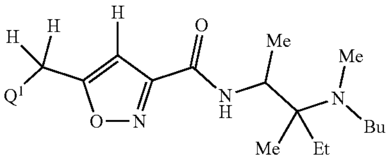
(Y-221)
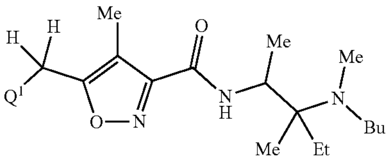
(Y-222)
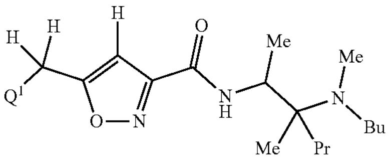
(Y-223)
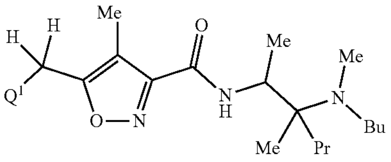
(Y-224)
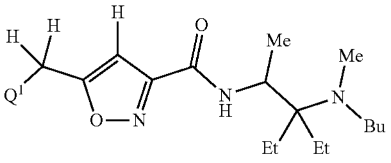
(Y-225)
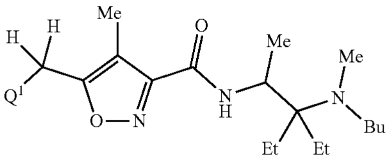
(Y-226)
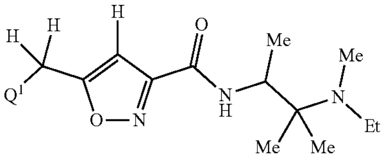
(Y-227)
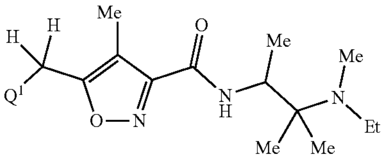
(Y-228)
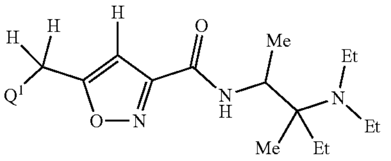

-continued
(Y-229)
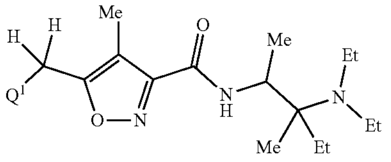
(Y-230)
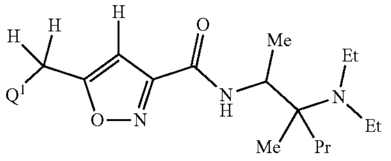
(Y-231)
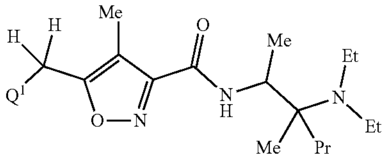
(Y-232)
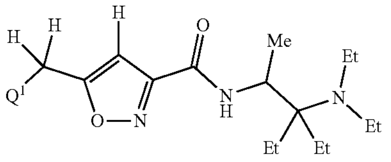
(Y-233)
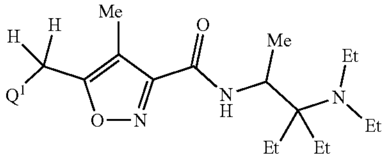
(Y-234)
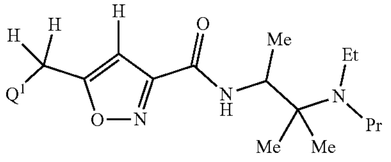
(Y-235)
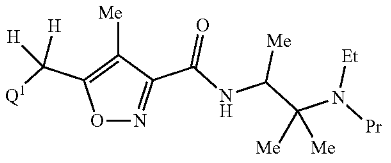
(Y-236)
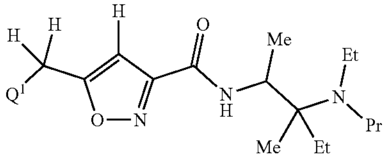
(Y-237)
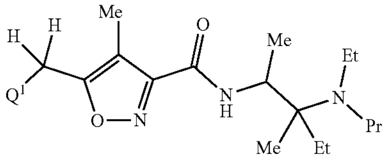
-continued
(Y-238)
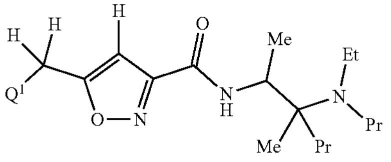
(Y-239)
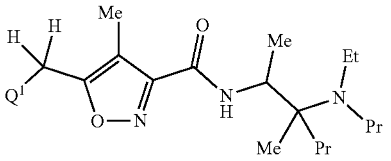
(Y-240)
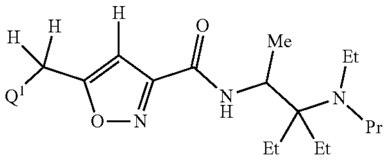
(Y-241)
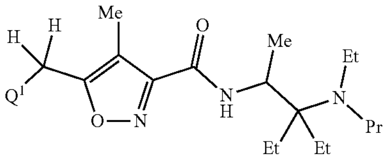
(Y-242)
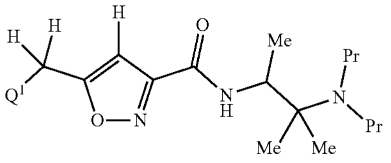
(Y-243)
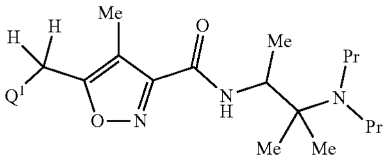
(Y-244)
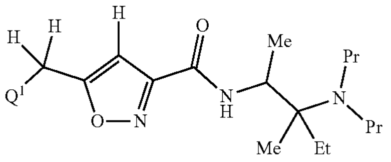
(Y-245)
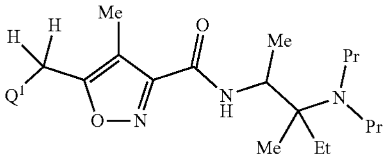
(Y-246)
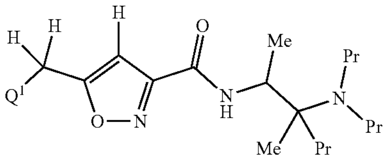

-continued
(Y-247)
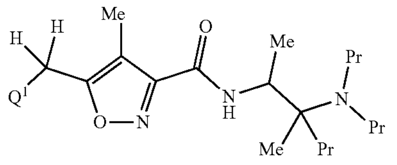
(Y-248)
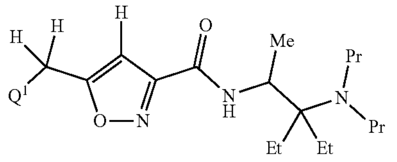
(Y-249)
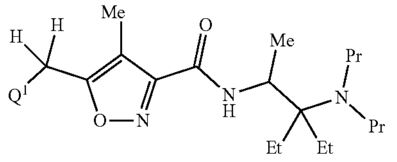
(Y-338)
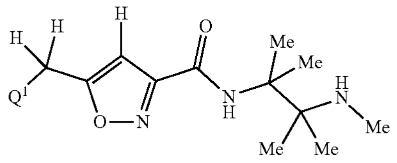
(Y-251)
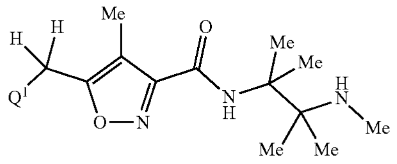
(Y-252)
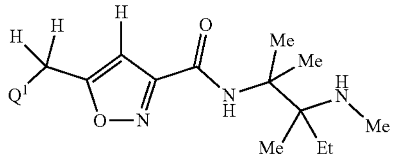
(Y-253)
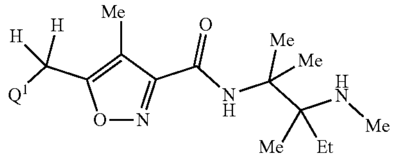
(Y-254)
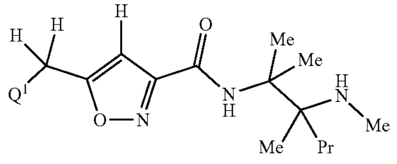
(Y-255)
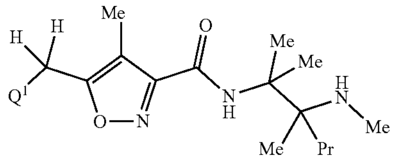
-continued
(Y-256)
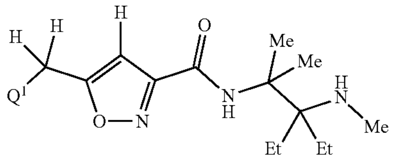
(Y-257)
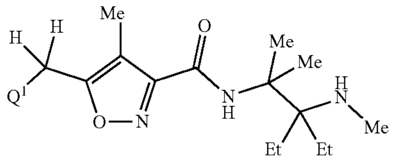
(Y-258)
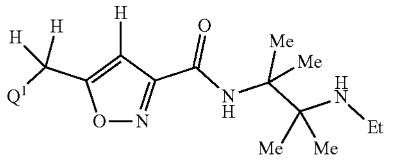
(Y-259)
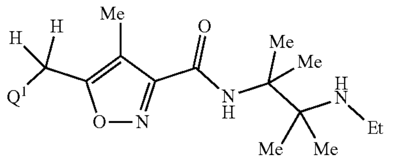
(Y-260)
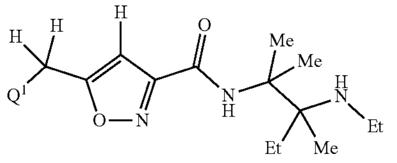
(Y-261)
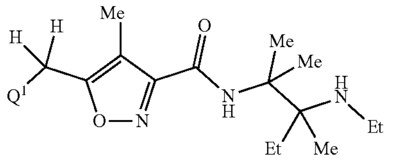
(Y-262)
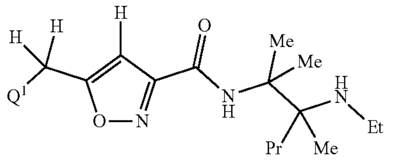
(Y-263)
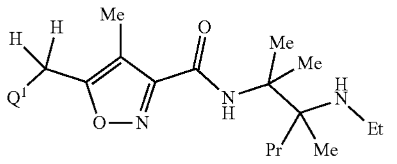
(Y-264)
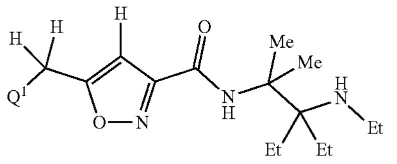

-continued
(Y-265)
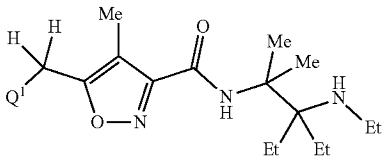
(Y-266)
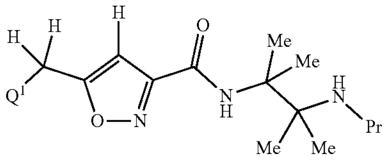
(Y-267)
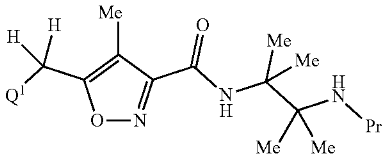
(Y-268)
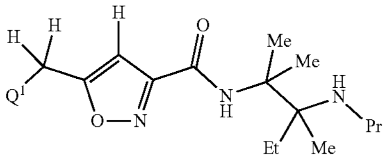
(Y-269)
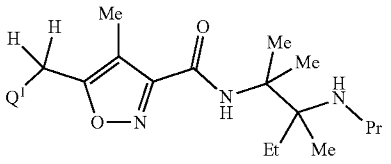
(Y-270)
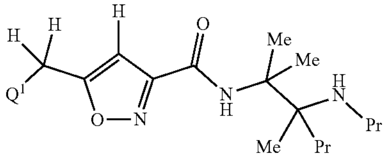
(Y-271)
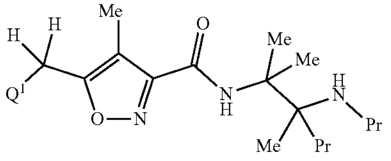
(Y-272)
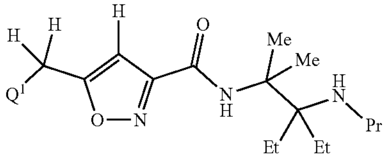
(Y-273)
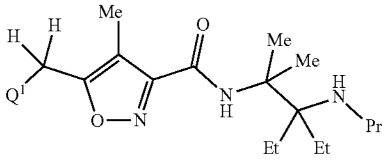
-continued
(Y-274)
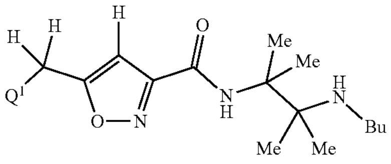
(Y-275)
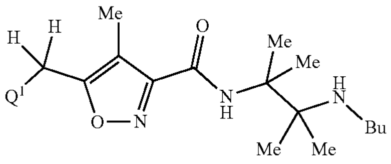
(Y-276)
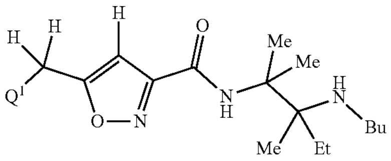
(Y-277)
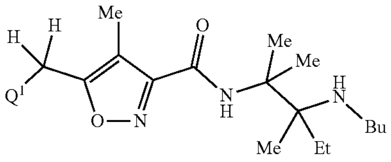
(Y-278)
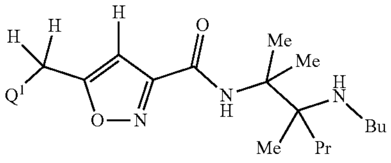
(Y-279)
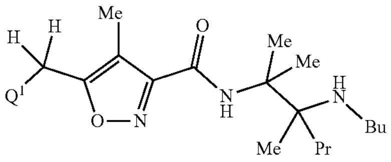
(Y-280)
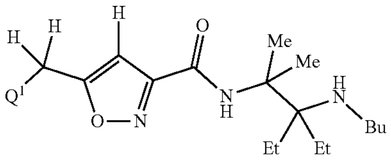
(Y-281)
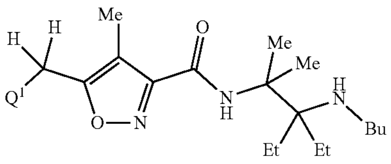
(Y-282)
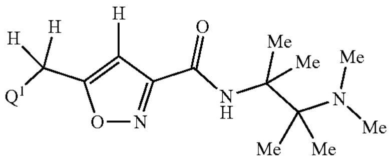

(Y-283)
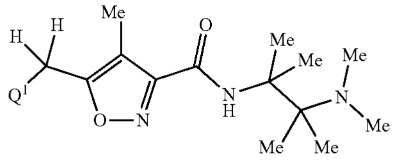
(Y-284)
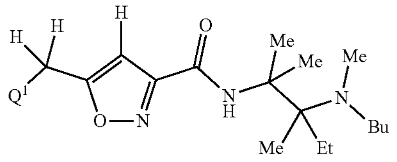
(Y-285)
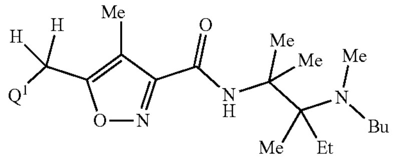
(Y-284)
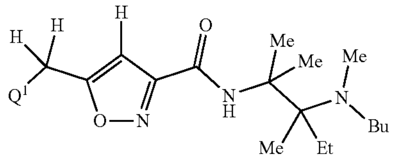
(Y-285)
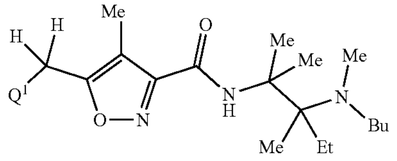
(Y-286)
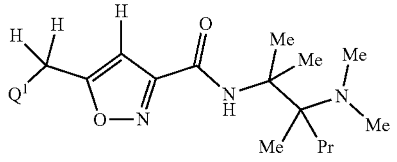
(Y-287)
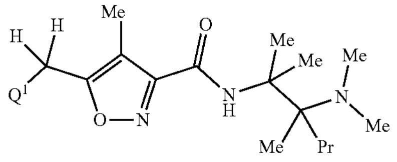
(Y-288)
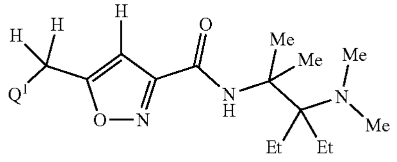
(Y-289)
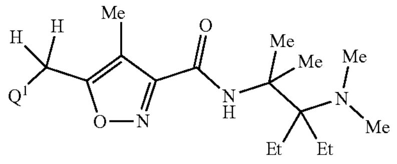
(Y-290)
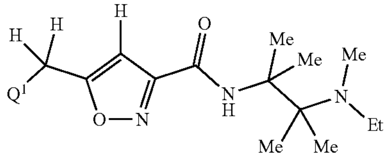
(Y-291)
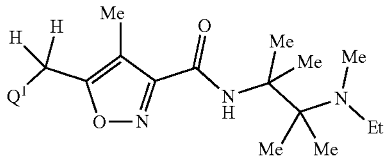
(Y-292)
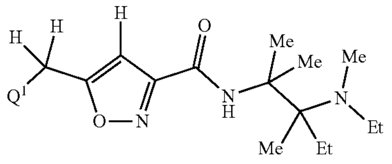
(Y-293)
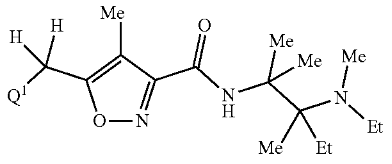
(Y-294)
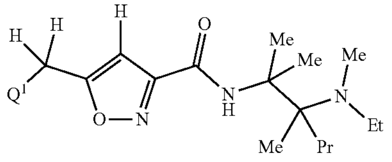
(Y-295)
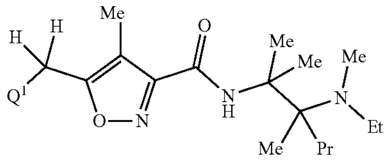
(Y-296)
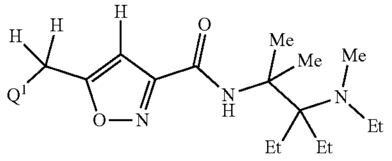
(Y-297)
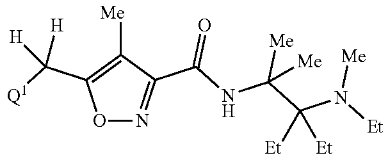
(Y-298)
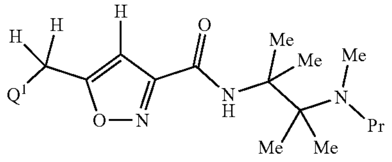

-continued
(Y-299)
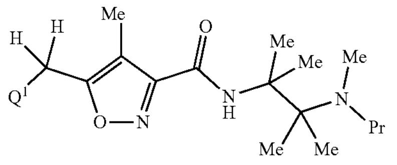
(Y-300)
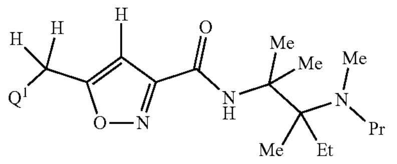
(Y-301)
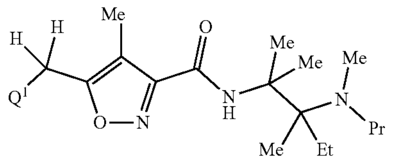
(Y-302)
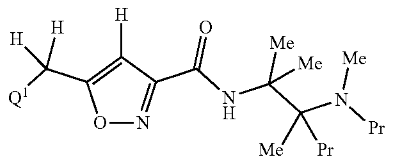
(Y-303)
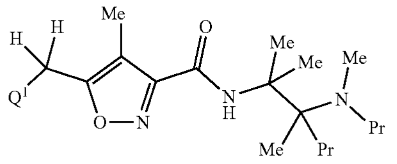
(Y-304)
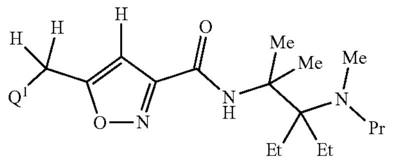
(Y-305)
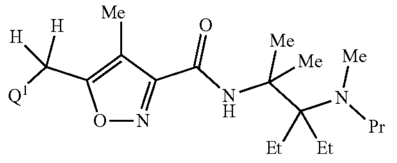
(Y-306)
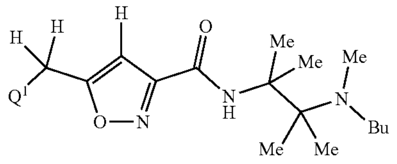
(Y-307)
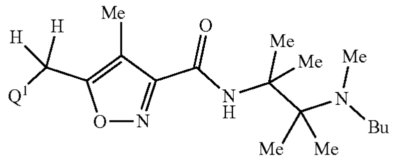
-continued
(Y-308)
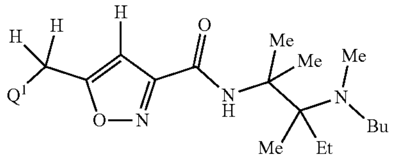
(Y-309)
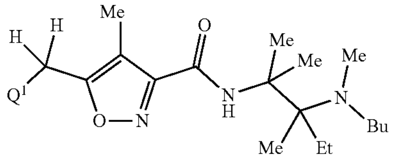
(Y-310)
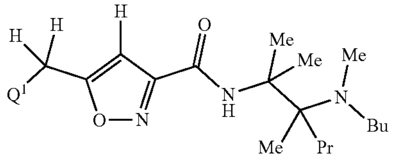
(Y-311)
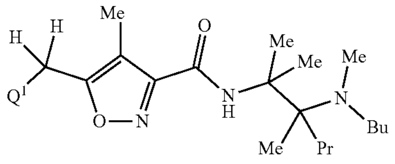
(Y-312)
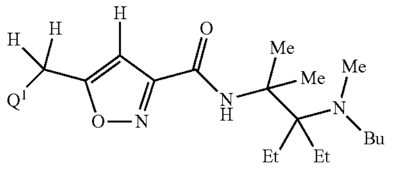
(Y-313)
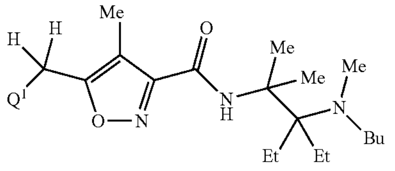
(Y-314)
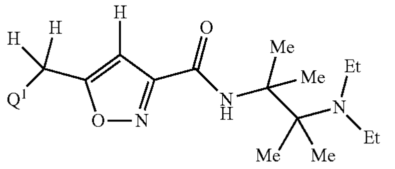
(Y-315)
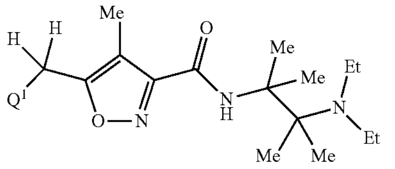
(Y-316)
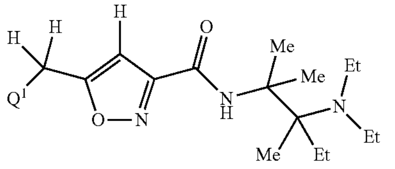

-continued
(Y-317)
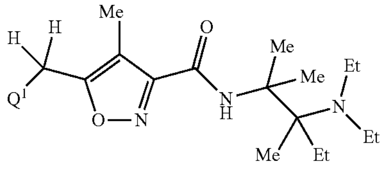
(Y-318)
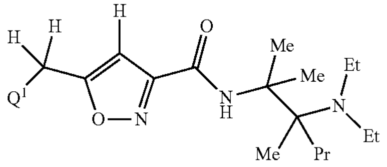
(Y-319)
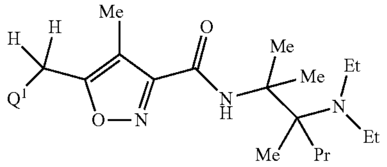
(Y-320)
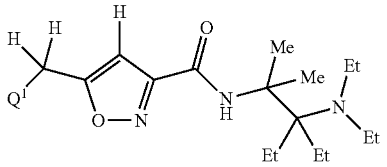
(Y-321)
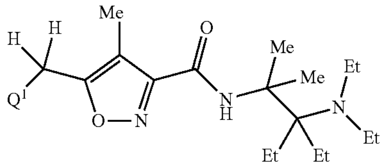
(Y-322)
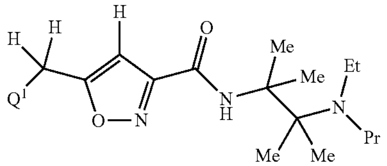
(Y-323)
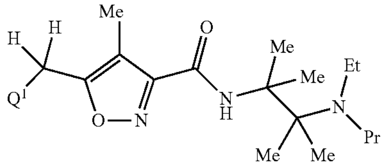
(Y-324)
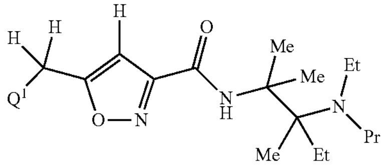
(Y-325)
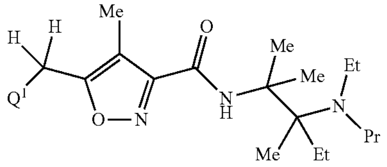
-continued
(Y-326)
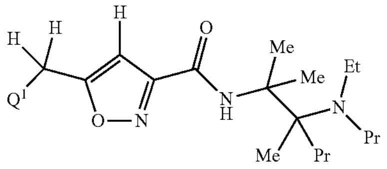
(Y-327)
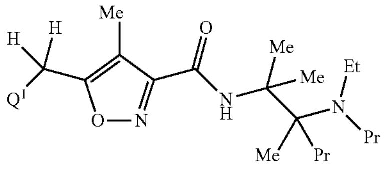
(Y-328)
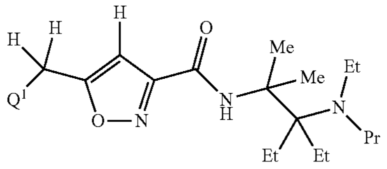
(Y-329)
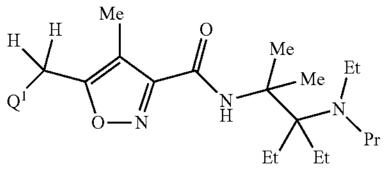
(Y-330)
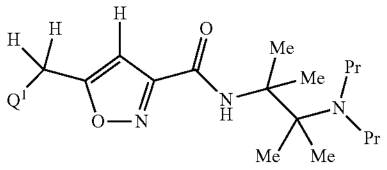
(Y-331)
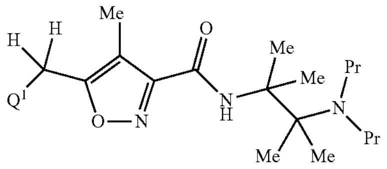
(Y-332)
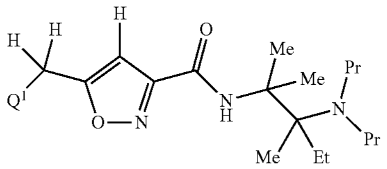
(Y-333)
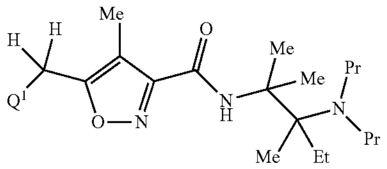
(Y-334)
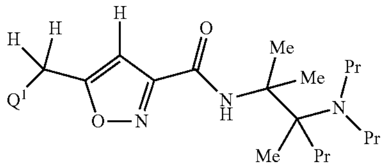

-continued
(Y-335)
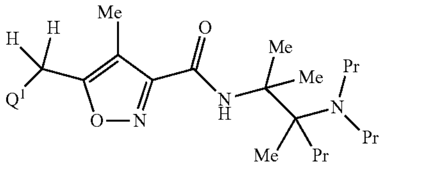
(Y-336)
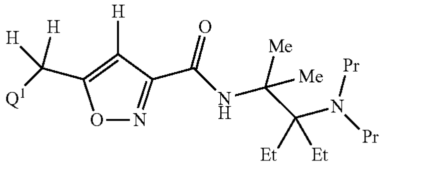
(Y-337)
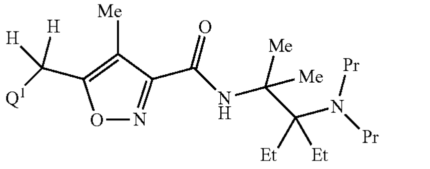
(Y-339)
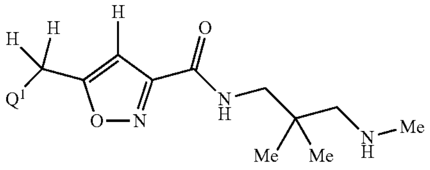
(Y-340)
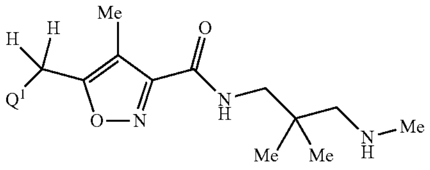
(Y-341)
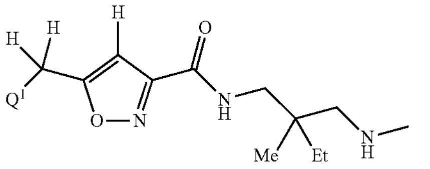
(Y-342)
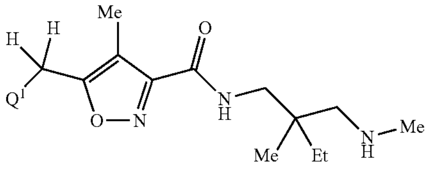
(Y-343)
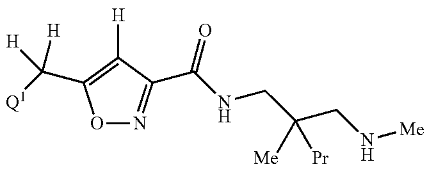
(Y-344)
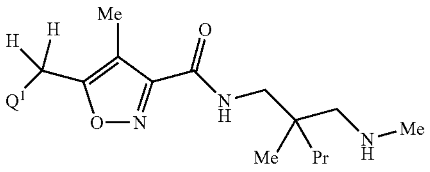
-continued
(Y-345)
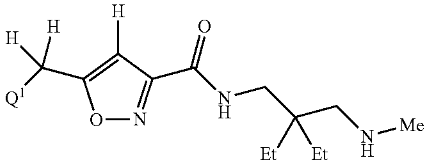
(Y-346)
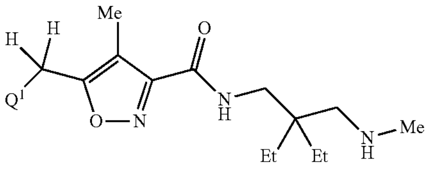
(Y-347)
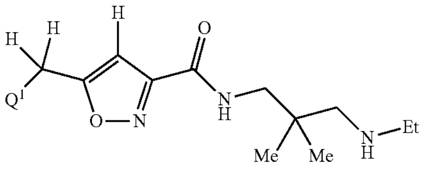
(Y-348)
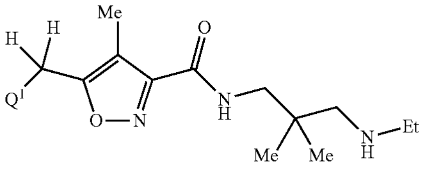
(Y-349)
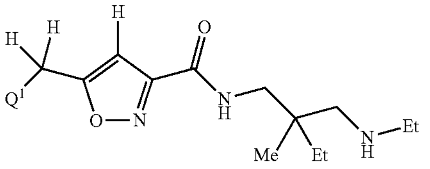
(Y-350)
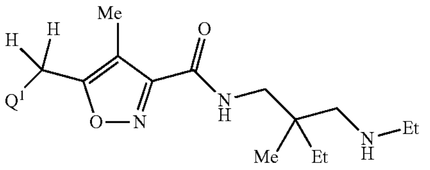
(Y-351)
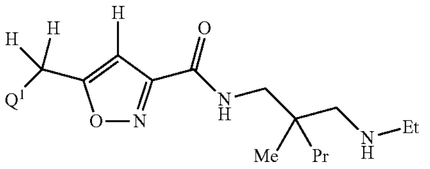
(Y-352)
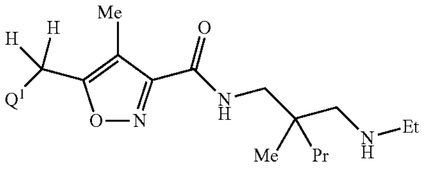
(Y-353)
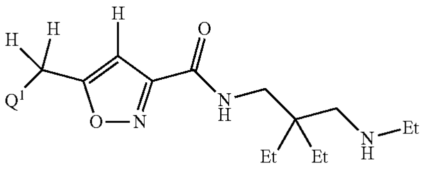

-continued
(Y-354)
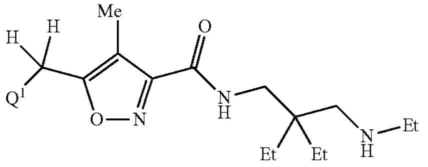
(Y-355)
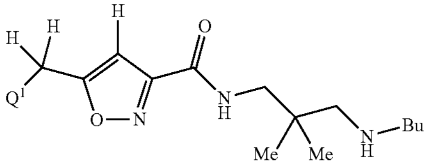
(Y-356)
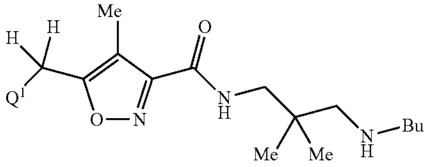
(Y-357)
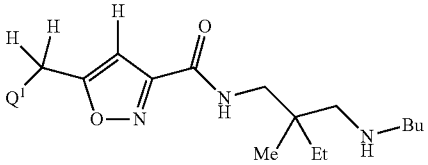
(Y-358)
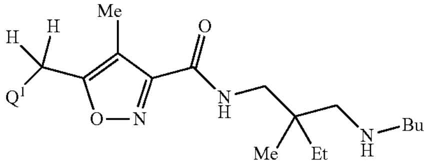
(Y-359)
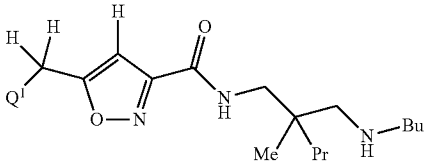
(Y-360)
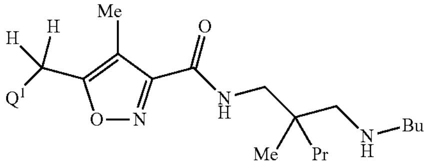
(Y-361)
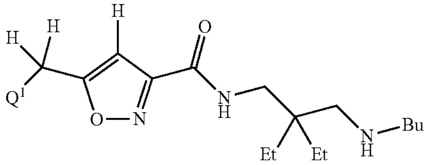
(Y-362)
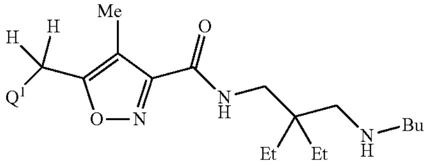
-continued
(Y-363)
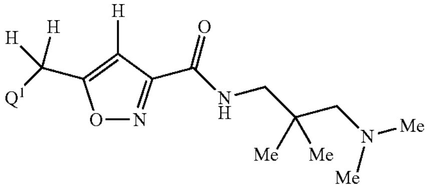
(Y-364)
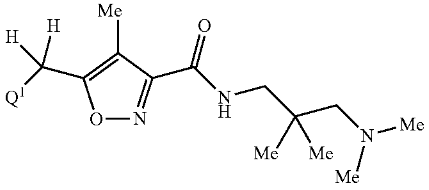
(Y-365)
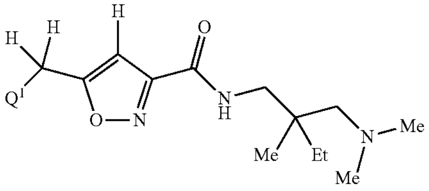
(Y-366)
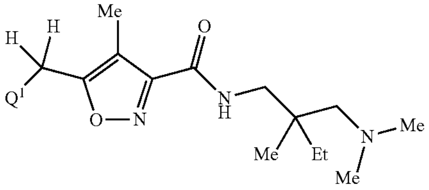
(Y-367)
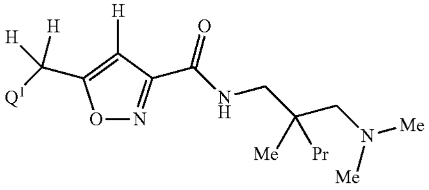
(Y-368)
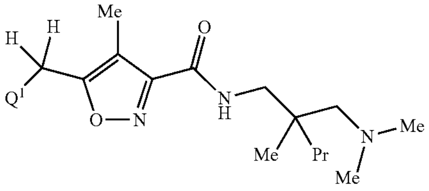
(Y-369)
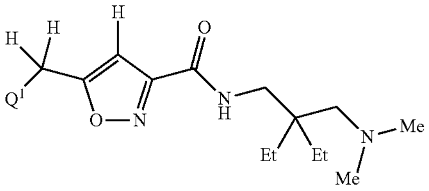
(Y-370)
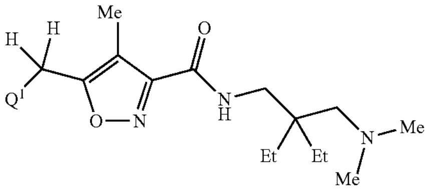

-continued
(Y-371)
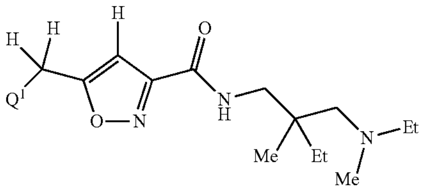
(Y-372)
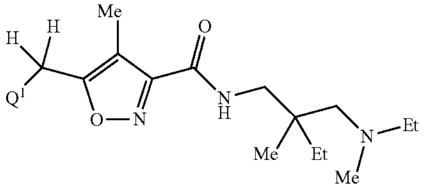
(Y-373)
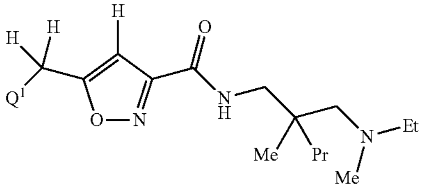
(Y-374)
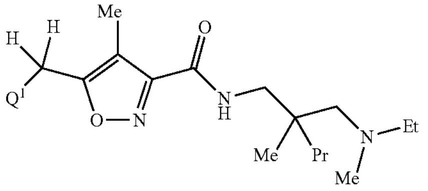
(Y-375)
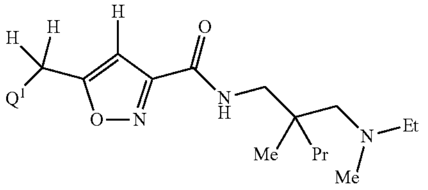
(Y-376)
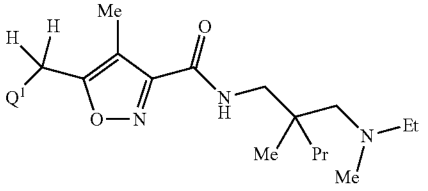
(Y-375)
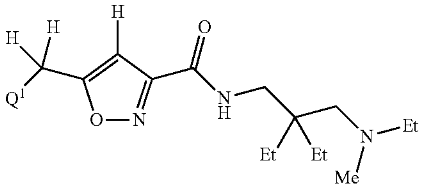
(Y-376)
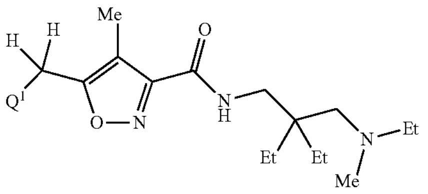
-continued
(Y-377)
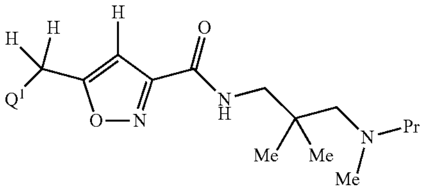
(Y-378)
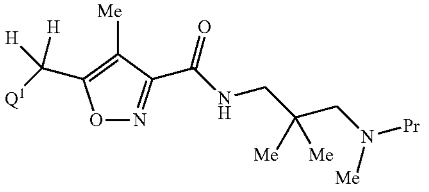
(Y-379)
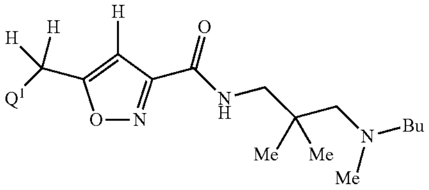
(Y-380)
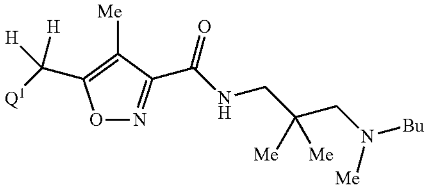
(Y-381)
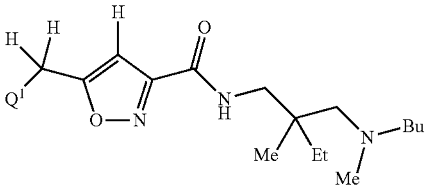
(Y-382)
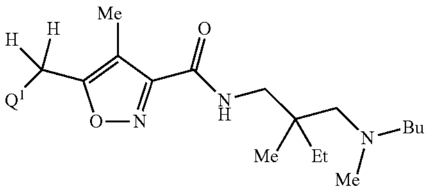
(Y-383)
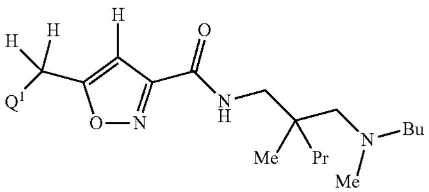
(Y-384)
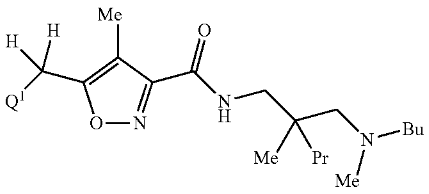

-continued
(Y-385)
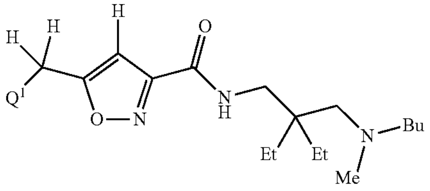
(Y-386)
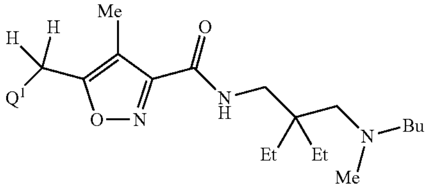
(Y-387)
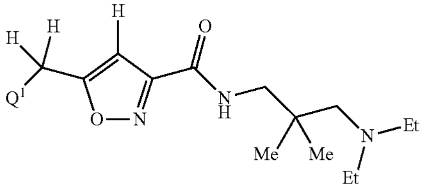
(Y-388)
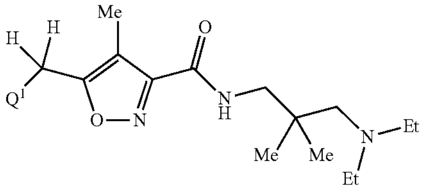
(Y-389)
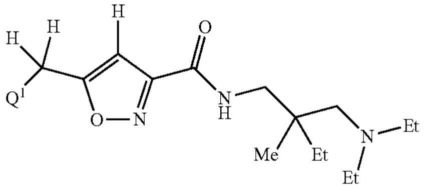
(Y-390)
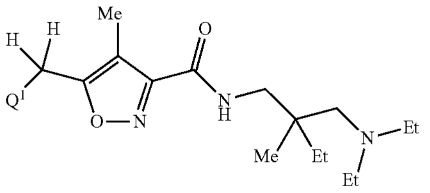
(Y-391)
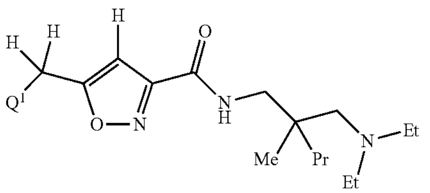
(Y-392)
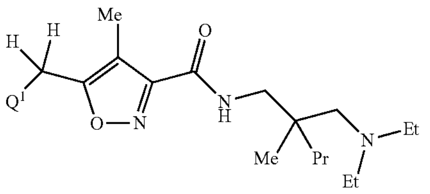
-continued
(Y-393)
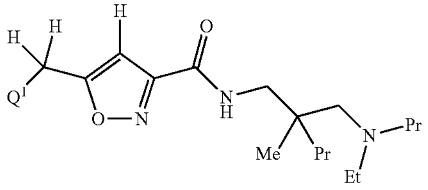
(Y-394)
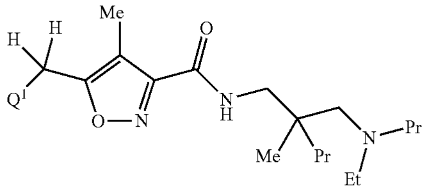
(Y-395)
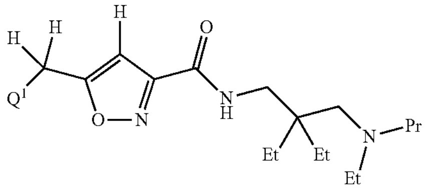
(Y-396)
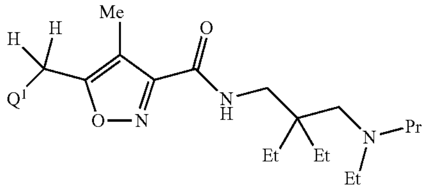
(Y-397)
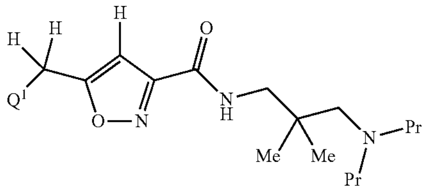
(Y-398)
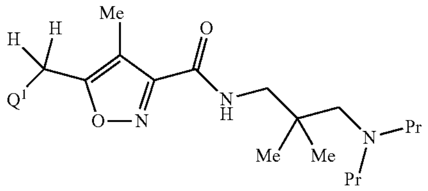
(Y-399)
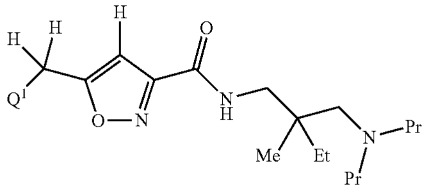
(Y-400)
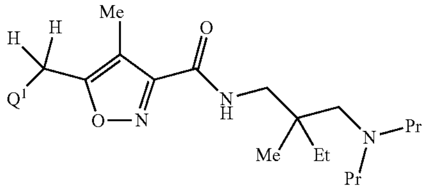

-continued
(Y-401)
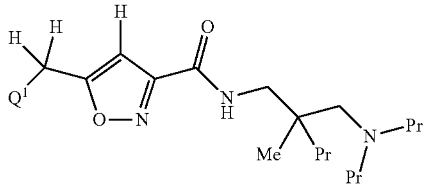
(Y-402)
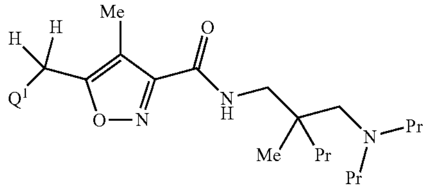
(Y-403)
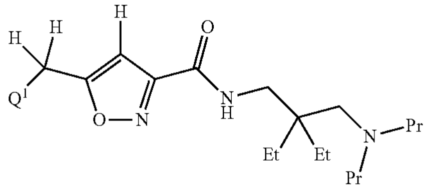
(Y-404)
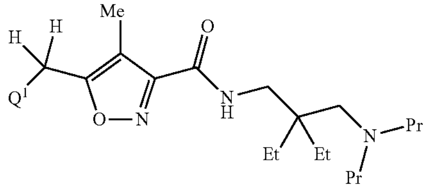
(Y-405)
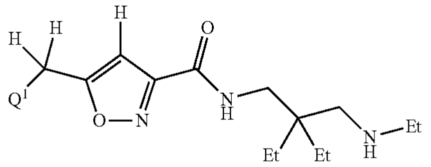
(Y-406)
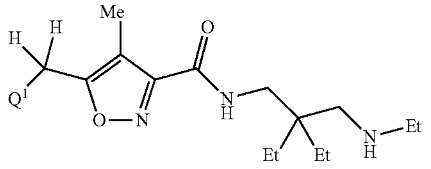
(Y-407)
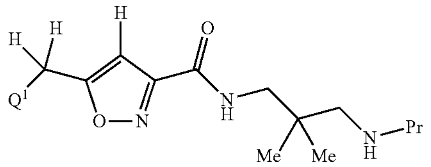
(Y-408)
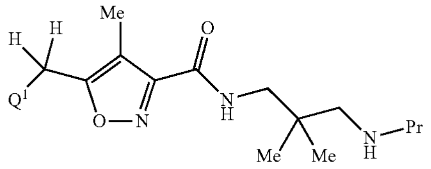
-continued
(Y-409)
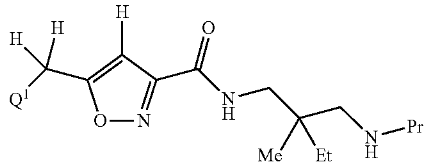
(Y-410)
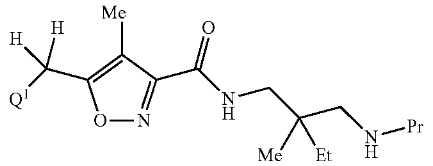
(Y-411)
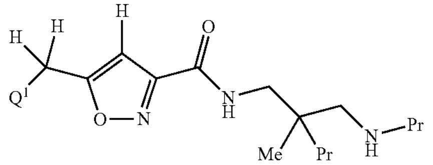
(Y-412)
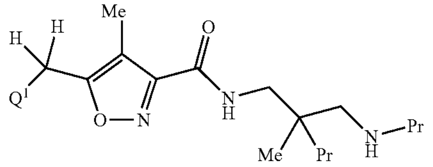
(Y-413)
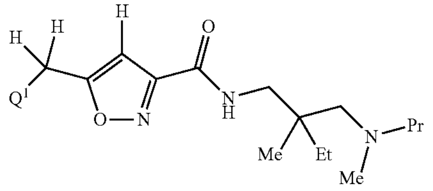
(Y-414)
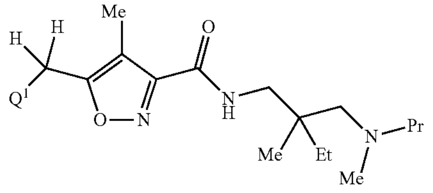
(Y-415)
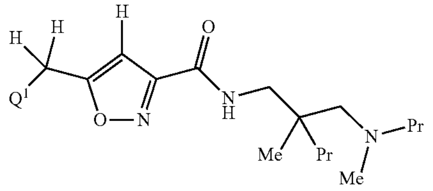
(Y-416)
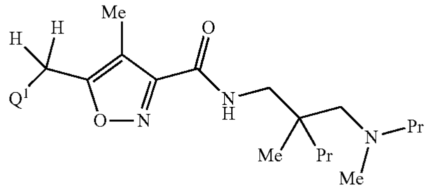

-continued
(Y-417)
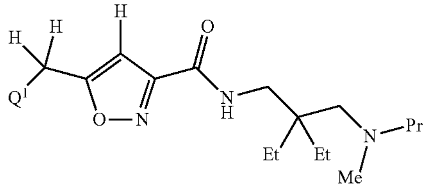
(Y-418)
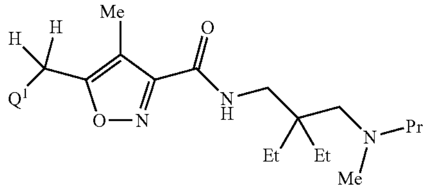
(Y-419)
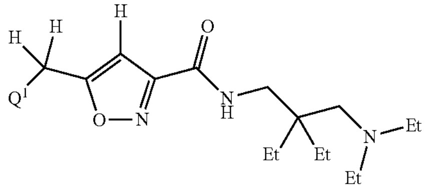
(Y-420)
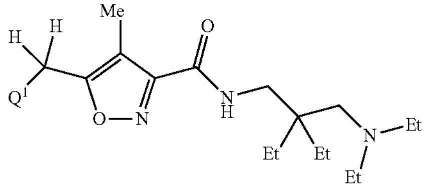
(Y-421)
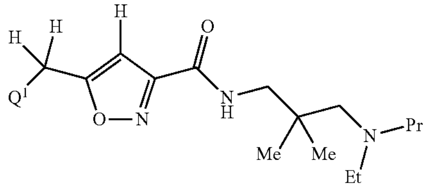
(Y-422)
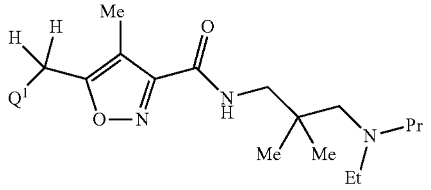
(Y-423)
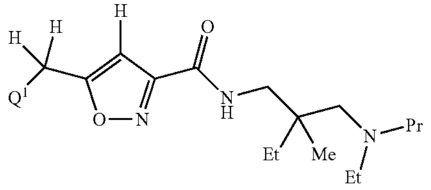
(Y-424)
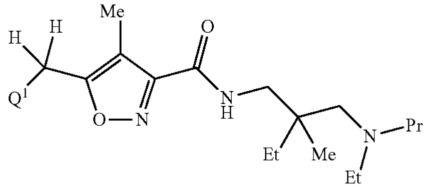
-continued
(Y-425)
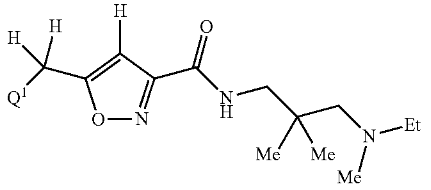
(Y-426)
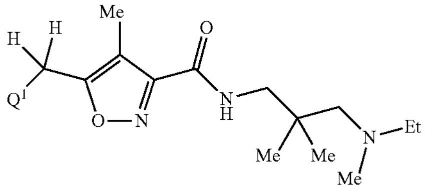
(Y-427)
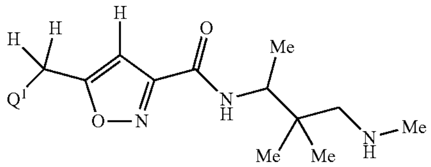
(Y-428)
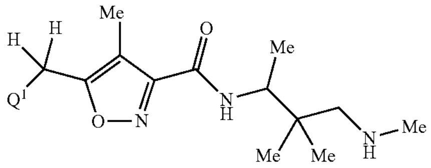
(Y-429)
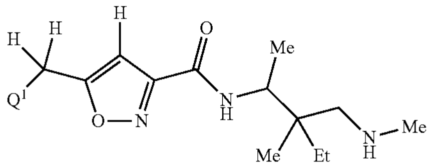
(Y-430)
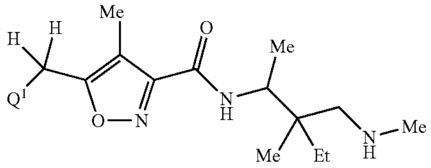
(Y-431)
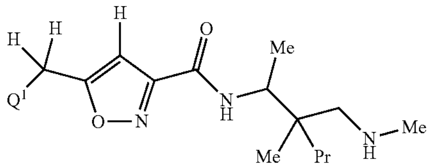
(Y-432)
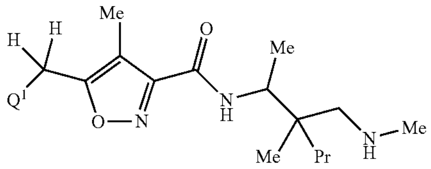
(Y-433)
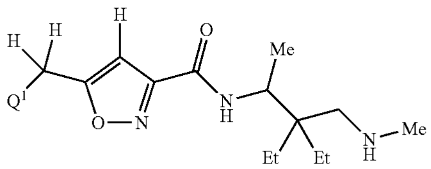

(Y-434)
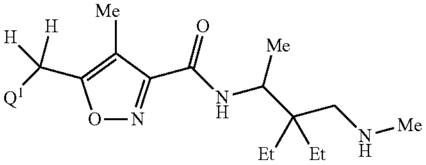
(Y-435)
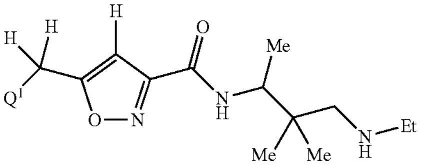
(Y-436)
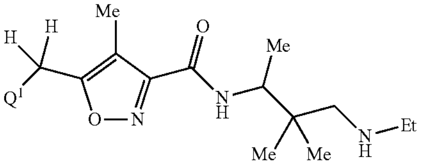
(Y-437)
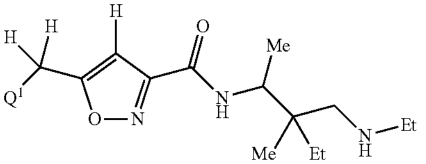
(Y-438)
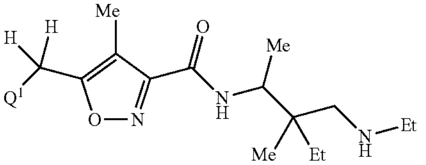
(Y-439)
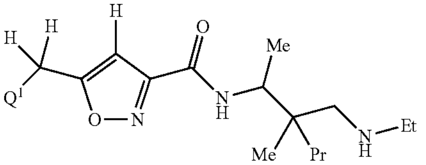
(Y-440)
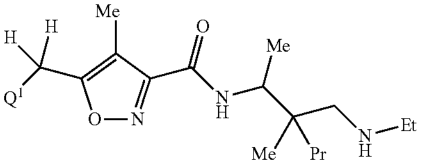
(Y-441)
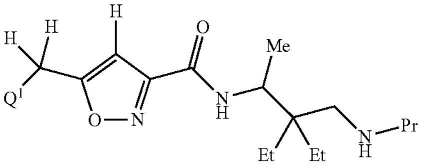
(Y-442)
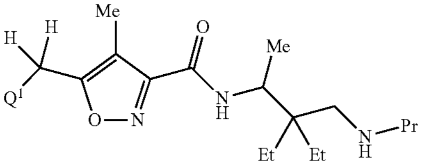
(Y-443)
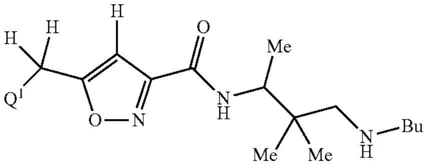
(Y-444)
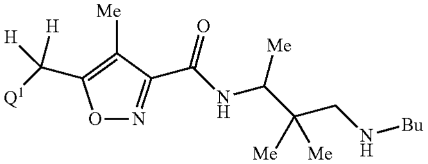
(Y-445)
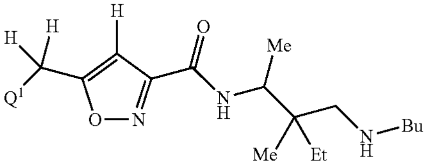
(Y-446)
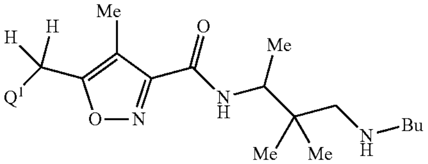
(Y-447)
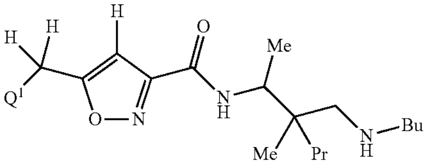
(Y-448)
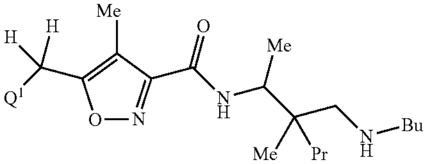
(Y-449)
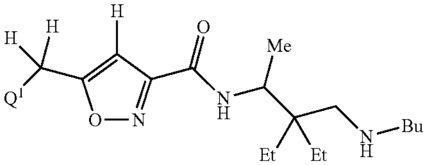
(Y-450)
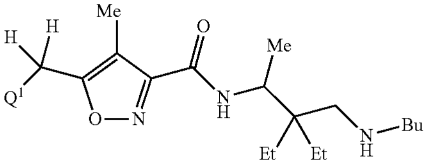
(Y-451)
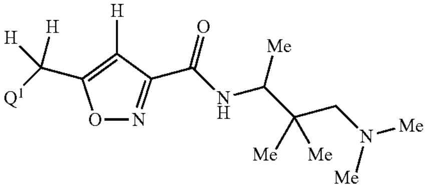

-continued
(Y-452)
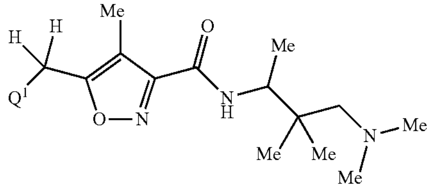
(Y-453)
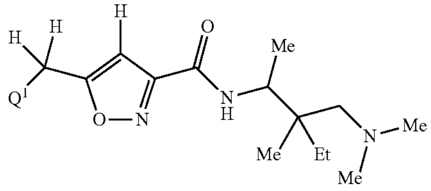
(Y-454)
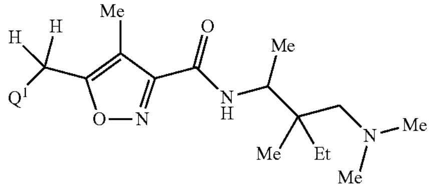
(Y-455)
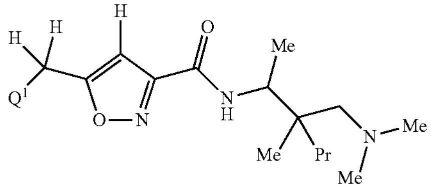
(Y-456)
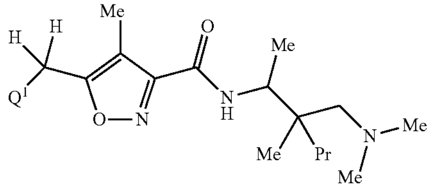
(Y-457)
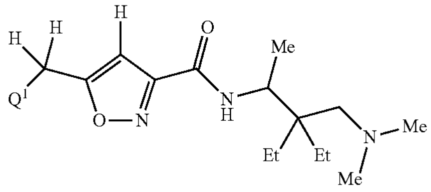
(Y-458)
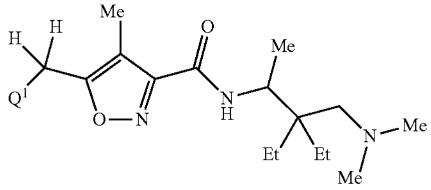
-continued
(Y-459)
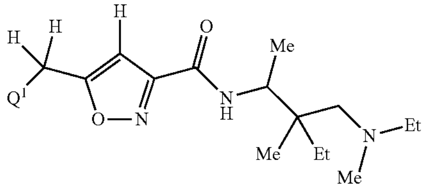
(Y-460)
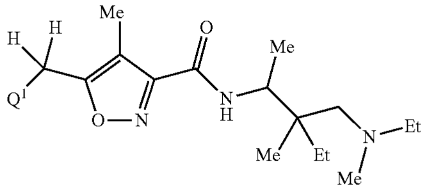
(Y-461)
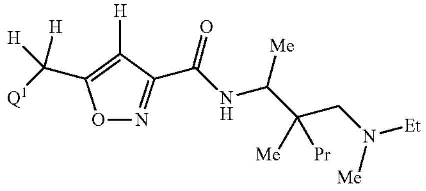
(Y-462)
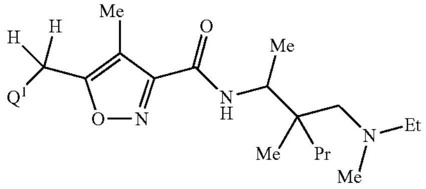
(Y-463)
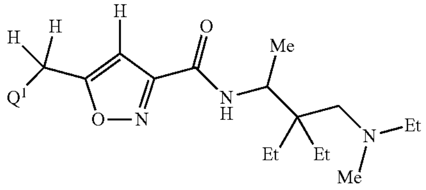
(Y-464)
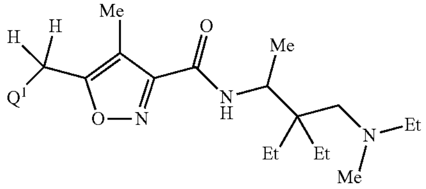
(Y-465)
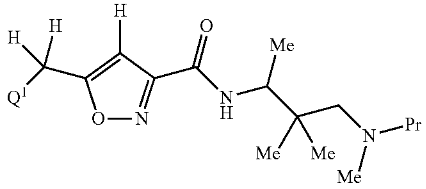
(Y-466)
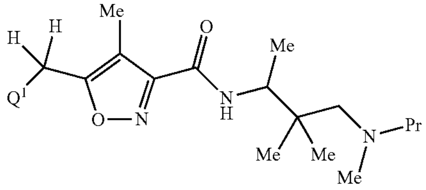

-continued
(Y-467)
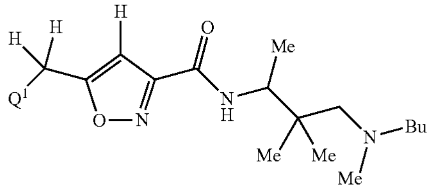
(Y-468)
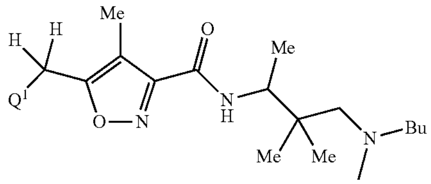
(Y-469)
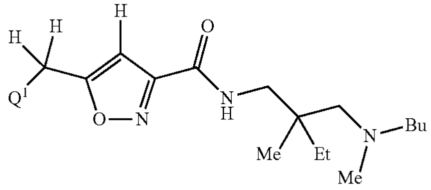
(Y-470)
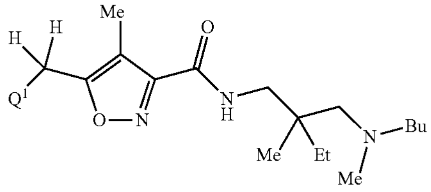
(Y-471)
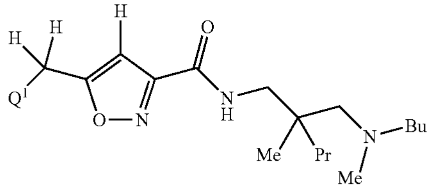
(Y-472)
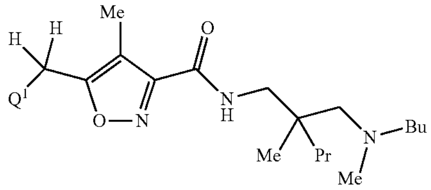
(Y-473)
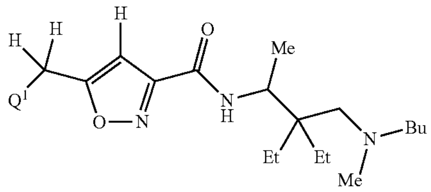
(Y-474)
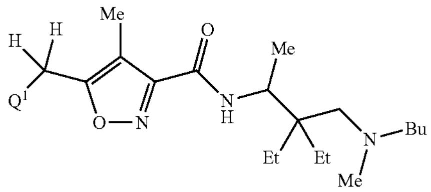
-continued
(Y-475)
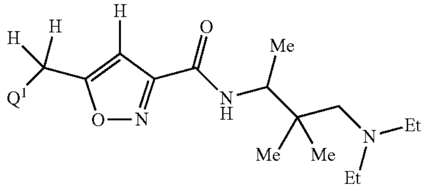
(Y-476)
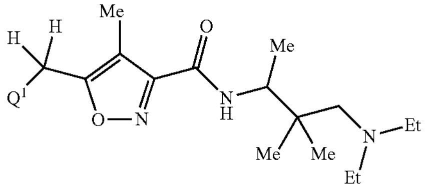
(Y-477)
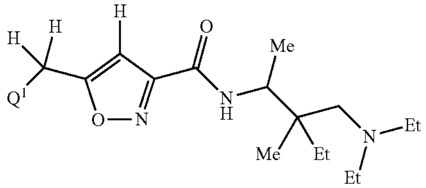
(Y-478)
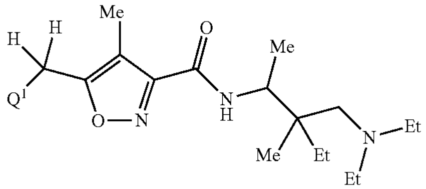
(Y-479)
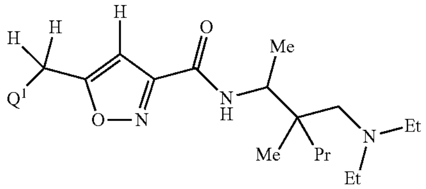
(Y-480)
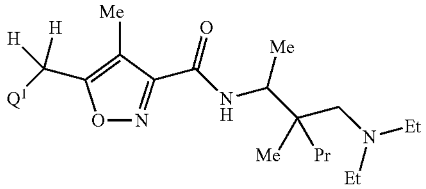
(Y-481)
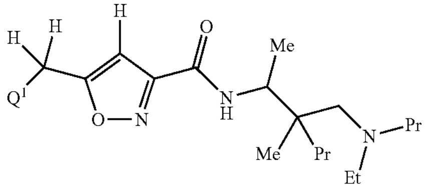
(Y-482)
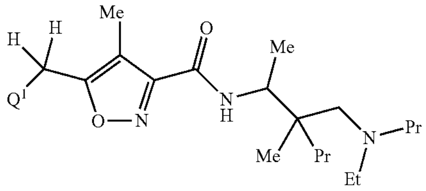

-continued
(Y-483)
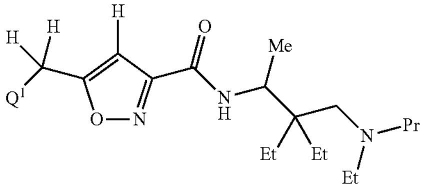
(Y-484)
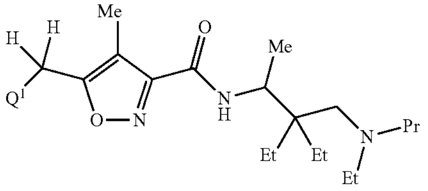
(Y-485)
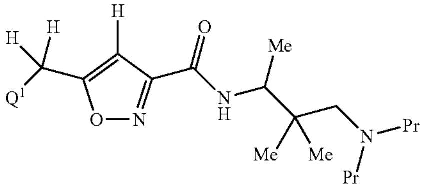
(Y-486)
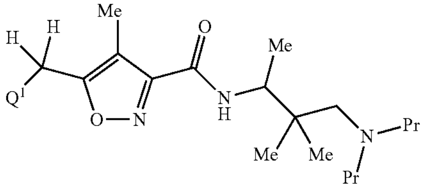
(Y-487)
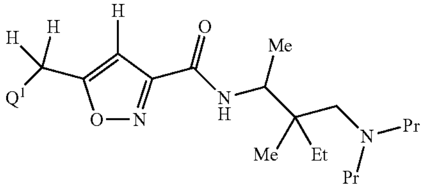
(Y-488)
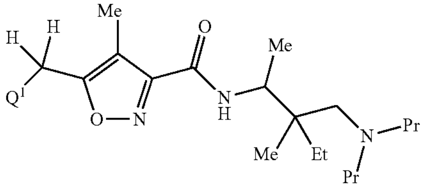
(Y-489)
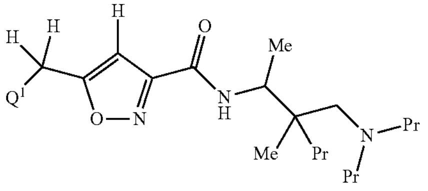
(Y-490)
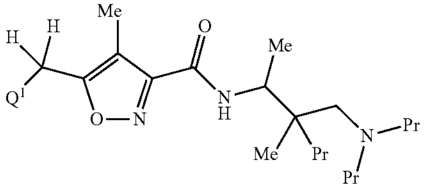
-continued
(Y-491)
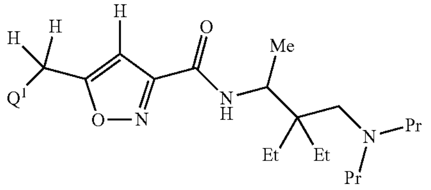
(Y-492)
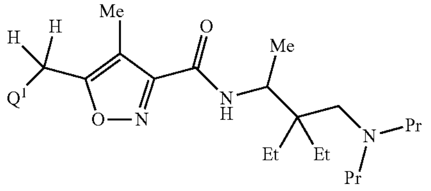
(Y-493)
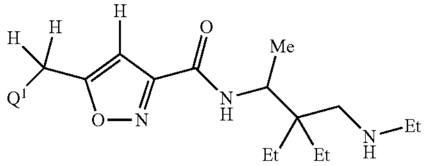
(Y-494)
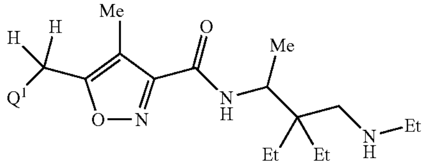
(Y-495)
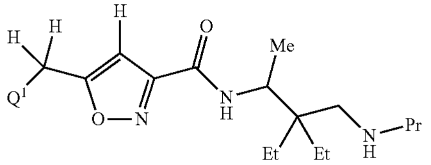
(Y-496)
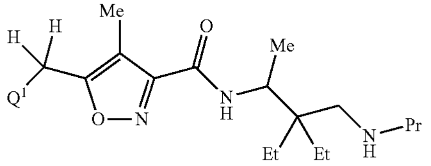
(Y-497)
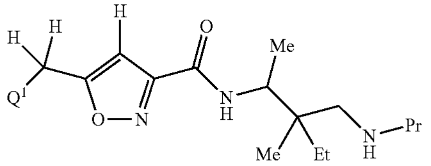
(Y-498)
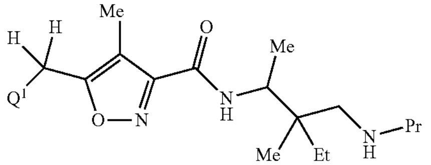
(Y-499)
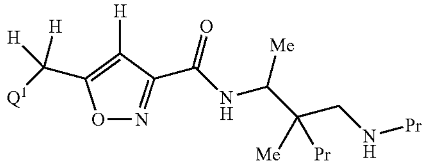

-continued
(Y-500)
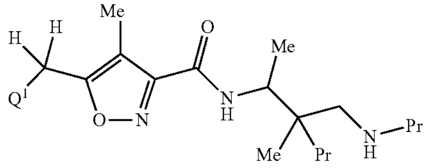
(Y-501)
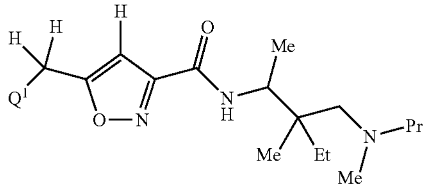
(Y-502)
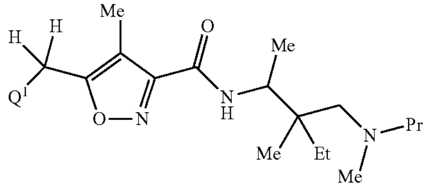
(Y-503)
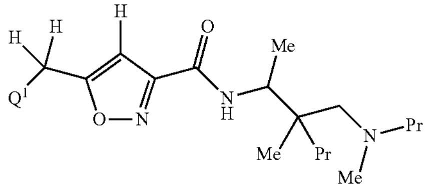
(Y-504)
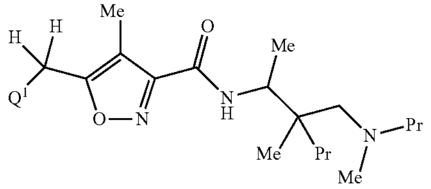
(Y-505)
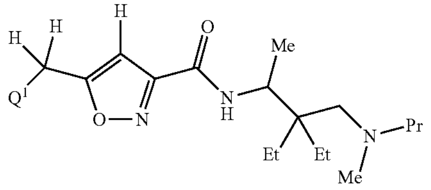
(Y-506)
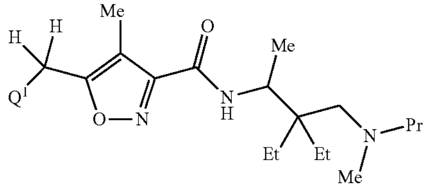
(Y-507)
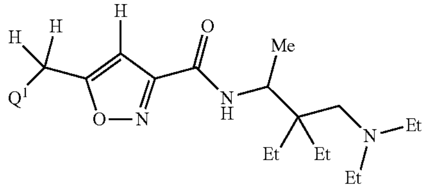
-continued
(Y-508)
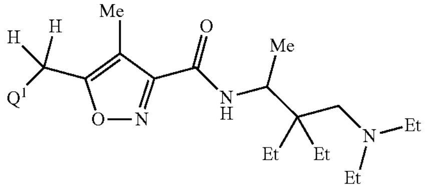
(Y-509)
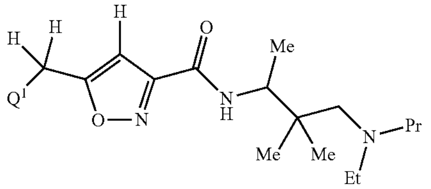
(Y-510)
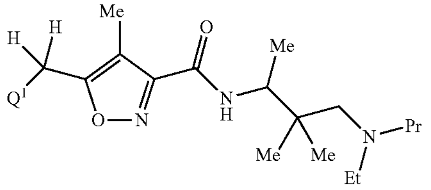
(Y-511)
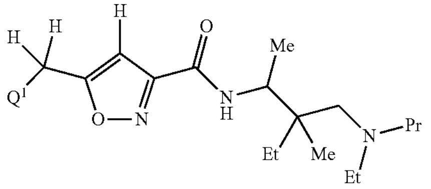
(Y-512)
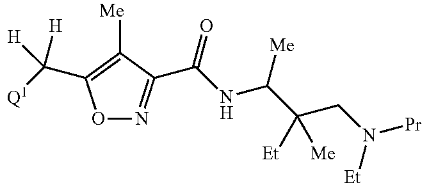
(Y-513)
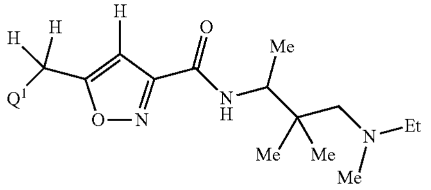
(Y-514)
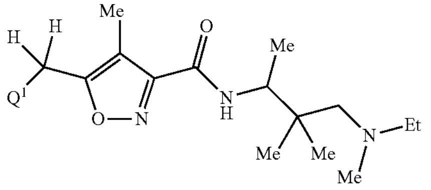
(Y-515)
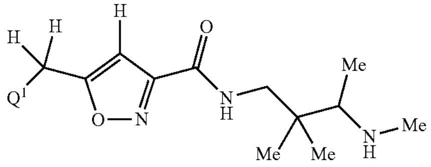

-continued
(Y-516)
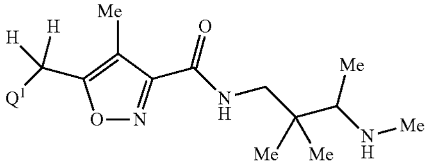
(Y-517)
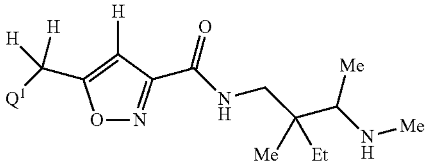
(Y-518)
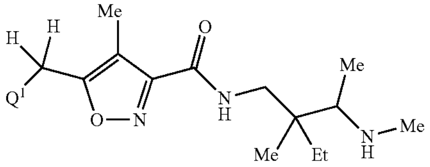
(Y-519)
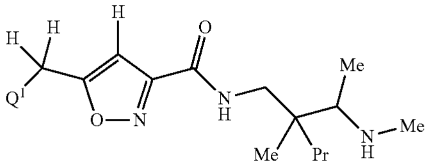
(Y-520)
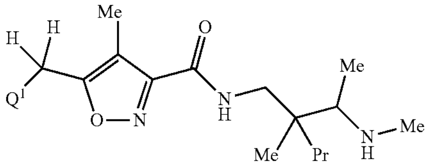
(Y-521)
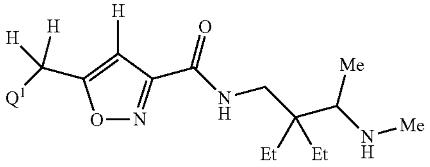
(Y-522)
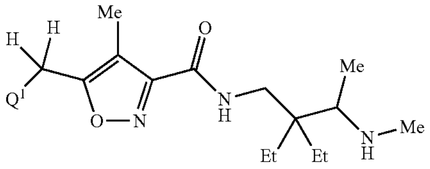
(Y-523)
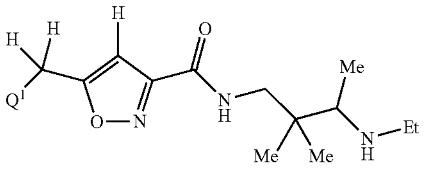
(Y-524)
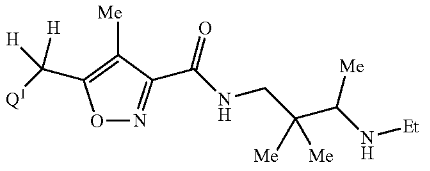
-continued
(Y-525)
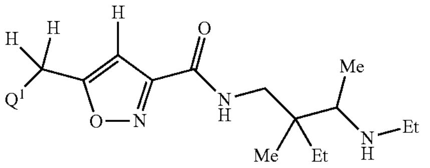
(Y-526)
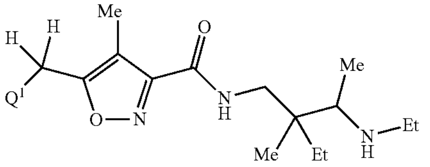
(Y-527)
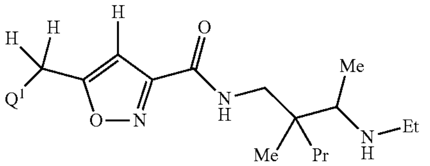
(Y-528)
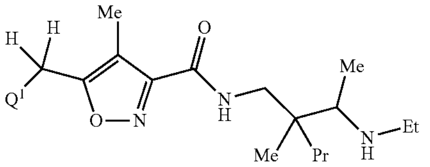
(Y-529)
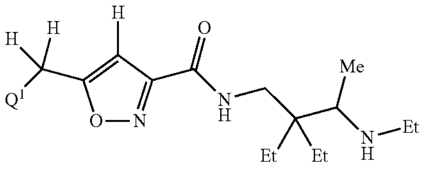
(Y-530)
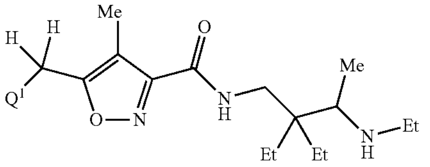
(Y-531)
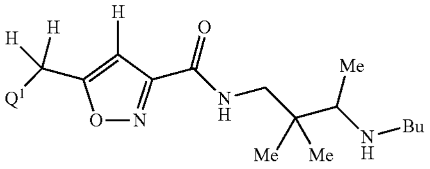
(Y-532)
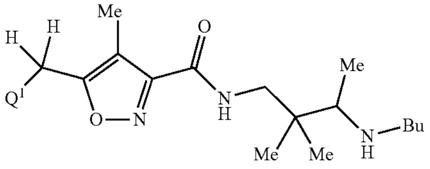
(Y-533)
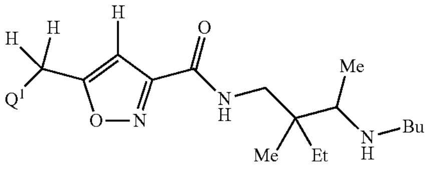

-continued
(Y-534)
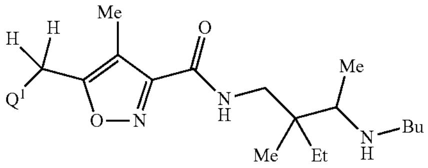
(Y-535)
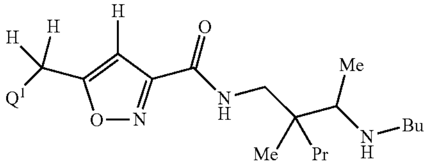
(Y-536)
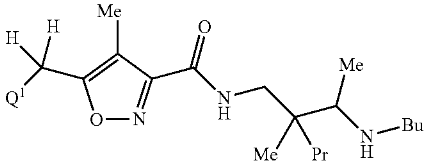
(Y-537)
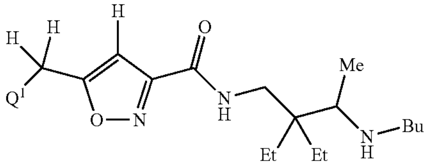
(Y-538)
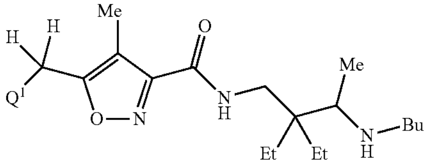
(Y-539)
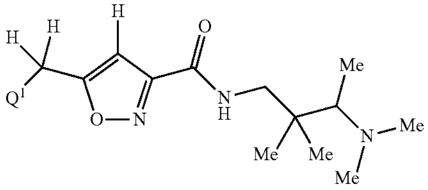
(Y-540)
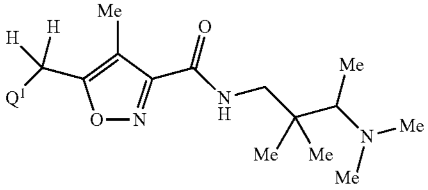
(Y-541)
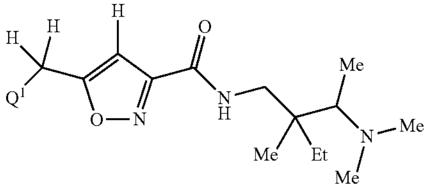
-continued
(Y-542)
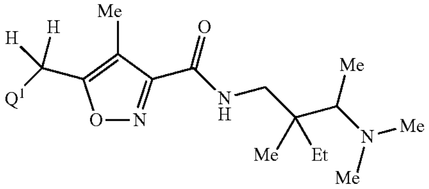
(Y-543)
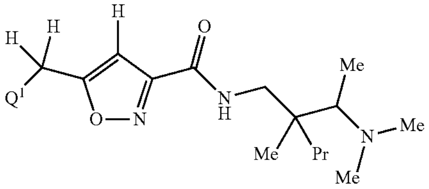
(Y-544)
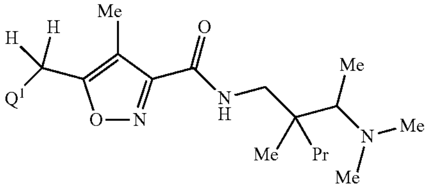
(Y-545)
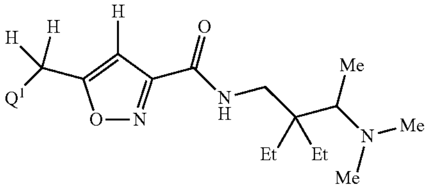
(Y-546)
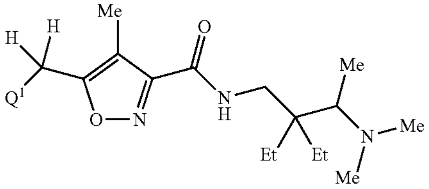
(Y-547)
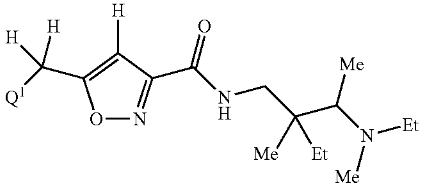
(Y-548)
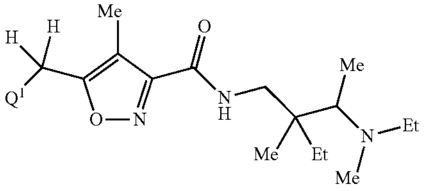
(Y-549)
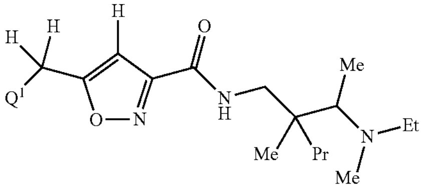

-continued
(Y-550)
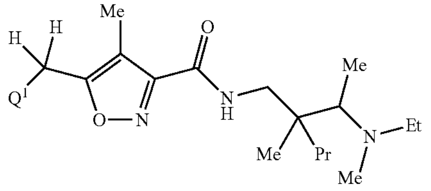
(Y-551)
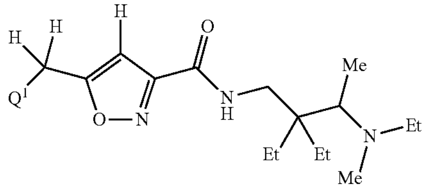
(Y-552)
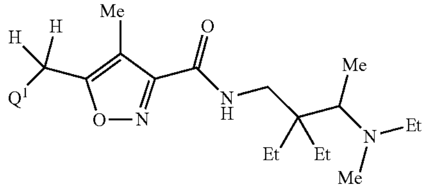
(Y-553)
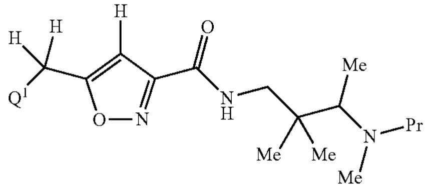
(Y-554)
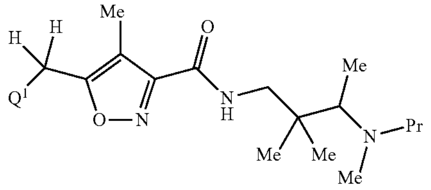
(Y-555)
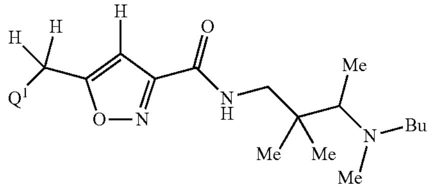
(Y-556)
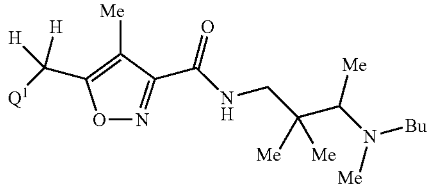
(Y-557)
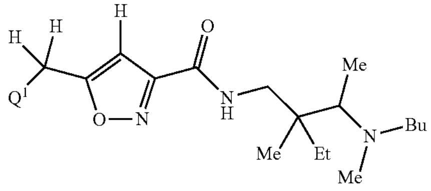
-continued
(Y-558)
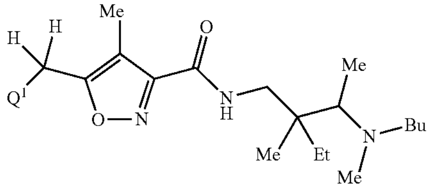
(Y-559)
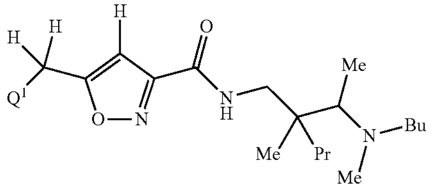
(Y-560)
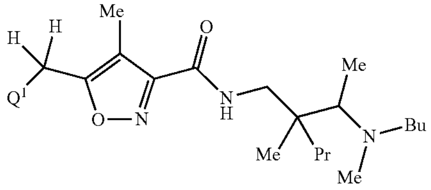
(Y-561)
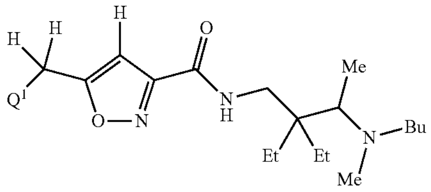
(Y-562)
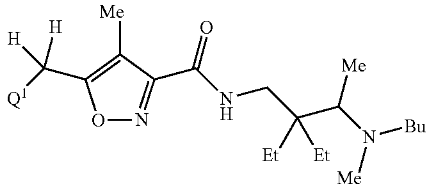
(Y-563)
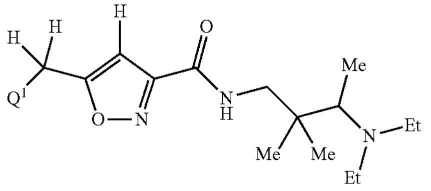
(Y-564)
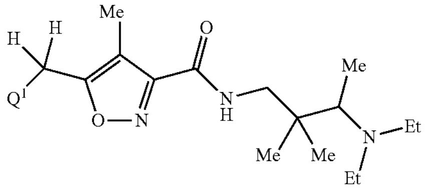
(Y-565)
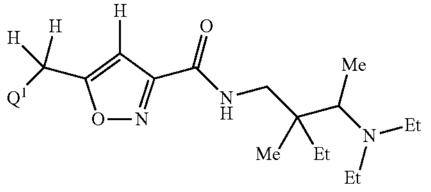

-continued
(Y-566)
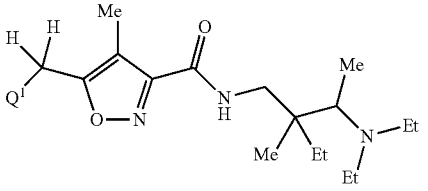
(Y-567)
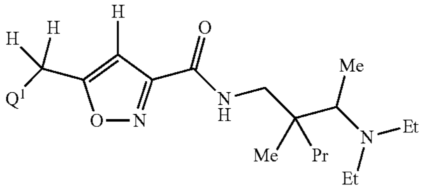
(Y-568)
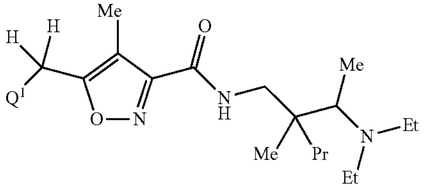
(Y-569)
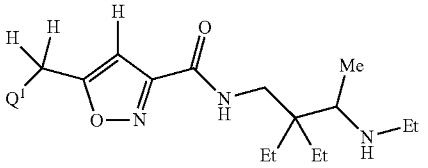
(Y-570)
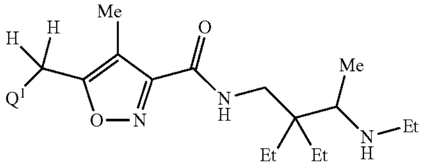
(Y-571)
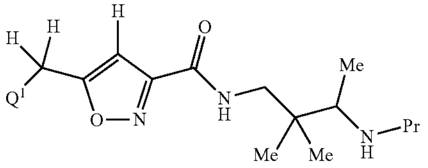
(Y-572)
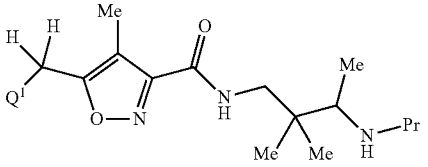
(Y-573)
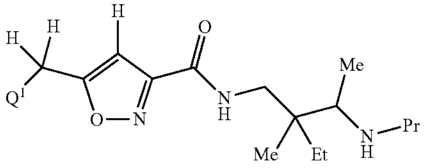
-continued
(Y-574)
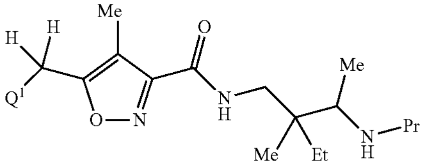
(Y-575)
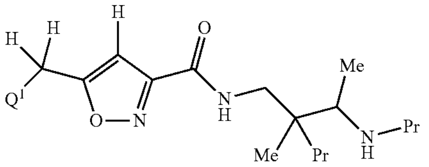
(Y-576)
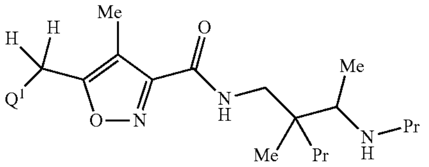
(Y-577)
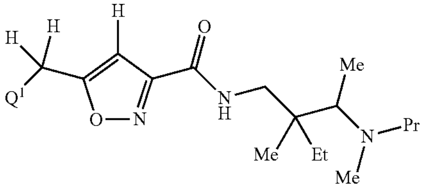
(Y-578)
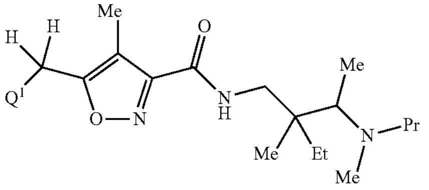
(Y-579)
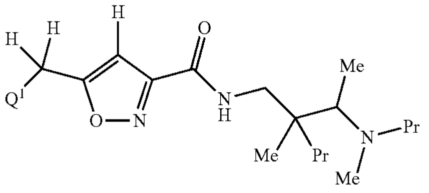
(Y-580)
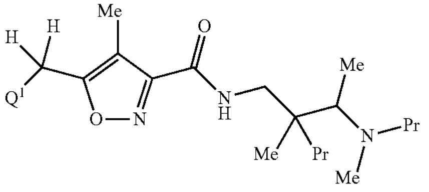
(Y-581)
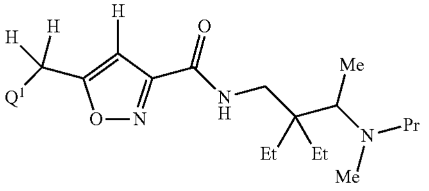

-continued
(Y-582)
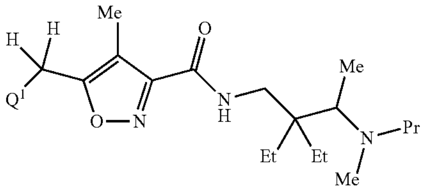
(Y-583)
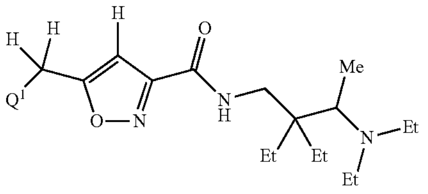
(Y-584)
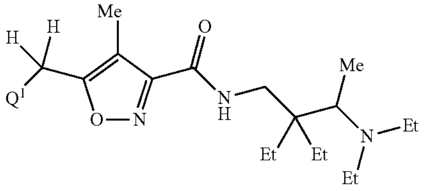
(Y-585)
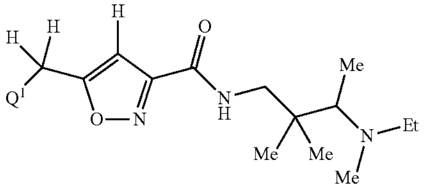
(Y-586)
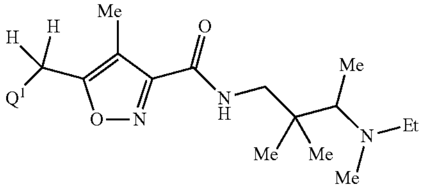
(Y-587)
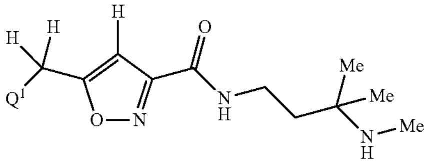
(Y-588)
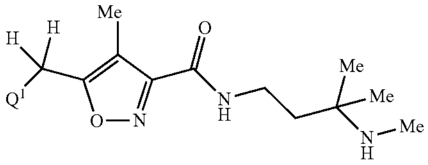
(Y-589)
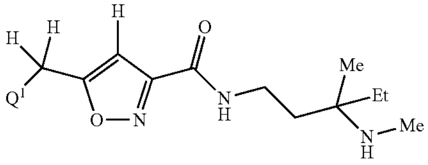
-continued
(Y-590)
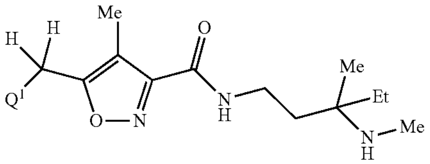
(Y-591)
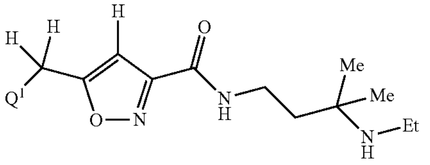
(Y-592)
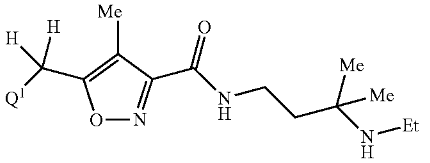
(Y-593)
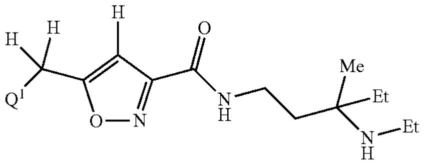
(Y-594)
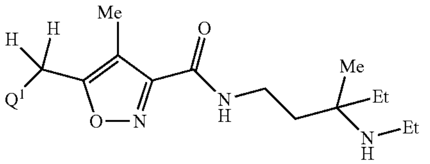
(Y-595)
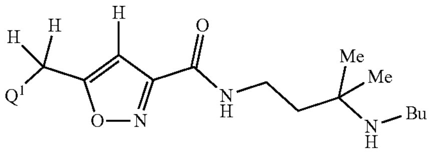
(Y-596)
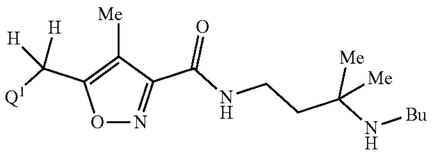
(Y-597)
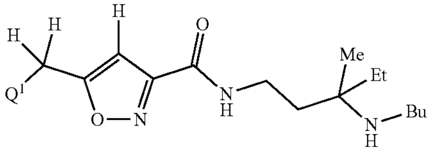
(Y-598)
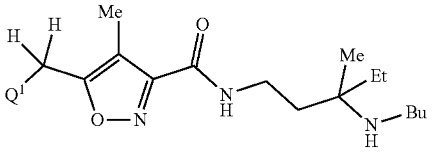

-continued
(Y-599)
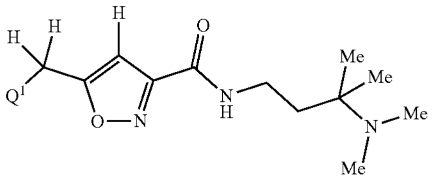
(Y-600)
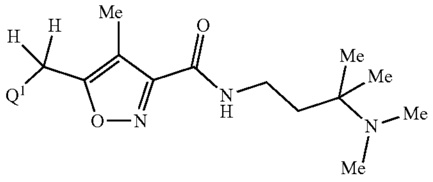
(Y-601)
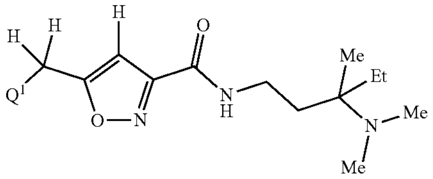
(Y-602)
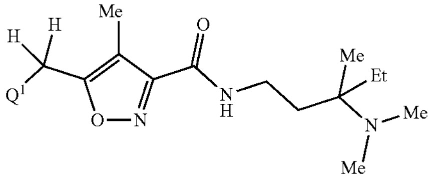
(Y-603)
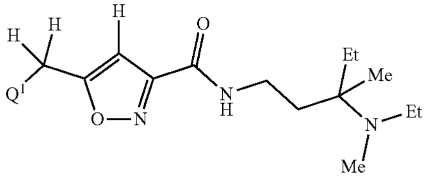
(Y-604)
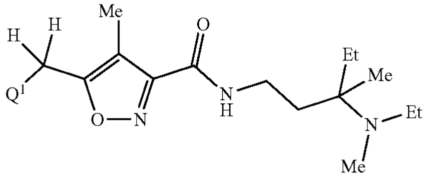
(Y-605)
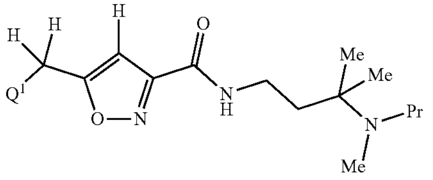
(Y-606)
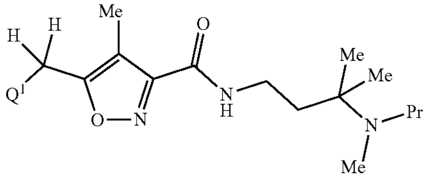
-continued
(Y-607)
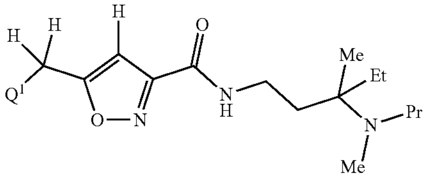
(Y-608)
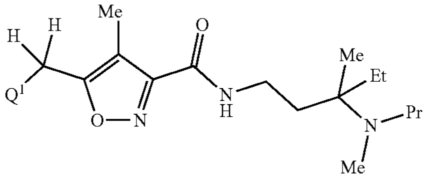
(Y-609)
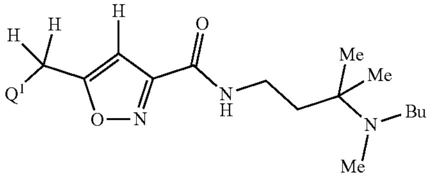
(Y-610)
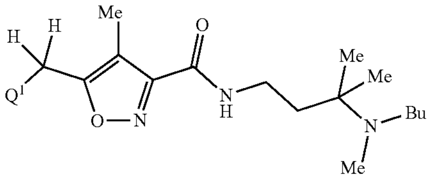
(Y-611)
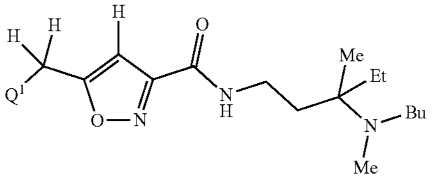
(Y-612)
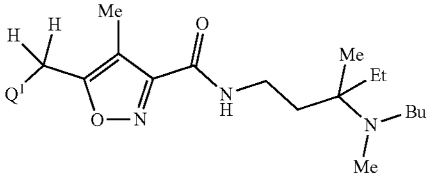
(Y-613)
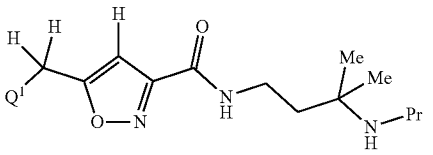
(Y-614)
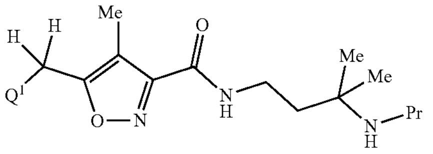
(Y-615)
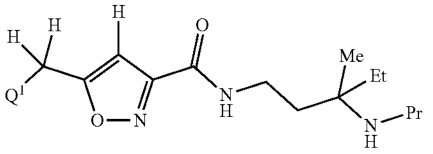

-continued
(Y-616)
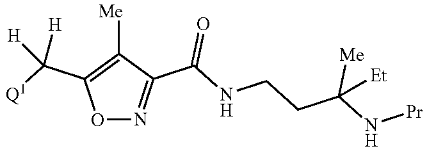
(Y-617)
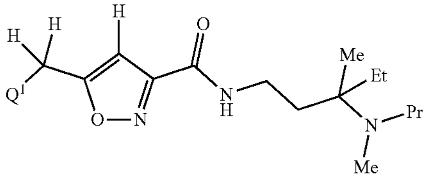
(Y-618)
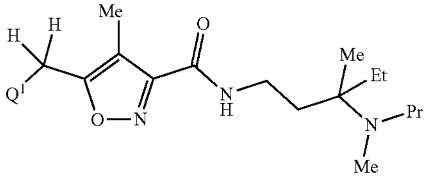
(Y-619)
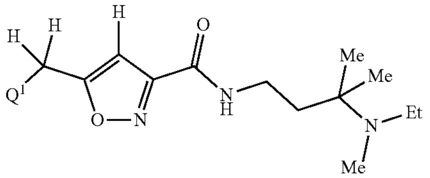
(Y-620)
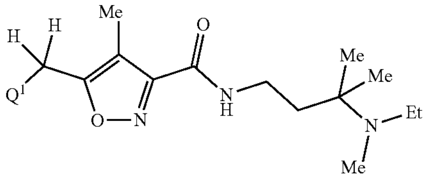
(Y-621)
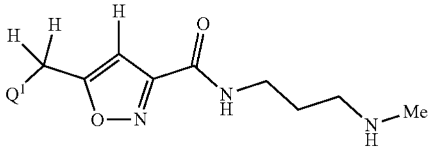
(Y-622)
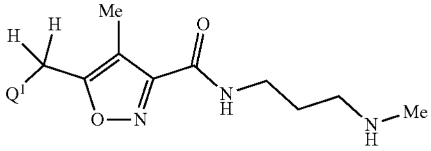
(Y-623)
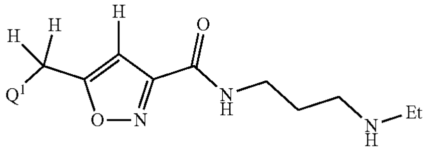
(Y-624)
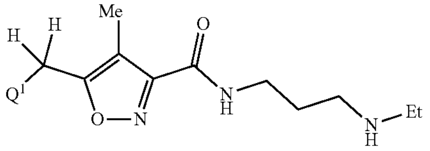
-continued
(Y-625)
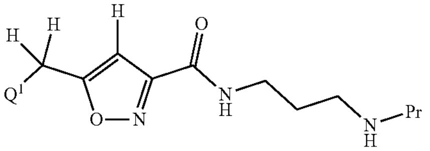
(Y-626)
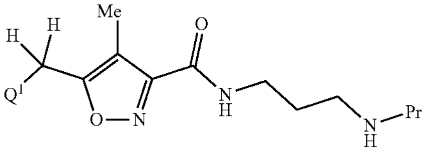
(Y-627)
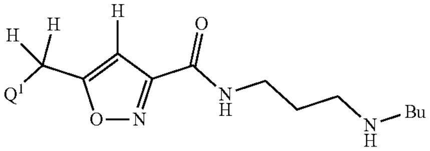
(Y-628)
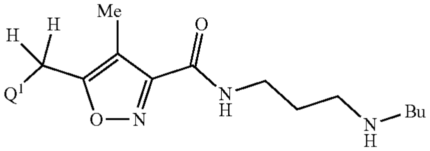
(Y-629)
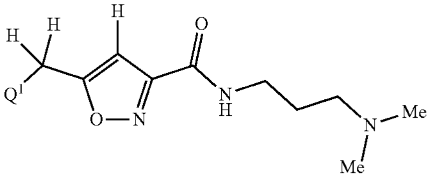
(Y-630)
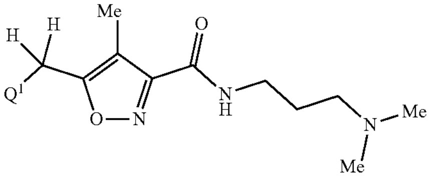
(Y-631)
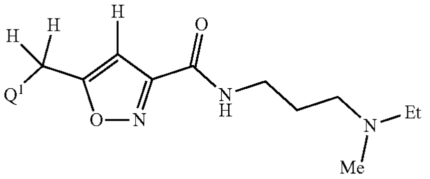
(Y-632)
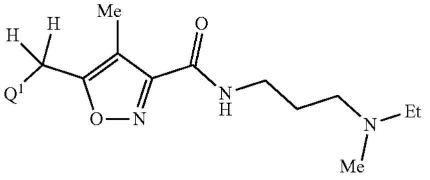
(Y-633)
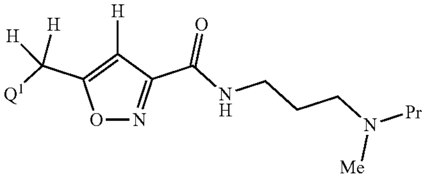

-continued
(Y-634)
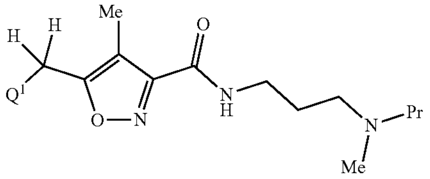
(Y-635)
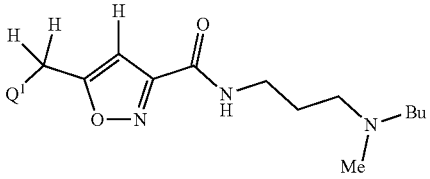
(Y-636)
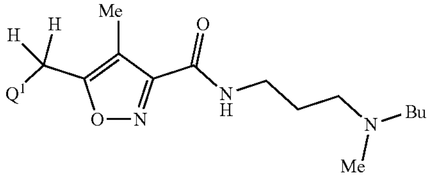
(Y-637)
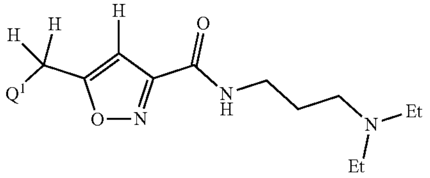
(Y-638)
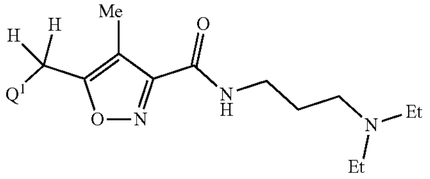
(Y-639)
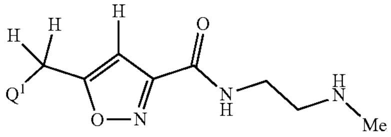
(Y-640)
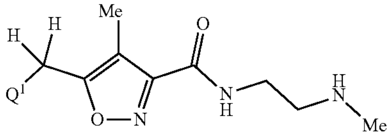
(Y-641)
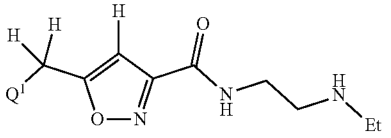
(Y-642)
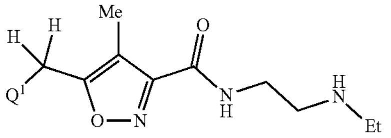
-continued
(Y-643)
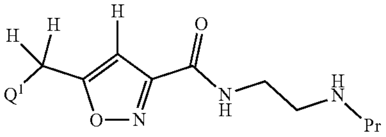
(Y-644)
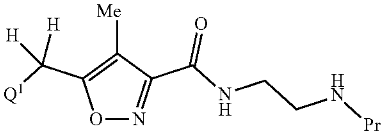
(Y-645)
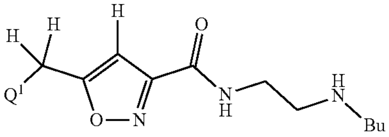
(Y-646)
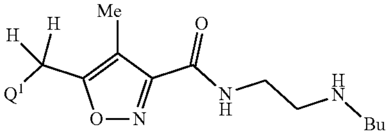
(Y-647)
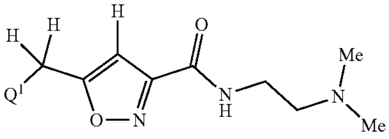
(Y-648)
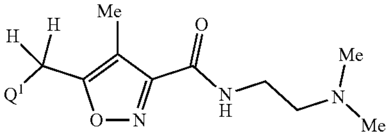
(Y-649)
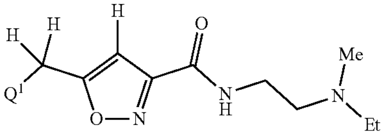
(Y-650)
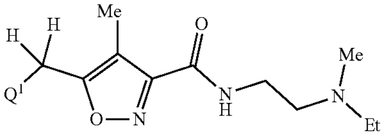
(Y-651)
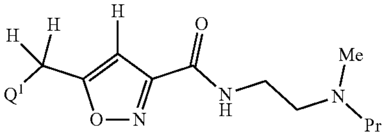
(Y-652)
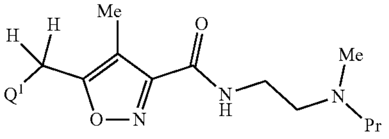
(Y-653)
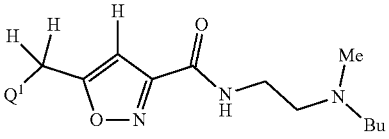

-continued
(Y-654)
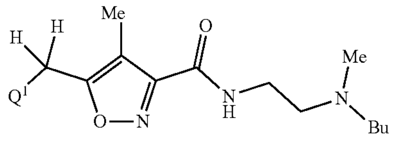
(Y-655)
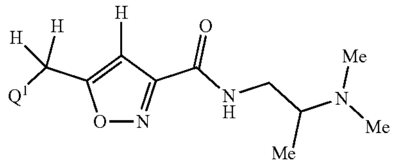
(Y-656)
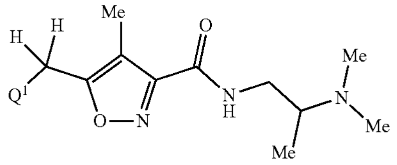
(Y-657)
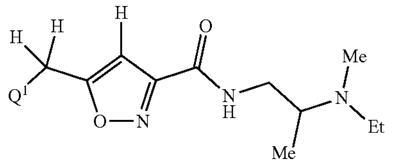
(Y-658)
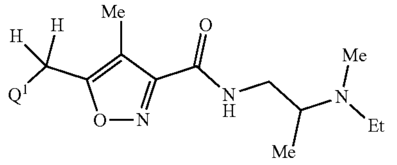
(Y-659)
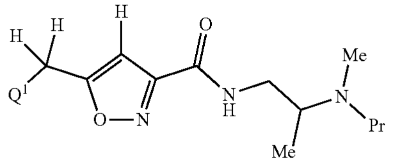
(Y-660)
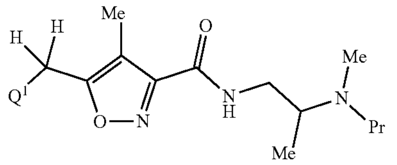
(Y-661)
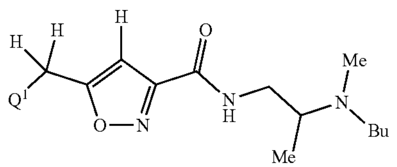
(Y-662)
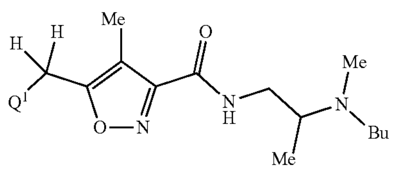
-continued
(Y-663)
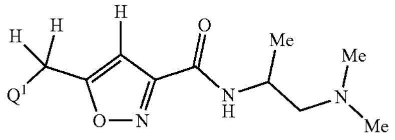
(Y-664)
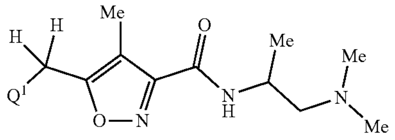
(Y-665)
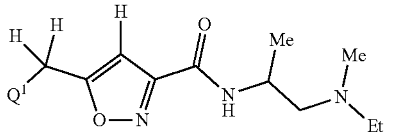
(Y-666)
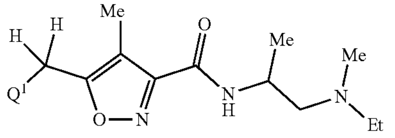
(Y-667)
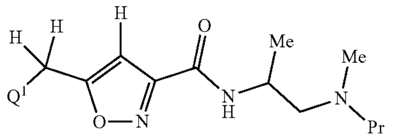
(Y-668)
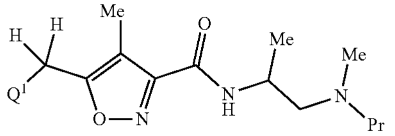
(Y-669)
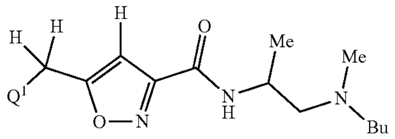
(Y-670)
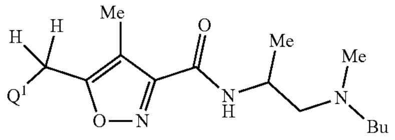
(Y-671)
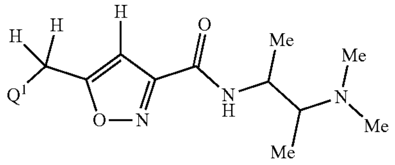
(Y-672)
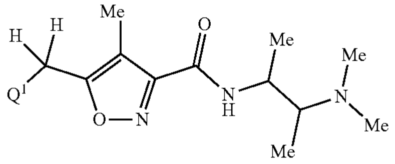

-continued
(Y-673)
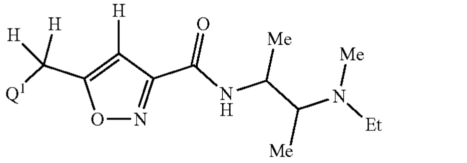
(Y-674)
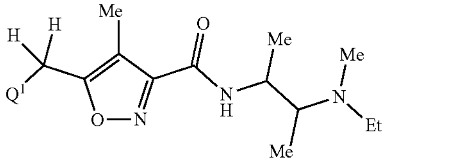
(Y-675)
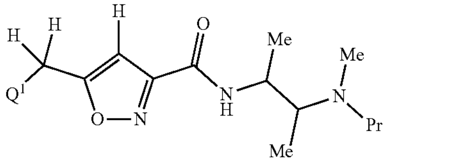
(Y-676)
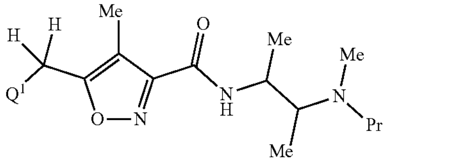
(Y-677)
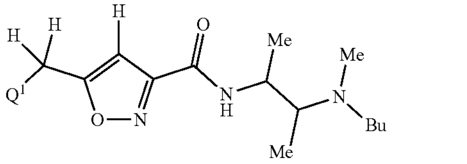
(Y-678)
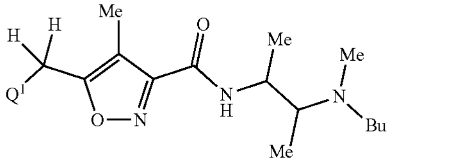
(Y-679)
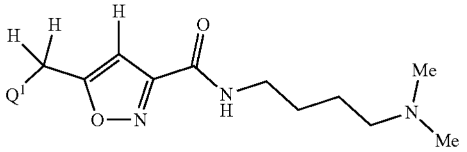
(Y-680)
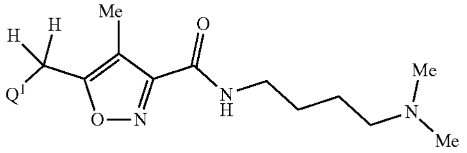
(Y-681)
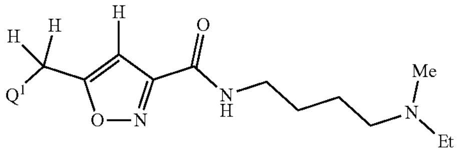
-continued
(Y-682)
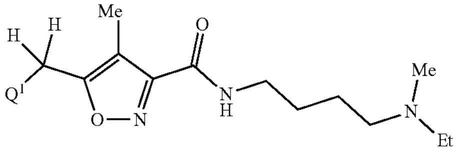
(Y-683)
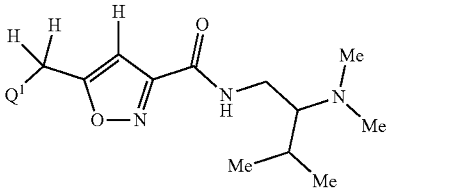
(Y-684)
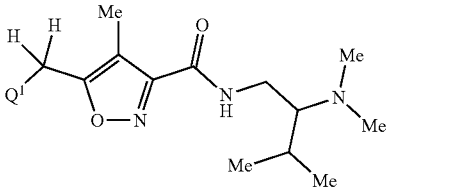
(Y-685)
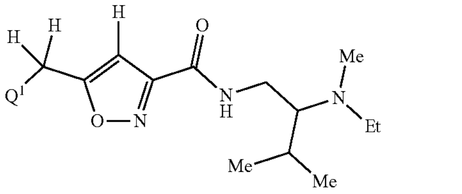
(Y-686)
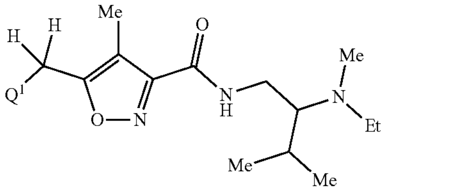
(Y-939)
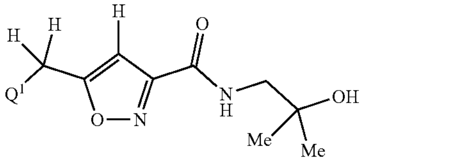
(Y-940)
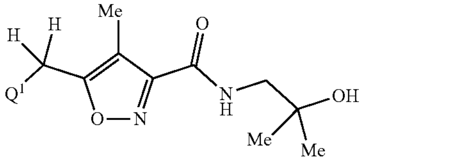
(Y-941)
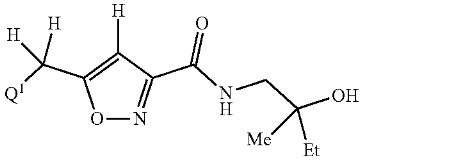

-continued (Y-942)

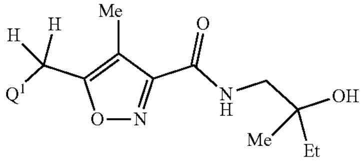

(Y-943)

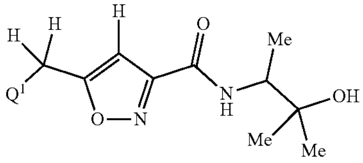

(Y-944)

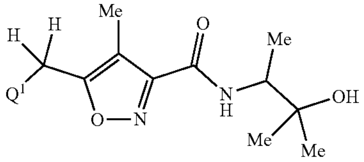

(Y-945)

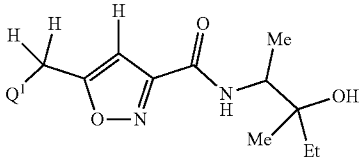

(Y-946)

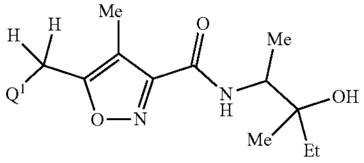

In formula (Y-1) to formula (Y-44), formula (Y-75) to formula (Y-686) and formula (Y-939) to formula (Y-946), Q$^1$ represents the following:

[Q$^1$]=[Et], [Pr], [Bu], [CH$_2$CH$_2$CH$_2$CH$_2$CH$_3$], [CH$_2$CF$_3$], [CH$_2$CH$_2$CF$_3$], [CH$_2$CH$_2$CH$_2$CF$_3$], [CH$_2$CH$_2$CH$_2$CH$_2$CF$_3$], [Ph], [CH$_2$Ph], [CH$_2$CH$_2$Ph], [CH$_2$CH$_2$CH$_2$Ph], [CH$_2$CH$_2$CH$_2$CH$_2$Ph], [2-F-Ph], [CH$_2$(2-F-Ph)], [CH$_2$CH$_2$(2-F-Ph)], [CH$_2$CH$_2$CH$_2$(2-F-Ph)], [CH$_2$CH$_2$CH$_2$CH$_2$(2-F-Ph)], [3-F-Ph], [CH$_2$(3-F-Ph)], [CH$_2$CH$_2$(3-F-Ph)], [CH$_2$CH$_2$CH$_2$(3-F-Ph)], [CH$_2$CH$_2$CH$_2$CH$_2$(3-F-Ph)], [4-F-Ph], [CH$_2$(4-F-Ph)], [CH$_2$CH$_2$(4-F-Ph)], [CH$_2$CH$_2$CH$_2$(4-F-Ph)], [CH$_2$CH$_2$CH$_2$CH$_2$(4-F-Ph)], [2-Cl-Ph], [CH$_2$(2-Cl-Ph)], [CH$_2$CH$_2$(2-Cl-Ph)], [CH$_2$CH$_2$CH$_2$(2-Cl-Ph)], [CH$_2$CH$_2$CH$_2$CH$_2$(2-Cl-Ph)], [3-Cl-Ph], [CH$_2$(3-Cl-Ph)], [CH$_2$CH$_2$(3-Cl-Ph)], [CH$_2$CH$_2$CH$_2$(3-Cl-Ph)], [CH$_2$CH$_2$CH$_2$CH$_2$(3-Cl-Ph)], [4-Cl-Ph], [CH$_2$(4-Cl-Ph)], [CH$_2$CH$_2$(4-Cl-Ph)], [CH$_2$CH$_2$CH$_2$(4-Cl-Ph)], [CH$_2$CH$_2$CH$_2$CH$_2$(4-Cl-Ph)], [2-Br-Ph], [CH$_2$(2-Br-Ph)], [CH$_2$CH$_2$(2-Br-Ph)], [CH$_2$CH$_2$CH$_2$(2-Br-Ph)], [CH$_2$CH$_2$CH$_2$CH$_2$(2-Br-Ph)], [3-Br-Ph], [CH$_2$(3-Br-Ph)], [CH$_2$CH$_2$(3-Br-Ph)], [CH$_2$CH$_2$CH$_2$(3-Br-Ph)], [CH$_2$CH$_2$CH$_2$CH$_2$(3-Br-Ph)], [4-Br-Ph], [CH$_2$(4-Br-Ph)], [CH$_2$CH$_2$(4-Br-Ph)], [CH$_2$CH$_2$CH$_2$(4-Br-Ph)], [CH$_2$CH$_2$CH$_2$CH$_2$(4-Br-Ph)], [3-Br-5-F-Ph], [CH$_2$(3-Br-5-F-Ph)], [CH$_2$CH$_2$(3-Br-5-F-Ph)], [CH$_2$CH$_2$CH$_2$(3-Br-5-F-Ph)], [CH$_2$CH$_2$CH$_2$CH$_2$(3-Br-5-F-Ph)], [2-CF$_3$-Ph], [CH$_2$(2-CF$_3$-Ph)], [CH$_2$CH$_2$(2-CF$_3$-Ph)], [CH$_2$CH$_2$CH$_2$(2-CF$_3$-Ph)], [CH$_2$CH$_2$CH$_2$CH$_2$(2-CF$_3$-Ph)], [3-CF$_3$-Ph], [CH$_2$(3-CF$_3$-Ph)], [CH$_2$CH$_2$(3-CF$_3$-Ph)], [CH$_2$CH$_2$CH$_2$(3-CF$_3$-Ph)], [CH$_2$CH$_2$CH$_2$CH$_2$(3-CF$_3$-Ph)], [4-CF$_3$-Ph], [CH$_2$(4-CF$_3$-Ph)], [CH$_2$CH$_2$(4-CF$_3$-Ph)], [CH$_2$CH$_2$CH$_2$(4-CF$_3$-Ph)], [CH$_2$CH$_2$CH$_2$CH$_2$(4-CF$_3$-Ph)], [2-OCF$_3$-Ph], [CH$_2$(2-OCF$_3$-Ph)], [CH$_2$CH$_2$(2-OCF$_3$-Ph)], [CH$_2$CH$_2$CH$_2$(2-OCF$_3$-Ph)], [CH$_2$CH$_2$CH$_2$CH$_2$(2-OCF$_3$-Ph)], [ 3-OCF$_3$-Ph], [CH$_2$(3-OCF$_3$-Ph)], [CH$_2$CH$_2$(3-OCF$_3$-Ph)], [CH$_2$CH$_2$CH$_2$(3-OCF$_3$-Ph)], [CH$_2$CH$_2$CH$_2$CH$_2$(3-OCF$_3$-Ph)], [OCF$_3$-Ph], [CH$_2$(4-OCF$_3$-Ph)], [CH$_2$CH$_2$(4-OCF$_3$-Ph)], [CH$_2$CH$_2$CH$_2$(4-OCF$_3$-Ph)], [CH$_2$CH$_2$CH$_2$CH$_2$(4-OCF$_3$-Ph)], [2-SCF$_3$-Ph], [CH$_2$(2-SCF$_3$-Ph)], [CH$_2$CH$_2$(2-SCF$_3$-Ph)], [CH$_2$CH$_2$CH$_2$(2-SCF$_3$-Ph)], [CH$_2$CH$_2$CH$_2$CH$_2$(2-SCF$_3$-Ph)], [3-SCF$_3$-Ph], [CH$_2$(3-SCF$_3$-Ph)], [CH$_2$CH$_2$(3-SCF$_3$-Ph)], [CH$_2$CH$_2$CH$_2$(3-SCF$_3$-Ph)], [CH$_2$CH$_2$CH$_2$CH$_2$(3-SCF$_3$-Ph)], [ 4-SCF$_3$-Ph], [CH$_2$(4-SCF$_3$-Ph)], [CH$_2$CH$_2$(4-SCF$_3$-Ph)], [CH$_2$CH$_2$CH$_2$(4-SCF$_3$-Ph)], [CH$_2$CH$_2$CH$_2$CH$_2$(4-SCF$_3$-Ph)], [NA1], [CH$_2$(NA1)], [CH$_2$CH$_2$(NA1)], [CH$_2$CH$_2$CH$_2$(NA1)], [CH$_2$CH$_2$CH$_2$CH$_2$(NA1)], [NA2], [CH$_2$(NA2)], [CH$_2$CH$_2$(NA2)], [CH$_2$CH$_2$CH$_2$(NA2)], [8-F-NA2], [CH$_2$(8-F-NA2)], [CH$_2$CH$_2$(8-F-NA2)], [CH$_2$CH$_2$CH$_2$(8-F-NA2)], [8-Cl-NA2], [CH$_2$(8-Cl-NA2)], [CH$_2$CH$_2$(8-Cl—N-A2)], [CH$_2$CH$_2$CH$_2$(8-Cl-NA2)], [8-Br-NA2], [CH$_2$(8-Br-NA2)], [CH$_2$CH$_2$(8-Br-NA2)], [CH$_2$CH$_2$CH$_2$(8-Br-NA2)], [CH$_2$CH$_2$OPh], [CH$_2$CH$_2$OCH$_2$Ph], [CH$_2$CH$_2$CH$_2$OPh], [CH$_2$CH$_2$CH$_2$OCH$_2$Ph], [CH$_2$CH$_2$CH$_2$CH$_2$OPh], [CH$_2$CH$_2$CH$_2$CH$_2$OCH$_2$Ph], [CH$_2$CH$_2$CH$_2$CH$_2$CH$_2$OPh], [CH$_2$CH$_2$CH$_2$CH$_2$CH$_2$OCH$_2$Ph], [CH$_2$CH$_2$O(NA2)], [CH$_2$CH$_2$OCH$_2$(NA2)], [CH$_2$CH$_2$CH$_2$O(NA2)], [CH$_2$CH$_2$CH$_2$OCH$_2$(NA2)], [CH$_2$CH$_2$CH$_2$CH$_2$O(NA2)], [CH$_2$CH$_2$CH$_2$CH$_2$OCH$_2$(NA2)], [CH$_2$CH$_2$CH$_2$CH$_2$CH$_2$O(NA2)], [CH$_2$CH$_2$CH$_2$CH$_2$CH$_2$OCH$_2$(NA2)], [CH$_2$CH$_2$(IN1)], [CH$_2$CH$_2$(IN2)], [CH$_2$CH$_2$(Py2)], [CH$_2$CH$_2$(Qun2)], [CH$_2$CH$_2$(Fur2)], [CH$_2$CH$_2$(Thi2)], [CH$_2$CH$_2$(BF5)], [CH$_2$CH$_2$(BF2)], [CH$_2$CH$_2$(BT5)], [CH$_2$CH$_2$(BT2)], [CH$_2$CH$_2$(BDXO5)], [CH$_2$CH$_2$(BDXA6)], [CH$_2$CH$_2$(3Cy)], [CH$_2$CH$_2$(5Cy)], [CH$_2$CH$_2$(8Cy)], [CH$_2$CH$_2$(2, 2-F$_2$-3Cy], [CH$_2$CH$_2$(2-CN-3Cy], [CH$_2$CH$_2$(2, 2-F$_2$-BDXO5], [CH$_2$CH$_2$(2, 2-F$_2$-3Cy)], [IN1], [Py2], [Thi2], [3Cy], [5Cy]

(Y-45)

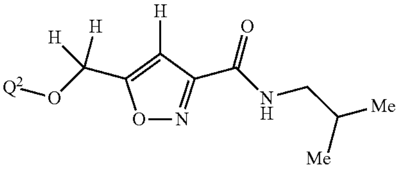

(Y-46)

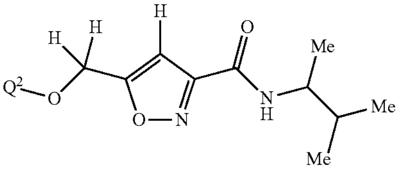

(Y-47)

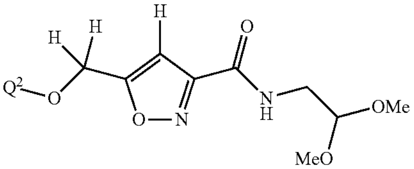

-continued
(Y-48)
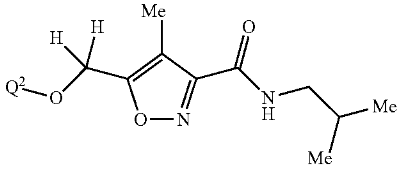
(Y-49)
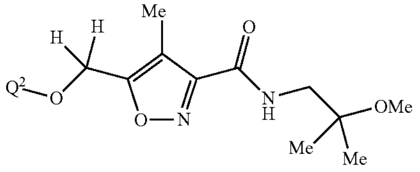
(Y-50)
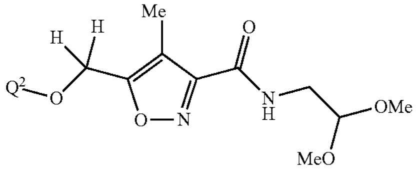
(Y-51)
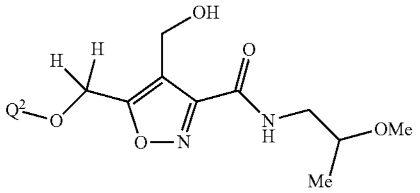
(Y-52)
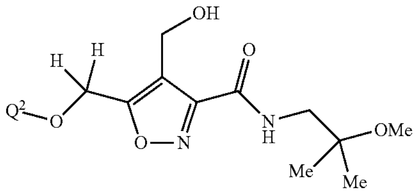
(Y-53)
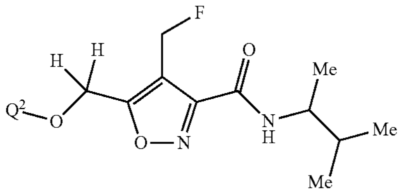
(Y-54)
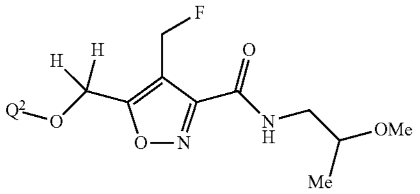
(Y-55)
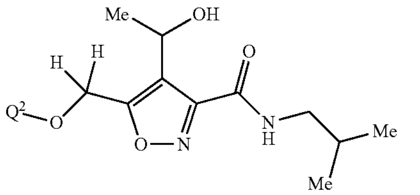
-continued
(Y-56)
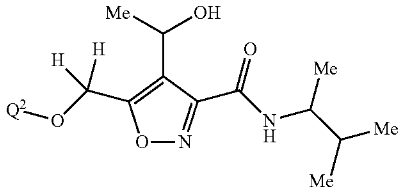
(Y-57)
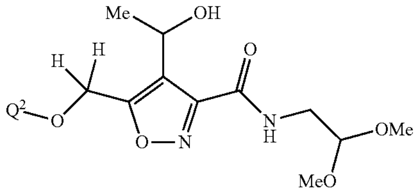
(Y-58)
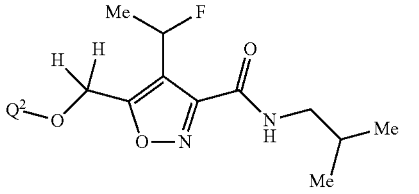
(Y-59)
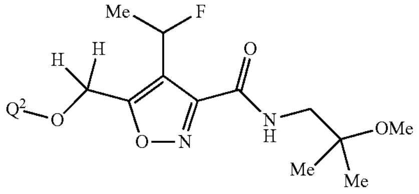
(Y-60)
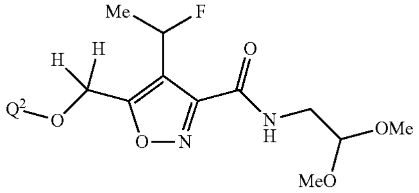
(Y-61)
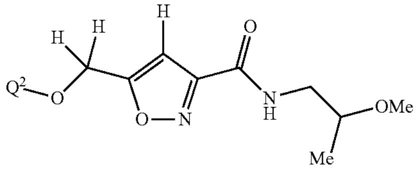
(Y-62)
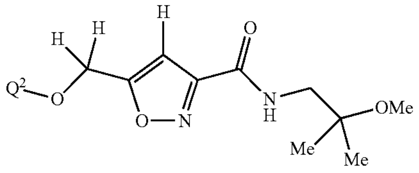
(Y-63)
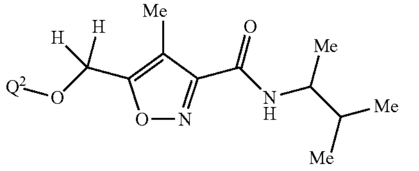

-continued
(Y-64)
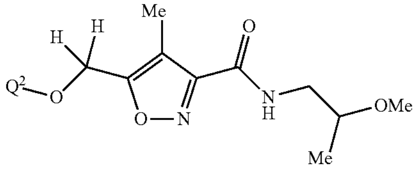
(Y-65)
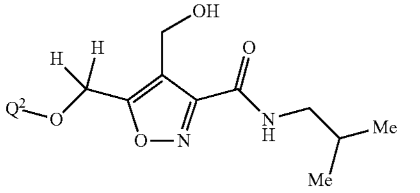
(Y-66)
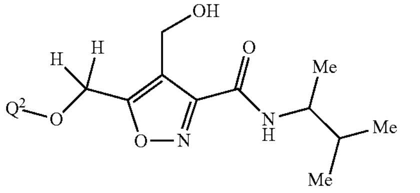
(Y-67)
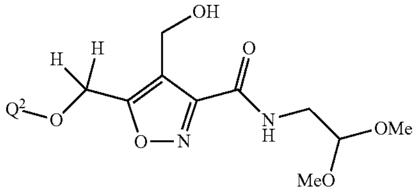
(Y-68)
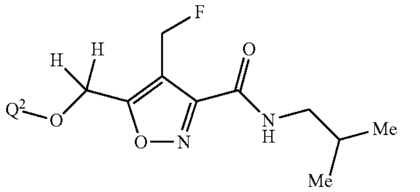
(Y-69)
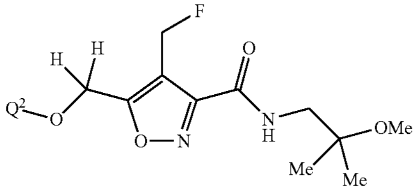
(Y-70)
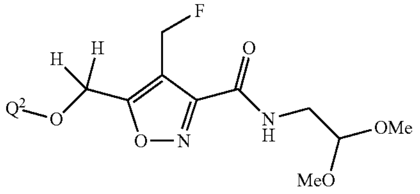
(Y-71)
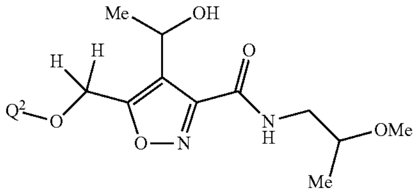
-continued
(Y-72)
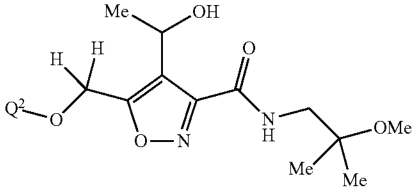
(Y-73)
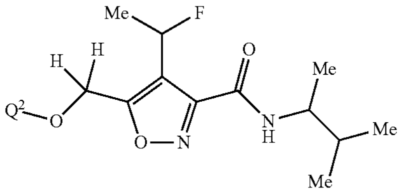
(Y-74)
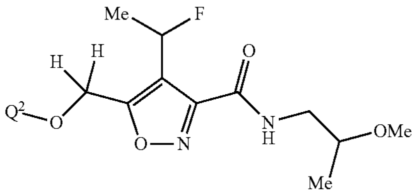
(Y-687)
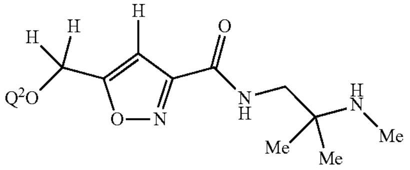
(Y-688)
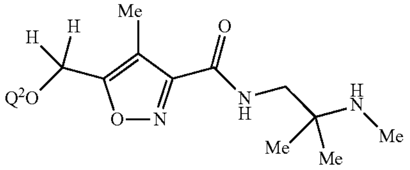
(Y-689)
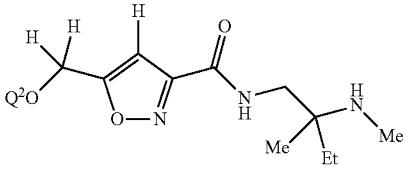
(Y-690)
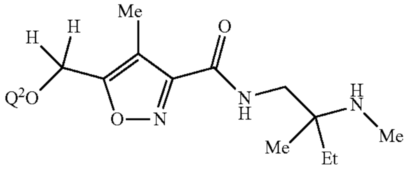
(Y-691)
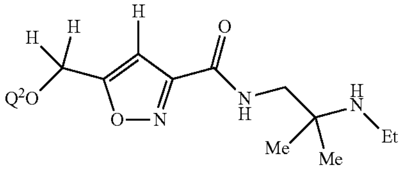

-continued
(Y-692)
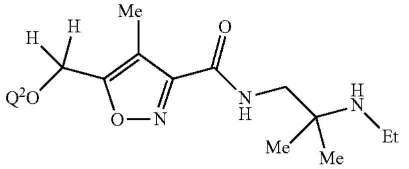
(Y-693)
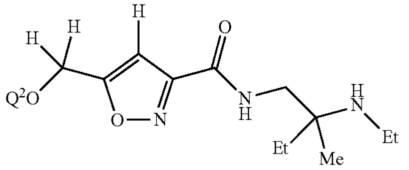
(Y-694)
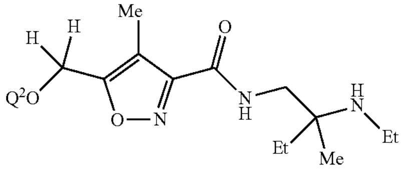
(Y-695)
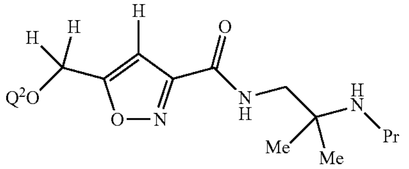
(Y-696)
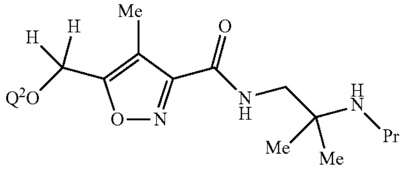
(Y-697)
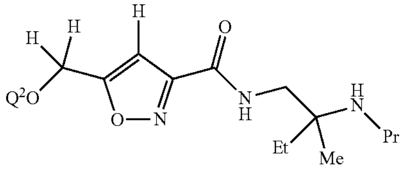
(Y-698)
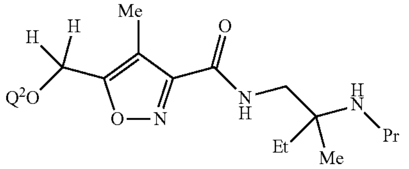
(Y-699)
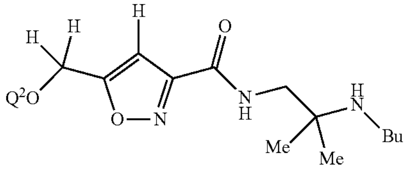
(Y-700)
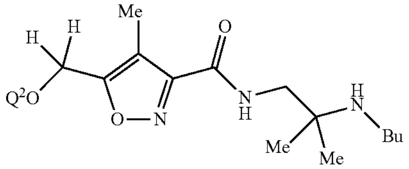
-continued
(Y-701)
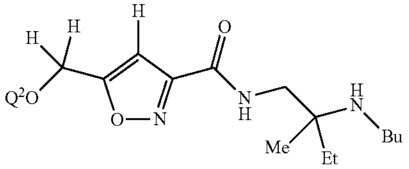
(Y-702)
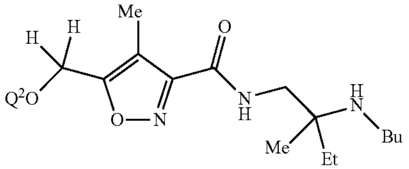
(Y-703)
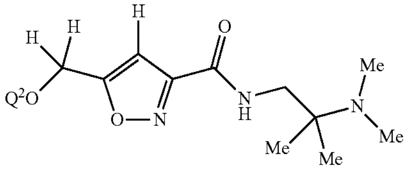
(Y-704)
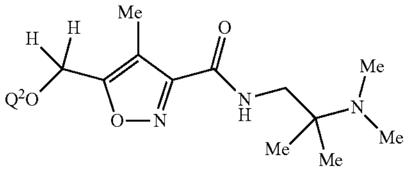
(Y-705)
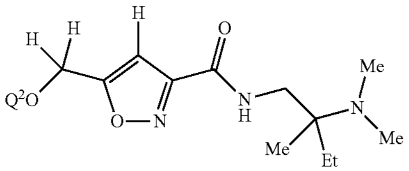
(Y-706)
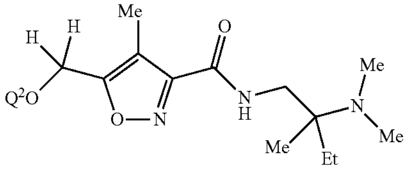
(Y-707)
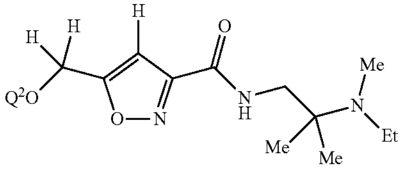
(Y-708)
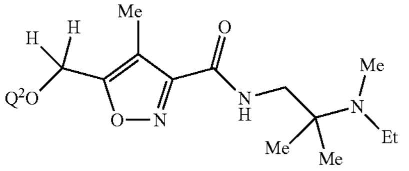
(Y-709)
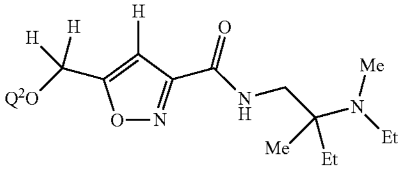

-continued
(Y-710)
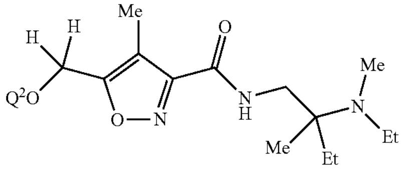
(Y-711)
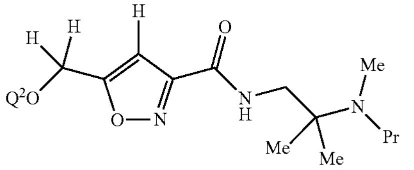
(Y-712)
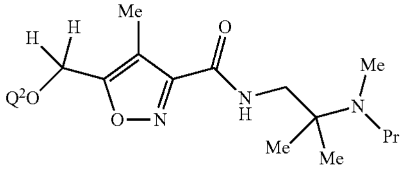
(Y-713)
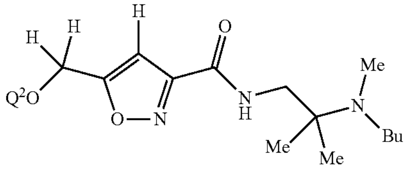
(Y-714)
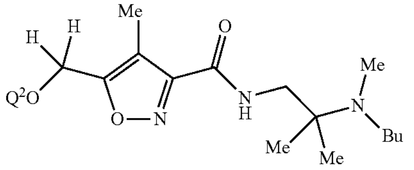
(Y-715)
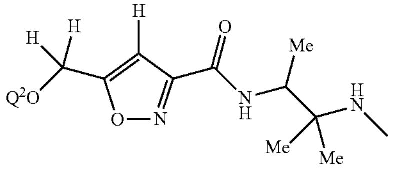
(Y-716)
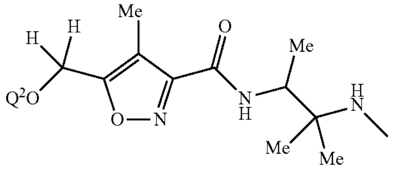
(Y-717)
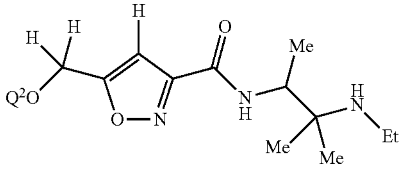
(Y-718)
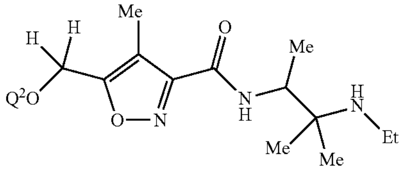
-continued
(Y-719)
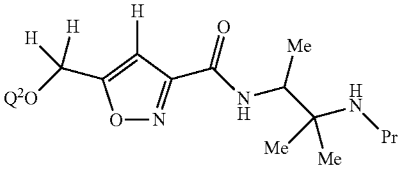
(Y-720)
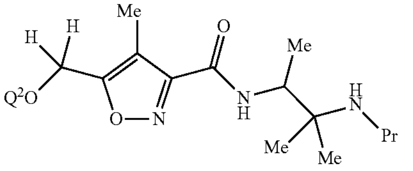
(Y-721)
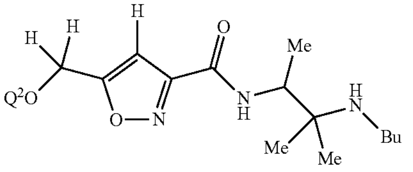
(Y-722)
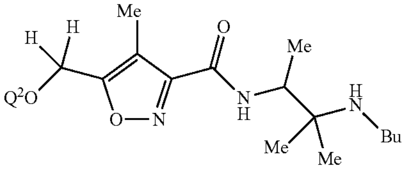
(Y-723)
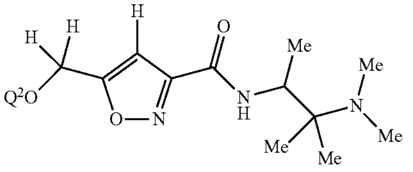
(Y-724)
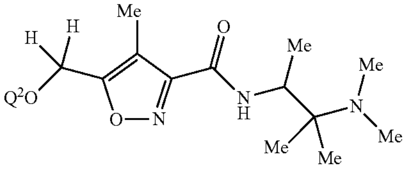
(Y-725)
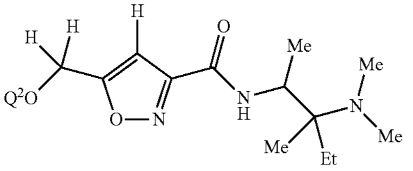
(Y-726)
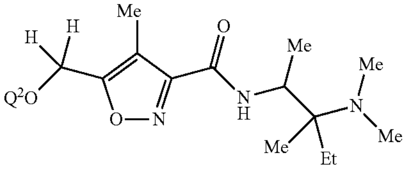
(Y-727)
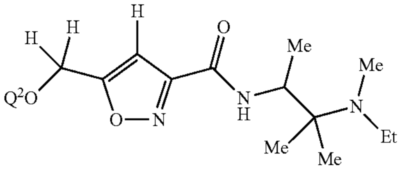

-continued
(Y-728)
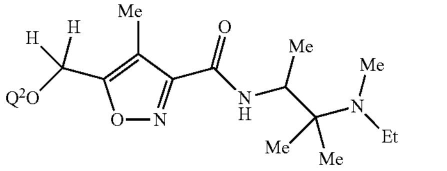
(Y-729)
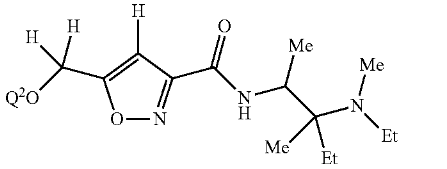
(Y-730)
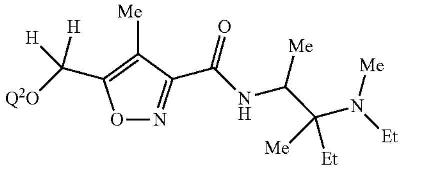
(Y-731)
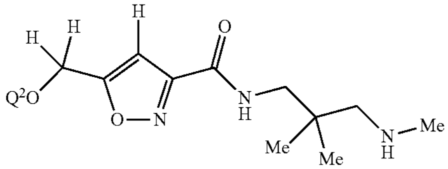
(Y-732)
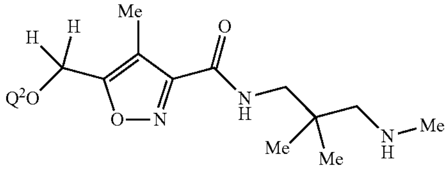
(Y-733)
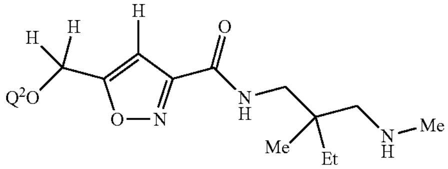
(Y-734)
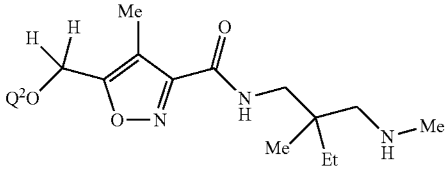
(Y-735)
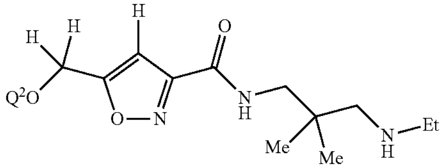
(Y-736)
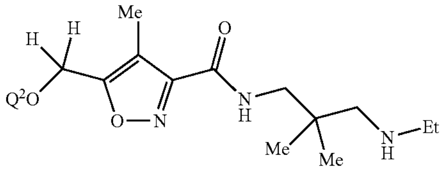
-continued
(Y-737)
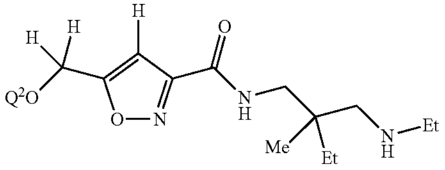
(Y-738)
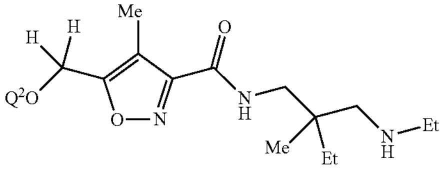
(Y-739)
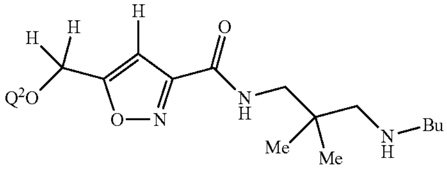
(Y-740)
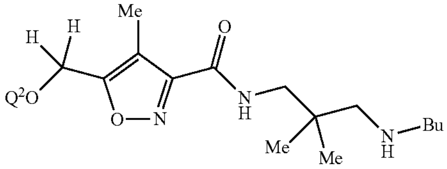
(Y-741)
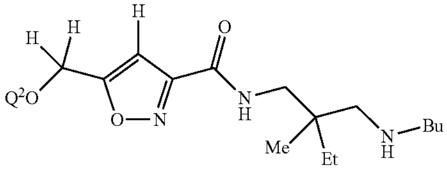
(Y-742)
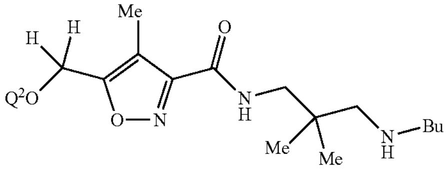
(Y-743)
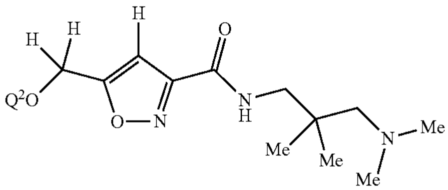
(Y-744)
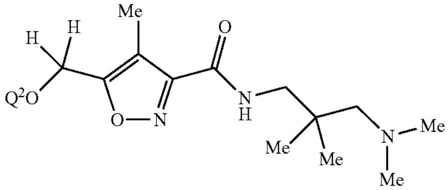

-continued
(Y-745)
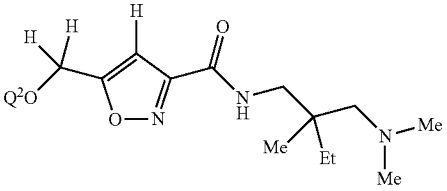
(Y-746)
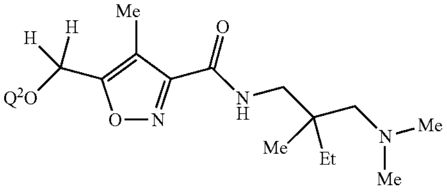
(Y-747)
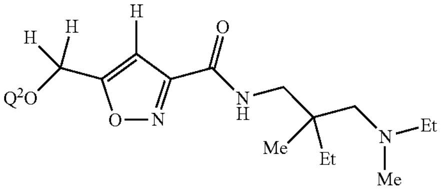
(Y-748)
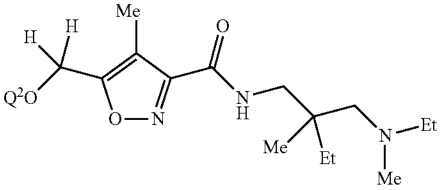
(Y-749)
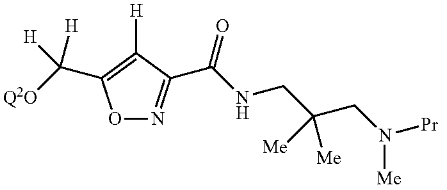
(Y-750)
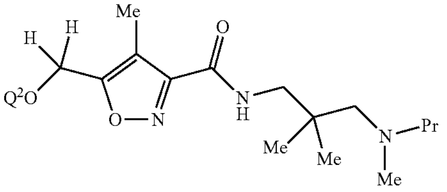
(Y-751)
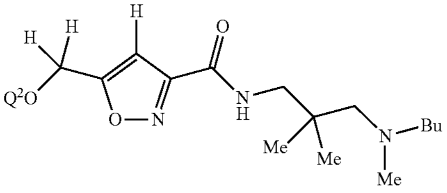
(Y-752)
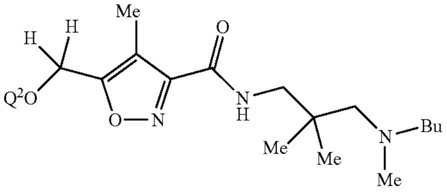
-continued
(Y-753)
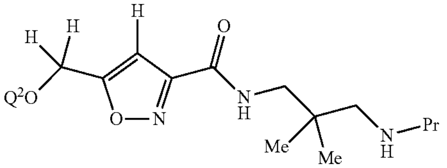
(Y-754)
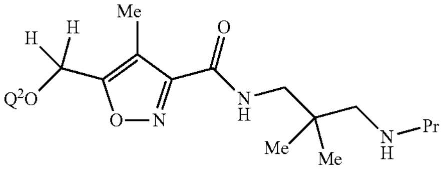
(Y-755)
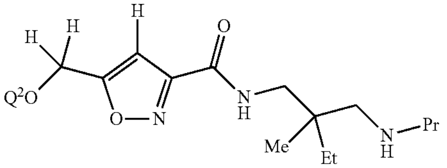
(Y-756)
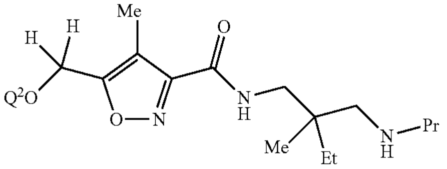
(Y-757)
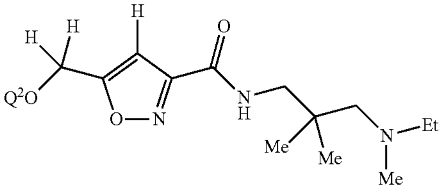
(Y-758)
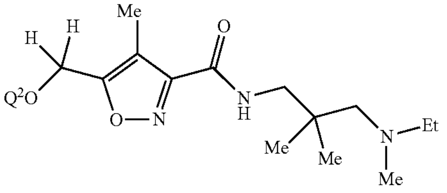
(Y-759)
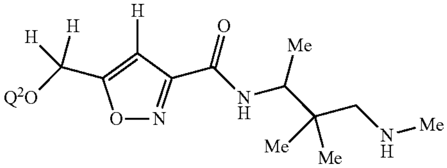
(Y-760)
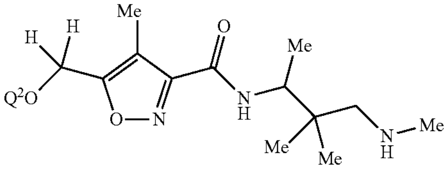

-continued
(Y-761)
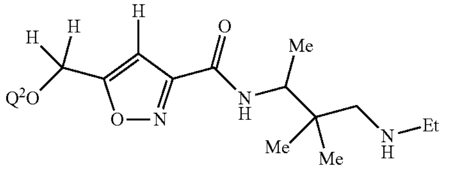
(Y-762)
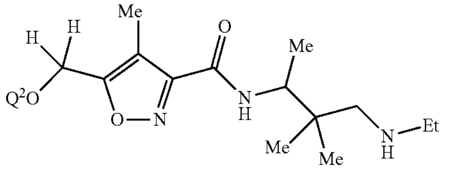
(Y-763)
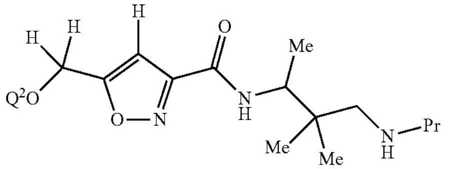
(Y-764)
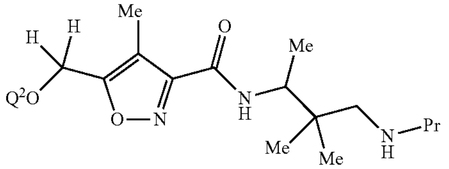
(Y-765)
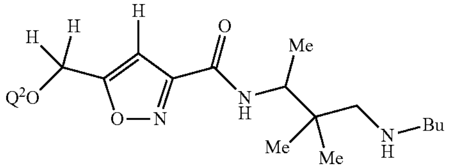
(Y-766)
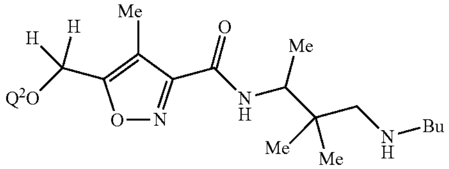
(Y-767)
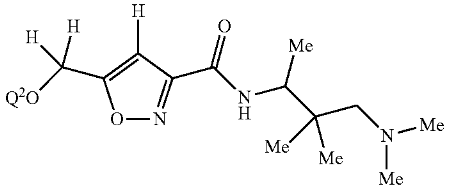
(Y-768)
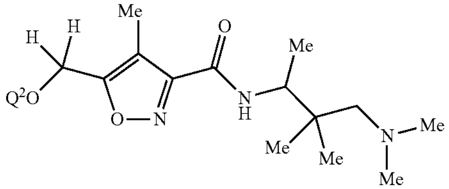
-continued
(Y-769)
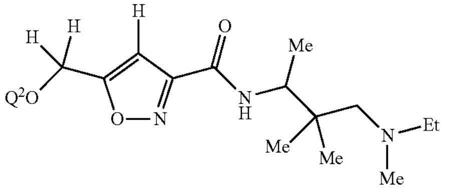
(Y-770)
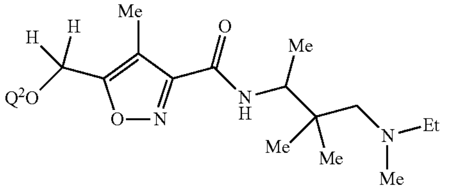
(Y-771)
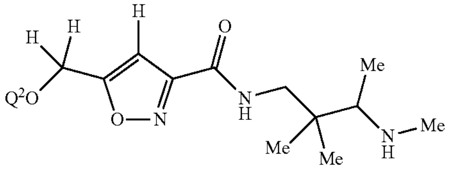
(Y-772)
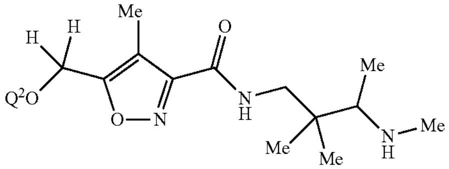
(Y-773)
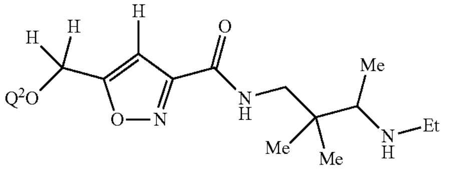
(Y-774)
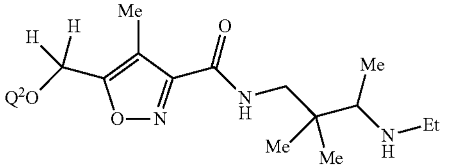
(Y-775)
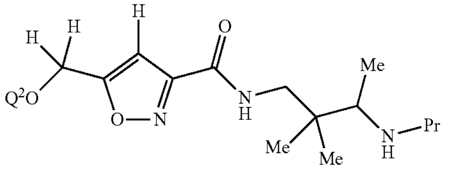
(Y-776)
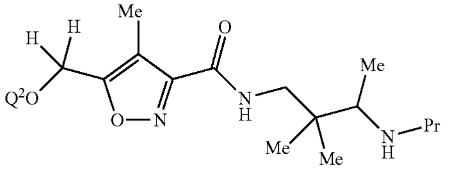

-continued
(Y-777)
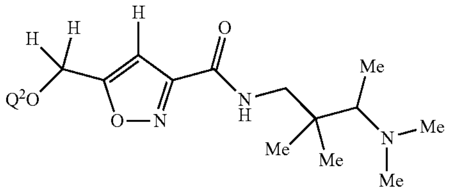
(Y-778)
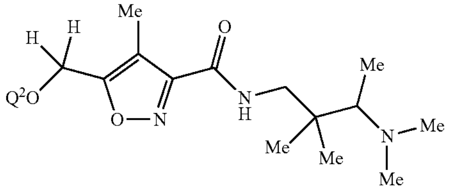
(Y-779)
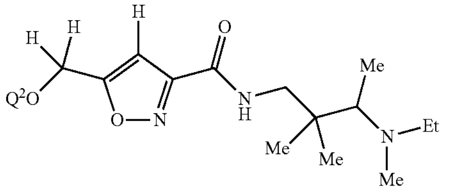
(Y-780)
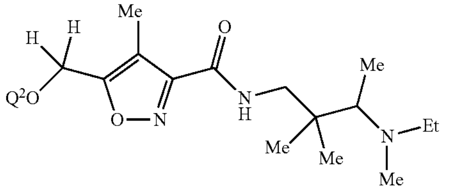
(Y-781)
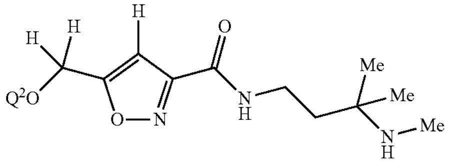
(Y-782)
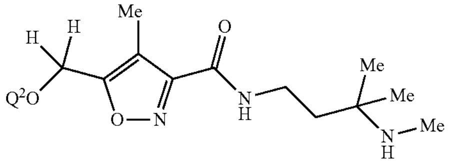
(Y-783)
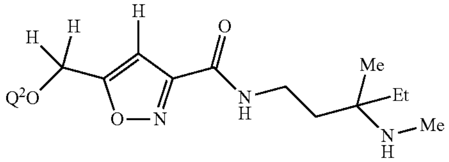
(Y-784)
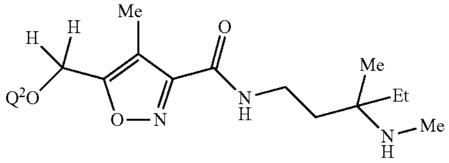
-continued
(Y-785)
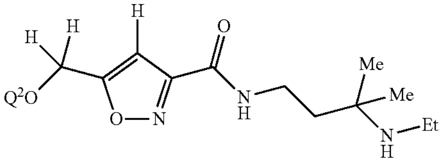
(Y-786)
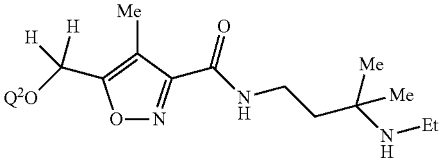
(Y-787)
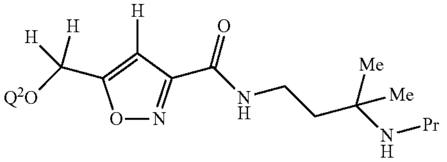
(Y-788)
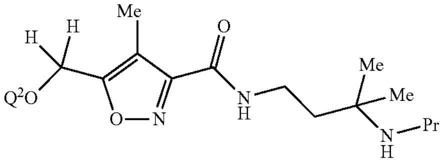
(Y-789)
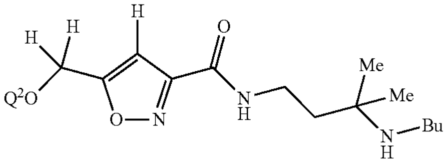
(Y-790)
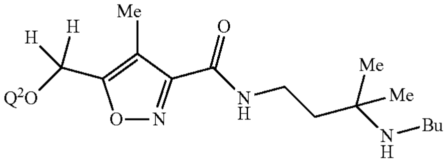
(Y-791)
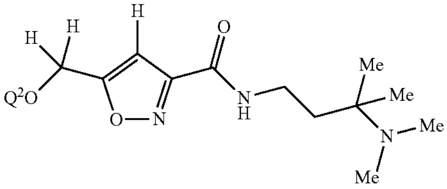
(Y-792)
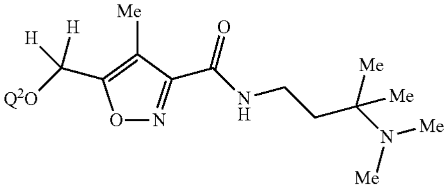
(Y-793)
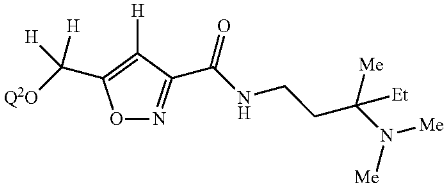

-continued
(Y-794)
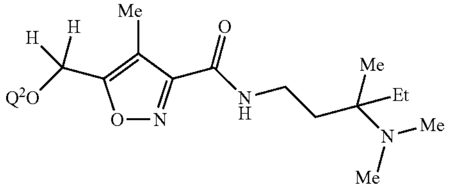
(Y-795)
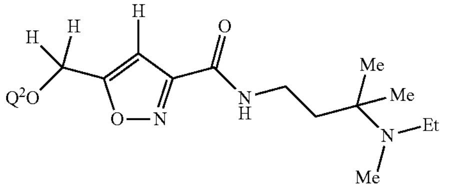
(Y-796)
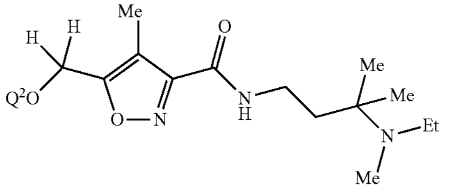
(Y-797)
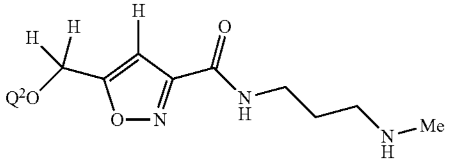
(Y-798)
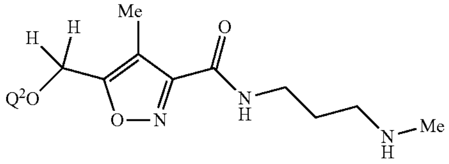
(Y-799)
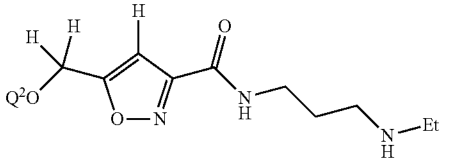
(Y-800)
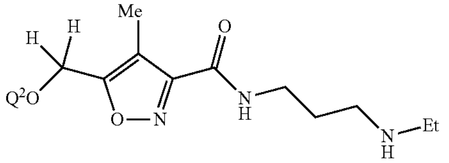
(Y-801)
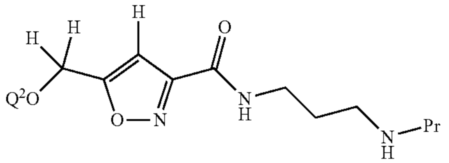
(Y-802)
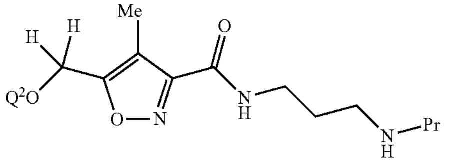
-continued
(Y-803)
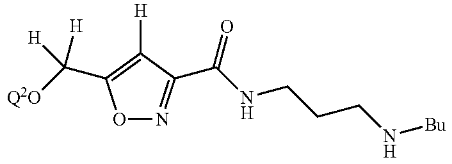
(Y-804)
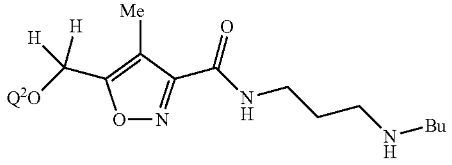
(Y-805)
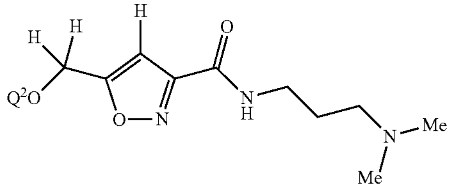
(Y-806)
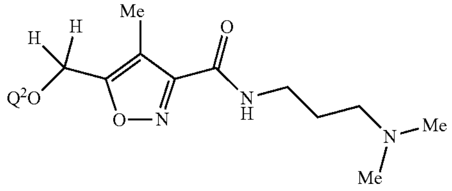
(Y-807)
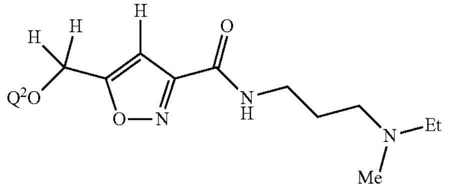
(Y-808)
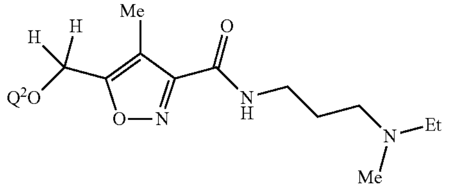
(Y-809)
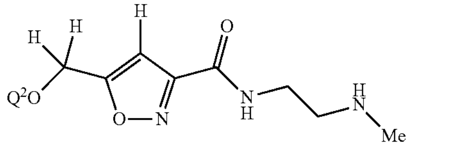
(Y-810)
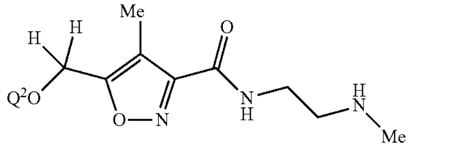
(Y-811)
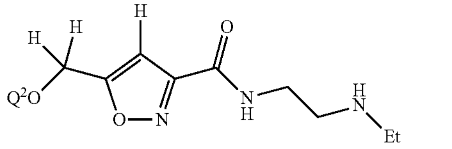

-continued
(Y-812)
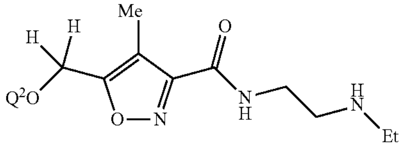
(Y-813)
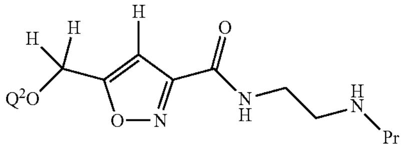
(Y-814)
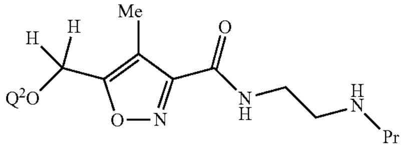
(Y-815)
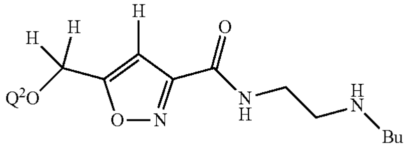
(Y-816)
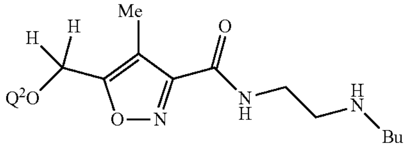
(Y-817)
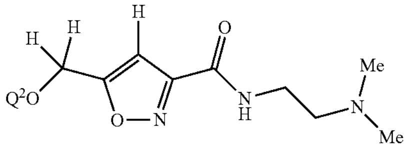
(Y-818)
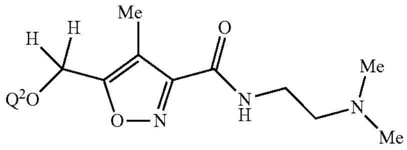
(Y-819)
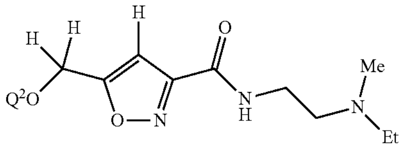
(Y-820)
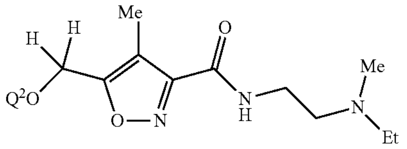
(Y-821)
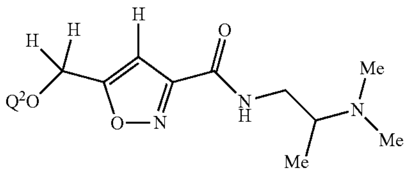
-continued
(Y-822)
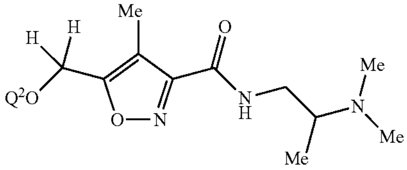
(Y-823)
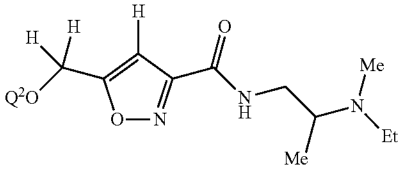
(Y-824)
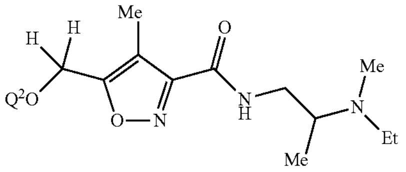
(Y-825)
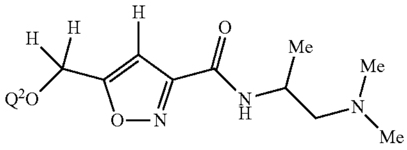
(Y-826)
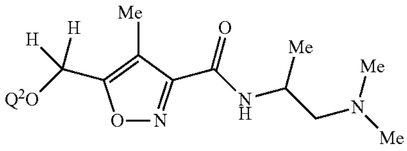
(Y-827)
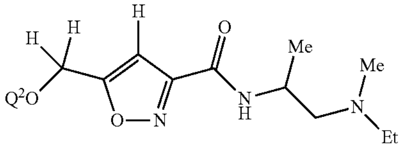
(Y-828)
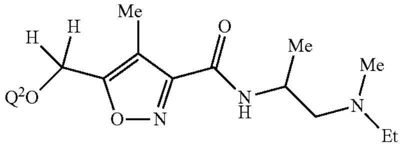
(Y-829)
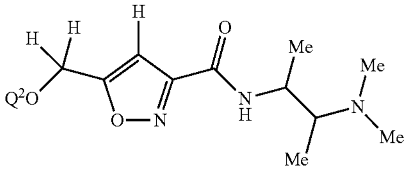
(Y-830)
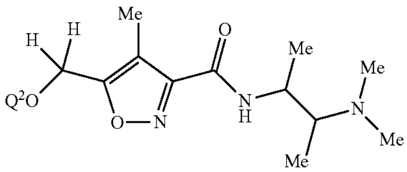

-continued
(Y-831)
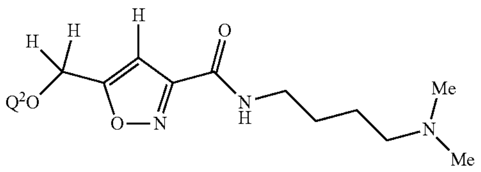
(Y-832)
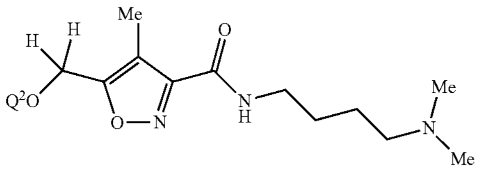
(Y-833)
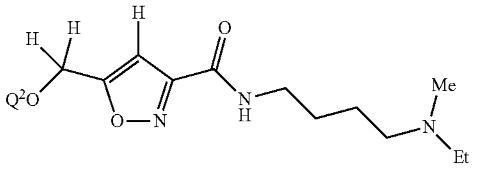
(Y-834)
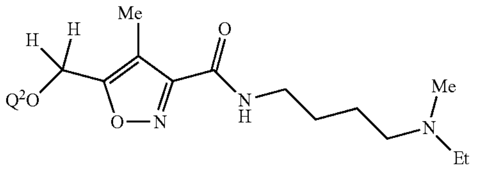
(Y-835)
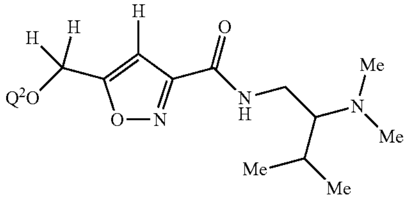
(Y-836)
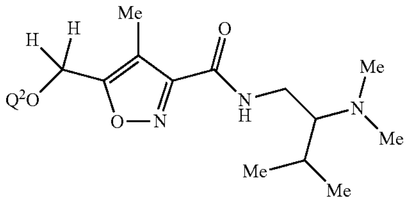
(Y-837)
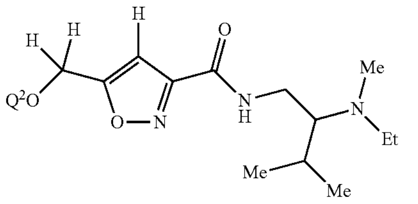
(Y-838)
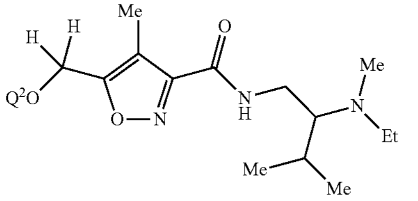
-continued
(Y-839)
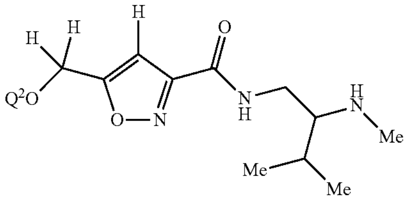
(Y-840)
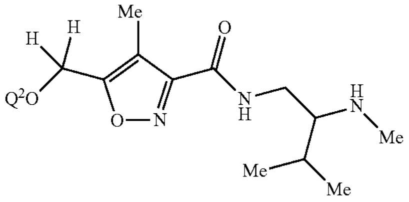
(Y-841)
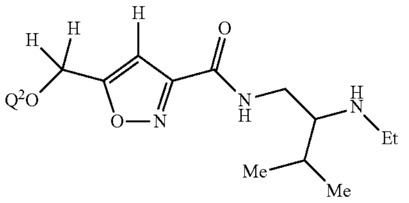
(Y-842)
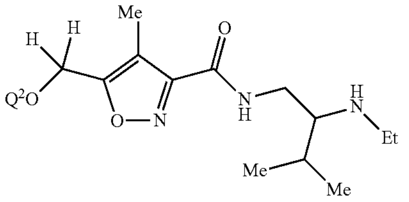
(Y-843)
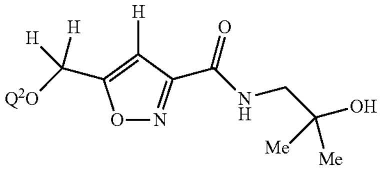
(Y-844)
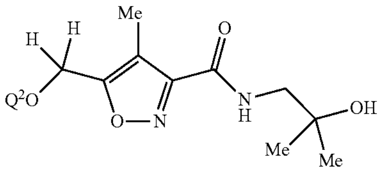
(Y-845)
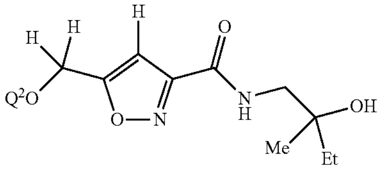
(Y-846)
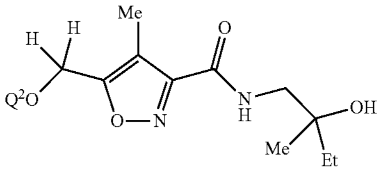

-continued
(Y-847)
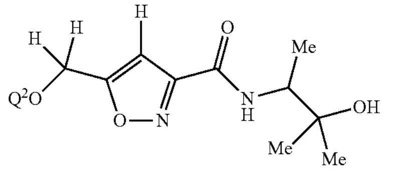
(Y-848)
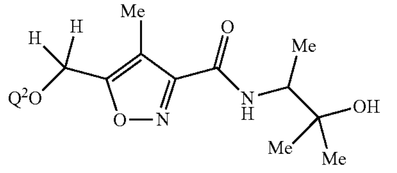
(Y-849)
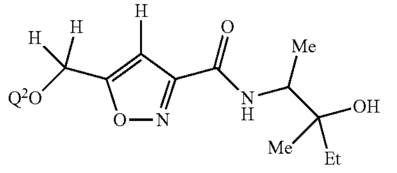
(Y-850)
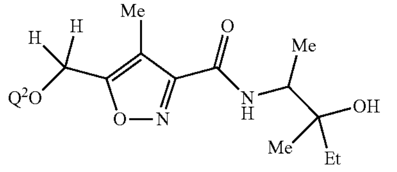
(Y-851)
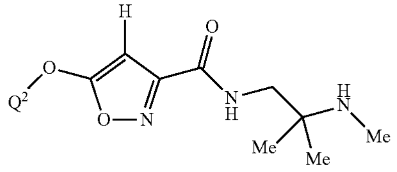
(Y-852)
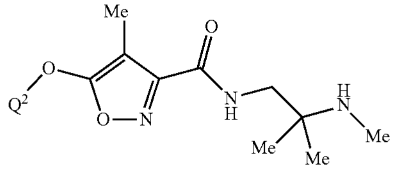
(Y-853)
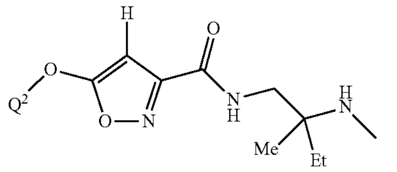
(Y-854)
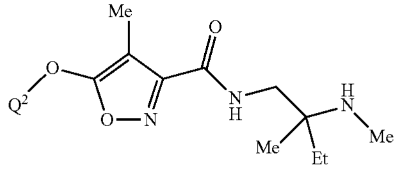
(Y-855)
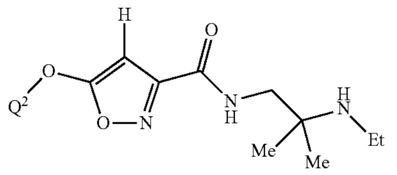
-continued
(Y-856)
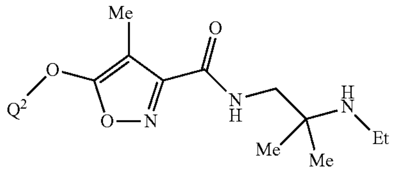
(Y-857)
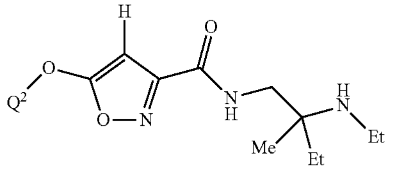
(Y-858)
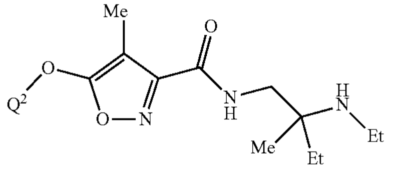
(Y-859)
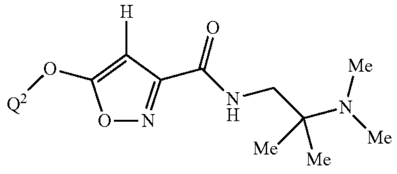
(Y-860)
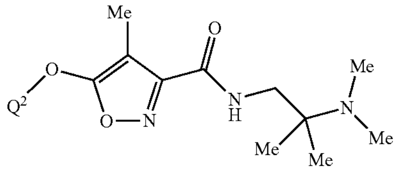
(Y-861)
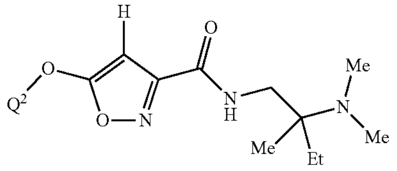
(Y-862)
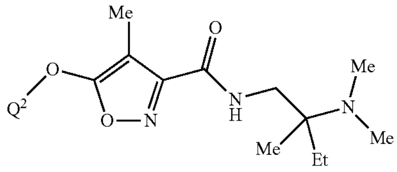
(Y-863)
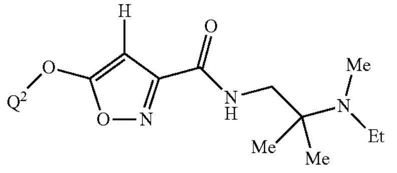
(Y-864)
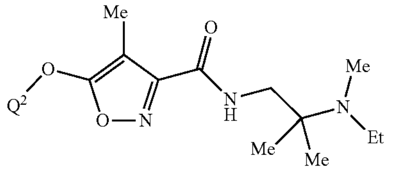

-continued
(Y-865)
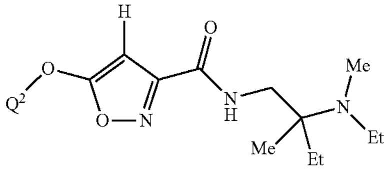
(Y-866)
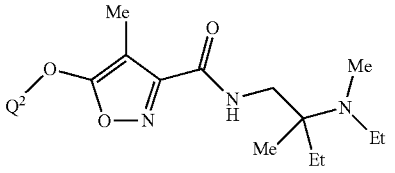
(Y-867)
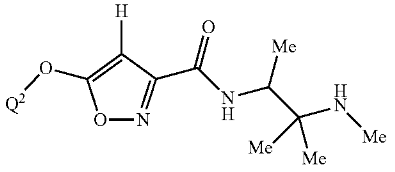
(Y-868)
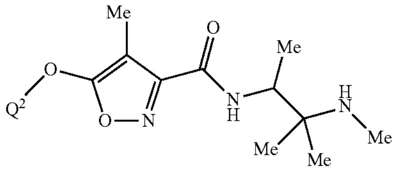
(Y-869)
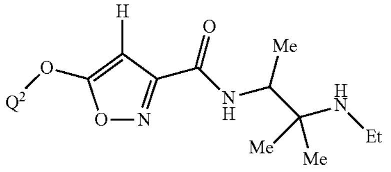
(Y-870)
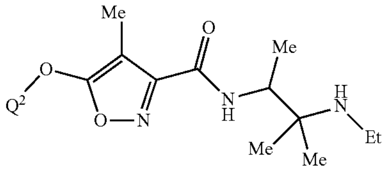
(Y-871)
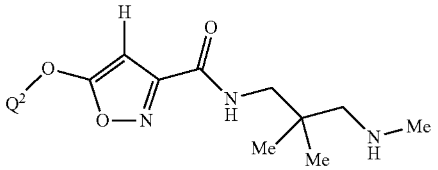
(Y-872)
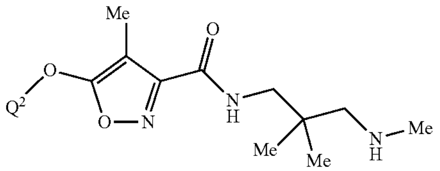
(Y-873)
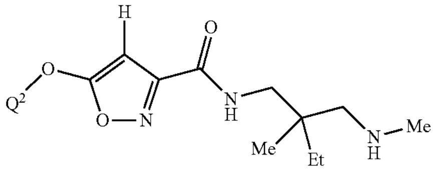
-continued
(Y-874)
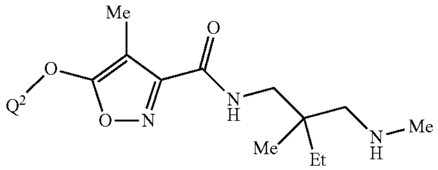
(Y-875)
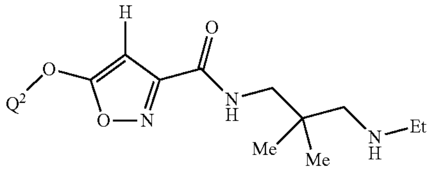
(Y-876)
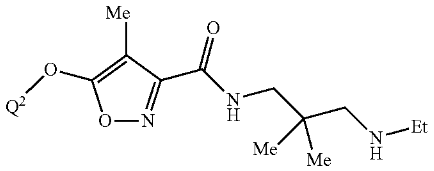
(Y-877)
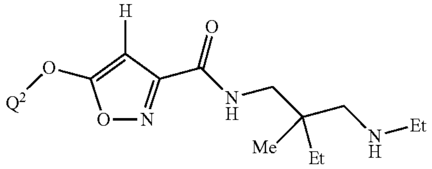
(Y-878)
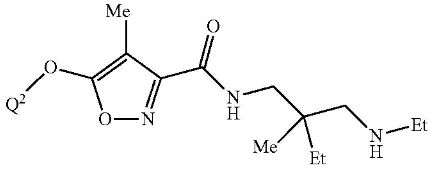
(Y-879)
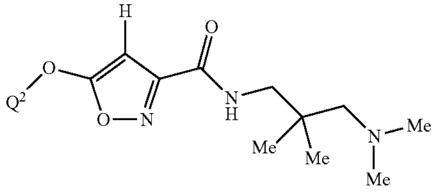
(Y-880)
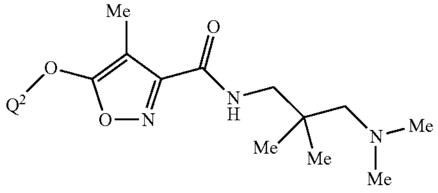
(Y-881)
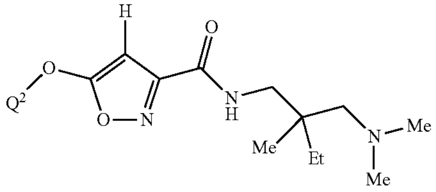

-continued
(Y-882)
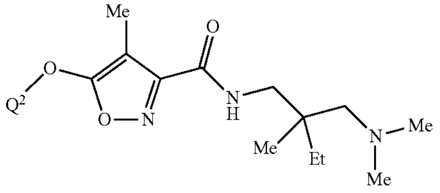
(Y-883)
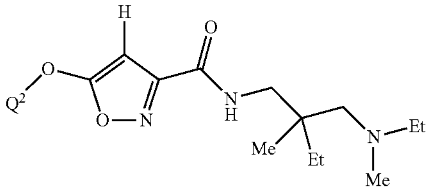
(Y-884)
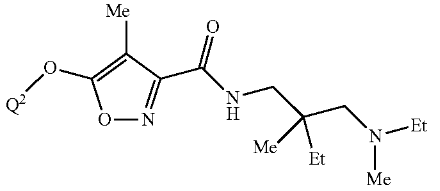
(Y-885)
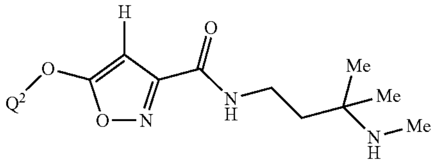
(Y-886)
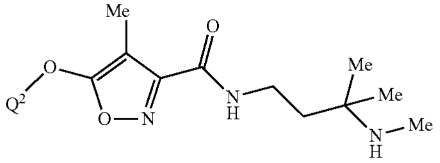
(Y-887)
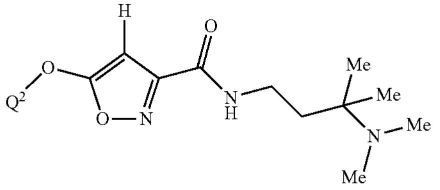
(Y-888)
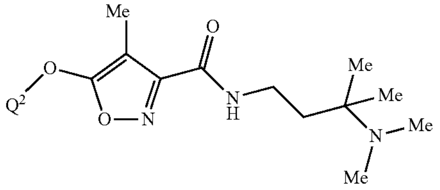
(Y-889)
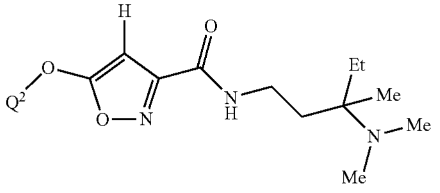
-continued
(Y-890)
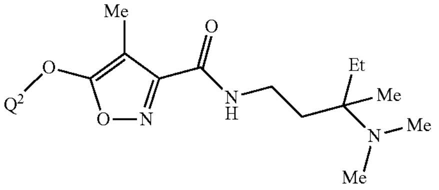
(Y-891)
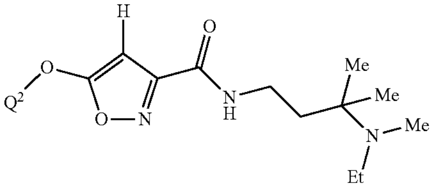
(Y-892)
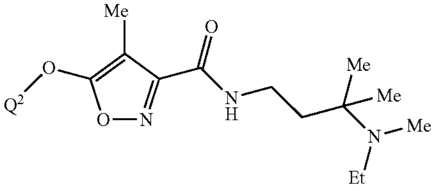
(Y-893)
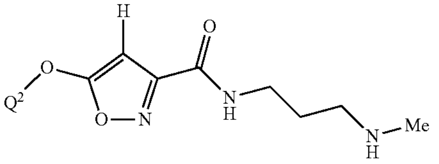
(Y-894)
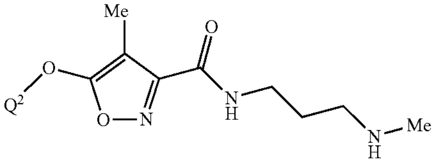
(Y-895)
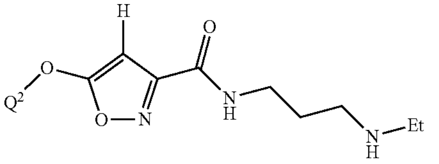
(Y-896)
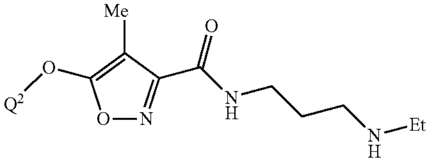
(Y-897)
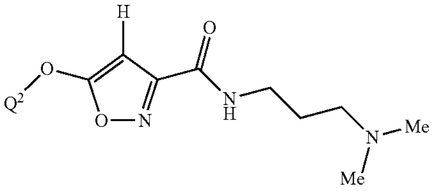

-continued
(Y-898)
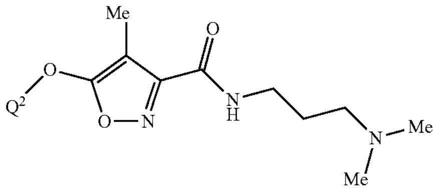
(Y-899)
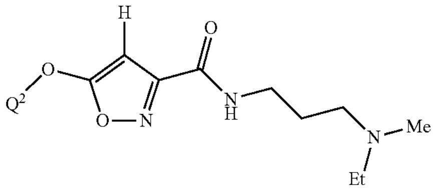
(Y-900)
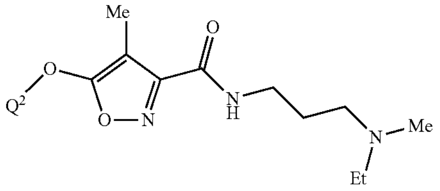
(Y-901)
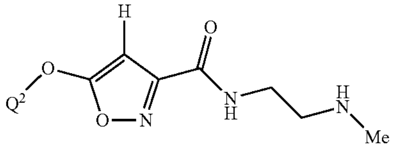
(Y-902)
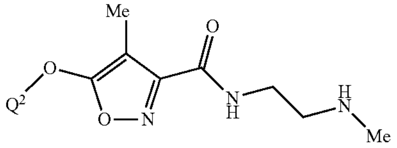
(Y-903)
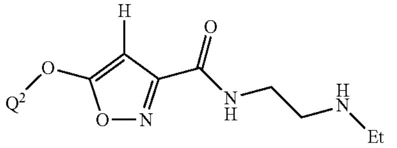
(Y-904)
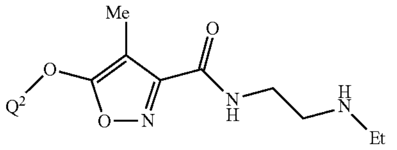
(Y-905)
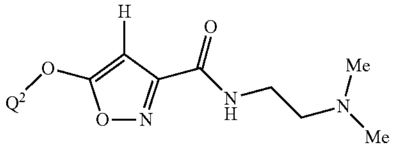
(Y-906)
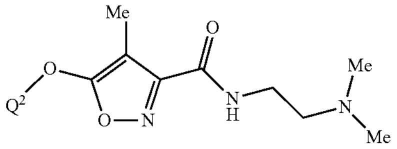
-continued
(Y-907)
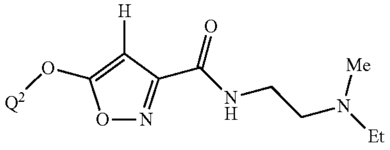
(Y-908)
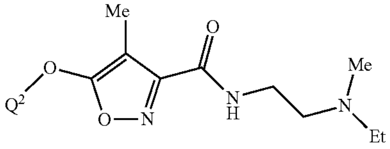
(Y-909)
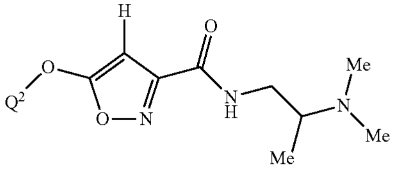
(Y-910)
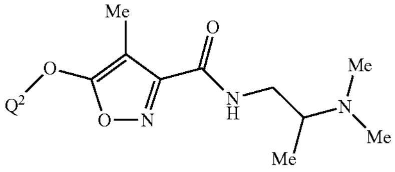
(Y-911)
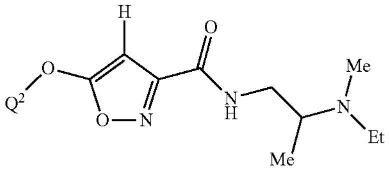
(Y-912)
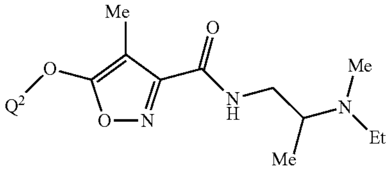
(Y-913)
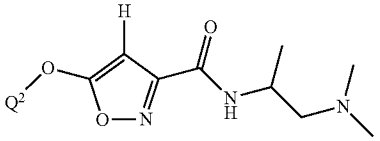
(Y-914)
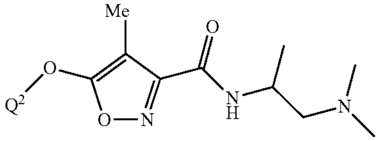
(Y-915)
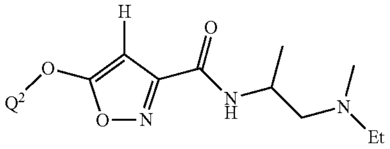

-continued
(Y-916)
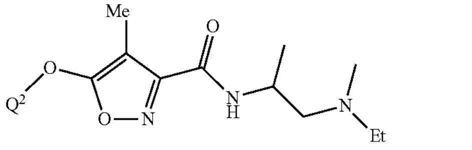
(Y-917)
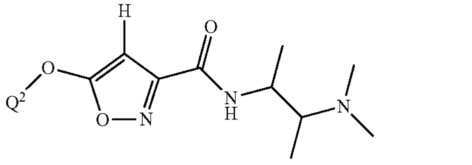
(Y-918)
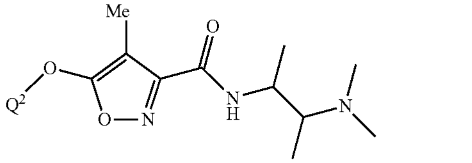
(Y-919)
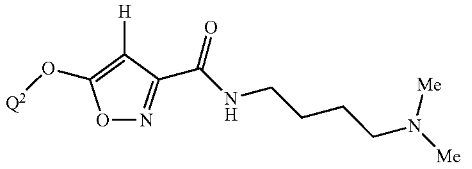
(Y-920)
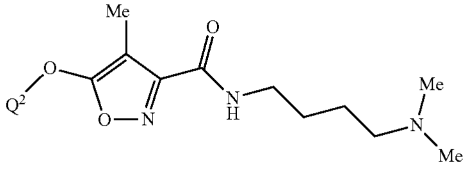
(Y-921)
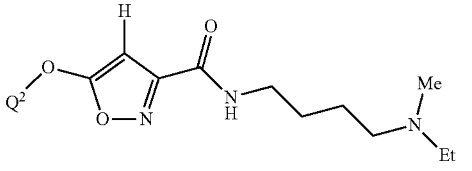
(Y-922)
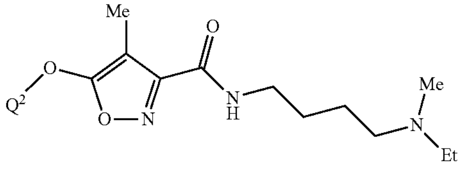
(Y-923)
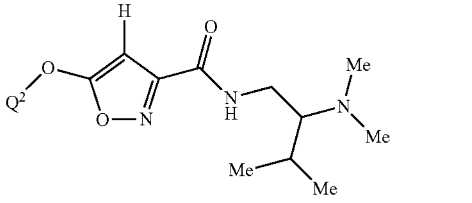
-continued
(Y-924)
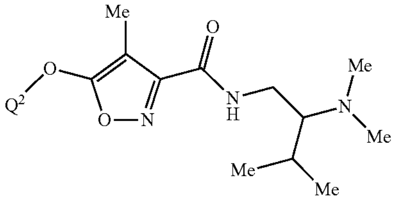
(Y-925)
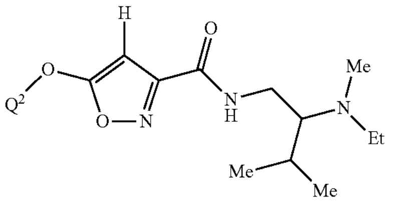
(Y-926)
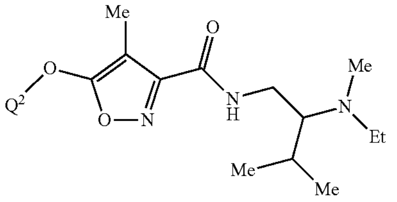
(Y-927)
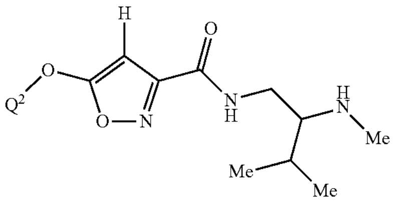
(Y-928)
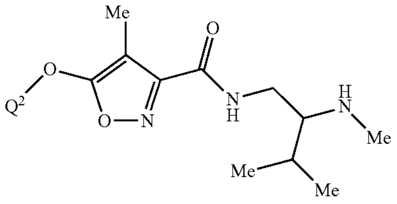
(Y-929)
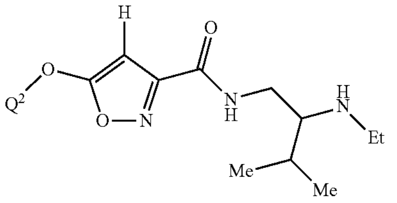
(Y-930)
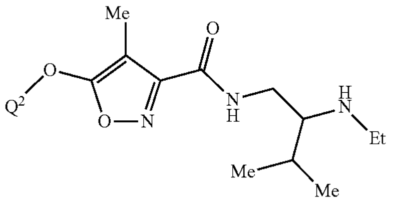
(Y-931)
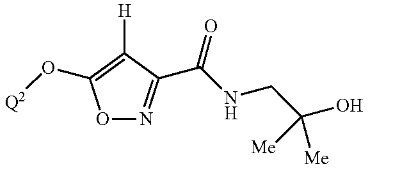

-continued (Y-932)

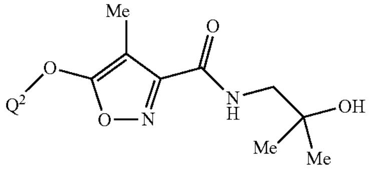

(Y-933)

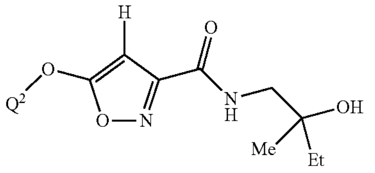

(Y-934)

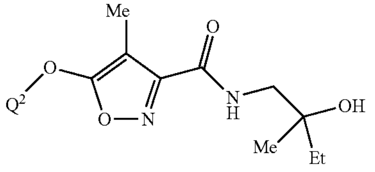

(Y-935)

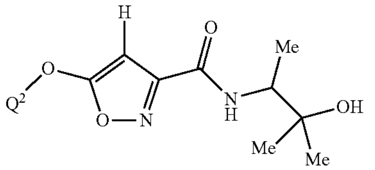

(Y-936)

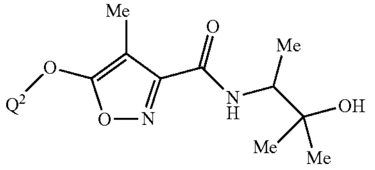

(Y-937)

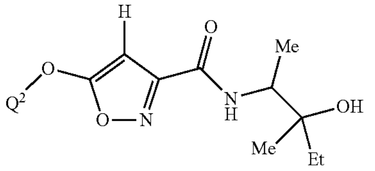

(Y-938)

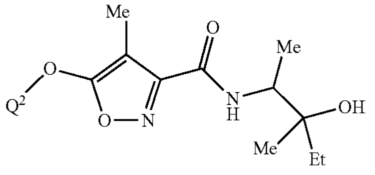

In formula (Y-45) to formula (Y-74) and formula (Y-687) to formula (Y-938), $Q^2$ represents the following:
[$Q^2$]=[Et], [Pr], [Bu], [$CH_2CH_2CH_2CH_2CH_3$], [$CH_2CF_3$], [$CH_2CH_2CF_3$], [$CH_2CH_2CH_2CF_3$], [Ph], [$CH_2$Ph], [$CH_2CH_2$Ph], [$CH_2CH_2CH_2$Ph], [$CH_2CH_2CH_2CH_2$Ph], [$CH_2CH_2CH_2CH_2CH_2$Ph], [2-F-Ph], [$CH_2$(2-F-Ph)], [$CH_2CH_2$(2-F-Ph)], [$CH_2CH_2CH_2$(2-F-Ph)], [3-F-Ph], [$CH_2$(3-F-Ph)], [$CH_2CH_2$(3-F-Ph)], [$CH_2CH_2CH_2$(3-F-Ph)], [4-P-Ph], [$CH_2$(4-F-Ph)], [$CH_2CH_2$(4-F-Ph)], [$CH_2CH_2CH_2$(4-F-Ph)], [2-Cl-Ph], [$CH_2$(2-Cl-Ph)], [$CH_2CH_2$(2-Cl-Ph)], [$CH_2CH_2CH_2$(2-Cl-Ph)], [3-Cl-Ph], [$CH_2$(3-Cl-Ph)], [$CH_2CH_2$(3-Cl-Ph)], [$CH_2CH_2CH_2$(3-Cl-Ph)], [4-Cl-Ph], [$CH_2$(4Cl-Ph)], [$CH_2CH_2$(4-Cl-Ph)], [$CH_2CH_2CH_2$(4-Cl-Ph)], [2-Br-Ph], [$CH_2$(2-Br-Ph)], [$CH_2CH_2$(2-Br-Ph)], [$CH_2CH_2CH_2$(2-Br-Ph)], [3-Br-Ph], [$CH_2$(3-Br-Ph)], [$CH_2CH_2$(3-Br-Ph)], [$CH_2CH_2CH_2$(3-Br-Ph)], [4-Br-Ph], [$CH_2$(4-Br-Ph)], [$CH_2CH_2$(4-Br-Ph)], [$CH_2CH_2CH_2$(4-Br-Ph)], [3-Br-5-F-Ph], [$CH_2$(3-Br-5-F-Ph)], [$CH_2CH_2$(3-Br-5-F-Ph)], [$CH_2CH_2CH_2$(3-Br-5-F-Ph)], [2-$CF_3$-Ph], [$CH_2$(2$CF_3$Ph)], [$CH_2CH_2$(2-$CF_3$-Ph)], [$CH_2CH_2CH_2$(2-$CF_3$-Ph)], [3-$CF_3$-Ph], [$CH_2$(3-$CF_3$-Ph)], [$CH_2CH_2$(3-$CF_3$-Ph)], [$CH_2CH_2CH_2$(3-$CF_3$-Ph)]$_1$ [4-$CF_3$-Ph], [$CH_2$(4-$CF_3$-Ph)], [$CH_2CH_2$(4-$CF_3$-Ph)], [$CH_2CH_2CH_2$(4-$CF_3$-Ph)], [2-$OCF_3$-Ph], [$CH_2$(2-$OCF_3$Ph)], [$CH_2CH_2$(2-$OCF_3$-Ph)], [$CH_2CH_2CH_2$(2-$OCF_3$-Ph)], [3 $OCF_3$-Ph], [$CH_2$(3-$OCF_3$-Ph)], [$CH_2CH_2$(3-$OCF_3$-Ph)], [$CH_2CH_2CH_2$(3-$OCF_3$-Ph)], [ 4-$OCF_3$-Ph], [$CH_2$(4-$OCF_3$-Ph)], [$CH_2CH_2$(4-$OCF_3$-Ph)], [$CH_2CH_2CH_2$(4-$OCF_3$-Ph)], [2-$SCF_3$-Ph], [$CH_2$(2-$SCF_3$Ph)], [$CH_2CH_2$(2-$SCF_3$-Ph)], [$CH_2CH_2CH_2$(2-$SCF_3$-Ph)], [3-$SCF_3$-Ph], [$CH_2$(3-$SCF_3$-Ph)], [$CH_2CH_2$(3-$SCF_3$-Ph)], [$CH_2CH_2CH_2$(3-$SCF_3$-Ph)], [$SCF_3$-Ph], [$CH_2$(4-$SCF_3$-Ph)], [$CH_2CH_2$(4-$SCF_3$-Ph)], [$CH_2CH_2CH_2$(4-$SCF_3$-Ph)], [NA1], [$CH_2$(NA1)], [$CH_2CH_2$(NA1)], [$CH_2CH_2CH_2$(NA1)], [NA2], [$CH_2$(NA2)], [$CH_2CH_2$(NA2)], [$CH_2CH_2CH_2$(NA2)], [$CH_2CH_2CH_2CH_2$(NA2)], [$CH_2CH_2CH_2CH_2CH_2$(NA2)], [8-Br-NA2], [$CH_2$(8-F-NA2)], [$CH_2CH_2$(8-F-NA2)], [$CH_2CH_2CH_2$(8-F-NA2)], [8-Cl-NA2], [$CH_2$(8-Cl-NA2)], [$CH_2CH_2$(8-Cl-NA2)], [$CH_2CH_2CH_2$(8-Cl-NA2)], [8-Br-NA2], [$CH_2$(8-Br-NA2)], [$CH_2CH_2$(8-Br-NA2)], [$CH_2CH_2CH_2$(8-Br-NA2)], [$CH_2CH_2$OPh], [$CH_2CH_2$O(NA2)], [$CH_2$(IN1)], [$CH_2CH_2$(IN2)], [$CH_2$(Py2)], [$CH_2$(Qun2)], [$CH_2$(Fur2)], [$CH_2$(Thi2)], [$CH_2$(BF5)], [$CH_2$(BF2)], [$CH_2$(BT5)], [$CH_2$(BT2)], [$CH_2$(BDXO5)], [$CH_2$(BDXA6)], [$CH_2$(3Cy)], [$CH_2$(5Cy)], [$CH_2$(8Cy)], [$CH_2$(2, 2-$F_2$-3 Cy)], [$CH_2$(2-CN-3Cy)], [$CH_2$(2, 2-$F_2$-BDXO5)], [$CH_2$(2, 2-$F_2$-3 Cy)], [Py2], [Thi2], [Fur2], [3Cy], or [5Cy].

Then, Formulation Examples will be shown. In addition, part indicates part by weight.

Formulation Example 1

20 parts of any one of the compounds A or Compounds (1) to (77) is dissolved in 65 parts of xylene, and 15 parts of SORPOL 3005X (registered trade name of TOHO Chemical Industry Co., Ltd.) is added thereto. The mixture is well stirred and mixed to obtain an emulsifiable concentrate.

Formulation Example 2

40 parts of any one of the compounds A or Compounds (1) to (77), and 5 parts of SORPOL 3005X are well mixed, and then 32 parts of Carplex #80 (synthetic hydrous silicon oxide, registered trade name of Shionogi & Co., Ltd.), and 23 parts of 300-mesh diatomaceous earth are added thereto. The mixture is stirred and mixed with a juice mixer to obtain a wettable powder.

Formulation Example 3

1.5 parts of any one of the compounds A or Compounds (1) to (77), 1 part of Tokuseal GUN (synthetic hydrous silicon oxide, manufactured by Tokuyama corporation), 2 parts of Reax 85A (sodium ligninsulfonate, manufactured by West vaco chemicals), 30 parts of Bentonite Fuji (bentonite, manufactured by HOJUN Co., Ltd.), and 65.5 parts of Shokozan A clay (kaolin clay, manufactured by SHOKOZAN MINING Co., Ltd.) are well pulverized and mixed, and water is added thereto. The mixture is then kneaded well, granulated with an extrusion granulator, and dried to obtain 1.5% granules.

Formulation Example 4

10 parts of any one of the compounds A or Compounds (1) to (77), 10 parts of phenylxylylethane, and 0.5 part of Sumijule L-75 (tolylene diisocyanate, manufactured by Sumitomo Bayer Urethane Co., Ltd.) are mixed, and then the mixture is added to 20 parts of a 10% aqueous solution of arabic gum, followed by stirring the resulting mixture with a homomixer to obtain an emulsion having an average particle diameter of 20 Thereto is added 2 parts of ethylene glycol, and the mixture is further stirred in a warm bath at 60° C. for 24 hours to obtain a microcapsule slurry. Separately, 0.2 parts of xanthan gum and 1.0 part of Veegum R (aluminum magnesium silicate, registered trade name of Vanderbilt Company) are dispersed in 56.3 parts of ion-exchanged water to obtain a thickening agent solution. 42.5 parts of the microcapsule slurry and 57.5 parts of the thickening agent solution are mixed to obtain a microcapsule formulation.

Formulation Example 5

10 parts of any one of the compounds A or Compounds (1) to (77), and 10 parts of phenylxylylethane are mixed, and then the mixture is added to 20 parts of 10% aqueous solution of polyethylene glycol, followed by stirring the resulting mixture with a homomixer to obtain an emulsion having an average particle diameter of 3 Separately, 0.2 parts of xanthan gum and 1.0 part of Veegum R (aluminum magnesium silicate, registered trade name of Vanderbilt Company) are dispersed in 58.8 parts of ion-exchanged water to obtain a thickening agent solution. 40 parts of the emulsion solution and 60 parts of the thickening agent solution are mixed to obtain a flowable.

Formulation Example 6

5 parts of any one of the compounds A or Compounds (1) to (77), 3 parts of Carplex #80 (a fine powder of synthetic hydrous silicon oxide, registered trade name of Shionogi & Co., Ltd.), 0.3 parts of PAP (a mixture of monoisopropyl phosphate and diisopropyl phosphate) and 91.7 parts of talc (300 mesh) are stirred and mixed with a juice mixer to obtain a dust formulation.

Formulation Example 7

0.1 parts of any one of the compounds A is dissolved in 10 parts of isopropyl alcohol, and the mixture is mixed with 89.9 parts of kerosene to obtain an oil solution.

Formulation Example 8

1 part of any one of the compounds A or Compounds (1) to (77), 5 parts of dichloromethane and 34 parts of kerosene are mixed and dissolved, and filled into an aerosol container, and a valve part is attached to the container, then 60 parts of a propellant (liquefied petroleum gas) is filled under pressure into the container through the valve part to obtain an oil-based aerosol.

Formulation Example 9

0.6 parts of any one of the compounds A or Compounds (1) to (77), 5 parts of xylene, 3.4 parts of kerosene and 1 part of ATMOS 300 (emulsifier, registered trade name of Atlas Chemical Company) are mixed and dissolved, and the resulting solution and 50 parts of water are filled into an aerosol container, and 40 parts of a propellant (liquefied petroleum gas) is filled under pressure into the container through the valve part to obtain an aqueous aerosol.

Formulation Example 10

0.3 g of any one of the compounds A or Compounds (1) to (77) is dissolved in 20 mL of acetone. The resulting solution is uniformly stirred and mixed with 99.7 g of a base material for an insecticidal coil (a mixture of Tabu powder, Pyrethrum marc and wood powder in a ratio of 4:3:3). Thereafter, 100 mL of water is added to the mixture, and the resulting mixture is sufficiently kneaded, and molded and dried to obtain an insecticidal coil.

Formulation Example 11

0.8 g of any one of the compounds A or Compounds (1) to (77), and 0.4 g of piperonyl butoxide are dissolved in acetone to have a total amount of 10 mL. A base material for an insecticidal mat for electric heating with a size of 2.5 cm×1.5 cm, 0.3 cm in thickness (a plate of compacted fibrils of the mixture of cotton linter and pulp) is uniformly impregnated with 0.5 mL of this solution to obtain an insecticidal mat for electric heating.

Formulation Example 12

3 parts of any one of the compounds A or Compounds (1) to (77) is dissolved in 97 parts of kerosene to obtain a solution, and this solution is put in a container made of polyvinyl chloride. Into the container is inserted an absorptive wick (which is prepared by solidifying powders of an inorganic powder with a binder followed by sintering them) whose upper portion can be heated by a heater, to obtain a part to be used for an absorptive wick type electric heating vaporizer.

Formulation Example 13

100 mg of any one of the compounds A or Compounds (1) to (77) is dissolved in an appropriate amount of acetone, and a porous ceramic plate with a size of 4.0 cm×4.0 cm, 1.2 cm in thickness is impregnated with the solution to obtain a fumigant for heating.

Formulation Example 14

100 μg of any one of the compounds A or Compounds (1) to (77) is dissolved in an appropriate amount of acetone, and the solution is uniformly applied on a filter paper of 2 cm×2 cm, 0.3 mm in thickness. Then, the filter paper is air-dried to remove acetone to obtain a formulation vaporizable at room temperature.

Formulation Example 15

10 parts of any one of the compounds A or Compounds (1) to (77), 35 parts of a mixture of polyoxyethylene alkyl ether sulfate ammonium salt and white carbon (weight ratio 1:1) as well as 55 parts of water are mixed, and the mixture is finely pulverized by wet grinding method to obtain each flowable agent.

Then, the noxious arthropod controlling effect of the compound is shown as test examples.

Test Example 1

A formulation containing each of the compounds (1), (3), (4), (5), (8), (11), (12) and (21) prepared in accordance with Formulation Example 7 was diluted with an isopropyl alcohol/kerosine=1/9 mixed liquid so that the concentration of each compound became 2.0% w/v, to obtain a diluted solution.

Ten vermin *Blattella germanica* (male female each five vermin) were allowed to release in a container for a test in which a butter was applied on an inner wall (diameter 8.75 cm, height 7.5 cm, bottom face covered with 16 mesh wire net), and the container was arranged on a bottom of a chamber for a test (bottom surface: 46 cm×46 cm, height: 70 cm). From a height of 60 cm from an upper surface of the container, 1.5 mL of the diluted solution was sprayed using a spray gun (spraying pressure 0.42 $kg/cm^2$). Thirty seconds after spraying, the container was taken out from the chamber for a test, the number of vermin which had been knocked down was counted for 15 minutes with time, and a knockdown ratio was obtained. The knockdown ratio was calculated by the following expression.

Knockdown ratio (%)=(number of knocked down vermin/number of test vermin)×100

As a result, the knockdown ratio of test vermin within 15 minutes was 80% or more, in treatment with the compounds (1), (3), (4), (5), (8), (11), (12) and (21), respectively.

Test Example 2

A formulation containing each of the compounds (1), (2), (4), (8), (11) and (21) prepared in accordance with Formulation Example 7 was diluted with an isopropyl alcohol/kerosine=1/9 mixed liquid so that the concentration of each compound became 2.0% w/v, to obtain a diluted solution.

Ten imagoes of *Musca domestica* (male female each five vermin) were allowed to release in a polyethylene cup (bottom surface diameter 10.6 cm), and the cup was covered with a 16 mesh nylon gauze. The polyethylene cup was arranged on a bottom of a chamber for a test (bottom surface: 46 cm×46 cm, height: 70 cm). From a height of 30 cm from an upper surface of the polyethylene cup, 0.5 mL of the diluted solution was sprayed using a spray gun (spraying pressure 0.9 $kg/cm^2$). After spraying, the cup was immediately taken out from the chamber for a test, and the number of knocked down vermin was counted for 15 minutes with time, and a knockdown ratio was obtained. The knockdown ratio was calculated by the following expression.

Knockdown ratio (%)=(number of knocked down vermin/number of test vermin)×100

As a result, the knockdown ratio of the test vermin within 15 minutes was 80% or more, in treatment with the compounds (1), (2), (4), (8), (11) and (21), respectively.

Test Example 3

A formulation containing each of the compounds (2), (4), (11), (12), (20), (21) and (24) to (32) prepared in accordance with Formulation Example 7 was diluted with an isopropyl alcohol/kerosine=1/9 mixed liquid so that the concentration of each compound became 0.1% w/v, to obtain a diluted solution.

Ten imagoes of Culexpipienspallens were allowed to release in a polyethylene cup (bottom surface diameter 10.6 cm), and the cup was covered with a 16 mesh nylon gauze. The polyethylene cup was arranged on a bottom of a chamber for a test (bottom surface: 46 cm×46 cm, height: 70 cm). From a height of 30 cm from an upper surface of the polyethylene cup, 0.5 mL of the diluted solution was sprayed using a spray gun (spraying pressure 0.4 $kg/cm^2$). After spraying, the cup was immediately taken out from the chamber for a test, the number of knocked down vermin was counted for 15 minutes with time, and a knockdown ratio was obtained. The knockdown ratio was calculated by the following expression.

Knockdown ratio (%)=(number of knocked down vermin/number of test vermin)×100

As a result, the knockdown ratio of the test vermin within 15 minutes was 80% or more in treatment with the compounds (2), (4), (11), (12), (20), (21), and (24) to (32), respectively.

Test Example 4

A formulation containing each of the compounds (7) and (19) prepared in accordance with Formulation Example 15 was diluted with water so that the concentration of each compound became 500 ppm, to prepare a diluted solution.

To 100 ml of ion-exchanged water was added 0.7 mL of the diluted solution (active ingredient concentration 3.5 ppm). Thirty last instar larvae of Culexpipienspallens were released in the solution, the life or death thereof was investigated after 1 day, and a dead vermin ratio was obtained. The dead vermin ratio was calculated by the following expression.

Dead vermin ratio (%)=(number of dead vermin/number of test vermin)×100

As a result, the dead vermin ratio showed 91% or more, in sections of treatment with the compounds (7) and (19), respectively.

Test Example 5

A formulation containing the compound (4) prepared in accordance with Formulation Example 15 was diluted with water so that the concentration became 500 ppm to obtain a diluted solution. On the other hand, a cucumber was planted in a polyethylene cup, and grown until a first true leaf developed. About 20 vermin of *Aphis gossypii* was parasitized therein. After one day, the diluted solution was sprayed to the cucumber at a ratio of 20 mL/cup. Six days after spraying, the number of live or dead vermin of *Aphis gossypii* was investigated, and a controlling value was obtained by the following expression.

$$\text{Controlling value } (\%)=\{1-(Cb\times Tai)/(Cai\times Tb)\}\times 100$$

In addition, letters in the expression indicate the following meanings.

Cb: Number of vermin before treatment of non-treated section

Cai: Number of live parasitic vermin at observation of non-treated section

Tb: Number of vermin before treatment of treated section

Tai: Number of live parasitic vermin at observation of treated section

As a result, in a section of treatment with the compound (4), the controlling value showed 90% or more.

Test Example 6

A formulation containing the compound (21) prepared in accordance with Formulation Example 15 was diluted with water so that the concentration became 500 ppm, to prepare a diluted solution.

On the other hand, the diluted solution was sprayed to a cabbage at a stage of three leaves planted in a polyethylene cup at a ratio of 20 mL/cup. After spraying, the plant was air-dried, foliage portions were cut and accommodated into a 50 mL cup, 5 second instar larvae of *Plutella xylostella* were released, and the cup was covered. This was stored at 25° C., and after 5 days, the number of dead vermin was counted, and a dead vermin ratio was obtained by the following expression.

Dead vermin ratio (%)=(Number of dead vermin/number of test vermin)×100

As a result, the section of treatment with the compound (21) showed 80% or more of the dead vermin ratio.

Test Example 7

In a cage (22×22×30 cm), 200 to 400 imagoes of *Aedes aegypti* (female male ratio about 1:1) are released. A circulating constant temperature tank and two brown bottles (bottom diameter 6 cm, height 10 cm) having the interior through which water can be circulated, are connected with a silicone tube, and water at 38° C. is circulated.

On one side of a semipermeable membrane (6×6 cm), 90 μL of an acetone solution of the compound (6.7 mg/mL) is applied. After air drying, a side which has not been applied with the compound, of the semipermeable membrane, is wetted with water, and is applied to an outer bottom surface of one of the brown bottles (hereinafter, the brown bottle is referred to as brown bottle A). On an outer bottom surface of the other brown bottle, the compound is not applied, and a semipermeable membrane which has been merely wetted with water is applied (hereinafter, the brown bottle is referred to as brown bottle B).

A bottom of each of the brown bottle A and the brown bottle B is adhered to the cage from an outer side of the cage. After adhesion, the total number of *Aedes aegypti* which has been attracted to each bottle is observed three times of after 2, 4 and 6 minutes.

A repellency ratio is obtained by the following expression. The repellency ratio 100% means that *Aedes aegypti* was not attracted to the brown bottle treated with the compound.

Repellency ratio (%)={1−(number of *Aedes aegypti* which has been attracted to brown bottle *A*)/(attraction number of *Aedes aegypti* which has been attracted to brown bottle *B*)}×100

As a result, in a section of treatment with the compound, the repelling effect is recognized in both of female and male.

Test Example 8

A test was performed referring to the method described in Journal of Medical Entomology 2000, 37 (1), 177-181 and Journal of Medical Entomology 2005, 42 (4), 643-646.

Each 6 ml of blood of an animal (cattle, rabbit etc.) is placed into each well of a hexaplicate well plate (in series), each well is covered with a collagen membrane, and the hexaplicate well plate is warmed to 38° C. with a water bath. On a net (5×5 cm) made of a plastic, an acetone solution of the compound (4.2 mg/mL) is applied so that an amount becomes 100 μL per each well. After air drying, the net is piled on a collagen membrane.

A K & D module {having a structure in which 6 small chambers (width 4.4 cm, length 5 cm, height 5 cm) are connected in series, a hole (diameter 1 cm) for placing *Aedes aegypti* is provided at a center on a side which is not contacted with a neighboring small chamber, in each small chamber and, in addition, a ceiling surface is closed, and a sliding-type partition plate is provided on a bottom surface} is placed on the hexaplicate well, and each 5 female imagoes of *Aedes aegypti* are placed into each small chamber.

A partition plate on a bottom surface of the K & D module is opened so that *Aedes aegypti* can suck the blood.

For 3 minutes after opening of the partition plate, the number of *Aedes aegypti* which has inserted a snout into each well and sucked the blood (biting) is counted. A test is repeated 6 times.

A biting inhibition ratio is obtained by the following expression. The biting inhibition ratio 100% means that there is no biting *Aedes aegypti.*

Biting inhibition ratio (%)={1−(number of biting vermin)/(number of test vermin)}×100

As a result, in a section of treatment with compound, the biting inhibitory effect is recognized.

Test Example 9

A formulation containing each of the compounds (42), (43), (45)-(49), (51)-(59), (61)-(64), (66), (67), (69), (71), (72), (74) and (75) prepared in accordance with Formulation Example 7 was diluted with an isopropyl alcohol/kerosine=1/9 mixed liquid so that the concentration of each compound became 0.5% w/v, to obtain a diluted solution.

Ten imagoes of Culexpipienspallens were allowed to release in a polyethylene cup (bottom surface diameter 10.6 cm), and the cup was covered with a 16 mesh nylon gauze. The polyethylene cup was arranged on a bottom of a chamber for a test (bottom surface: 46 cm×46 cm, height: 70 cm). From a height of 30 cm from an upper surface of the polyethylene cup, 0.5 mL of the diluted solution was sprayed using a spray gun (spraying pressure 0.4 kg/cm$^2$). After spraying, the cup was immediately taken out from the chamber for a test, the number of knocked down vermin was counted for 15 minutes with time, and a knockdown ratio was obtained. The knockdown ratio was calculated by the following expression.

Knockdown ratio (%)=(number of knocked down vermin/number of test vermin)×100

As a result, the knockdown ratio of the test vermin within 15 minutes was 80% or more in treatment with the compounds (42), (43), (45)-(49), (51)-(59), (61)-(64), (66), (67), (69), (71), (72), (74) and (75), respectively.

INDUSTRIAL APPLICABILITY

The present noxious arthropod controlling agent has controlling efficacy on a noxious arthropod, and is useful.

The invention claimed is:

1. A method for controlling a noxious arthropod, comprising applying an effective amount of an amide compound of formula (I):

(I)

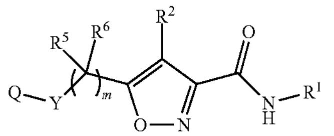

wherein $R^1$ is a C2-C8 alkyl group having one or more groups selected from the group consisting of a hydroxy group, a methoxy group, a C1-C6 alkylamino group and a di(C1-C6 alkyl)amino group, $R^2$ is a methyl group, a fluoromethyl group, a hydroxymethyl group, a 1-fluoroethyl group or a hydrogen atom, and Q-Y—$(CR^5R^6)_m$ is a C1-C4 alkoxy group or a C3-C8 hydrocarbon chain group optionally having one or more substituents selected from the group consisting of a halogen atom and a cyano group, to a noxious arthropod or a habitat of a noxious arthropod.

2. The method for controlling a noxious arthropod according to claim 1, wherein Q-Y—$(CR^5R^6)_m$ is a C3-C8 hydrocarbon chain group optionally having one or more substituents selected from the group consisting of a halogen atom and a cyano group.

3. The method for controlling a noxious arthropod according to claim 1, wherein Q-Y—$(CR^5R^6)_m$ is a C1-C4 alkoxy group optionally having one or more substituents selected from the group consisting of a halogen atom and a cyano group.

* * * * *